(12) United States Patent
Silverman et al.

(10) Patent No.: US 6,331,396 B1
(45) Date of Patent: Dec. 18, 2001

(54) ARRAYS FOR IDENTIFYING AGENTS WHICH MIMIC OR INHIBIT THE ACTIVITY OF INTERFERONS

(75) Inventors: Robert H. Silverman, Beachwood; Bryan R. G. Williams; Sandy Der, both of Cleveland, all of OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/405,438

(22) Filed: Sep. 23, 1999

Related U.S. Application Data
(60) Provisional application No. 60/101,497, filed on Sep. 23, 1998.

(51) Int. Cl.[7] .............................. C12Q 1/68; C12M 1/36; C07H 21/04

(52) U.S. Cl. .................. 435/6; 435/287.2; 536/23.1; 536/23.52; 536/24.3; 536/24.31

(58) Field of Search .................. 435/6, 287.2; 536/23.1, 536/24.31, 23.52

(56) References Cited

U.S. PATENT DOCUMENTS

| | | | |
|---|---|---|---|
| 5,700,637 | 12/1997 | Southern | 435/6 |
| 6,040,138 | * 3/2000 | Lockhart et al. | 435/6 |
| 6,077,673 | * 6/2000 | Chenchik | 435/6 |

FOREIGN PATENT DOCUMENTS

| | | |
|---|---|---|
| 97/10365 | 3/1997 | (WO) . |

OTHER PUBLICATIONS

Darnell et al. "Jak–STAT pathways and transacriptional activation in response to IFNs and other extracellular signaling proteins" Science, 1994, 264: 1415–1421.*

"A direct signaling pathway through tyrosine kinase activation of SH2 domain–containing transcription factors " by Xin–Yuan Fu, *Journal of Leukocyte Biology*, vol.57, Apr. 1995, pp. 529–535.

"A Nuclear Tyrosine Phosphatase Downregulates Interferon–Induced Gene Expression" by David, et al., *Molecular and Cellular Biology*, vol. 13, No. 12, Dec. 1993, pp. 7515–7521.

Abstract #95, "Probing Mechanisms of IFN Action with Gene Knockout Mice and Gene Chips" by Silverman, et al. Second Joint Meeting of the International Cytokine Society and the International Society for Interferon Rearch, Jerusalem, Israel, Oct. 25–30, 1998.

"The neuregulin, glial growth factor 2, diminishes autoimmune demyelination and enchances remyelination in a chronic relapsing model for multiple sclerosis"by Cannella, et al., *Proc. Natl. Acad. Sci. USA*, vol. 95, Aug. 1998, pp. 10100–10105.

"Accessing Genetic Information with High–Density DNA Arrays" by Chee, et al., *Science*, vol. 274, Oct. 25, 1996, pp. 610–614.

"Rapid genetic sequence analysis using a DNA probe array system" by Kreiner, *American Laboratory*, Mar. 1996.

"Light–generated oligonucleotide arrays for DNA sequence analysis" by Pease, et al., *Proc. Natl. Acad. Sci. USA*, vol. 91, May 1994, pp. 5022–5026.

"Polycystin, the polycystic kidney disease 1 protein, is expressed by epithelial cells in fetal, adult and polycystic kidney" by Ward, et al., *Proc. Natl. Acad. Sci. USA*, vol. 93, Feb. 1996, pp. 1524–1528.

"Dissecting the Regulatory Circuitry of a Eukaryotoic Genome" by Holstege, et al., *Cell*, vol.95, Nov. 25, 1998, pp. 717–728.

"Role of HIF–1 β in hypoxia–mediated aptosis, cell proliferation and tumor angiogenesis" by Carmeliet, et al., *Nature*, vol. 394, Jul. 30, 1998, pp. 485–490.

"The Murine Gene for Cellular Retinoic Acid–binding Protein Type II: Genomic Organization, Chromosomal Localization, and Post–Transcriptional Regulation by Retinoic Acid" by MacGregor, et al., *The Joural of Biological Chemistry*, vol. 267, No. 11, Apr. 15, 1992, pp. 7777–7783.

"Functional Dissection of Eukayotic Initiation Factor 4F: the 4A Subunit and the Central Domain of the 4 Subunit are Sufficient to Mediate Internal Entry of 43S Preinitiation Complexes" by Pestova, et al., *Molecular and Cellular Biology*, vol. 16, No. 12, Dec. 1996, pp. 6870–6878.

"Two Forms of Mouse Syntrophin, a 58 kd Dystrophin–Associated Protein, Differ in Primary Structure and Tissue Distribution" by Adams, et al., *Neuron*, vol. II, Sep. 1993, pp. 531–540.

"The Murine Decorin: Complete cDNA Cloning, Genomic Organization, Chromosomal Assignment, and Expression During Organogenesis and Tissue Differentiation" by Scholzen, et al.., *The Journal of Biological Chemistry*, vol. 269, No. 45, Nov. 11, 1994, pp. 28270–28281.

(List continued on next page.)

*Primary Examiner*—Stephanie Zitomer
*Assistant Examiner*—B J Forman
(74) *Attorney, Agent, or Firm*—Calfee, Halter & Griswold LLP

(57) ABSTRACT

Methods and model systems for identifying and characterizing new therapeutic agents, particularly proteins, which mimic or inhibit the activity of all interferons, Type I interferons, IFN-α, IFN-β, or IFN-γ. The method comprises administering an interferon selected from the group consisting of IFN-α, IFN β, IFN-τ, IFN-ω, IFN-γ, and combinations thereof to cultured cells, administering the candidate agent to a duplicate culture of cells; and measuring the effect of the candidate agent and the interferon on the transcription or translation of one or, preferably, a plurality of the interferon stimulated genes or the interferon repressed genes (hereinafter referred to as "ISG's" and "IRGs", respectively). The model system is an array with gene probes that hybridize with from about 100 to about 5000 ISG and IRG transcripts.

8 Claims, No Drawings-

OTHER PUBLICATIONS

"Molecular Cloning of Human Plasma Membrane Phospholipid Scramblase: A Protein Mediating Transbilayer Movement of Plasma Membrane Phospolipids" by Zhou, et al., *The Journal of Biochemistry*, vol. 281, Aug. 21, 1998, pp. 18240–28244.

"Direct Allelic Variation Scanning of the Yeast Genome" by Winzeler, et al., *Science*, vol. 281, Aug. 21, 1998, pp. 1194–1197.

"Exploiting Chemical Libraries, Structure and Genomics in the Search for Kinase Inhibitors" by Gray, et al., *Science*, vol., 281, Jul. 24, 1998, pp. 533–538.

"DNA Chips Survey an Entire Genome" by Service, *Science*, vol. 281, Aug. 21, 1998, P. 1122.

"Advances in polycystic kidney disease" by Schneider, *Molecular Medicine Today*, Feb. 1996, pp. 70–75.

"Cellular gene expression altered by human cytomegalovirus: Global monitoring with oligonucleotide arrays" by Zhu, et al., *Proc. Natl. Acad. Sci. USA*, vol. 95, Nov. 1998, pp. 14470–14474.

"A Genome–Wide Transcriptional Analysis of the Mitotic Cell Cycle" by Cho, et al., *Molecular Cell*, vol. 2, Jul. 1998, pp. 65–73.

"Cloning and Functional Analysis of BAG–1: A Novel Bcl–2 Binding Protein with Anti–Cell Death Activity" by Takayama, et al., *Cell*, vol. 80, Jan. 27, 1995, pp. 279–284.

"RAP46 Is a Negative Regulator of Glucocorticoid Receptor Acton and Hormone–induced Aptosis" by Kullman, et al., *The Journal of Biological Chemistry*, vol. 273, No. 23, Jun. 5, 1998, pp. 14620–14625.

"Identification of genes differentially regulated by interferon α, β, or γ using oligonucloetid arrays" by Der, et al. *Proc. Natl. Acad. Sci. USA*, vol. 95, Dec. 1998, pp. 15623–15628.

"Discovery and analysis of inflammatory disease–related genes using cDNA microarrays" by Heller, et al., *Proc. Natl. Acad. sci. USA*, vol. 94, Mar. 1997, pp. 2150–2155.

"Parallel human genome analysis: Microarray–based expression monitoring of 1000 genes" by Schena, et al., *Proc. Natl. Acad. Sci. USA*, vol. 93, Oct. 1996, pp. 10614–10619.

"Going global" by Phimister, *Nature Genetics*, vol. 21, No. 1, Jan. 1999, p.1.

"Microarrays and macroconsequences" Collins, *Nature Genetics*, vol. 21, No. 1, Jan. 1999, p.2.

"Array of Hope" by Lander, *Nature Genetics*, vol. 21, No. 1, Jan. 1999, pp. 3–4.

"Molecular interactions on microarrays" by Southern, et al., *Nature Genetics*, vol. 21, No. 1, Jan. 1999, pp. 5–9.

"Expression profiling using cDNA microarrays" by Duggan, et al., *Nature Genetics*, vol. 21, No. 1, Jan. 1999, pp. 10–14.

"Making and reading microarrays", by Cheung, et al., *Nature Genetics*, vol. 21, No. 1, Jan. 1999, pp. 15–19.

"High density synthetic oligonucleotide arrays" by Lupshutz, et al., *Nature Genetics*, vol. 21, No. 1, Jan. 1999, pp. 20–24.

"Options available—from start to finish—for obtaining expression data by microarray" by Bowtell, *Nature Genetic*, vol. 21, No. 1, Jan. 1999, pp. 25–32.

"Exploring the new world of the genome with DNA microarrays" by Brown, et al., *Nature Genetics*, vol. 21, No. 1, Jan 1999, pp. 33–37.

"The genetics of cancer—a 3D model" Cole, et al., *Nature Genetics*, vol. 21, No. 1, Jan. 1999, pp. 38–41.

"Resequencing and mutational analysis using oligonucleotide microarrays" by Hacia, *Nature Genetics*, vol. 21 No. 1, Jan. 1999, pp. 42–47.

"DNA microarrays in drug discover and development" by Debouck, et al, *Nature Genetics*, vol. 21, No. 1, Jan. 1999, pp. 48–50.

"Gene expression informatics—its all in your mine" by Bassett, et al. *Nature Genetics*, vol. 21 No. 1, Jan. 1999, pp. 51–55.

"Population genetics—making sense out of sequence" by Chakravarti, *Nature Genetics*, vol. 21, No. 1, Jan. 1999, pp. 56–60.

Jones et al. "Profiling the growth inhibitorymechanisms of interfereon–gamma by microarray expression analysis" Feb. 1999, 47(2): 61.*

* cited by examiner

ARRAYS FOR IDENTIFYING AGENTS WHICH MIMIC OR INHIBIT THE ACTIVITY OF INTERFERONS

This application claims the benefit of U.S. Provisional No. 60/101,497, filed Sep. 23, 1998.

The present invention was made with support from National Institutes of Health Grant NOs. AI 34039, CA 44059, and CA 62220. The United States Government has certain rights in the invention.

BACKGROUND OF THE INVENTION

Interferons (IFNS) are a family of related cytokines that mediate a range of diverse functions including antiviral, antiproliferative, antitumor and immunomodulatory activities. The pleiotropic activities of IFNs are mediated primarily through the transcriptional regulation of many downstream effector genes. IFNs bind to their cognate receptors and initiate a signaling cascade, involving the JAK-family of tyrosine kinases and STAT-family of transcription factors, that leads to the transcriptional induction of a number of IFN-stimulated genes (ISGs). IFN actions are largely mediated by the proteins encoded by ISGs, the best studied of which include the dsRNA-activated protein kinase (PKR), the 2'-5' oligoadenylate (2-5A) synthetases and 2-5A-dependent ribonuclease (RNaseL), and the Mx proteins. The other well-characterized category of ISGs include the STAT and IRF families of transcription factors which are involved in the regulation of both ISG and IFN gene expression. However, the biological functions for many ISGs, including 6-16, 9-27 and the ISG-54 gene family, remain unclear despite, in some cases, extensive investigation of the 5' regulatory regions of those genes.

ISGs exhibit unique patterns of transcriptional inducibility by different types of IFNs. Type I IFNs, representing the IFN-alpha ($\alpha$), -beta ($\beta$), -omega ($\omega$), and -tau ($\tau$) genes, are grouped together since they bind to common Type I IFN receptor, while IFN-gamma ($\gamma$) is designated as Type II IFN since it is the unique ligand for the distinct Type II IFN receptor. In general, engagement of the Type I IFN receptor results in activation of the multimeric transcription factor, ISGF3, and leads to the transcriptional initiation of gene promoters containing IFN-Stimulated Response Elements (ISRE). Type II IFN receptor stimulation typically activates STAT1 homodimers which can regulate transcription from gene promoters containing IFN-$\gamma$ Activated Sites (GAS). In accordance with this model, the differential inducibility of certain ISGs by Type I, Type II IFN, or by both, can be attributed to the presence of canonical ISRE or GAS elements.

Despite their common utilization of the same receptor complex, distinct Type I IFN proteins can mediate different biological responses. Numerous studies, using recombinant or purified natural, IFN-$\alpha$ or IFN-$\beta$ proteins, have shown that individual Type I IFNs can be distinguished by their unique profiles of specific biological activities including antiviral and antiproliferative finctions, natural killer cell stimulation, and receptor binding affinities. While the molecular mechanisms underlying these differences are not yet known, a likely possibility involves the differential expression of ISGs by the various Type I IFNs. The best documented example of this concept involves betaRI ($\beta$RI), a chemokine gene whose expression is preferentially inducible by IFN-$\beta$ but not by IFN-$\gamma$ nor several IFN-$\alpha$ subtypes.

Considerable efforts have been devoted to exploit the therapeutic potential of IFNs. Currently both IFN-$\alpha$ and IFN-$\beta$ are used to treat patients with serious diseases. Presently, IFN-$\alpha$ is used in the treatment of chronic myelogenous leukemia (CML), hairy cell leukemia, renal cell carcinoma, melanoma, hepatitis C virus infections, Kaposi sarcoma and hepatitis B infections. IFN-$\beta$ is used for the treatment of multiple sclerosis. Unfortunately, patients who have been treated with the currently available forms of IFN-$\alpha$ and IFN-$\beta$, which include purified naturally occurring IFNs and recombinant IFNs, have experienced serious side-effect including including fever, malaise, myalgia, and depression.

Accordingly, it is desirable to have new methods and tools for identifying new therapeutic agents (hereinafter referred to as "IFN mimics") which upregulate the ISGs that cause desirable effects in patients but which do not upregulate the ISGs that cause the detrimental side-effects associated with treating patients with IFNs. It is also desirable to have methods and tools which can be used to identify agents that selectively inhibit upregulation of the ISGs that cause the detrimental side-effects which result from treatment with IFNs, particularly IFN-$\alpha$ and IFN-$\beta$. It is also desirable to have a method for establishing patient sensitivity to interferon before beginning treatment protocols. It is also desirable to have methods and tools for monitoring the efficacy of treatment of patients with the currently used interferons and with any new interferon-like agents which are being developed. It is also desirable to have new treatment protocols which can make interferon therapy for cancer more effective. It is also desirable to have new methods and tools for identifying the biochemical pathways by which IFNs mediate their therapeutic effects.

SUMMARY OF THE INVENTION

The present invention provides novel methods and model systems for identifying and characterizing new therapeutic agents, particularly proteins, which mimic the activity of all interferons, Type I interferons, IFN-$\alpha$, IFN $\beta$, IFN-$\tau$, IFN-$\omega$, and IFN-$\gamma$,. The method comprises administering an interferon selected from the group consisting of IFN-$\alpha$, IFN $\beta$, IFN-$\tau$, IFN-$\omega$, IFN-$\gamma$, and combinations thereof to cultured cells, administering the candidate agent to a duplicate culture of cells; and measuring the effect of the candidate agent and the interferon on the transcription or translation of one or, preferably, a plurality of the interferon stimulated genes or the interferon repressed genes (hereinafter referred to as "ISG's" and "IRGs", respectively). The model system is an array with gene probes that hybridize with from about 100 to about 5000 ISG and IRG transcripts.

In another aspect the present invention provides new methods for identifying and characterizing new therapeutic agents which block the activity of all interferons, Type I interferons, select Type I interferons, or IFN-$\gamma$. The method comprises administering an interferon selected from the group consisting of IFN-$\alpha$, IFN $\beta$, IFN-$\tau$, IFN-$\omega$, IFN-$\gamma$, and combinations thereof to cultured cells, administering the interferon and the candidate agent to a duplicate cell culture; and assaying for changes in the levels of transcription of one or, preferably, a plurality of ISGs and IRGs, particularly those new ISGs and IRGs which are listed in Table 2 and Table 3, respectively.

In another aspect the present invention provides new methods for identifying and characterizing new agents which inhibit the transcription or translation of a new ISG that has been uncovered by the present study. The method comprises administering the interferon which has been shown to stimulate transcription of the new ISG to a set of cultured cells, administering the interferon and the candidate inhibitor to a duplicate set of cultured cells; and measuring the levels of mRNA or the levels of protein or factor encoded by the ISG gene in the two sets of cultured cells. This method is especially useful for identifying inhibitors for those ISGs whose transcription is increased by 2-fold or greater by treatment with the interferon.

In another aspect, the present invention provides a method of determining the sensitivity of a patient to prospective interferon therapy. The method comprises exposing cell samples obtained from a patient who is a candidate for interferon therapy to the interferon and measuring the levels of one or, preferably, a plurality of the ISG and IRG transcripts that are produced in response to the exposure. An increase in the levels of ISG transcripts and a decrease in the level of IRG transcripts in the interferon treated cells relative to the levels found in untreated control cells indicates that the patient is responsive to treatment with the interferon. A finding of no or little difference in the levels of ISGs and IRGs transcripts in the interferon-treated cells and control cells indicates that the patient is not responsive to treatment with the interferon.

In another aspect the present invention provides a method for monitoring the efficacy of interferon therapy in a patient. The method comprises measuring levels of transcripts of one or, preferably, a plurality of ISGs which are known to be stimulated by the interferon in a first cell sample obtained from the patient prior to administration of the interferon and in a second cell sample obtained from the patient subsequent to administration of the interferon. An increase in levels of the ISG transcript in the sample obtained from the patient subsequent to treatment relative to the sample obtained from the patient prior to treatment indicates that the patient is responsive to treatment with the interferon at the dosages administered.

In another aspect the present invention provides a method for monitoring the expression of genes which are specifically regulated by INF-β and therefore will determine the efficacy of INF-β therapy.

In another aspect the present invention provides a method for diagnosing the presence of viral infection in a patient. The method comprises assaying for elevated levels of transcripts of one or, preferably, a set of ISGs in cells which have been obtained from the patient relative to levels found in healthy subjects.

In another aspect the present invention relates to a method of identifying new ISGs and IRGs, particularly the ISGs and IRGs whose expression is regulated by IFN-β. The method comprises administering interferon to cultured cells for a period of time, such as for example 2 hours, 4 hours, 6 hours or 8 hours, measuring the levels of gene transcripts from untreated control cells and in cells treated with the interferon using arrays which comprise probes that are known to hybridize with transcripts of known ISGs and IRGs and with transcripts of genes whose products are not known to be ISGs or IRGs; and comparing the levels of transcripts for each gene in the control and interferon-treated cell cultures to provide a set of genes that are stimulated by treatment with interferon and a set of genes that are repressed by treatment with the interferon.

DETAILED DESCRIPTION OF THE INVENTION

The mRNA profiles from IFN-α, -β or -γ treatments of the human fibrosarcoma cell line, HT1080, were determined using oligonucleotide arrays with probe sets corresponding to more than 6800 human genes. Among these were transcripts for 48 known IFN-stimulated genes, the expression of which were consistent with previous studies in which the particular ISG was characterized as responsive to either Type I (α, β) or Type II (γ) IFNs, or both. Novel IFN stimulated genes were identified which were diverse in their known biological functions and included genes implicated in regulating apoptosis (RAP46/Bag-I and phospholipid scramblase), stress-activated protein kinase pathways (mixed lineage kinase-2), and growth factor signaling (vascular endothelial growth factor-related protein). Furthermore, gene transcripts were also identified whose expression was reduced by IFNs including COX17, histone H4, and TRAF6. These results demonstrate the usefulness of arrays comprising gene probes in monitoring the effect of IFNs on mammalian gene expression.

In accordance with these findings, new model systems useful for identifying new therapeutic agents and for identifying the biochemical pathways by which IFNs mediate their therapeutic effects are provided.

In one aspect the model system is a customized array which comprises gene probes that hybridize with from about 100 to about 5000 ISG and IRG transcripts. As used herein the term "array" refers to an arrangement of the gene probes on a substrate or support system. Preferably, the gene probes are arranged in a particular order and attached to the substrate or support system. As used herein the term "ISG" refers to any mammalian gene whose expression is increased at least 1.2 fold in cells treated with an interferon. (See Table 4 or the data set displayed at www. lerner.ccf.org/ri/labs/williams.html for a list of such genes.) As used herein the term "IRG" refers to any mammalian gene whose expression is decreased at least 1.2 fold in cells treated with an interferon. (See Table 4 or the data set displayed at the above-described website for a list of such genes.) As used herein the term "interferon" refers to a naturally-occurring interferon, a recombinant interferon which is at least 50% homologous to a naturally occurring interferon, interferon mixtures, and chemically-modified interferons, such as a polyethylene glycol (PEG)-interferon. Naturally-occurring interferons include all subtypes of IFN α, IFN-β, and IFN-γ. Preferably, the array comprises probes to fewer than 100 genes which are not ISGs or IRGs.

Examples of the types of molecules which may be used as a probe are cDNA molecules, oligonucleotides which contain at least 10 nucleotides, preferably from about 10 to about 30 nucleotides, and other gene probes which comprise nucleobases including synthetic gene probes such as, for example, peptide nucleic acids (PNAs). Preferably, the probes are attached to a solid support such as for example a glass substrate. Among the probes are molecules which hybridize under stringent conditions with transcripts of the newly-discovered ISGs shown in Table 2, i.e. the ISGs that are not preceded by a + sign. Preferably, the array comprises probes which hybridize a plurality of the ISGs shown in Table 2 and the IRGs shown in Table 3.

Hybridization conditions are based on the melting temperature ($T_m$) the nucleic acid binding complex or probe, as described in Berger and Kimmel (1987) Guide to Molecular Cloning Techniques, Methods in Enzymology, vol 152, Academic Press. The term "stringent conditions, as used herein, is the "stringency" which occurs within a range from about Tm-5 (5° below the melting temperature of the probe) to about 20° C. below Tm. As used herein "highly stringent" conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Alternatively, the customized array comprises probes that hybridize with transcripts of ISGs and IRGs responsive to select interferons or to transcripts of ISGs and IRGs that are highly responsive to one or more interferons. In one embodiment the array comprises probes to ISGs and IRGs responsive to Type I interferons, including all IFN alpha, IFN beta, IFN-omega, and IFN-tau and lacking probes that hybridize with Type II interferons, including IFN-gamma. In another array comprises probes that hybridize with transcripts of ISGs and IRGs responsive to Type II interferons, and lacking probes that hybridize with Type I interferons. In another embodiment the array comprises gene probes that hybridize with genes whose expression is decreased or increased at least 3 fold by treatment with a Type I interferon. Preferably, the gene probes on such array hybridize to fewer than 100 different transcripts of genes whose expression is not increased at least 3 fold by treatment with a Type I interferon. In another embodiment the array comprises gene probes that hybridize with genes whose expression is decreased or increased at least 3 fold by treatment with a Type II interferon. Preferably, the gene probes on such array hybridize to fewer than 100 different transcripts of genes whose expression is not increased at least 3 fold by treatment with a Type II interferon.

Methods of Identifying New Therapeutic Agents

The present invention provides novel methods for identifying and characterizing new therapeutic agents, particularly proteins, which mimic the activity of all interferons, Type I interferons, IFN-γ, or select Type I interferons, such as, for example, IFN-β. The method comprises administering an interferon selected from the group consisting of IFN-α, IFN β, IFN-γ, and combinations thereof to a sample or samples of cells, administering the candidate agent to a duplicate sample of cells; and measuring the effect of the candidate agent and the interferon on the transcription or translation of one or, preferably, a plurality of ISGs and IRGs including the new ISGs that are not preceded by a + sign in Table 2. More preferably, the effect of the interferon is measured using a mini-array as described above or an array that comprises gene probes to all of the ISGs and IRGs shown in the attached data set. Preferably, separate cultures of cells are exposed to different dosages of the candidate agent.

Any cell line which is capable of being maintained in culture may be used in the method. Preferably, the cell line is a human cell line, such as, for example, a human fibrosarcoma cell line, Daudi cells, HeLa cells, and human primary cells including peripheral blood mononuclear cells, epithelial cells, endothelial cells, neural cells, muscle cells, or fibroblast cells. Nearly identical amounts of the interferon and the candidate agent are added to the culture medium of separate representative cultures of the cells. The cells are then incubated in the medium for a sufficient amount of time for transcription of the ISGs to occur or for turnover of the basal amounts of mRNA encoded by the IRGs. Preferably the cells are incubated in the medium for about 0.5 hours to about 24 hours, more preferably for from about 1 to about 8 hours. Control cultures are incubated in medium lacking the interferon and the candidate agent.

Alternatively, cells from individuals that have been treated with the interferon or with the agent are used. For example peripheral blood mononuclear cells from such individuals, as well as cells from untreated individuals are used. Preferably, RNA is extracted from such cells, converted to cRNA and used to probe arrays and mini-arrays, as described above.

The effect of the candidate agent on transcription is determined by measuring the relative amounts of the ISG transcripts that are present in the interferon treated cultures and the candidate agent-treated cultures as compared to the control cultures. Preferably, the relative amounts of IRG transcripts that are also present in the control culture, interferon-treated culture, and candidate agent-treated culture are also measured. Alternatively, the relative amounts of transcripts for a preselected subset of ISGs, or a preselected subset of IRGs or a single ISG such as for example, 2-5-A-synthetases, hypoxia inducible factor −1, scramblase, fas, BAK, PKR, RING4(TAP1), LMP7, MHC1, or a single IRG such as for example, bcr, PKD1, and COX17 are measured in the three cultures. The methods are especially useful for identifying therapeutic agents that are more potent than the known interferons and for identifyng therapeutic agents that do not have the same deleterious effects as the interferon which is used in the assay. The method is also useful for identifying IFN mimics that can be used in patients that fail IFN therapy due to anti-IFN antibody production in such patients.

Suitable methods for measuring the relative amounts of the transcripts are Northern blots, RT-PCR, or real-time RT-PCR, or RNase protection assays. For ease in measuring the transcripts for a plurality of the ISGs that are induced by the interferon or for a plurality of the IRGs that are repressed by the interferon, it is preferred that arrays and the mini-arrays as described above be used.

Optionally, the relative amounts of gene products that are produced in response to treatment with the interferon and the candidate therapeutic agent are also measured in the three cultures. In those cases where the gene product is a protein, the method used for assaying production of the gene products include, by way of example, western blots probed with specific antibody to the protein encoded by the ISG or IRG.

In another aspect the present invention provides new methods for identifying and characterizing new therapeutic agents which block the activity of all interferons, Type I interferons, IFN-γ, or select Type I interferons, such as, for example, IFN-β. The method comprises administering an interferon selected from the group consisting of IFN-α, IFN β, IFN-γ, and combinations thereof to a sample or samples of cultured cells, administering the interferon and the candidate inhibitor to a duplicate sample of cells; assaying for differences between the levels of transcription of the ISGs and IRGs in the two samples of cells. The differences are determined by measuring the relative levels of ISG transcripts and IRG transcripts in the cells treated with interferon and no inhibitor and in the cells that are treated with interferon plus the candidate inhibitor. Preferably, the levels of the ISG and IRG transcripts are also measured in untreated control cultures which are incubated in medium lacking both the interferon and the candidate inhibitor. Preferably, the levels of the transcripts of the genes listed in Table 2 and Table 3 are assayed.

Alternatively, cells from individuals that have been treated with the interferon or with the interferon plus the candidate inhibitor are used. For example peripheral blood mononuclear cells from such individuals, as well as cells from untreated individuals are used. RNA is extracted from such cells, converted to cRNA and used in conjunction with an array or mini-array as described above.

This method is especially useful for identifying potential therapeutic agents which block or avoid the unwanted, harmful side-effects of current IFN therapy. The agents which inhibit IFN function, i.e., the IFN antagonists, are useful for treating conditions such as AIDS, SLE, and rheumatoid arthritis, in which IFNs contribute to the disease.

In another aspect the present invention provides new methods for identifying and characterizing new agents which inhibit the transcription or translation of one of the new interferon-regulated genes that have been uncovered by the present study. The method comprises administering the interferon which has been shown to stimulate transcription of a particular gene to a cell culture, administering the interferon and the candidate inhibitor to a duplicate cell culture; and measuring the levels of mRNA or the levels of protein encoded by the gene in the two cell cultures. This method is especially useful for identifying inhibitors for those genes whose transcription is increased by 2-fold or greater by treatment with the interferon.

Method for Determining the Interferon Sensitivity of a Subject

In another aspect, the present invention provides a method of determining the sensitivity of a patient to prospective interferon therapy. The patient may be a veterinary patient or a human patient. The method comprises exposing cell samples obtained from a patient who is a candidate for interferon therapy to the interferon and measuring the levels of one or, preferably, a plurality of the ISG and IRG transcripts that are produced in response to the exposure. Suitable cells include, for example, nucleated blood cells, leukemia cells, tumor cells, liver cells obtained by biopsy. An increase in the levels of ISG transcripts and a decrease in the level of IRG transcripts in the interferon treated cells relative to the levels found in untreated control cells indicates that the patient is responsive to treatment with the interferon. A finding of little to no difference, for example a difference of less than 5%, in the levels of ISGs and IRGs transcripts in the interferon-treated cells and control cells indicates that the patient is not responsive to treatment with the interferon and that treatment with the interferon is not likely to produce the desired therapeutic effect.

Methods of Monitoring the Efficacy of Treatment with Interferon.

In another aspect the present invention provides a method for monitoring the efficacy of interferon therapy in a patient. In one embodiment, the method is used to identify non-responders, i.e., patients who are not expected to be responsive to treatment with a specific interferon or interferon mimic, or to determine minimum dosages which are expected to induce a beneficial therapeutic response in the patient, or to determine optimum dosages of the IFN or IFN mimic. The method comprises obtaining a first sample from the patient, administering the interferon or interferon mimic to the patient, obtaining a second sample from the patient, and measuring levels of a transcript for one or more genes that are down-regulated or upregulated by the interferon. The samples may be blood samples or tissue samples obtained by biopsy. Suitable cells include, for example, nucleated blood cells, leukemia cells, tumor cells, liver cells obtained by biopsy.

Preferably, the levels of one or more of the ISGs identified in Table II as not being known (i.e., the ISGs in Table 2 which are not preceded by a + sign) or one or more of the IRGs in Table 3 are measured. For example, the method may comprise isolating PBMCs from the patient before and after treatment with the IFN, isolating RNA from the PBMCs and performing RT-PCR or Northern blots on isolated RNA to determine if the transcripts of one or more of the IRGs in Table 3 have been downregulated. Alternatively, protein may be extracted from the PBMCs and then assayed by western blots using antibody to one or more of the proteins encoded by the IRGs in Table 3. More preferably the pre-treatment and post-treatment levels of the transcripts of all the ISGs in Table 2 and all the IRGs in Table 3 are determined.

In one preferred embodiment the method comprises administering IFN-β or a candidate INF-β mimic to the patient and measuring the levels of the phospholipid scramblase gene transcript in cells from the two samples, i.e., in cells from the sample obtained prior to administration of the interferon and after administration of the interferon. The levels of phospholipid scramblase gene transcript may be measured in peripheral blood mononuclear cells (PBMCs). A finding that treatment with INF-β or the IFN-β mimic has not elevated the levels of phospholipid scramblase transcript in the sample obtained from the patient as compared to the levels of phospholipid scramblase transcript in the PBMCs obtained from the patient before treatment, i.e., a finding that treatment with INF-β did not upregulate the phospholipid scramblase gene in PBMCs from the patient, indicates that the treatment with the INF-β or IFN β mimic is not likely to produce the desired therapeutic effect. Such method is useful for determining whether treatment with INF-β will decrease the duration and frequency of relapse in a patient with multiple sclerosis. This method is also useful for determining the proper dosing schedule or concentration of INF-β or INF-β mimic that must be used to treat the patient or the modifications to IFN-βw which must be made in order for treatment with IFN-α to have a more positive effect on suppressing disease in the patient. The method is also useful to determine optimum dosages of INF-β or an INF-β mimic.

In another preferred embodiment the method comprises administering IFN-α or IFN-γ to a patient with chronic myelogenous leukemia (CML) and measuring the levels of bcr/abl gene transcript in the leukemia cells from these patients both before and after administration of the IFN-α or IFN-γ to the patient. IFN-α and IFN-γ cause decreases in bcr expression. Because the bcr/abl oncogene which causes CML is also driven by the bcr promoter, IFN-α or IFN-γ treatment is expected to lead to decreases in bcr/abl mRNA levels, thus, leading to a therapeutic benefit for CML patients. Also ex vivo treatments of bone marrow or peripheral stem cell autologous transplants can be treated with IFN-α or IFN-γ as a method for purging the leukemia cells from the transplant.

Method of Diagnosing a Viral Infection in a Patient

In another aspect, the present invention provides a method for diagnosing a viral infection. The method comprises obtaining a cell sample from the patient, and measuring levels of a transcript for a gene which is down-regulated or upregulated by a Type I interferon in the cell sample. Preferably, levels of such transcripts are compared to the levels that are present in healthy subjects, i.e., persons who do not have a viral infection. Preferably, levels of the genes which are listed in Table 2 and Table 3 are measured.

Suitable methods for measuring the relative amounts of the ISG and IRG transcripts are Northern blots, RT-PCR, or real-time RT-PCR, or RNase protection assays. For ease in measuring the transcripts for all of the ISGs that are induced by the Type I interferon or interferons and for all of the IRGs that are repressed by the Type I interferon or interferons, it is preferred that arrays and the mini-arrays as described above be used.

Methods for Identifying Antiviral Proteins

Such methods are based on knowledge of which genes are induced or repressed by IFNs. In one aspect, a human cell line is transfected with a cDNA of an ISG or IRG, preferably a newly-identified ISG or IRG and grown under conditions that permit expression of the ISG or IRG The cells are then challenged with a virus. If the ISG encodes an antiviral protein, virus replication will be inhibited in cells transfected with the ISG cDNA.

Alternatively, the ISG in a culture of human cells is suppressed by transfecting the cells with antisense cDNA, or antisense oligonucleotide, or PNA, or a dominant negative mutant ISG. Cells in which the ISG expression is inhibited or suppressed are expected to have a defect in the biological action of IFNs, such as for instance the antiviral activity of IFN.

Method of Identifying New ISGs and IRGs.

In another aspect the present invention relates to a method of identifying new ISGs and IRGs. The method comprises administering IFN-α and IFN-β, and IFN-γ to separate sets of cultured cells for a period of time, such as for example 2 hours, 4 hours, 6 hours or 8 hours, assaying the transcripts present in untreated control cells and in the IFN-treated sets of cultured cells using arrays comprising probes to genes that are known to be induced or repressed by treatment with one or more interferons and to genes that are not known to be induced or repressed by treatment with one or more interferons. The results of the assay provide a set of genes which are stimulated by IFN-α and IFN-β, IFN-γ or combinations thereof and a set of genes that are repressed by treatment with IFN-α, INF-β, IFN-γ or combinations thereof. Such method is useful for identifying genes that are upregulated or down regulated by all Type I and Type II interferons, genes that are preferentially upregulated or downregulated by a subset of IFNs, e.g. Type I interferons as opposed to Type II interferons, and genes that are exclusively upregulated or down regulated by one interferon, such as for example, IFN-α or one subtype of IFN-α, INF-β, or IFN-γ.

The following examples are for purposes of illustration only and are not intended to limit the scope of the claims which are appended hereto.

EXAMPLE 1

To identify novel ISGs and obtain a comprehensive profile of differential ISG expression by distinct IFNs, oligonucleotide arrays containing probe sets for an 6800 human genes were used to assay for changes in mRNA expression following stimulation of the human fibrosarcoma cell line, HT1080, with either IFNα, -β or γ. Monitoring of gene expression by this method is based on hybridization of labeled RNA populations to high-density arrays of oligonucleotides, synthesized on a glass substrate by a combination of photolithography and conventional oligonucleotide chemistry as described in Fry, A. M., S. J. Schultz, J. Bartek, E. A. Nigg (1995) JBC 270, 12899–12905. Several hundred genes were determined to be IFN-regulated including many of which represented novel ISGs. Significantly, the identification of novel ISGs with known biological functions provides new and informative insights into the mechanisms of IFN action.

Materials and Methods

Cell Culture and RNA Isolation. HT1080 cells were cultured using DMEM supplemented with fetal bovine serum (10%) and antibiotics. Cells ($10^7$) were plated on 15 cm tissue culture plates and cultured overnight before being treated with 1000 IU/ml of each IFN, IFN-α (IFNalpha2a, Roche, specific activity $2.7 \times 10^8$ IU/mg), IFN-β (IFN-beta, Berlex, specific activity $2 \times 10^8$ IU/mg), or IFN-γ (IFN-gamma, Gibco-BRL, specific activity $10^7$ IU/mg). After treatment with the IFNs for 6 hours, total RNA was isolated (Trizol, Gibco-BRL).

Preparation of cRNA. The methods for preparation of cRNA and subsequent steps leading to hybridization and scanning of the Hu6800 GeneChip Arrays were provided by the manufacturer (Affymetrix). Briefly, poly A+RNA was isolated from 100 µg total RNA of each sample with Oligotex (Qiagen) and converted into double-stranded cDNA using a cDNA synthesis kit (SuperScript Choice, Gibco-BRL) with a special oligo dT(24) primer containing a T7 RNA polymerase promoter site added 3' of the poly T tract (Genset). After second-strand synthesis, labeled cRNA was generated from the cDNA sample by an in vitro transcription (IVT) reaction (T7 MegaScript System, Ambion) supplemented with biotin-11-CTP and biotin-16-TTP (Enzo Diagnostics). The labeled cRNA was purified using RNeasy spin columns (Qiagen).

Fifty µg of cRNA from each sample was used to prepare 1 ml of master hybridization mix which also contained a cocktail of 4 control cRNAs for bacterial genes, added in known concentrations (BioB, BioC, BioD and cre, at 1.5, 5, 25 and 100 pM, respectively; referred to as "staggered spikes"), to serve as tools for comparing hybridization efficiency between arrays. A biotinylated oligonucleotide, B2, was also added which hybridizes to unique features at the center and 4 corners of each chip to facilitate accurate orientation and mapping of the probe sets.

Microarray Hybridization and Scanning. Fifty µg of each cRNA sample was fragmented by mild alkaline treatment, at 94° C. for 35 min in fragmentation buffer (200 mM Trisacetate, pH 8.1, 500 mM potassium acetate, 150 magnesium acetate). A final complete hybridization mix for each sample was prepared which contained the fragmented cRNA, 50 pM of a control biotinylated oligonucletide, B2 (Affymetrix), staggered control cRNA cocktail (final concentrations: 1.5 pM BioB, 5 pM BioC, 25 pM BioD and 100 pM cre), 0.1 mg/ml herring sperm DNA (Sigma), and 2×Affy buffer, in 1 ml total volume. Prior to hybridization, the cRNA samples were heated to 94° C. for 5 min, equilibrated to 40° C. for 5 min, and clarified by centrifugation (14,000 g) at room temperature for 5 min. Aliquots of each sample (200 µl) were hybridized to Hu6800 GeneChip arrays at 40° C. for 16 h, in a rotisserie oven set at 60 rpm. The Hu6800 GeneChip array represents a set of 4 individual chips, A–D, each containing unique probe sets to over 1700 genes, collectively representing more than 6800 human genes. Following hybridization, the arrays were washed with 6×SSPE and 0.5×SSPE according to manufacturer's protocol stained with strepavidin-phycoerythrin (Molecular Probes), washed again and read using a confocal microscope scanner with the 560mm longpass filter (Molecular Dynamics, Affymetrix). Data Analysis. Data analysis were performed using GeneChip 3.0 software. Comparison files were created by scaling the 6 probe sets for 5', M and 3' of actin and GAPDH in all data sets to an arbitrary value, 50,000, and normalizing to all genes.

Results

To assess variability in array hybridization and cDNA synthesis efficiency between samples, two types of hybridization controls were examined. Hybridization efficiency between arrays was assessed by comparing the signal intensities for the 4 control bacterial gene cRNA "spikes", BioB, BioC, BioD and cre, which had been added to the hybridization mixtures at known concentrations (1.5, 5, 25 and 100 pM, respectively). Among the 16 total arrays screened, BioB was usually detected as absent, while BioC, BioD and cre were detected as present in all data sets. This established that, under these hybridization conditions, the lower detection limit was in the range of 1.5 to 5 pM. Each array also contained distinct probe sets corresponding to the 5', middle (M), and 3' regions for both actin and GAPDH. The cumulative hybridization intensities for either of these gene transcripts were used to provide normalization between different RNA samples, as is commonly done in conventional mRNA detection methods. Furthermore, the efficiency of full-length cDNA synthesis for a given cRNA sample can be assessed by comparing the respective 3' signal intensities to that of the upstream 5' and middle regions.

Since each sample was hybridized to 4 separate DNA arrays, it was essential to determine the consistency among arrays by calculating the average intensities for all of the actin and GAPDH probe set among the data sets (See Table 1 below). Importantly, the average hybridization signals for each of the 6 different actin and GAPDH probe sets differed by less than 20% among the four samples. To compare the efficiency of cDNA synthesis between samples, the ratios for the 5' and middle intensities relative to the 3'-intensities were calculated for actin and GAPDH. Among the 4 samples, the intensities for 5'-GAPDH signals were 81–86% of the 3'-GAPDH intensities, while M-GAPDH signals were 101–110% of the 3'-GAPDH values; the 5'- and M-actin intensities relative to that of the 3'-actin values, were 130–146% and 146–157%, respectively. The higher signal intensities for the M- and 5'-GAPDH regions as compared to the 3'-region are reflective of the intrinsic hybridization characteristics of these probes sets. Also, a high degree of similarity was observed in the overall patterns of 5', middle, and 3' intensities between samples. Specifically, the 5'-actin intensities were lower than M-actin, but higher than 3'-actin signals in all 4 samples; all M-GAPDH intensities were uniformly higher than those of the 3'-GAPDH regions which, in turn, were higher than M GAPDH signals. Taken together, these data indicate that a high level of both efficiency and consistency was achieved in the cDNA and cRNA synthesis for these 4 samples.

TABLE 1

Average intensity values for actin and GAPDH. The average intensity values for the probe sets indicated were calculated from the respective values obtained by hybridization of each sample to the 4 arrays which comprise a Hu6800 GeneChip set.

| Sample | 5' | M | 3' |
|---|---|---|---|
| Actin | | | |
| 1 | 5662(1.46) | 6089(1.57) | 3875(1) |
| 2 | 7195(1.30) | 8073(1.46) | 5532(1) |
| 3 | 7311(1.33) | 8167(1.48) | 5484(1) |
| 4 | 7860(1.49) | 8254(1.56) | 5281(1) |
| GAPDH | | | |
| 1 | 6314(0.82) | 8493(1.10) | 7707(1) |
| 2 | 8107(0.86) | 10230(1.09) | 9417(1) |
| 3 | 6949(0.81) | 8635(1.01) | 8542(1) |
| 4 | 8101(0.85) | 10319(1.09) | 9441(1) |

We next determined which gene transcripts were detectable and their respective signal intensities. The total number of mRNAs detected as present among the 4 samples was similar: untreated, 2207; IFN-α, 2225; IFN-β, 2403; and IFN-γ 2320. The intensities for gene transcripts detected as present represented a range spanning 3 orders of magnitude, from approximately 20 to the highest recorded value of 18,524 for metallothionein. The majority of these mRNAs, approximately 85–90%, were detected with intensities of less than 1000. The genes associated with intensities greater than 1000 (~300 genes) include many of the ribosomal genes and commonly known high-abundance genes such as tubulin, elongation factor 1-a and ubiquitin. It is interesting to note that among this set of highly abundant mRNAs, stimulation by any of the 3 IFNs did not cause dramatic changes in their expression levels, with any detectable changes being less than 2-fold. The singular exception was β2 microglobulin, a known ISG, with a basal expression level of 1111 that was increased 1.9-, 2.3- and 1.3-fold, respectively, by IFN-α, -β or -γ (Table 2).

To identify IFN-regulated genes, pairwise comparisons were generated between the data sets from each of the IFN-treated samples and the untreated HT1080 cell data set. Over 1000 genes were identified whose mRNA expression levels changed following IFN stimulation (See FIG. 4 and the data set posted at www.lerner.ccf.org/ri/labs/williams.html). The majority of these (>75%) represented genes for which the degree of change was less than 2-fold. The number of genes whose expression changed more than 10-, 4- or 2-fold was 10, 26 and 94 for IFN-α; 14, 56 and 268 for INF-β; and 4, 25 and 129 for IFN-γ, respectively.

To select the genes most likely to represent IFN-regulated genes which are strongly induced or repressed by IFNs, we empirically tested different criteria to make further selections from the list of over 1000 differentially expressed genes. By using known ISGs as "guideposts", we determined reasonable but conservative delineations for fold change values. After applying a given criteria to yield a shortened list of genes, its effectiveness was assessed by the number of known ISGs remaining and in particular, how many remained near the bottom of the list. Three criteria were ultimately applied to generate a list of 128 genes (Table 2): 1) gene transcripts with at least 4-fold increased expression by any IFN type, 2) gene transcripts with at least 3-fold increase by any IFN type and detected as absent in untreated HT1080 cells, and 3) gene transcripts with at least 2-fold increase in response to all 3 types of IFNs. These genes were then ordered in 3 subgroups by first listing genes on the basis of highest fold change in response to IFN-α, followed by responses to INF-β and finally, IFN-γ. A useful aspect of the GeneChip 3.0 software involves the special identification of genes whose expression was called as absent from the untreated or baseline sample, but present in the IFN-treated sample. In these cases, the fold change is calculated by dividing the intensity value for the gene from the IFN treated data set, by an arbitrary value of 20 (which approximates the lower limit of detection) and thus, the calculated fold change most likely represents a underestimation of the true fold change. The genes falling into this category are identified in Table 2 with a "greater than" sign (>) preceding the fold change value.

Among the 128 genes in Table 2, at least 48 genes represent known ISGs as indicated in previous published studies while the remaining 80 represent novel IFN-regulated genes. The characteristic induction profiles for these genes allows for them to be categorized as 1) genes which are induced by all 3 types of IFNs, 2) genes inducible by IFN-α or IFN-β, 3) genes preferentially induced by IFN-β, and 4) genes preferentially induced by IFN-γ; 9–27, 2–5A synthetase, HIF-1 and IRF-1 represent examples for each of categories, respectively (FIG. 1, Table 2). There were no convincing examples of genes preferentially induced by IFN-α but not by IFN-β. While there are examples of genes listed in Table 2 with significant fold increases in response to IFN-α, but with 0 representing the fold increase by INF-β, the respective IFN-induced intensity values are in fact similar. As examples, the respective IFN-α- and INF-β treated intensities for alpha-1 type XVI collagen are 220 and 184, and for PML-I are 84 and 88, despite 0-fold increase by IFN-β displayed for both genes. When analyzing two data sets, the GeneChip software uses a decision matrix which includes other parameters in addition to the net change in intensity values, in order to decide whether a given gene is differentially expressed. Consequently, once a decision is made that there was no significant difference in expression, "0" is automatically entered as the fold change value for that gene regardless of the actual ratio between the two intensity values. Therefore in the overall analysis, it is important to consider actual intensity values in addition to the fold-change.

The results for specific known ISGs are as follows: 6-16 was absent in untreated cells and induced at least 20- and 21-fold by IFN-α or INF-β respectively, but not at all by IFN-γ. 9-27 was induced 23- and 22-fold by IFN-α or INF-β and 8-fold by IFN-γ (FIG. I and Table 2). The consistency between our data and previous studies regarding IFN-specific inducibility further extends to several other genes.

ISGs which are preferentially induced by IFN-α but not IFN-γ include the 2-5' oligoadenylate synthetase family of genes, MxA and MxB genes, and the gene family comprising ISG54, ISG56, ISG58, and RIG-G. ISGs preferentially induced by IFN-γ include IRF-1, IP-30 and IITA; ISGs which are responsive to both IFN-α and IFN-γ include MHC Class I genes, STATI and GBP. The differential induction of 2-5A synthetase mRNA by IFN-α and IFN-γ was confirmed by Northern blot analysis prior to using the same RNA samples to prepare cRNA for this analysis. It is noteworthy that although the mRNA expression profiles for most of the above genes were established using a variety of different cell types including HeLa, Daudi and NB4 cells, their IFN-specific induction characteristics were similar in HT 1080 cells.

In the analysis of our data using known ISGs as guideposts, we determined that it was reasonable to attribute greater significance towards genes whose expression levels changed from absent in untreated cells to detectable in IFN-treated cells. The 3 criteria we applied to select the 128 IFN-regulated genes described in Table 2 represent conservative cutoffs. Known ISGs were also among the hundreds of genes which were originally detected as differentially expressed but excluded by our cutoff criteria and therefore, by inference, other genuine and novel ISGs were also likely represented. It is possible that the mRNA levels for many genuine ISGs simply do not change by more than 3-fold at the 6 h timepoint we used to prepare cRNA. These results demonstrate that the present method of using oligonucleotide arrays to identify ISGs is effective.

The results for specific unknown ISGs are as follows: The expression levels of scramblase were increased 8- and 10-fold by IFN-α and INF-β, respectively, while IFN-γ conferred a more modest 3-fold increase (Table 2). This enzyme has an important role in the apoptosis programmed by flipping phosphatidylserine from the inner to the outer leaf of the cell membrane. Exposed phosphatidylserine serves as a surface marker for recruited phagocytes to recognize and eliminate apoptotic bodies. Therefore, increased levels of phospholipid scramblase in response to IFN may serve as a mechanism which enables more efficient removal of virus-infected cells undergoing apoptosis. Two anti-apoptotic IFN-regulated genes were identified. Expression of RAP46, the human homologue for the mouse gene, BAG-1, was consistently induced about 3-fold by all IFNs. In addition, Bcl-2 expression was modestly increased by IFN-α or IFN-β.

Our analysis has now identified several IFN-regulated serine/threonine kinase genes. For example, mixed lineage kinase 2 (MLK2) was inducible by all 3 IFNs. MLK2 has been characterized as a participant in the JNK/SAPK pathway, capable of activating SEK1 and MKK7. Thus, IFNs may sensitize JNK/SAPK signaling pathways by upregulating MLK2.

Previously, βRI. was the only known ISG which is selectively induced by IFN-β, but not IFN-α nor IFN-γ. Our data identifies over 20 potential candidate genes whose mRNA levels are upregulated by IFN-β but not by IFN-α. These include a gene encoding a clathrin-like protein, PKR, hypoxia-inducible factor (HIF-1), and the fos family member, Fra-1. Two other candidate IFN-β-specific genes are ISG54 and ISG58. Interestingly, the two other members of this gene family, ISG56 and RIG-G, both exhibit a consistently higher level of inducibility in response to INF-β as compare to IFN-α (Table 2). Other genes which also appear to be preferentially induced by INF-β over IFN-α include IFI16, STATI, and GBP-2. Although probe sets for βR1 are encoded on the Hu6800 set of chips, no basal nor inducible expression of βR1 was detectable among of our samples, possibly because βR1 mRNA levels usually peak later than the 6 h timepoint used in this study.

Unexpectedly, PKR was characterized by the oligo array data as inducible by INF-β, but not IFN-α. However, as evident from Table 2, the actual untreated and IFN-α-treated intensities for PKR are 42 and 83, respectively, a 2-fold increase. Previous studies involving Northern blot and nuclear run-on analyses determined that PKR gene transcription in Daudi cells reaches maximal levels 2 hours following IFN-α stimulation and that PKR mRNA levels are significantly elevated by 4 hours. These results suggest the intriguing possibilities that not only may PKR be preferentially induced by IFN-β, cellular background may also contribute distinct characteristics to the profile of PKR mRNA induction by distinct IFN subtypes. Furthermore, the concept of differential responsiveness by certain IFNs in a cell type-specific manner may also be generalized to other ISGS, Stimulation by either IFN-α or IFN-γ resulted in similar results, approximately 100 genes with differences greater than 2-fold, and 25 genes with greater than 4-fold change. INF-β stimulation, on the other hand, resulted in more than double these amounts, 268 genes with greater than 2-fold increases, and 56 genes with greater than 4-fold change. Since the molar amounts of IFN-α and -β protein used in our experiments were similar and the respective intensity values for the majority of ISGs induced by both IFN-α and IFN-β were also generally similar, this suggests that IFN-β may regulate a wider range of ISGs, at least in fibrosarcoma cells. In addition, it also suggests that ISGs which are inducible by IFN-α or INF-β may be distinguished into 3 categories, ISGs which are similarly regulated by IFN-α/β, ISGs which are preferentially regulated by INF-β and ISGs which are differentially regulated by IFN-α and IFN-β but still inducible by both. We did not detect ISGs which are preferentially induced by IFN-α but not INF-β.

Genes which were not previously known to be preferentially regulated by IFN-α include the IL-15α receptor and NF-IL6α. The AAD14 gene was upregulated 3 fold by IFN-γ and while it encodes for a protein of unknown function, mutant alleles of this gene having expanded CAG repeats are present in patients with spinocerebellar ataxia.

Finally, a group of genes exhibited decreased mRNA levels following IFN treatment. By applying 2 criteria, any genes with at least 3-fold decrease by any IFN and genes with at least 2-fold decrease by all 3 IFNs, 12 genes were identified as IFN-repressed genes (Table 3). These genes include the histone H4 gene and the COX 17 gene. Expression of the histone H4 gene is known to be cell cycle-regulated and is coupled to DNA replication and G1/S transition. The reduction of histone H4 mRNA levels by all 3 IFNs may represent one of the regulatory mechanisms required for IFN-induced growth arrest. COX17 has been best characterized in yeast as a specific transporter of copper ions to enzymes such as cytochrome oxidase and copper/zinc superoxide dismutase. Expression of the zinc transporter, ZnT-3, was also decreased by INF-β but it is not known whether ZnT-3 has any role in regulating superoxide dismutase enzymes. ZnT-3 and four other genes, clone 23748, clone 1D2, C1 and insulin-like growth factor 2 (IGF-2), all appear to be preferentially downregulated by IFN-β, but not IFN-α or IFN-γ. IGF-2 has previously been shown to be downregulated by IFN-γ and this was suggested as a possible mechanism involved in IFN-γ-mediated growth inhibition. Such genes may serve as better markers to monitor the effectiveness of IFN therapies.

Table 2. Genes Upregulated by IFNs. IFN-regulated genes identified by GeneChip analysis were divided into three subgroups, separated by a space. The first subgroup was organized in decreasing order on the basis of fold increase in response to IFN-α, while the second and third were similarly ordered by decreasing fold increase in response to IFN-β and IFN-γ, respectively. A plus sign in the "Known ISG" column indicates that previous studies had identified the given gene as being regulated by IFNs. An asterisk beside an intensity value indicates that the given-gene transcript was determined by the GeneChip software as absent from that particular sample. A "greater than" sign (>) beside a fold increase value for a given gene indicates that this likely represents an underestimation since expression of the gene was determined as absent in the untreated sample and consequently, the GeneChip software used 20 as an arbitrary divisor in order to calculate the fold change for the IFN-treated sample.

TABLE 2

| GenBank Accession | Known ISG | Gene Description | Untreated Intensity | | IFN- alpha Intensity | IFN- alpha Fold Increase | IFN- beta Intensity | IFN- beta Fold Increase | IFN- gamma Intensity | IFN- gamma Fold Increase |
|---|---|---|---|---|---|---|---|---|---|---|
| M24594 | + | ISG-56K | 16 | * | 588 | >29.4 | 2492 | >124.6 | 15 | 0 |
| X02875 | + | 2-5A synthetase (1.8 kb RNA) | 18 | * | 584 | >29.2 | 505 | >25.2 | 24 | 0 |
| X57522 | + | RING4 | 29 | * | 800 | 28 | 602 | 21 | 1407 | 49.2 |
| J04164 | + | 9-27 | 62 | * | 1431 | 23.2 | 1349 | 21.9 | 504 | 8.2 |
| M33882 | + | MxA | 19 | * | 426 | >21.3 | 625 | >31.3 | 25 | 0 |
| M13755 | + | IFN4nduced 17/15-kDa protein | 148 | | 3054 | 20.7 | 2409 | 16.3 | 268 | 1.8 |
| U22970 | + | 6-16 | −12 | * | 405 | >20.2 | 433 | >21.7 | −7 | .0 |
| U52513 | + | RIG-G | 19 | * | 358 | >17.9 | 583 | >29.2 | 63 | >3.1 |
| M62800 | | 52-kD SS-A/Ro autoantigen | −34 | * | 204 | >10.2 | 131 | >6.6 | 126 | >6.3 |
| M87503 | + | p48ISGF3γ | 50 | * | 499 | 10.1 | 478 | 9.6 | 392 | 7.9 |
| U72882 | + | IFP35 | 55 | | 460 | 8.4 | 395 | 7.2 | 258 | 4.7 |
| Z14982 | + | LMP7 | 47 | * | 389 | 8.3 | 342 | 7.3 | 535 | 11.4 |
| AF008445 | | Phospholipid scramblase | 72 | | 594 | 8.2 | 723 | 10.0 | 268 | 2.9 |
| X02874 | + | 2-5A synthetase (1.6 kb RNA) | 33 | * | 262 | 8 | 217 | 6.6 | 43 | 0 |
| L22342 | + | IFN-induced nuclear phosphoprotein | 4 | * | 156 | >7.8 | 199 | >10.0 | 119 | >6.0 |
| M30818 | + | MxB | 3 | * | 114 | >5.7 | 254 | >12.7 | 36 | 0 |
| M97936 | + | STAT1 (84 kDa) | −31 | * | 111 | >5.6 | 224 | >11.2 | 40 | >2.0 |
| U43142 | | VEGF-C/VRP | 37 | | 198 | 5.3 | 150 | 0 | 264 | 7.1 |
| M87434 | + | 2-5A synthetase (71 kDa) | 10 | * | 104 | >5.2 | 181 | >9.1 | 25 | 0 |
| Z36591 | | RAP46/Bag-1 | −2 | * | 99 | >5.0 | 134 | >6.7 | 86 | >4.3 |
| X74262 | | RbAp48 | 24 | * | 119 | 5 | 175 | 7.3 | 100 | 4.2 |
| D49824 | | Human HLA-B null allele | 79 | | 395 | 5 | 527 | 6.7 | 360 | 4.6 |
| M63838 | + | IFI 16 | 8 | * | 98 | >4.9 | 254 | >12.7 | 67 | >3.3 |
| M97935 | | STAT1 (91 kDa) | 52 | | 258 | 4.9 | 446 | 8.5 | 155 | 3 |
| D50919 | | KIAA0129 | 33 | | 155 | 4.7 | 198 | 6 | 76 | 0 |
| M92642 | | Alpha-1 type XVI collagen | 43 | * | 179 | 4.2 | 153 | 0 | 190 | 4.4 |
| M55542 | + | GBP-2 | 12 | * | 82 | >4.1 | 175 | >8.7 | 147 | >7.3 |
| X14454 | + | IRF-1 | 22 | * | 88 | 4 | 117 | 5.3 | 682 | 31.1 |
| M79463 | + | PML-2 | 70 | | 280 | 4 | 279 | 4 | 250 | 3.6 |
| X82200 | | Staf50 mRNA | 46 | | 177 | 3.9 | 274 | 6 | 55 | 0 |
| X66401 | + | LMP2 | 108 | | 388 | 3.6 | 250 | 2.3 | 581 | 6.4 |
| D28137 | | BST-2 | 22 | * | 86 | 3.9 | 100 | 4.5 | 32 | 1.4 |
| X90846 | | Mixed lineage kinase 2 | 17 | * | 71 | >3.6 | 95 | >4.8 | 95 | >4.8 |
| X04602 | | Interleukin BSF-2 | 21 | * | 76 | 3.6 | 65 | 3.1 | 65 | 3 |
| U59321 | | DEAD-box protein p72 | −37 | * | 70 | >3.5 | 32 | >1.6 | −32 | 0 |

TABLE 2-continued

| GenBank Accession | Known ISG | Gene Description | Untreated Intensity | | IFN-alpha Intensity | IFN-alpha Fold Increase | IFN-beta Intensity | IFN-beta Fold Increase | IFN-gamma Intensity | IFN-gamma Fold Increase |
|---|---|---|---|---|---|---|---|---|---|---|
| U04285 | | Lysosomal acid lipase (LIPA) | 17 | * | 69 | >3.5 | 81 | >4.0 | 31 | 0 |
| M79462 | + | PML-1 | 35 | * | 121 | 3.5 | 134 | 0 | 124 | 3.6 |
| M24470 | | Glucose-6-P dehydrogenase | 18 | * | 68 | >3.4 | 71 | 0 | 45 | 0 |
| U89606 | | Pyridoxal kinase | 28 | * | 89 | 3.2 | 168 | 6 | 93 | 0 |
| U83463 | | Scaffold protein Pbp1 | 13 | * | 64 | >3.2 | 64 | 0 | 37 | >1.9 |
| J04080 | + | Complement component C1r | 11 | * | 62 | >3.1 | 65 | >3.3 | 103 | >5.2 |
| U32849 | | Hou | 18 | * | 59 | >3.0 | 92 | >4.6 | 49 | >2.4 |
| M20022 | + | MHC Class 1 | 151 | | 445 | 3 | 536 | 3.6 | 912 | 6.1 |
| X58536 | + | MHC Class 1 | 120 | | 337 | 2.8 | 363 | 3 | 276 | 2.3 |
| D28915 | | Hepatitis C-associated p44 | 27 | * | 74 | 2.8 | 128 | 4.8 | 26 | 0 |
| L40387 | | TRIP14 | 117 | * | 318 | 2.7 | 416 | 3.5 | 110 | 0 |
| M22877 | | Somatic cytochrome c | 93 | | 253 | 2.7 | 333 | 3.6 | 163 | 1.7 |
| U09825 | | Acid finger protein | 76 | * | 200 | 2.6 | 214 | 2.8 | 153 | 2 |
| X15949 | + | IRF-2 | 5 | * | 50 | >2.5 | 77 | >3.9 | 42 | 0 |
| U41515 | | DSS1 | 67 | | 168 | 2.5 | 201 | 3 | 117 | 1.8 |
| X83492 | + | Fas/Apo-I | 6 | * | 48 | >2.4 | 51 | 0 | 52 | >2.6 |
| L14778 | | PPP3CA | 7 | * | 47 | >2.4 | 76 | >3.8 | 26 | >1.3 |
| X61123 | | BTG1 | 80 | | 192 | 2.4 | 158 | 2 | 183 | 2.3 |
| J04611 | | Lupus p70 (Ku) autoantigen | 524 | | 1250 | 2.4 | 1253 | 2.4 | 1025 | 2 |
| X75755 | | PR264 | 150 | | 364 | 2.4 | 342 | 2.3 | 326 | 2.2 |
| D89052 | | Proton-ATPase-like protein | 408 | | 912 | 2.2 | 720 | 1.8 | 1005 | 2.5 |
| U84573 | | PLOD2 | 58 | | 28 | 2.1 | 162 | 2.8 | 23 | 2.5 |
| U10439 | + | DsRNA adenosine deaminase | 152 | | 324 | 2.1 | 450 | 3 | 304 | 2 |
| Z47087 | | Pol II elongation factor-like protein | 134 | | 263 | 2 | 201 | 1.5 | 238 | 1.8 |
| M94556 | | Mitochondrial SSB | 309 | | 542 | 1.8 | 619 | 2 | 581 | 1.9 |
| D32129 | + | HLA class-I (HLA-A26) heavy chain | 252 | | 449 | 1.8 | 461 | 1.8 | 518 | 2.1 |
| J00105 | + | Beta-2 microglobulin | 1019 | | 1700 | 1.7 | 2150 | 2.1 | 1296 | 1.3 |
| L25081 | | GTPase (rhoC) | 432 | | 696 | 1.6 | 652 | 1.5 | 912 | 2.1 |
| U20998 | | SRP9 | 105 | | 157 | 1.5 | 277 | 2.6 | 137 | 1.3 |
| X95648 | | eIF-2B alpha subunit | 90 | | 138 | 1.5 | 167 | 1.9 | 196 | 2.2 |
| U07802 | | TisIId | 10 | * | 28 | >1.4 | 39 | >2.0 | 30 | >1.5 |
| U49837 | | LIM protein MLP | −16 | * | 26 | >1.3 | 50 | >2.5 | 24 | >1.2 |
| X16707 | | Fra-1 | 18 | * | 44 | 0 | 214 | >10.7 | 254 | >12.7 |
| M21388 | | Unproductively rearranged IgM | −7 | | 180 | 0 | 193 | >9.7 | 251 | >12.5 |
| D38293 | | Clathrin-like protein | 28 | * | 27 | 0 | 246 | 8.9 | 15 | 0 |
| Y09836 | | 3'UTR of unknown protein | 11 | * | −19 | 0 | 150 | >7.5 | 35 | 0 |
| U22431 | | Hypoxia-inducible factor −1 | 29 | * | 33 | 0 | 204 | 7.1 | 50 | 0 |
| M35663 | + | Pkr | 39 | * | 68 | 0 | 271 | 7 | 33 | 0 |
| X89416 | | Protein phosphatase 5 | 49 | | 103 | 0 | 305 | 6.2 | 160 | 3.3 |
| U88047 | | DRX | −40 | * | 77 | 0 | 107 | >5.4 | 106 | 0 |
| Z50194 | | PO-rich protein | 46 | | 103 | 0 | 245 | 5.3 | 210 | 4.5 |
| U41766 | | MDC9 | 25 | * | 30 | 0 | 135 | 5.3 | 19 | 0 |
| U79291 | | Clone 23721 | 16 | * | −2 | 0 | 97 | >4.9 | 20 | 0 |
| U58046 | | p167 | 21 | | 17 | 0 | 100 | 4.7 | 14 | 0 |
| D79999 | | KIAAo177 | 32 | * | 21 | 0 | 140 | 4.4 | 43 | 0 |
| U41387 | | Gu protein | 53 | | 56 | 0 | 226 | 4.3 | 57 | 0 |

TABLE 2-continued

| GenBank Accession | Known ISG | Gene Description | Untreated Intensity | | IFN-alpha | | IFN-beta | | IFN-gamma | |
|---|---|---|---|---|---|---|---|---|---|---|
| | | | | | Intensity | Fold Increase | Intensity | Fold Increase | Intensity | Fold Increase |
| X63563 | | RNA polymerase II 140 kDa | 56 | | 105 | 1.9 | 230 | 4.1 | 88 | 0 |
| X70649 | | Clone 1042 of DEAD box family | 49 | * | 81 | 0 | 199 | 4.1 | 50 | 0 |
| D29640 | | KIAA0051 | 26 | | 32 | 0 | 103 | 4 | 37 | 0 |
| Z29064 | | AF-1p | 23 | * | 54 | 2.4 | 88 | 3.9 | 42 | 1.8 |
| D79986 | | K1AA0164 | 4 | * | 30 | 0 | 76 | >3.8 | 19 | 0 |
| U44378 | | DPC4 | 15 | * | 34 | >1.7 | 77 | >3.8 | 16 | 0 |
| J03473 | | Poly (ADP-vibose) polymerase | 61 | | 130 | 0 | 224 | 3.7 | 146 | 2.4 |
| D90070 | | PMA-responsive gene (APR) | 4 | * | 28 | >1.4 | 69 | >3.5 | 42 | >2.1 |
| D63875 | | KIAA0155 | 14 | | 13 | 0 | 70 | >3.5 | 26 | 0 |
| M85164 | | SAP-1 | 11 | * | 21 | 0 | 67 | >3.4 | 32 | >1.6 |
| U34605 | + | ISG-58K | 8 | * | 15 | 0 | 66 | >3.3 | 20 | 0 |
| D14043 | | MGC-24 | 55 | | 94 | 1.7 | 182 | 3.3 | 33 | 0 |
| J04102 | | Ets-2 | 20 | * | 14 | 0 | 67 | 3.3 | 34 | 0 |
| D16481 | | Mitochondrial 3-ketoacyl-CoA thiolase | 45 | * | 86 | 0 | 147 | 3.2 | 103 | 2.3 |
| Z69915 | | Clone ICRFp507L1876 | 23 | * | 28 | 0 | 73 | 3.2 | 28 | 0 |
| X98260 | | M-phase phosphoprotein, mpp11 | −9 | * | 7 | 0 | 61 | >3.1 | −6 | 0 |
| M14660 | + | ISG-54K | −62 | * | −5 | >1.0 | 61 | >3.1 | −4 | >1.0 |
| M82882 | | Human cis-acting sequence | 2 | * | 21 | 0 | 63 | >3.1 | 9 | 0 |
| U05040 | | FUSE binding protein | 60 | * | 84 | 0 | 189 | 3.1 | 63 | 0 |
| M28249 | | Collagen receptor alpha-2 subunit | 31 | * | 28 | 0 | 97 | 3.1 | 22 | 0 |
| X74039 | | uPA receptor | 22 | * | 52 | 0 | 68 | 3.1 | 49 | 0 |
| M83216 | | Caldesmon | 3 | * | 9 | 0 | 62 | >3.1 | 5 | 0 |
| AB001106 | | Glia maturation factor | 6 | * | 14 | 0 | 61 | >3.0 | 21 | 0 |
| U19252 | | Putative transmembrane protein | 11 | * | 24 | 0 | 59 | >3.0 | 30 | 0 |
| M63896 | | TEF1 | 15 | * | 22 | 0 | 59 | >3.0 | 9 | 0 |
| X54326 | | Glutaminyl-tRNA synthetase | 49 | * | 39 | 0 | 150 | 3 | 44 | 0 |
| J03909 | + | IP-30 | 4 | * | 44 | >2.2 | 35 | >1.8 | 239 | >12.0 |
| U82987 | | Bcl-2 binding component 3 (bbc3) | −27 | * | 46 | >2.3 | 8 | 0 | 102 | >5.1 |
| M83667 | | NF-IL6-beta | 24 | | 30 | 0 | 59 | 2.5 | 108 | 4.5 |
| M24283 | + | ICAM-1 | −8 | * | −4 | 0 | −15 | 0 | 86 | >4.3 |
| U63824 | | RTEF-1 | 40 | * | 87 | 2.2 | 64 | 0 | 162 | 4 |
| M21533 | + | MHC Class 1 | 239 | * | 437 | 1.8 | 517 | 2.2 | 938 | 3.9 |
| X96752 | | L-3-hydroxyacyl-CoA dehydrogenase | 17 | * | 32 | 0 | 50 | >2.5 | 77 | >3.8 |
| U31628 | | IL15RA | 36 | * | 87 | 0 | 111 | 0 | 135 | 3.8 |
| X85237 | | Splicing factor SF3a120 | 52 | * | 49 | 0 | 101 | 0 | 192 | 3.7 |
| X98172 | | MACH-1 | 23 | * | 53 | 2.3 | 65 | 2.8 | 74 | 3.2 |
| X71874 | | MECL-1 | 184 | | 312 | 1.7 | 292 | 1.6 | 563 | 3.1 |
| X84213 | + | BAK | 57 | | 78 | 0 | 82 | 0 | 190 | 3.3 |
| U18009 | | Human 17q21 clone LF 113 | 30 | * | 64 | 0 | 52 | 0 | 94 | 3.1 |

TABLE 2-continued

|  |  |  |  | IFN-alpha | | IFN-beta | | IFN-gamma | |
| --- | --- | --- | --- | --- | --- | --- | --- | --- | --- |
| GenBank Accession | Known ISG | Gene Description | Untreated Intensity | Intensity | Fold Increase | Intensity | Fold Increase | Intensity | Fold Increase |
| U65011 |  | PRAME | 37 * | 72 | 0 | 67 | 0 | 111 | 3 |
| L07633 |  | IFN-γ-tinducible gene, I-5111 | 250 | 478 | 1.9 | 411 | 1.6 | 714 | 2.9 |

TABLE 3

Genes downregulated by IFNs.

|  |  |  | IFN-alpha | | IFN-beta | | IFN-gamma | |
| --- | --- | --- | --- | --- | --- | --- | --- | --- |
| GenBank Accession | Gene Description | Untreated Intensity | Intensity | Fold Increase | Intensity | Fold Increase | Intensity | Fold Increase |
| L77701 | COX17 | 107 | 17 | >5.3 | 60 | 0 | 28 | 3.8 |
| D86971 | KIAA0217 | 74 | 14 | >3.7 | 63 | 0 | 54 | 1.4 |
| U07000 | BCR | 77 | 24 | 3.2 | 30 | 0 | 21 | 3.7 |
| M16707 | Histone H4 | 62 | 8 | >3.1 | 1 | >3.1 | −16 | >3.1 |
| U60062 | FEZ1-T | 60 | 22 | 2.8 | 30 | 0 | 18 | >3.0 |
| U62962 | Int-6 | 237 | 121 | 2 | 473 | (2) | 158 | 1.5 |
| Z78289 | clone 1D2 | 182 | 101 | 0 | 24 | 7.6 | 151 | 0 |
| X03562 | Insulin-Like Growth Factor 2 | 129 | 92 | 0 | 0 | >6.4 | 115 | 0 |
| U79294 | clone 23748 | 366 | 140 | 2.6 | 74 | 5 | 165 | 0 |
| X78817 | H. sapiens partial C1 mRNA | 206 | 145 | 0 | 46 | 4.5 | 175 | 0 |
| U76010 | Zinc transporter ZnT-3 | 469 | 289 | 0 | 118 | 4 | 296 | 0 |
| U62437 | Nicotinic acetylcholine receptor | 78 | −11 | 0 | −28 | >3.9 | 20 | 0 |
| U61232 | Tubulin-folding cofactor E | 69 | 51 | 0 | 10 | >3.5 | 51 | 0 |
| U30894 | N-sulphoglucosamine sulphohydrolase | 71 | 39 | 0 | 16 | >3.5 | 56 | 0 |
| U82311 | Unknown protein | 231 | 187 | 1.2 | 66 | 3.5 | 200 | 0 |
| X17025 | Homolog of IPP isomerase | 109 | 55 | 0 | 147 | 0 | 8 | >5.5 |
| U78798 | TRAF6 | 117 | 44 | 0 | 41 | 2.8 | 28 | 4.1 |
| Z31695 | Inositol polyphosphate 5-phosphatase. | 79 | 37 | 0 | 50 | 0 | 17 | >3.9 |
| M15841 | U2 RNA-associated B antigen | 129 | 104 | 0 | 121 | 0 | 38 | 3.4 |
| X97748 | PTX3 | 90 | 63 | 0 | 107 | 0 | 26 | 3.5 |
| L33243 | Polycystic kidney disease 1 protein | 60 | 33 | 0 | 38 | 0 | 4 | >3.0 |

EXAMPLE 2

Murine ISGs and IRGs were identified from cultures of primary mouse embryo fibroblasts prepared from C57/B16 mice at 16 days of gestation. Cells were treated for 6 hours with 10,000 units per ml of IFN-αBBDB. Total/mRNA was isolated from treated and untreated control cells as described above in Example 1. The levels of transcripts in the untreated and treated cells were assayed using Mu6500 chip set which contains probes to about 6500 rodent genes. The results are shown in Table 5. A subset of the genes stimulated or repressed by treatment with the interferon are shown in Table 7 As shown in Table 5 and 7 below, a number of murine genes are stimulated or repressed by treatment with the interferon. Some of these genes are the murine or rat homolog of the human genes identified in Example 1 above. Because the array contains probes to rodent genes which have no counterpart on the Hu6800 GeneChip Arrays, these results also identify novel ISGs and IRGs that were not identified in Example 1.

EXAMPLE 3

Murine ISGs and IRGs were identified from cultures of primary mouse embryo fibroblasts incubated in the presence or absence of encephalomyocarditis virus and IFN-αBBD. Fibroblasts were obtained as described in Example 2 and The levels of transcripts in cells incubated in the presence of IFNα-BBDB and in the presence and absence of virus and in cells incubated in the absence of IFN-αBBDB and in the presence and absence of virus were assayed as described above in example 2. The results are shown in Table 6 below. These results shows that virus enhances the expression of certain IFN-a stimulated genes (see Table 8) and represses expression of certain IFN-a stimulated genes.

TABLE 4

ISGs and IRGs identified from human fibrosarcoma cells incubated in IFN-α, IFN-β or IFN-γ

| GenBank Accession. | Entrez Definition — Afix Definition | Un-treated In-tensity | B = A | IFN-a In-tensity | Incr Decr | Fold Change | Sig | IFN-b In-tensity | Incr Decr | Fold Change | Sig | IFN-g In-tensity | Incr Decr | Fold Change | Sig |
|---|---|---|---|---|---|---|---|---|---|---|---|---|---|---|---|
| X67325 | *H. sapiens* p27 mRNA | −7 | | 1423 | I | −70.8 | 30.33 | 1018 | I | −50.6 | 23.03 | 167 | I | −8.0 | 3.23 |
| M13755 | Human interferon-induced 17-kDa/15-kDa protein "mRNA," complete cds | 148 | * | 2906 | I | 20.7 | 26.59 | 2262 | I | 16.3 | 20.49 | 120 | MI | 1.8 | 0.26 |
| J04164 | Human interferon-inducible protein 27-Sep "mRNA," complete cds | 62 | * | 1369 | I | 23.2 | 19.36 | 1288 | I | 21.9 | 18.22 | 442 | I | 8.2 | 5.37 |
| X57522 | *H. sapiens* RING4 cDNA | 29 | * | 771 | I | 28 | 15.87 | 573 | I | 21 | 11.89 | 1379 | I | 49.2 | 26.56 |
| M24594 | Human interferon-inducible 56 Kd protein "mRNA," complete cds | 16 | * | 572 | I | −29.4 | 13.97 | 2477 | I | −124.6 | 46.62 | 0 | NC | 0 | 0 |
| X02875 | Human mRNA (3'-fragment) for (2'-5') oligo A synthetase E "(1,8" kb RNA) — Also Rep | 18 | * | 566 | I | −29.2 | 13.84 | 486 | I | −25.2 | 12 | 6 | NC | 0 | 0 |
| M33882 | Human p78 protein "mRNA," complete cds | 19 | * | 407 | I | −21.3 | 10.07 | 606 | I | −31.3 | 14.77 | 6 | NC | 0 | 0 |
| U22970 | 16 Jun gene (interferon-inducible peptide precursor) extracted from Human interferon | −12 | | 417 | I | −20.2 | 9.93 | 446 | I | −21.7 | 10.63 | 6 | NC | 0 | 0 |
| U52513 | Human RIG-G "mRNA," complete cds | 19 | * | 338 | I | −17.9 | 8.33 | 564 | I | −29.2 | 13.82 | 43 | I | −3.1 | 0.49 |
| M87503 | Human IFN-responsive transcription factor subunit "mRNA," complete cds | 50 | | 449 | I | 10.1 | 6.48 | 428 | I | 9.6 | 6.11 | 342 | I | 7.9 | 4.58 |
| AF008445 | *Homo sapiens* phospholipid scramblase "mRNA," complete cds. /gb = AF008445 /ntyp | 72 | | 521 | I | 8.2 | 5.86 | 650 | I | 10 | 7.76 | 135 | I | 2.9 | 0.75 |
| U72882 | Human interferon-induced leucine zipper protein (IFP35) "mRNA," partial cds — Also | 55 | * | 405 | I | 8.4 | 5.28 | 340 | I | 7.2 | 4.18 | 203 | I | 4.7 | 1.98 |
| Z14982 | MHC-encoded proteasome subunit gene LAMP7-E1 gene (proteasome subunit LMP | 47 | * | 342 | I | 8.3 | 4.77 | 295 | I | 7.3 | 3.91 | 488 | I | 11.4 | 7.45 |
| M62800 | Human 52-kD SS-A/Ro autoantigen "mRNA," complete cds | −34 | | 238 | I | −10.2 | 4.74 | 165 | I | −6.6 | 2.62 | 160 | I | −6.3 | 2.47 |
| X02874 | Human mRNA for (2'-5') oligo A synthetase E (1,6 kb RNA). | 33 | * | 229 | I | 8 | 3.78 | 184 | I | 6.6 | 2.8 | 10 | I | 0 | 0 |
| L22342 | Human nuclear phosphoprotein "mRNA," complete cds | 4 | | 153 | I | −7.8 | 3.01 | 195 | I | −10.0 | 4.21 | 115 | I | −6.0 | 1.97 |
| D49824 | Human HLA-B null allele mRNA — "Also Represents: L42345, L11570, L11571, HG29 | 79 | * | 317 | I | 5 | 2.69 | 449 | I | 6.7 | 4.46 | 282 | I | 4.6 | 2.25 |
| M97935 | Human transcription factor ISGF-3 mRNA sequence — Also Represents: HUMISGF3A | 52 | | 205 | I | 4.9 | 2.11 | 394 | I | 8.5 | 5.27 | 103 | I | 3 | 0.7 |
| U43142 | Human vascular endothelial growth factor related protein VRP "mRNA," complete cds | 37 | * | 161 | I | 5.3 | 2.05 | 113 | NC | 0 | 0 | 227 | I | 7.1 | 3.35 |
| M97936 | Human transcription factor ISGF-3 mRNA sequence | −31 | * | 142 | I | −5.6 | 2.01 | 255 | I | −11.2 | 5.3 | 70 | I | −2.0 | 0.24 |
| M30818 | Human interferon-induced cellular resistance mediator protein (MxB) "mRNA," compl | 3 | | 111 | I | −5.7 | 1.84 | 251 | I | −12.7 | 5.76 | 32 | NC | 0 | 0 |
| M79463 | Human PML-2 "mRNA," complete CDS — "Also Represents: HG560-HT560, M82827" | 70 | | 210 | I | 4 | 1.6 | 209 | I | 4 | 1.58 | 180 | I | 3.6 | 1.24 |
| X66401 | LMP2 gene extracted from *H. sapiens* genes "TAP1," "TAP2," "LMP2," "LMP7 and DO | 108 | * | 280 | I | 3.6 | 1.58 | 142 | I | 2.3 | 0.5 | 473 | I | 5.4 | 3.59 |
| D50919 | Human mRNA for KIAA0129 "gene," complete cds | 33 | | 122 | I | 4.7 | 1.54 | 165 | I | 6 | 2.4 | 44 | NC | 0 | 0 |
| L77701 | *Homo sapiens* COX17 "mRNA," complete cds | 107 | | −90 | D | −5.3 | 1.53 | −47 | NC | 0 | 0 | −79 | D | 3.8 | 0.92 |
| M87434 | Human 71 kDa 2'5' oligoadenylate synthetase (p69 2-5A synthetase) "mRNA," comp | 10 | | 94 | I | −5.2 | 1.51 | 171 | I | −9.1 | 3.65 | 14 | NC | 0 | 0 |
| Z35491 | *H. sapiens* mRNA for novel glucocorticoid receptor-associated protein | −2 | | 101 | MD | −5.0 | 1.48 | 136 | I | −6.7 | 2.43 | 88 | I | −4.3 | 1.14 |
| X74262 | *H. sapiens* mRNA RbAp48 mRNA encoding retinoblastoma binding protein | 24 | | 95 | MD | −4.0 | 1.08 | 151 | I | 7.3 | 2.79 | 76 | I | 4.2 | 1.02 |
| M63838 | Human interferon-gamma induced protein isoform I (GBP-2) "mRNA," complete cds | 8 | | 91 | I | −4.0 | 0.98 | 246 | I | −12.7 | 5.7 | 59 | I | −3.3 | 0.64 |
| M92642 | Human DEAD-box protein p72 (P72) "mRNA," complete cds | 43 | | 136 | I | −4.1 | 0.96 | 163 | I | 0 | 0 | 147 | I | 4.4 | 1.54 |
| J04611 | *Homo sapiens* alpha-1 type XVI collagen (COL16A1) "mRNA," complete cds | 524 | * | 726 | I | −3.5 | 0.92 | 69 | I | −1.6 | 1.22 | 501 | I | 2 | 0.64 |
| X82200 | Human lupus p70 (Ku) autoantigen protein "mRNA," complete cds | 46 | | 131 | I | 2.8 | 0.91 | 243 | I | 3 | 1.1 | 9 | NC | 0 | 0 |
| G2915-HT305 | Major Histocompatibility "Complex," Class "I," E (Gb:M20022) | 151 | | 294 | I | 4 | 0.89 | 95 | I | 5.3 | 1.57 | 761 | I | 6.1 | 5.2 |
| K03460 | Human alpha-tubulin isotype H2-alpha "gene," last exon | 77 | | 177 | I | 3.9 | 0.88 | 228 | I | 2.4 | 0.38 | 150 | I | 0 | 0 |
| AB000464 | Human "mRNA," clone "RES4-24A," exon "1," "2," "3," 4 | 89 | | −72 | MD | 3.3 | 0.87 | 385 | I | 3.6 | 1.82 | −29 | NC | 0 | 0 |
| Z84483 | Human DNA sequence from PAC "46H23;" BRCA2 gene region chromosome 13q12 | 80 | * | −79 | MD | −4.5 | 1.09 | 117 | NC | 0 | 0.97 | 25 | NC | 0 | 0 |
| M55542 | Human guanylate binding protein isoform I (GBP-2) "mRNA," complete cds | 12 | | 70 | I | −4.0 | 1.08 | −26 | NC | −4.0 | 3.44 | 135 | I | −7.3 | 2.65 |
| U59321 | Human DEAD-box protein p72 (P72) "mRNA," complete cds | −37 | | 107 | I | −4.1 | 0.98 | −77 | D | −8.7 | 0.13 | 5 | I | 0 | 0 |
| IG658-HT658 | Major Histocompatibility "Complex," Class "I," C (Gb:X58536) — "Also Similar To: L42 | 120 | | 217 | I | −3.5 | 0.96 | 163 | I | −1.6 | 1.1 | 156 | I | 2.3 | 0.52 |
| L05072 | *Homo sapiens* interferon regulatory factor 1 "gene," complete cds — Also Represents: | 22 | | 66 | I | 2.8 | 0.92 | 69 | I | 3 | 1.1 | 660 | I | 31.1 | 15.38 |
| D89052 | Human mRNA for proton-ATPase-like "protein, complete cds | 408 | | 504 | I | 4 | 0.91 | 243 | I | 5.3 | 1.57 | 598 | I | 2.5 | 1.18 |
| D85815 | Human DNA for "rhoHP1," complete cds | 81 | | −62 | MD | 2.2 | 0.88 | 95 | I | 1.8 | 0.38 | −28 | NC | 0 | 0 |
| D28137 | Human mRNA for "BST-2," complete cds | 22 | | 64 | I | 3.9 | 0.84 | 78 | I | 4.5 | 1.15 | 10 | I | 1.4 | 0.04 |
| D63160 | Human DNA for lectin P35 | 78 | | −65 | D | −3.9 | 0.84 | −27 | NC | 0 | 0 | −41 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| M79462 | Human PML-1 "mRNA," complete CDS | 35 | | 86 | MI | 3.5 | 0.83 | 100 | D | 0 | 0 | 90 | I | 3.6 | 0.88 |
| U79294 | Human clone 23748 "mRNA," complete cds. | 366 | * | −226 | D | 2.6 | 0.82 | −292 | D | 5 | 2.54 | −201 | NC | 0 | 0 |
| L40387 | Homo sapiens thyroid receptor interactor (TRIP14) "gene," 3' end of cds. /gb = L40387 | 117 | * | 201 | I | 2.7 | 0.82 | 299 | I | 3.5 | 1.6 | −8 | NC | 0 | 0 |
| D84557 | Human mRNA for "HsMcm6," complete cds | 166 | | −113 | D | 3.1 | 0.79 | 68 | NC | 0 | 0 | −37 | NC | 0 | 0 |
| D86971 | Human mRNA for KIAA0217 "gene," partial cds | 74 | | −60 | MD | −3.7 | 0.76 | −11 | I | 0 | 0 | −20 | MD | 1.4 | 0.04 |
| M22877 | Human somatic cytochrome c (HCS) "gene," complete cds | 93 | | 159 | I | 2.7 | 0.73 | 239 | I | 3.6 | 1.44 | 70 | MI | 1.7 | 0.17 |
| M16424 | Human beta-hexosaminidase alpha chain (HEXA) gene | 67 | * | −73 | MD | −3.3 | 0.71 | −12 | NC | 0 | 0 | −1 | NC | 0 | 0 |
| X90846 | H. sapiens mRNA for mixed lineage kinase 2 — Also Represents: Z48615 | 17 | | 54 | I | −3.6 | 0.68 | 79 | MI | −4.8 | 1.24 | 79 | MI | −4.8 | 1.24 |
| X75755 | H. sapiens PR264 gene — Also Represents: HG3088-HT3261 Same Unigene Cluster | 150 | | 214 | I | 2.4 | 0.68 | 192 | I | 2.3 | 0.57 | 176 | I | 2.2 | 0.49 |
| X04602 | Human mRNA for interleukin BSF-2 (B-cell differentiation factor) — "Also Represents: | 21 | | 55 | I | 3.6 | 0.68 | 44 | I | 3.1 | 0.48 | 43 | I | 3 | 0.46 |
| U04285 | Human lysosomal acid "lipase," cholesteryl ester hydrolase (LIPA) gene — "Also Repr | 17 | | 52 | I | −3.5 | 0.63 | 64 | I | −4.0 | 0.89 | 14 | NC | 0 | 0 |
| U09825 | Human acid finger protein "mRNA," complete cds | 76 | | 124 | I | 2.6 | 0.61 | 138 | I | 2.8 | 0.73 | 77 | I | 2 | 0.27 |
| M24470 | Human glucose-6-phosphate "dehydrogenase," complete cds | 18 | | 50 | MI | −3.4 | 0.61 | 53 | NC | 0 | 0 | 27 | NC | 0 | 0 |
| U89606 | Human pyridoxal kinase "mRNA," complete cds. | 28 | | 61 | MI | 3.2 | 0.6 | 140 | I | 6 | 2.19 | 65 | I | 0 | 0 |
| U07000 | BCR gene (unknown) extracted from Human breakpoint cluster region (BCR) "gene," | 77 | | −53 | MD | 3.2 | 0.58 | −47 | NC | 0 | 0 | −56 | D | 3.7 | 0.71 |
| U83463 | Human scaffold protein Pbp1 "mRNA," complete cds. | 13 | | 52 | I | −3.2 | 0.56 | 52 | NC | 0 | 0 | 25 | I | −1.9 | 0.12 |
| U88964 | Human HEM45 "mRNA," complete cds. | 276 | | 287 | I | 2 | 0.54 | 180 | I | 1.7 | 0.24 | 29 | NC | 0 | 0 |
| M16707 | Human histone H4 "gene," complete "cds," clone FO108 — Also Represents: X00038 | 62 | | −53 | D | −3.1 | 0.53 | −61 | D | −3.1 | 0.56 | −78 | D | −3.1 | 0.64 |
| J04080 | Human complement component C1r "mRNA," complete cds | 11 | * | 51 | I | −3.1 | 0.52 | 55 | I | −3.3 | 0.59 | 93 | I | −5.2 | 1.5 |
| Z97054 | DNA binding protein from Human DNA sequence from PAC 339A18 on chromosome | 145 | | −90 | MD | 2.6 | 0.52 | −24 | NC | 0 | 0 | −21 | NC | 0 | 0 |
| U41515 | Human deleted in split hand/split foot 1 (DSS1) "mRNA," complete cds | 67 | | 102 | I | 2.5 | 0.51 | 134 | I | 3 | 0.81 | 50 | I | 1.8 | 0.15 |
| U15641 | Human transcription factor E2F-4 "mRNA," complete cds — Also Represents: S75174 | 141 | | −87 | D | 2.6 | 0.51 | −39 | NC | 0 | 0 | 2 | NC | 0 | 0 |
| U65785 | Human 150 kDa oxygen-regulated protein ORP150 "mRNA," complete cds | 776 | | −365 | D | 1.9 | 0.5 | −292 | D | 1.6 | 0.28 | −354 | D | 1.8 | 0.46 |
| M31520 | Human ribosomal protein S24 mRNA — Also Represents: HG3214-HT3391 | 1583 | | 948 | I | 1.6 | 0.5 | 562 | I | 1.4 | 0.21 | 91 | NC | 0 | 0 |
| G3342-HT351 | Id1 — Also Represents: S78825 | 851 | | 609 | I | 1.7 | 0.49 | 433 | I | 1.5 | 0.27 | 153 | I | 2.3 | 0.42 |
| X61123 | Human BTG1 mRNA | 80 | * | 112 | I | 2.4 | 0.49 | 78 | I | 2 | 0.26 | 103 | I | 1.3 | 0.11 |
| J00105 | Human beta-2 microglobulin gene "mRNA," 3' end — Also Represents: V00567 | 1019 | | 681 | I | 1.7 | 0.48 | 1131 | I | 2.1 | 1.15 | 277 | NC | 0 | 0 |
| X57351 | Human 1-8D gene from interferon-inducible gene family — Also Represents: HG1538- | 264 | | 261 | I | 2 | 0.48 | 311 | I | 2.2 | 0.65 | 68 | I | 0 | 0 |
| U93205 | Human nuclear chloride ion channel protein (NCC27) "mRNA," complete cds | 2328 | | 1224 | I | 1.5 | 0.48 | 1071 | I | 1.5 | 0.38 | 24 | I | 1.6 | 0.37 |
| U90426 | Human nuclear RNA "helicase," complete cds | 708 | | 528 | I | 1.7 | 0.48 | 325 | I | 1.5 | 0.21 | 449 | I | 1.6 | 0 |
| G4063-HT433 | Transcription Factor Hbf-2 — Also Represents: X74142 | 59 | | −50 | MD | −3.0 | 0.48 | −18 | MI | 0 | 0 | −29 | I | 0 | 0 |
| U10439 | Human double-stranded RNA adenosine deaminase "mRNA," complete cds | 152 | | 172 | I | 2.1 | 0.46 | 298 | I | 3 | 1.18 | 153 | I | 2 | 0.37 |
| L26247 | Homo sapiens su11iso1 "mRNA," complete cds | 1468 | | 853 | I | 1.6 | 0.45 | 406 | I | 1.3 | 0.13 | 483 | I | 1.3 | 0.17 |
| | | 1001 | | 645 | I | 1.6 | 0.45 | 269 | I | 1.3 | 0.1 | 10 | NC | 0 | 0 |
| U32849 | Human Hou "mRNA," complete cds | 80 | | −52 | MD | 2.8 | 0.45 | −58 | NC | 0 | 0 | −36 | I | 0 | 0 |
| G4322-HT459 | "Tubulin," Beta | 18 | * | 42 | I | −3.0 | 0.44 | 74 | I | −4.6 | 1.14 | 31 | MI | −2.4 | 0.26 |
| | | 306 | * | 275 | I | 1.9 | 0.44 | 231 | I | 1.8 | 0.32 | 253 | I | 1.8 | 0.38 |
| | | 1744 | | 946 | I | 1.6 | 0.44 | 391 | I | 1.2 | 0.1 | 206 | NC | 0 | 0 |
| Z54367 | H. sapiens gene for plectin — Also Represents: U53204 | 124 | | 145 | I | 2.2 | 0.44 | −10 | NC | 0 | 0 | 88 | NC | 0 | 0 |
| D38048 | Human mRNA for proteasome subunit "z," complete cds | 195 | | −110 | D | 2.3 | 0.44 | −38 | NC | 0 | 0 | −46 | NC | 0 | 0 |
| Z12962 | H. sapiens mRNA for homologue to yeast ribosomal protein L41 | 764 | | 524 | I | 1.7 | 0.43 | 415 | I | 1.5 | 0.29 | 206 | I | 1.3 | 0.09 |
| X95404 | H. sapiens mRNA for non-muscle type cofilin | 14040 | | −3328 | D | 1.3 | 0.43 | −2342 | MD | 1.2 | 0.22 | −2409 | NC | 0 | 0 |
| | | 6834 | | −1921 | D | 1.4 | 0.43 | −1444 | NC | 0 | 0 | −1117 | NC | 0 | 0 |
| D28915 | Human gene for hepatitis C-associated microtubular aggregate protein p44 | 27 | * | 48 | MI | 2.8 | 0.42 | 102 | I | 4.8 | 1.44 | 0 | NC | 0 | 0 |
| M60858 | Human nucleolin "gene," complete cds | 740 | | −332 | D | 1.8 | 0.42 | 365 | I | 1.5 | 0.24 | −281 | D | 1.6 | 0.28 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| D10704 | Human mRNA for choline kinase | 80 | | -51 | D | 2.7 | 0.42 | -25 | NC | 0 | 0 | -41 | NC | 0 | 0 |
| X02751 | Human N-ras mRNA and flanking regions | 2 | * | 52 | I | -2.7 | 0.41 | 47 | I | -2.4 | 0.31 | 16 | NC | 0 | 0 |
| L07633 | Homo sapiens (clone 1950.2) interferon-gamma IEF SSP 5111 "mRNA," complete cd | 250 | | 228 | I | 1.9 | 0.41 | 161 | I | 1.6 | 0.22 | 464 | I | 2.9 | 1.38 |
| U29680 | Human A1 protein "mRNA," complete cds | 26 | * | 46 | I | 2.8 | 0.41 | 22 | NC | 0 | 0 | 23 | NC | 0 | 0 |
| M64174 | Human protein-tyrosine kinase (JAK1) "mRNA," complete cds | 8662 | | -2225 | D | 1.3 | 0.4 | -2314 | D | 1.4 | 0.43 | -1605 | D | 1.2 | 0.21 |
| V00563 | Human gene for immunoglobulin mu, part of exon 8. | 54 | | -48 | D | -2.7 | 0.4 | 11 | NC | 0 | 0 | -34 | NC | 0 | 0 |
| U07550 | Human chaperonin 10 "mRNA," complete cds | 123 | | -73 | D | 2.4 | 0.4 | -57 | NC | 0 | 0 | -35 | NC | 0 | 0 |
| D63486 | Human mRNA for KIAA0152 "gene," complete cds | 271 | | 236 | I | 1.9 | 0.39 | 30 | NC | 0 | 0 | 166 | I | 1.6 | 0.21 |
| M94362 | Human lamin.B2 (LAMB2) "mRNA," partial cds | 221 | | -118 | D | 2.1 | 0.39 | 3 | NC | 0 | 0 | -61 | NC | 0 | 0 |
| Z25521 | H. sapiens integrin associated protein mRNA, complete CDS, — Also Represents: X69 | 574 | | -261 | D | 1.8 | 0.39 | 199 | NC | 0 | 0 | -14 | NC | 0 | 0 |
| Z29066 | H. sapiens nek2 mRNA for protein kinase — Also Represents: U11050 | 99 | | 112 | I | 2.1 | 0.37 | 138 | I | 2.4 | 0.53 | 75 | I | 1.8 | 0.18 |
| U60062 | Human FEZ1-T "mRNA," alternatively spliced "form," complete cds | 26 | * | 43 | I | 2.7 | 0.37 | 46 | I | 2.8 | 0.41 | 22 | NC | 0 | 0 |
| M34516 | Human omega light chain protein 14.1 (Ig lambda chain related) gene | 60 | | -38 | D | 2.8 | 0.37 | -30 | MI | -2.7 | 0 | -42 | MD | -3.0 | 0.45 |
| U82987 | Human Bcl-2 binding component 3 (bbc3) "mRNA," partial cds | 14 | * | 41 | MI | -2.7 | 0.37 | 8 | NC | 0 | 0 | 19 | NC | 0 | 0 |
| Z14244 | H. sapiens cox VIIb mRNA for cytochrome c oxidase subunit VIIb | -27 | | 74 | I | -2.3 | 0.36 | 35 | NC | 0 | 0 | 130 | I | -5.1 | 1.74 |
| D38521 | Human mRNA for KIAA0077 "gene," partial cds | 441 | | 320 | I | 1.7 | 0.36 | 180 | NC | 0 | 0 | 195 | I | 1.4 | 0.16 |
| G3859-HT412 | Mage-4a Antigen | 80 | | -49 | D | 2.6 | 0.36 | 29 | NC | 0 | 0 | -33 | NC | 0 | 0 |
| U63090 | Human Gal "beta-1,3" GalNAc "alpha-2,3" sialyltransferase (ST3Gal II) "mRNA," com | 53 | | -45 | D | -2.6 | 0.36 | -47 | NC | 0 | 0 | -29 | NC | 0 | 0 |
| J02923 | Human 65-kilodalton phosphoprotein (p65) "mRNA," complete cds | 12 | * | 41 | MI | -2.7 | 0.36 | -10 | NC | 0 | 0 | 11 | NC | 0 | 0 |
| G2917-HT306 | Major Histocompatibility "Complex," Class "I," E (Gb:M21533) | 102 | | 109 | MI | 2.1 | 0.34 | 195 | I | 2.9 | 0.92 | 70 | I | 1.7 | 0.16 |
| U67122 | Human ubiquitin-related protein SUMO-1 "mRNA," complete cds. — "Also Represents | 239 | | 198 | I | 1.8 | 0.34 | 278 | I | 2.2 | 0.6 | 700 | I | 3.9 | 2.87 |
| G1400-HT140 | Carboxyl "Methyltransferase," "Aspartate," Alt. Splice 1 — Also Represents: D13892 | 107 | | 113 | I | 2.1 | 0.34 | 151 | I | 2.4 | 0.56 | 19 | NC | 0 | 0 |
| G2815-HT293 | "Myosin," Light "Chain," "Alkali," Smooth Muscle "(Gb:U02629)," "Non-Muscle," Alt. S | 100 | | 108 | I | 2.1 | 0.34 | 80 | I | 1.8 | 0.2 | 39 | I | 1.4 | 0.06 |
| | | 2243 | | 974 | I | 1.4 | 0.34 | 415 | I | 1.2 | 0.08 | 370 | I | 0 | 0 |
| D87071 | Human mRNA for KIAA0233 "gene," complete cds | 8595 | | -2055 | D | 1.3 | 0.34 | -1055 | NC | 0 | 0 | -1952 | D | 1.3 | 0.31 |
| M87860 | Human S-lac lectin L-14-II (LGALS2) gene | 126 | | -71 | D | 2.3 | 0.34 | 19 | NC | 0 | 0 | 12 | MI | 1.1 | 0.01 |
| X15949 | Human mRNA for interferon regulatory factor-2 (IRF-2) | -10 | * | 59 | MI | -2.4 | 0.34 | 49 | NC | 0 | 0 | -4 | NC | 0 | 0 |
| Z47087 | H. sapiens mRNA for RNA polymerase II elongation factor-like protein | 5 | * | 45 | MI | -2.5 | 0.33 | 72 | NC | 0 | 0 | 36 | NC | 0 | 0 |
| M58028 | Human ubiquitin-activating enzyme E1 (UBE1) "mRNA," complete cds | 134 | | 129 | I | 2 | 0.33 | 68 | NC | 0 | 0 | 105 | I | 1.8 | 0.23 |
| S73591 | brain-expressed HHCPA78 homolog [human,] HL-60 acute promyelocytic leukemia | 626 | | -263 | D | 1.7 | 0.33 | -180 | NC | 0 | 0 | -208 | D | 1.5 | 0.18 |
| M94556 | Human mitochondrial specific single stranded DNA binding protein "mRNA," complete | 4 | * | 46 | MI | -2.5 | 0.33 | 29 | NC | 0 | 0 | 13 | NC | 0 | 0 |
| X02530 | Human mRNA for gamma-interferon inducible early response gene (with homology to | 309 | | 233 | I | 1.8 | 0.32 | 310 | I | 2 | 0.53 | 272 | I | 1.9 | 0.42 |
| Z26491 | H. sapiens gene for catechol O-methyltransferase — Also Represents: M65213 | 54 | | -34 | D | 2.7 | 0.32 | -47 | D | -2.7 | 0.38 | -17 | I | 0 | 0 |
| U67319 | Human Lice2 beta cysteine protease "mRNA," complete cds. | 381 | | 268 | I | 1.7 | 0.32 | 178 | I | 1.5 | 0.16 | 239 | I | 1.6 | 0.26 |
| X01703 | Human gene for alpha-tubulin (b alpha 1) | 31 | * | 46 | MI | 2.5 | 0.32 | 27 | NC | 0 | 0 | 38 | NC | 0 | 0 |
| X60489 | Human mRNA for elongation factor-1-beta | 316 | | 237 | I | 1.7 | 0.32 | 118 | NC | 0 | 0 | 263 | I | 1.8 | 0.39 |
| U90546 | Human butyrophilin (BTF4) "mRNA," complete cds | 2705 | | 1065 | I | 1.4 | 0.32 | -219 | NC | 0 | 0 | 645 | I | 1.2 | 0.14 |
| | 1-8D gene from interferon-inducible gene family — Also Represents: HG1538- | 40 | | -116 | D | -2.0 | 0.31 | -25 | NC | 0 | 0 | -26 | NC | 0 | 0 |
| U62962 | Human Int-6 "mRNA," complete cds | 11471 | | -2433 | D | 1.3 | 0.31 | -3146 | D | 1.4 | 0.52 | -1252 | D | 1.5 | 0.12 |
| U32129 | Human mRNA for HLA class-I (HLA-A26) heavy "chain," complete cds (clone cMIY-1 | 237 | | -117 | D | 2 | 0.31 | 236 | I | 2 | 0.46 | -79 | MD | 2.1 | 0.52 |
| X57351 | Human plectin (PLEC1) "mRNA," complete cds | 252 | | 196 | I | 1.8 | 0.31 | 208 | I | 1.8 | 0.34 | 266 | I | 0 | 0 |
| U53204 | Human cyclin B "mRNA," 3' end | 5002 | | 1593 | I | 1.3 | 0.31 | 856 | I | 1.2 | 0.11 | 557 | NC | 1.1 | 0.02 |
| M25753 | | 460 | | -200 | D | 1.8 | 0.31 | -125 | D | 1.4 | 0.1 | -53 | MD | 0 | 0.02 |
| | | 345 | | 247 | I | 1.7 | 0.31 | 122 | NC | 0 | 0 | 255 | I | 1.7 | 0.33 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| M22760 | *Homo sapiens* nuclear-encoded mitochondrial cytochrome c oxidase Va subunit "mR | 528 | | 331 | I | 1.6 | 0.31 | 131 | NC | 0 | 0 | 292 | I | 1.6 | 0.25 |
| U62136 | Human putative enterocyte differentiation promoting factor "mRNA," partial cds | 63 | | −38 | D | 2.5 | 0.31 | 20 | NC | 0 | 0 | −31 | D | 2 | 0.16 |
| X07315 | Human gene for PP15 (placental protein 15) | 528 | | 332 | I | 1.6 | 0.31 | 38 | NC | 0 | 0 | 145 | MI | 1.3 | 0.08 |
| | | 51 | * | 63 | MI | 2.2 | 0.31 | 30 | NC | 0 | 0 | 26 | NC | 0 | 0 |
| L25851 | *Homo sapiens* integrin alpha E "mRNA," complete cds | 33 | | 46 | MI | 2.4 | 0.31 | 21 | NC | 0 | 0 | 38 | NC | 0 | 0 |
| V00594 | Human mRNA for metallothionein from cadmium-treated cells — Also Represents: J00 | 17001 | | −3191 | D | 1.2 | 0.3 | −4549 | D | 1.4 | 0.6 | −2617 | NC | 0 | 0.48 |
| X89398 | ung gene "(uracil-DNA-glycosylase," UNG2) extracted from *H. sapiens* ung gene for u | 105 | | 104 | I | 2 | 0.3 | 8 | NC | 0 | 0 | 136 | I | 2.3 | 0.37 |
| IG162-HT316 | Tyrosine "Kinase," Receptor "Axl," Alt. Splice 2 | 240 | | 185 | MI | 1.8 | 0.3 | 110 | NC | 0 | 0 | 210 | I | 1.9 | 0.27 |
| U73824 | Human p97 "mRNA," complete cds | 1652 | | −544 | MI | 1.5 | 0.3 | −490 | NC | 0 | 0 | −524 | D | 1.5 | 0 |
| | | 48 | | 59 | I | 2.2 | 0.3 | 21 | NC | 0 | 0 | 8 | NC | 0 | 0 |
| | | 1261 | | 601 | MI | 1.5 | 0.3 | 261 | NC | 0 | 0 | −164 | NC | 0 | 0 |
| J03260 | Human transducin alpha-subunit (GNAZ) "mRNA," complete cds — Also Represents: | −8 | * | 54 | I | −2.3 | 0.3 | 31 | NC | 0 | 0 | 36 | NC | 0 | 0 |
| D45248 | Human mRNA for proteasome activator hPA28 subunit "beta," complete cds | 418 | | 269 | I | 1.6 | 0.29 | 254 | I | 1.6 | 0.26 | 339 | I | 1.8 | 0.43 |
| M10942 | Human metallothionein-ie gene (hMT-ie) | 832 | | −314 | I | 1.6 | 0.29 | −214 | D | 1.3 | 0.12 | −141 | NC | 0 | 0 |
| X83492 | *H. sapiens* mRNA for Fas/Apo-1 (clone "pCRTM11-Fasdelta(4,7)." /gb = X83492 /ntyp | 6 | * | 43 | I | −2.4 | 0.29 | 45 | NC | 0 | 0 | 46 | I | −2.6 | 0.35 |
| Y08614 | *H. sapiens* mRNA for CRM1 protein | 157 | | −80 | MD | 2.1 | 0.29 | 26 | NC | 0 | 0 | −78 | NC | 0 | 0 |
| L14778 | Human calmodulin-dependent protein phosphatase catalytic subunit (PPP3CA) "mRN | 7 | * | 40 | I | −2.4 | 0.28 | 69 | I | −3.8 | 0.84 | 19 | I | −1.3 | 0.03 |
| M17885 | Human acidic ribosomal phosphoprotein P0 "mRNA," complete cds | 8139 | | −1797 | D | 1.3 | 0.28 | −2105 | D | 1.3 | 0.39 | −739 | NC | 0 | 0 |
| U06711 | Human Ly-6-related protein-9804 "gene," complete cds — Also Represents: U56145 | 274 | | 197 | I | 1.7 | 0.28 | 230 | I | 1.8 | 0.37 | 132 | NC | 0 | 0 |
| X71490 | *H. sapiens* mRNA for vacuolar proton "ATPase," subunit D | 135 | | 118 | MI | 1.9 | 0.28 | 88 | NC | 0 | 0 | 146 | MI | 2.1 | 0.4 |
| | | 10371 | | −2123 | D | 1.3 | 0.28 | −38 | NC | 0 | 0 | −2241 | D | 1.3 | 0.31 |
| U90313 | Human glutathione-S-transferase homolog "mRNA," complete cds. | 1571 | | 676 | I | 1.4 | 0.28 | −117 | NC | 0 | 0 | 559 | I | 1.4 | 0.21 |
| L00426 | Human 26S protease (S4) regulatory subunit "mRNA," complete cds | 310 | | 210 | I | 1.7 | 0.27 | 430 | I | 2.4 | 0.93 | 144 | NC | 0 | 0 |
| K01900 | Human lymphocyte interferon alpha type 201 "mRNA," complete cds | 46 | | −43 | D | −2.3 | 0.27 | −48 | D | −2.3 | 0.29 | −28 | D | −2.3 | 0.22 |
| L25081 | Human GTPase (rhoC) "mRNA," complete cds | 432 | | 264 | I | 1.6 | 0.27 | 221 | I | 1.5 | 0.2 | 480 | I | 2.1 | 0.75 |
| Z22548 | *H. sapiens* thiol-specific antioxidant protein mRNA | 147 | | 124 | I | 1.8 | 0.27 | 98 | I | 1.7 | 0.18 | 135 | I | 1.9 | 0.32 |
| M15958 | Human gastrin "gene," complete cds | 41 | * | −69 | MD | −2.1 | 0.27 | −37 | NC | 0 | 0 | −56 | NC | 0 | 0.24 |
| D14689 | Human mRNA for KIAA0023 "gene," complete cds | 96 | | −52 | MD | 2.2 | 0.27 | −22 | NC | 0 | 0 | −20 | NC | 0 | 0 |
| D80000 | Human mRNA for KIAA0178 "gene," partial cds | 49 | | −34 | D | −2.4 | 0.27 | 29 | NC | 0 | 0 | 2 | NC | 0 | 0 |
| X74794 | *H. sapiens* P1-Cdc21 mRNA | 437 | | −183 | D | 1.7 | 0.27 | −97 | NC | 0 | 0 | −145 | NC | 0 | 0 |
| | | 10791 | | −2116 | MD | 1.2 | 0.26 | −2350 | MD | 1.3 | 0.32 | −1440 | D | −2.4 | 0.29 |
| L17128 | *Homo sapiens* (clone H4/H16) gamma-glutamic carboxylase "mRNA," complete cds | 9 | * | 37 | I | −2.3 | 0.26 | 27 | NC | 0 | 0 | 39 | I | 0 | 0 |
| D85131 | Human mRNA for Myc-associated zinc-finger protein of human "islet," complete cds | 66 | | −38 | D | 2.3 | 0.26 | −24 | NC | 0 | 0 | 13 | NC | 0 | 0 |
| X54936 | *H. sapiens* mRNA for placenta growth factor (PIGF) | 118 | | 104 | MI | 1.9 | 0.28 | 36 | NC | 0 | 0 | 8 | NC | 0 | 0 |
| Z29064 | *H. sapiens* AF-1p mRNA | 23 | | 32 | I | 2.4 | 0.25 | 66 | I | 3.9 | 0.85 | 19 | I | 1.8 | 0.11 |
| M19267 | Human tropomyosin "mRNA," complete cds — Also Represents: X12369 Same Unige | 680 | | 347 | I | 1.5 | 0.25 | 366 | I | 1.5 | 0.27 | 143 | NC | 0 | 0 |
| G1153-HT115 | Nucleoside Diphosphate Kinase Nm23-H2s | 1130 | | 496 | MI | 1.4 | 0.25 | 470 | MI | 1.4 | 0.23 | 449 | I | 1.4 | 0.21 |
| U96915 | *Homo sapiens* sin3 associated polypeptide p18 (SAP18) "mRNA," complete cds. | 537 | | 296 | I | 1.6 | 0.25 | 78 | MI | 1.1 | 0.03 | −16 | NC | 0 | 0 |
| D50405 | Human mRNA for RPD3 "protein," complete cds | 223 | | 160 | I | 1.7 | 0.25 | 139 | NC | 0 | 0 | 286 | I | 2.3 | 0.69 |
| X05610 | Human mRNA for type IV collagen alpha-2 chain | 660 | | −244 | D | 1.6 | 0.25 | −42 | NC | 0 | 0 | −205 | D | 1.4 | 0.16 |
| U23946 | Human putative tumor suppressor (LUCA15) "mRNA," complete cds | 54 | | −32 | MD | 2.4 | 0.25 | −5 | NC | 0 | 0 | −13 | NC | 0 | 0 |
| U76272 | Human diadenosine triphosphate (Ap3A) hydrolase (FHIT) "gene," 5' of | −10 | * | 53 | I | −2.1 | 0.25 | −1 | NC | 0 | 0 | 23 | NC | 0 | 0 |
| U54644 | Human tub homolog "mRNA," complete cds — Also Represents: U82467 | 148 | | −72 | D | 1.9 | 0.24 | −66 | MD | 1.8 | 0.19 | −51 | NC | 0 | 0 |
| G3044-HT374 | "Fibronectin," Alt. Splice 1 — "Also Represents: HG3044-HT2527, X02761" | 673 | | −245 | D | 1.6 | 0.24 | 193 | I | 1.3 | 0.09 | −235 | D | 1.5 | 0.22 |
| G2815-HT293 | "Myosin," Light "Chain," "Alkali," "Non-Muscle," Alt. S | 1347 | | 555 | I | 1.4 | 0.24 | 245 | I | 1.2 | 0.06 | 5 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| U63824 | Human transcription factor RTEF-1 (RTEF1) "mRNA," complete cds | 40 | | 47 | I | 2.2 | 0.24 | 23 | NC | 0 | 0 | 122 | I | 4 | 1.23 |
| X65463 | H. sapiens mRNA for MHC class I promoter binding protein | 65 | * | 64 | MI | 2 | 0.24 | 33 | NC | 0 | 0 | 91 | MI | 2.4 | 0.44 |
| | | 46 | | −34 | MD | −2.3 | 0.24 | −22 | NC | 0 | 0 | −25 | NC | 0 | 0 |
| L37042 | Homo sapiens casein kinase I alpha isoform (CSNK1A1) "mRNA," complete cds | 102 | | −53 | D | 2.1 | 0.24 | 47 | NC | 0 | 0 | −13 | NC | 0 | 0 |
| M87284 | Human 69 kDa 2'5' oligoadenylate synthetase (P69 2-5A synthetase) "mRNA," comp | 52 | * | 56 | I | 2.1 | 0.23 | 86 | I | 1.5 | 0.23 | 6 | NC | 0 | 0 |
| X72727 | H. sapiens tunp mRNA for transformation upregulated nuclear protein | 523 | | 274 | I | 1.5 | 0.23 | 277 | I | 1.5 | 0.13 | 101 | NC | 0 | 0 |
| D00760 | Human mRNA for proteasome subunit HC3 | 231 | | 156 | I | 1.7 | 0.23 | 110 | I | 1.5 | 0.12 | 67 | NC | 0 | 0 |
| J03909 | Human gamma-interferon-inducible protein (IP-30) "mRNA," complete cds | 4 | * | 40 | MI | −2.2 | 0.23 | 31 | MI | −1.8 | 0 | 235 | I | −12.0 | 5.33 |
| X79234 | H. sapiens mRNA for ribosomal protein L11 | 5490 | | −1212 | D | 1.3 | 0.23 | −1371 | NC | 0 | 0 | −1487 | D | 1.4 | 0.35 |
| M62810 | Human mitochondrial transcription factor 1 "mRNA," complete cds | 46 | | 50 | MI | 2.1 | 0.23 | 82 | NC | 0 | 0 | −20 | NC | 0 | 0 |
| X64707 | H. sapiens BBC1 mRNA | 3338 | | 1023 | MI | 1.3 | 0.23 | 549 | NC | 0 | 0 | 860 | NC | 0 | 0 |
| G1980-HT202 | "Tubulin," Beta 2 | 6620 | | −1350 | D | 1.3 | 0.22 | −1817 | D | 1.4 | 0.4 | −461 | NC | 0 | 0.55 |
| X98172 | H. sapiens mRNA for MACH-alpha-1 protein | 23 | * | 30 | MI | 2.3 | 0.22 | 42 | I | 2.8 | 0.39 | 51 | I | 3.2 | 0 |
| U86782 | Human 26S proteasome-associated pad1 homolog (POH1) "mRNA," complete cds. / | 293 | | 181 | I | 1.6 | 0.22 | 228 | I | 1.8 | 0.33 | 9 | NC | 0 | 0 |
| M84349 | Human transmembrane protein (CD59) gene | 401 | | 220 | I | 1.5 | 0.22 | 217 | I | 1.5 | 0.21 | 185 | I | 1.5 | 0.16 |
| X71874 | proteasome-like subunit MECL-1 gene extracted from H. sapiens genes for proteason | 184 | | 128 | I | 1.7 | 0.22 | 108 | I | 1.6 | 0.16 | 379 | I | 3.1 | 1.41 |
| D00763 | Human mRNA for proteasome subunit HC9 | 268 | | 170 | I | 1.6 | 0.22 | 95 | MI | 1.4 | 0.08 | 13 | NC | 0 | 0 |
| U09964 | Human serine kinase "mRNA," complete cds | 87 | | −45 | D | 2.1 | 0.22 | −10 | NC | 0 | 0 | −48 | D | 2.3 | 0.28 |
| M11353 | Human H3.3 histone class C "mRNA," complete cds | 914 | | 397 | I | 1.4 | 0.22 | 39 | NC | 0 | 0 | 17 | NC | 0 | 0 |
| M17886 | Human acidic ribosomal phosphoprotein P1 "mRNA," complete cds | 7275 | | −1429 | MD | 1.2 | 0.21 | −1968 | D | 1.4 | 0.4 | −979 | NC | 0 | 0 |
| U47634 | Human beta-tubulin class III isotype (beta-3) "mRNA," complete cds | 348 | | 197 | I | 1.6 | 0.21 | 210 | I | 1.6 | 0.24 | 290 | I | 1.8 | 0.41 |
| AB000584 | Human mRNA for TGF-beta superfamily "protein," complete cds | 1134 | | 445 | I | 1.4 | 0.21 | 406 | I | 1.4 | 0.18 | 222 | I | 1.2 | 0.07 |
| X13794 | H. sapiens lactate dehydrogenase B gene exon 1 and 2 (EC 1.1.1.27) (and joined CD | 1551 | | −448 | D | 1.4 | 0.21 | −211 | NC | 0 | 0 | −699 | D | 1.8 | 0.62 |
| M63180 | Human threonyl-tRNA synthetase "mRNA," complete cds | 218 | | −95 | D | 1.8 | 0.21 | 119 | NC | 0 | 0 | −90 | D | 1.7 | 0.18 |
| | | 87 | | 73 | I | 1.8 | 0.21 | 53 | NC | 0 | 0 | 29 | NC | 0 | 0 |
| D12686 | Human mRNA for eukaryotic initiation factor 4 gamma (eIF-4 gamma) | 426 | | −162 | D | 1.6 | 0.2 | −3 | NC | 0 | 0 | −70 | NC | 0 | 0 |
| D31762 | Human mRNA for KIAA0057 "gene," complete cds | 148 | | −69 | D | 1.9 | 0.2 | 52 | NC | 0 | 0 | −24 | NC | 0 | 0 |
| G4334-HT460 | Glycogenin — Also Represents: U31525 | 270 | | 164 | I | 1.6 | 0.2 | 116 | NC | 0 | 0 | 53 | NC | 0 | 0 |
| U00802 | Human drebrin E2 mRNA "(DBN1)," complete cds — Also Represents: D17530 | 83 | | −42 | D | 2 | 0.21 | −15 | NC | 0 | 0 | −4 | NC | 0 | 0 |
| U05681 | Human proto-oncogene BCL3 gene — Also Represents: M31732 | 169 | | −77 | D | 1.8 | 0.21 | −61 | NC | 0 | 0 | 7 | NC | 0 | 0 |
| U46571 | Human tetratricopeptide repeat protein (tpr2) "mRNA," complete cds | 82 | | −42 | D | 2.1 | 0.21 | −7 | NC | 0 | 0 | −43 | NC | 0 | 0 |
| X14329 | Human mRNA for carboxypeptidase N small subunit (EC 3.4.17.3) | 79 | * | −41 | MD | 2.1 | 0.21 | −66 | NC | 0 | 0 | −29 | NC | 0 | 0 |
| X89894 | H. sapiens mRNA for nuclear receptor | 18 | * | 28 | I | −2.3 | 0.21 | 4 | NC | 0 | 0 | 37 | NC | 0 | 0 |
| M19311 | Human calmodulin "mRNA," complete cds — Also Represents: D45887 | 2009 | | 661 | I | 1.3 | 0.2 | 640 | I | 1.3 | 0.19 | −200 | NC | 0 | 0 |
| U37689 | Human RNA polymerase II subunit (hsRPB8) "mRNA," complete cds | 573 | | 269 | I | 1.5 | 0.2 | 223 | I | 1.4 | 0.14 | 400 | I | 1.7 | 0.39 |
| D38583 | Human mRNA for "calgizzarin," complete cds | 802 | | 348 | I | 1.4 | 0.2 | 199 | I | 1.2 | 0.08 | 424 | I | 1.5 | 0.29 |
| M34539 | Human FK506-binding protein (FKBP) "mRNA," complete cds | 1008 | | −310 | D | 1.4 | 0.2 | −134 | D | 1.2 | 0.04 | −306 | D | 1.4 | 0.19 |
| M14091 | Human thyroxine-binding globulin "mRNA," complete cds | 43 | | −30 | D | −2.2 | 0.19 | −10 | NC | 0 | 0 | −58 | D | −2.2 | 0.27 |
| X68277 | H. sapiens CL 100 mRNA for protein tyrosine phosphatase | 155 | | 109 | I | 1.7 | 0.2 | 38 | NC | 0 | 0.27 | 92 | I | 1.6 | 0.15 |
| J04029 | Homo sapiens keratin 10 type I intermediate filament (KRT 10) "mRNA," complete cds | 401 | | 210 | I | 1.5 | 0.2 | 59 | NC | 0 | 0.22 | 93 | NC | 0 | 0 |
| L32977 | Homo sapiens (clone I17252) ubiquinol cytochrome c reductase Rieske iron-sulphur | 460 | * | 229 | I | 1.5 | 0.2 | 78 | NC | 0 | 0.19 | 50 | NC | 0 | 0 |
| U57341 | Human neurofilament triplet L protein "mRNA," partial cds. /gb = U57341 /ntype = RNA | 695 | | −229 | D | −2.2 | 0.19 | −265 | D | 1.6 | 0 | −124 | D | 1.8 | 0.11 |
| J04168 | Human leukoslatin "mRNA," complete cds | 44 | | −25 | MD | −2.1 | 0.19 | −33 | D | −2.2 | 0.27 | −20 | NC | 0 | 0 |
| D87465 | Human mRNA for KIAA0275 "gene," complete cds | 43 | | −31 | MD | −2.1 | 0.19 | −29 | D | −2.1 | 0.22 | −30 | NC | 0 | 0 |
| U49441 | Human mitochondrial trifunctional protein beta subunit "mRNA," partial cds. /gb = U49 | 54 | * | −29 | MD | 2.2 | 0.19 | −27 | D | 2 | 0.15 | −3 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| U17760 | Human laminin S B3 chain (LAMB3) gene | 541 | | −189 | D | 1.5 | 0.19 | −80 | D | 1.2 | 0.03 | −113 | NC | 0 | 0 |
| X76717 | H. sapiens MT-11 mRNA | 425 | | 210 | I | 1.5 | 0.19 | −208 | NC | 0 | 0 | 331 | I | 1.8 | 0.4 |
| M20778 | Homo "sapiens," alpha-3 (VI) collagen — Also Represents: X52022 | 51 | | −28 | D | 2.2 | 0.19 | −15 | NC | 0 | 0 | −38 | D | −2.6 | 0.32 |
| M20902 | Human apolipoprotein C-I (VLDL) "gene," complete cds | 65 | | −33 | D | 2.1 | 0.19 | −29 | NC | 0 | 0 | −18 | D | 1.4 | 0.04 |
| M22538 | Human nuclear-encoded mitochondrial NADH-ublquinone reductase 24Kd subunit "m | 430 | | 214 | I | 1.5 | 0.19 | 104 | NC | 0 | 0 | 67 | NC | 0 | 0 |
| X69111 | H. sapiens HLH 1R21 mRNA for helix-loop-helix protein | 591 | | 268 | I | 1.5 | 0.19 | 122 | NC | 0 | 0 | 67 | NC | 0 | 0 |
| X63563 | H. sapiens mRNA for RNA polymerase II 140 kDa subunit | 1185 | | 432 | I | 1.4 | 0.19 | 45 | NC | 0 | 0 | −1 | NC | 0 | 0 |
| U84573 | Homo sapiens lysyl hydroxylase isoform 2 (PLOD2) "mRNA," complete cds | 56 | | 49 | I | 1.9 | 0.18 | 174 | I | 4.1 | 1.51 | 32 | D | 2.5 | 0.29 |
| M23114 | Homo sapiens calcium-ATPase (HK1) "mRNA," complete cds | 58 | | −30 | MD | 2.1 | 0.18 | 103 | I | 2.8 | 0.61 | −35 | I | 1.6 | 0.17 |
| U07806 | Human camptothecin resistant clone CEM/C2 DNA topoisomerase I "mRNA," partial | 205 | | 125 | MI | 1.6 | 0.18 | 194 | I | 1.9 | 0.39 | 119 | D | 1.7 | 0.13 |
| X55954 | Human mRNA for HI23 ribosomal protein homologue | 89 | | −43 | D | 1.9 | 0.18 | 103 | I | 2.2 | 0.36 | −38 | D | 1.3 | 0.29 |
| Z25749 | H. sapiens gene for ribosomal protein S7 | 5404 | | −1034 | D | 1.2 | 0.18 | −1065 | MD | 1.2 | 0.19 | −1330 | NC | 0 | 0 |
| M73780 | Human integrin beta-8 subunit "mRNA," complete cds | 3451 | | 878 | I | 1.3 | 0.18 | 636 | I | 1.2 | 0.1 | −24 | D | −2.0 | 0.14 |
| X51956 | Human ENO2 gene for neuron specific (gamma) enolase | 40 | | −38 | D | −2.0 | 0.18 | 0 | NC | 0 | 0 | −24 | MI | 1.5 | 0.07 |
| M16937 | Human homeo box c1 "protein," "mRNA," complete cds | 65 | * | 54 | I | 1.8 | 0.18 | 2 | NC | 0 | 0 | 33 | NC | 0 | 0 |
| M27318 | Human interferon (IFN-alpha-MI) "mRNA," complete cds | 29 | * | 31 | MI | 2.1 | 0.18 | 19 | NC | 0 | 0 | 12 | NC | 0 | 0 |
| M60854 | Human ribosomal protein S16 "mRNA," complete cds | 69 | | −35 | D | 2 | 0.18 | −37 | NC | 0 | 0 | −25 | NC | 0 | 0 |
| U01120 | Human glucose-6-phosphatase "mRNA," complete cds | 9238 | | −1571 | MD | 1.2 | 0.18 | −1818 | NC | 0 | 0 | −1395 | NC | 0 | 0 |
| U04209 | Human associated microfibrillar protein "mRNA," complete cds | 43 | * | −26 | D | −2.1 | 0.18 | −16 | NC | 0 | 0 | −16 | NC | 0 | 0 |
| U04241 | Human homolog of Drosophila enhancer of split m9/m10 "mRNA," complete cds | 16 | | 26 | I | −2.1 | 0.18 | 41 | NC | 0 | 0 | 20 | NC | 0 | 0 |
| U07132 | Human steroid hormone receptor Ner-I "mRNA," complete cds | 496 | | −173 | D | 1.5 | 0.18 | −129 | NC | 0 | 0 | −74 | NC | 0 | 0 |
| U59423 | Human Smad1 "mRNA," complete cds. | 183 | | −77 | MD | 1.7 | 0.18 | −38 | NC | 0 | 0 | −12 | NC | 0 | 0 |
| V00599 | Human mRNA fragment encoding beta-tubulin. (from clone D-beta-1) — Also Represe | 66 | | −33 | D | 2 | 0.18 | −19 | NC | 0 | 0 | −11 | NC | 0 | 0 |
| U61397 | Human ubiquitin-homology domain protein PIC1 "mRNA," complete cds — Also Repre | 5508 | | −1071 | D | 1.2 | 0.18 | −669 | NC | 0 | 0 | −612 | NC | 0 | 0 |
| D26599 | Human mRNA for proteasome subunit "HsC7-1," complete cds | 119 | | 82 | I | 1.7 | 0.17 | 101 | I | 1.8 | 0.25 | −14 | NC | 0 | 0.31 |
| G1071-HT107 | Bone Morphogenetic Protein 3 | 807 | | 319 | I | 1.4 | 0.17 | 329 | I | 1.4 | 0.18 | 446 | I | 1.6 | 0.13 |
| M59465 | Human tumor necrosis factor alpha inducible protein A20 "mRNA," complete cds | 39 | * | −35 | D | −2.0 | 0.17 | −34 | D | −2.0 | 0.16 | −23 | MD | −2.0 | 0 |
| U11861 | Human G10 homolog (edg-2) "mRNA," complete cds | 93 | | −43 | MD | 1.9 | 0.17 | −26 | MD | 1.4 | 0.05 | −36 | NC | 0 | 0 |
| U94586 | Human NADH:ublquinone oxidoreductase MLRQ subunit "mRNA," complete cds. | 619 | | 264 | I | 1.4 | 0.17 | 189 | NC | 0 | 0 | 255 | I | 1.2 | 0.07 |
| M22382 | Human mitochondrial matrix protein P1 (nuclear encoded) "mRNA," complete cds | 1441 | | 471 | I | 1.3 | 0.17 | −527 | NC | 0 | 0 | −145 | MI | 1.3 | 0.04 |
| L48513 | Homo sapiens paraoxonase 2 (PON2) "mRNA," complete cds | 880 | | 326 | I | 1.4 | 0.16 | 966 | I | 2.1 | 1.05 | 67 | NC | 0 | 0 |
| D63475 | Homo sapiens mRNA for KIAA0109 "gene," complete cds | 37 | | 34 | I | 1.9 | 0.16 | 44 | I | 2.2 | 0.25 | 4 | NC | 0 | 0 |
| U09813 | Homo sapiens ATP synthase subunit "9," P3 gene "copy," "mRNA," nuclear g | 2343 | * | 634 | I | 1.3 | 0.16 | 215 | I | 1.1 | 0.03 | −1 | NC | 0 | 0 |
| D87075 | Human mRNA for KIAA0238 "gene," partial cds | 1679 | | 502 | I | 1.3 | 0.16 | 276 | NC | 0 | 0 | 578 | I | 1.3 | 0.2 |
| L12723 | Human heat shock protein 70 (hsp70) "mRNA," complete cds | 39 | | −32 | D | −1.9 | 0.16 | 0 | NC | 0 | 0 | −9 | NC | 0 | 0 |
| L32137 | Human germline oligomeric matrix protein (COMP) "mRNA," complete cds | 105 | | −48 | MD | 1.8 | 0.16 | 101 | NC | 0 | 0 | −20 | NC | 0 | 0 |
| M32886 | Human sorcin CP-22 "mRNA," complete cds | 37 | * | −46 | D | −1.8 | 0.16 | −40 | NC | 0 | 0 | −32 | NC | 0 | 0 |
| Y57650 | Homo sapiens mRNA for "WSL-LH," WSL-S1 and WSL-S2 proteins — Also Represents: U | 392 | | 182 | I | 1.5 | 0.16 | −60 | NC | 0 | 0 | 47 | NC | 0 | 0 |
| Y09392 | H. sapiens mRNA for "WSL-LH," WSL-S1 and WSL-S2 proteins — Also Represents: U | 39 | | −30 | MD | −2.0 | 0.16 | 17 | NC | 0 | 0 | −13 | NC | 0 | 0 |
| Y09392 | H. sapiens SH2-containing inositol 5-phosphatase (hSHIP) "mRNA," complete cds | 41 | | −27 | D | −2.0 | 0.15 | 1 | NC | 0 | 0 | −25 | NC | 0 | 0 |
| X71428 | H. sapiens fus mRNA | 738 | | 274 | I | 1.4 | 0.15 | 476 | I | 1.6 | 0.38 | 226 | I | 1.3 | 0.11 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| V00572 | Human mRNA encoding phosphoglycerate kinase | 3020 | | 724 | I | 1.2 | 0.15 | −840 | D | 1.4 | 0.28 | 301 | NC | 0 | 0 |
| X03689 | Human mRNA fragment for elongation factor TU (N-terminus). /gb = X03689 /ntype = R | 4846 | | 1000 | I | 1.2 | 0.15 | 665 | I | 1.1 | 0.08 | 202 | I | 1 | 0.01 |
| G4073-HT434 | Cytosolic Acetoacetyl-Coenzyme A Thiolase | 196 | | 107 | I | 1.5 | 0.15 | 38 | NC | 1.2 | 0.03 | 60 | I | 1.3 | 0.06 |
| U19147 | Human GAGE-6 protein "mRNA," complete cds — "Also Represents: U19145, U19148 | 500 | | 206 | MD | 1.4 | 0.15 | 98 | NC | 0 | 0 | 198 | I | 1.4 | 0.14 |
| Z49099 | H. sapiens mRNA for spermine synthase | 1160 | | −299 | D | 1.3 | 0.15 | 60 | NC | 0 | 0 | −244 | D | 1.3 | 0.1 |
| D26362 | Human mRNA KIAA0043 "gene," complete cds | 62 | | −30 | D | 2 | 0.15 | −6 | NC | 0 | 0 | −2 | NC | 0 | 0 |
| M95178 | Human non-muscle alpha-actinin "mRNA," complete cds | 432 | | −142 | D | 1.5 | 0.15 | −53 | NC | 0 | 0 | −77 | NC | 0 | 0 |
| X79865 | H. sapiens Mrp17 mRNA | 885 | | −247 | D | 1.4 | 0.15 | −151 | NC | 0 | 0 | −72 | NC | 0 | 0 |
| U54778 | Human 14-3-3 epsilon "mRNA," complete cds | 317 | | 145 | I | 1.5 | 0.14 | 254 | I | 1.8 | 0.36 | 155 | I | 1.5 | 0.16 |
| M34079 | Human immunodeficiency virus fat transactivator binding protein-1 (fbp-1) "mRNA," c | 962 | | −252 | MD | 1.4 | 0.14 | −221 | D | 1.3 | 0.11 | −294 | D | 1.4 | 0.19 |
| J04973 | Human cytochrome bc-1 complex core protein II "mRNA," complete cds | 139 | | 82 | MI | 1.6 | 0.14 | 72 | I | 1.5 | 0.11 | 37 | I | 1.3 | 0.04 |
| U91316 | Human acyl-CoA thioester hydrolase "mRNA," complete cds | 4 | * | 34 | MI | −1.9 | 0.14 | 27 | I | −1.5 | 0.07 | 11 | NC | 0 | 0 |
| U14971 | Human ribosomal protein S9 "mRNA," complete cds | 572 | | 217 | I | 1.4 | 0.14 | 31 | NC | 0 | 0 | 340 | I | 1.6 | 0.29 |
| M21142 | guanine nucleotide-binding protein G-s-alpha-3 gene extracted from Human guanine | 3866 | | 831 | I | 1.2 | 0.14 | −89 | NC | 0 | 0 | 955 | I | 1.2 | 0.18 |
| X90840 | H. sapiens mRNA for axonal transporter of synaptic vesicles | 1344 | | −330 | MD | 1.3 | 0.14 | −179 | NC | 0 | 0 | −207 | MD | 1.2 | 0.06 |
| A28102 | Human GABAa receptor alpha-3 subunit. — "Also Similar To: AF002255, L41347, AF0 | 4 | * | 33 | I | −1.8 | 0.14 | −5 | NC | 0 | 0 | 23 | I | −1.3 | 0.04 |
| G2238-HT232 | Nuclear Mitotic Apparatus Protein "1," Alt. Splice Form 2 — "Also Represents: HG2238 | 52 | | −25 | D | 1.9 | 0.14 | 29 | NC | 0 | 0 | −12 | NC | 0 | 0 |
| M12125 | Human fibroblast muscle-type tropomyosin "mRNA," complete cds | 110 | | −46 | MD | 1.7 | 0.14 | −7 | NC | 0 | 0 | −24 | NC | 0 | 0 |
| M23892 | Human 15-lipoxygenase "mRNA," complete cds — Also Represents: U88317_rna1 | 1087 | | −282 | MD | 1.4 | 0.14 | −153 | NC | 0 | 0 | −144 | NC | 0 | 0 |
| U63541 | Human mRNA expressed in HC/HCC livers and MoIT-4 proliferating "cells," partial se | 23 | | 23 | I | 2 | 0.14 | 5 | NC | 0 | 0 | 11 | NC | 0 | 0 |
| X59543 | Human mRNA for M1 subunit of ribonucleotide reductase | 61 | | 45 | MI | 1.7 | 0.14 | 61 | NC | 0 | 0 | 51 | NC | 0 | 0 |
| Z22780 | H. sapiens cylicin mRNA | 200 | | 104 | I | 1.5 | 0.14 | 58 | NC | 0 | 0 | 14 | NC | 0 | 0 |
| M63175 | Human autocrine motility factor receptor mRNA | 37 | | −33 | D | −1.8 | 0.13 | −27 | NC | 0 | 0 | −20 | NC | 0 | 0 |
| Z24727 | H. sapiens tropomyosin isoform "mRNA," complete CDS | 58 | | 42 | I | 1.7 | 0.13 | 51 | MI | 1.9 | 0.18 | 30 | MI | 1.5 | 0.08 |
| U79254 | Human clone 23693 mRNA sequence | 1056 | | 324 | I | 1.3 | 0.13 | 222 | MI | 1.2 | 0.07 | 179 | I | 1.2 | 0.05 |
| D21852 | Human mRNA for KIAA0029 "gene," partial cds | 631 | | −176 | D | 1.4 | 0.13 | −4 | NC | 0 | 0 | −323 | D | 2 | 0.57 |
| D79989 | Human mRNA for KIAA0167 "gene," complete cds | 84 | | −37 | D | 1.8 | 0.13 | 20 | NC | 0 | 0 | −6 | NC | 0 | 0 |
| HG870-HT870 | "Golgin," 165 Kda Polypeptide | 36 | * | −31 | MD | −1.8 | 0.13 | −13 | NC | 0 | 0 | −20 | NC | 0 | 0 |
| J05032 | Human aspartyl-tRNA synthetase alpha-2 subunit "mRNA," complete cds | 39 | * | −23 | MD | −1.9 | 0.13 | −14 | NC | 0 | 0 | −16 | NC | 0 | 0 |
| M21904 | Human 4F2 glycosylated heavy chain (4F2HC) antigen gene | 52 | * | −25 | MD | 1.9 | 0.13 | 22 | NC | 0 | 0 | −15 | NC | 0 | 0 |
| Y07867 | H. sapiens mRNA for "Pirin," isolate 1 | 409 | | 162 | I | 1.4 | 0.13 | 20 | NC | 0 | 0 | 67 | NC | 0 | 0 |
| D14043 | Human mRNA for "MGC-24," complete cds | 43 | * | 33 | I | 1.8 | 0.13 | 14 | NC | 0 | 0 | 29 | NC | 0 | 0 |
| U08021 | Human nicotinamide N-methyltransferase (NNMT) "mRNA," complete cds | 55 | | 39 | MI | 1.7 | 0.12 | 127 | I | 3.3 | 0.92 | −22 | NC | 0 | 0 |
| U51010 | Human nicotinamide N-methyltransferase "gene," exon 1 and 5′ flanking region. /gb = | 742 | | 239 | I | 1.3 | 0.12 | −27 | NC | 0 | 0 | 1261 | I | 2.7 | 2.05 |
| U09587 | Human glycyl-tRNA synthetase mRNA, complete cds. | 401 | | 156 | I | 1.4 | 0.12 | 62 | NC | 0 | 0 | 659 | I | 2.6 | 1.42 |
| Z47055 | Human partial cDNA "sequence," farnesyl pyrophosphate synthetase like-4. /gb = Z47 | 1573 | | −346 | D | 1.3 | 0.12 | −109 | NC | 0 | 0 | −387 | D | 1.3 | 0.15 |
| M36430 | Human transducin beta-1 subunit "mRNA," 3′ end — Also Represents: X04526 | 485 | | 182 | I | 1.3 | 0.12 | 70 | NC | 0 | 0 | 207 | I | 1.4 | 0.15 |
| D50663 | Human mRNA for TCTEL1 "gene," complete cds | 469 | | −137 | D | 1.4 | 0.12 | 2 | NC | 0 | 0 | −109 | D | 1.3 | 0.08 |
| U01691 | Human annexin V (ANX5) "gene," 5′-untranslated region — "Also Represents: X12454 | 389 | | 153 | I | 1.3 | 0.12 | 106 | NC | 0 | 0 | 18 | NC | 0 | 0 |
| U76764 | Human CD97 "mRNA," complete cds — "Also Represents: X84700, X94630_ma1″ | 937 | | 278 | I | 1.4 | 0.12 | 94 | NC | 0 | 0 | 39 | NC | 0 | 0 |
| X52979 | SmB protein gene extracted from Human gene for small nuclear ribonucleoproteins S | 39 | | −20 | MD | −1.9 | 0.12 | 11 | NC | 0 | 0 | −1 | NC | 0 | 0 |
| X56687 | H. sapiens mRNA for autoantigen NOR-90 — "Also Represents: X53461, X53390, U65 | 1575 | | 399 | I | 1.3 | 0.12 | 86 | NC | 0 | 0 | 228 | I | 1.4 | 0.15 |
| X62691 | H. sapiens mRNA for ribosomal protein (homologous to yeast S24) | 34 | | −42 | MD | −1.7 | 0.12 | −20 | NC | 0 | 0 | −32 | NC | 0 | 0 |
| X12671 | hnrnp a1 protein gene extracted from Human gene for heterogeneous nuclear ribonu | 4511 | | 850 | I | 1.2 | 0.11 | 650 | NC | 0 | 0.5 | 226 | I | 1.3 | 0 |
| | | 880 | | 260 | I | 1.3 | 0.11 | 627 | | 1.7 | | −5 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| X78136 | *H. sapiens* hnRNP-E2 mRNA | 1073 | | 298 | I | 1.3 | 0.11 | 534 | I | 1.5 | 0.3 | 541 | I | 1.5 | 0.3 |
| X86809 | *H. sapiens* mRNA for major astrocytic phosphoprotein PEA-15 | 986 | | −235 | D | 1.3 | 0.11 | −345 | MD | 1.5 | 0.26 | −257 | MD | 1.4 | 0.14 |
| U68105 | Human poly(A)-binding protein (PABP) "gene," promoter region and — Also Represen | 996 | | 278 | I | 1.3 | 0.11 | 351 | I | 1.4 | 0.16 | 256 | I | 1.3 | 0.1 |
| X85373 | *H. sapiens* mRNA for Sm protein G | 613 | | 202 | I | 1.3 | 0.11 | 156 | MI | 1.3 | 0.16 | 82 | MI | 1.1 | 0.03 |
| U14969 | Human ribosomal protein L28 "mRNA," complete cds | 5725 | | 934 | I | 1.2 | 0.11 | 400 | I | 1.1 | 0.07 | 1680 | I | 1.3 | 0.29 |
| L76568 | S26 from *Homo sapiens* excision and cross link repair protein (ERCC4) "gene," comp | 398 | | 149 | I | 1.4 | 0.11 | 45 | I | 1.1 | 0.03 | 101 | NC | 0 | 0 |
| M64929 | Human protein phosphatase 2A alpha subunit "mRNA," complete cds | 94 | | −38 | MD | 1.7 | 0.11 | 50 | NC | 0 | 0.02 | −43 | MD | 1.8 | 0.16 |
| X65867 | *H. sapiens* mRNA for adenylosuccinate lyase | 634 | | 202 | I | 1.3 | 0.11 | −127 | I | 1.3 | 0 | 228 | I | 1.4 | 0.13 |
| U47101 | Human NitU-like protein (hNitU) "mRNA," partial cds | 112 | | 61 | I | 1.5 | 0.11 | 8 | MI | 1.5 | 0 | 53 | MI | 1.5 | 0.09 |
| | | 720 | | 227 | I | 1.3 | 0.11 | −94 | NC | 0 | 0 | 16 | NC | 0 | 0 |
| | | 475 | | 166 | I | 1.3 | 0.11 | −14 | NC | 0 | 0 | 131 | NC | 0 | 0 |
| D13640 | Human mRNA for KIAA0015 "gene," complete cds | 261 | | −85 | D | 1.5 | 0.11 | −103 | NC | 0 | 0 | −64 | NC | 0 | 0 |
| D14827 | Human mRNA for Tax helper protein "1," complete cds | 32 | * | −50 | MD | −1.6 | 0.11 | −23 | NC | 0 | 0 | −28 | NC | 0 | 0 |
| D31846 | Human gene for aquaporin-2 water "channel," "exon1-4," complete cds | 202 | | −70 | MD | 1.5 | 0.11 | −58 | NC | 0 | 0 | −79 | NC | 0 | 0 |
| D86974 | Human mRNA for KIAA0220 "gene," partial cds | 168 | | −58 | MD | 1.5 | 0.11 | 32 | NC | 0 | 0 | −34 | NC | 0 | 0 |
| L28010 | *Homo sapiens* HnRNP F protein "mRNA," complete cds | 196 | | −67 | D | 1.5 | 0.11 | 76 | NC | 0 | 0 | 46 | NC | 0 | 0 |
| L38951 | *Homo sapiens* importin beta subunit "mRNA," complete cds | 177 | | −61 | D | 1.5 | 0.11 | 115 | NC | 0 | 0 | −37 | NC | 0 | 0 |
| M19989 | Human platelet-derived growth factor (PDGFA) A chain gene | 32 | * | 25 | MI | 1.8 | 0.11 | 18 | NC | 0 | 0 | 11 | NC | 0 | 0 |
| M33336 | Human cAMP-dependent protein kinase type I-alpha subunit (PRKAR1A) "mRNA," c | 93 | | −37 | D | 1.7 | 0.11 | 76 | NC | 0 | 0 | −7 | NC | 0 | 0 |
| U24166 | Human EB1 "mRNA," complete cds | 230 | | 101 | MI | 1.4 | 0.11 | 91 | NC | 0 | 0 | 50 | NC | 0 | 0 |
| X93920 | *H. sapiens* mRNA for protein-tyrosine-phosphatase (tissue type: foreskin) | 30 | * | 24 | I | 1.8 | 0.11 | −7 | NC | 0 | 0 | 36 | NC | 0 | 0 |
| X95648 | *H. sapiens* mRNA for eIF-2B alpha subunit | 90 | | 48 | I | 1.5 | 0.11 | 78 | I | 1.9 | 0.22 | 106 | MI | 2.2 | 0.38 |
| D79995 | Human mRNA for KIAA0173 "gene," complete cds | 37 | | −18 | D | −1.9 | 0.1 | −23 | D | −1.9 | 0.12 | −12 | NC | 0 | 0 |
| D78132 | Human mRNA for Ras homologue enriched in brain (RHEB) "gene," Ras-related GT | 524 | | 171 | MI | 1.3 | 0.1 | 168 | I | 1.3 | 0.1 | 7 | NC | 0 | 0 |
| X99584 | *H. sapiens* mRNA for SMT3A protein | 100 | * | 54 | I | 1.5 | 0.1 | 45 | I | 1.5 | 0.08 | 95 | I | 2 | 0.28 |
| M64595 | Human small G protein (Gx) "mRNA," 3' end | 200 | | −65 | MD | 1.5 | 0.09 | −59 | MD | 1.4 | 0.08 | −28 | NC | 0 | 0 |
| U48959 | Human myosin light chain kinase (MLCK) "mRNA," complete cds | 127 | | −46 | D | 1.6 | 0.09 | −43 | D | 0 | 0 | −71 | D | 2.3 | 0.34 |
| D32050 | Human mRNA for alanyl-tRNA "synthetase," complete cds | 396 | | −109 | D | 1.4 | 0.09 | −24 | NC | 0 | 0 | −20 | NC | 0 | 0 |
| D89077 | Human mRNA for Src-like adapter "protein," complete cds | 33 | | −36 | MI | −1.6 | 0.09 | −22 | NC | 0 | 0 | −11 | NC | 0 | 0 |
| U18291 | Human CDC16Hs "mRNA," complete cds | 46 | | 31 | MI | 1.7 | 0.09 | 26 | NC | 0 | 0 | 17 | NC | 0 | 0 |
| U89942 | Human lysyl oxidase-related protein (WS9-14) "mRNA," complete cds | 618 | | −153 | D | 1.3 | 0.09 | 26 | NC | 0 | 0 | −118 | NC | 0 | 0 |
| X72964 | *H. sapiens* mRNA for calltractin | 178 | | 79 | MI | 1.4 | 0.1 | 4 | NC | 0 | 0 | 15 | NC | 0 | 0 |
| X84709 | *H. sapiens* mRNA for mediator of receptor-induced toxicity | 295 | | 115 | I | 1.4 | 0.1 | −48 | NC | 0 | 0 | 87 | NC | 0 | 0 |
| Z24724 | *H. sapiens* polyA site DNA | 33 | | −27 | D | −1.7 | 0.09 | 80 | I | 3.4 | 0.77 | −17 | I | 1.3 | 0.04 |
| U20098 | *Homo sapiens* signal recognition particle subunit 9 (SRP9) "mRNA," complete cds | 105 | | 52 | I | 1.5 | 0.09 | 172 | I | 2.6 | 0.72 | 32 | NC | 0 | 0 |
| X61615 | *H. sapiens* mRNA for leukemia inhibitory factor (LIF) receptor | 80 | | −30 | D | 1.6 | 0.09 | −51 | D | 2.7 | 0.42 | −24 | NC | 0 | 0 |
| M29277 | Human isolate JuSo MUC18 glycoprotein mRNA (3' "variant)," complete cds — "Also R | 320 | | −91 | MD | 1.4 | 0.09 | −160 | MD | 2 | 0.38 | −75 | NC | 0 | 0 |
| U07919 | Human aldehyde dehydrogenase 6 "mRNA," complete cds | 8 | | 25 | I | −1.6 | 0.09 | 42 | I | −2.5 | 0.31 | 6 | NC | 0 | 0 |
| J05448 | Human RNA polymerase subunit hRPB "33," mRNA | 115 | | 55 | MI | 1.5 | 0.09 | 57 | NC | 0 | 0 | 116 | I | 2 | 0.32 |
| D14811 | *H. sapiens* mRNA for KIAA0110 "gene," complete cds | 99 | | −35 | MD | 1.5 | 0.09 | −26 | NC | 0 | 0 | −50 | MD | 2 | 0.21 |
| U14972 | Human ribosomal protein S10 "mRNA," complete cds | 3771 | | 617 | I | 1.2 | 0.09 | −171 | NC | 0 | 0 | 964 | I | 1.3 | 0.18 |
| M20471 | Human brain-type clathrin light-chain a "mRNA," complete cds | 793 | | 205 | I | 1.3 | 0.09 | 91 | NC | 0 | 0 | 314 | MI | 1.4 | 0.17 |
| X90392 | *H. sapiens* mRNA for DNase X gene | 94 | | −34 | MI | 1.6 | 0.09 | −4 | NC | 0 | 0 | −37 | D | 1.6 | 0.11 |
| X91788 | *H. sapiens* mRNA for lcin protein | 279 | | 100 | I | 1.4 | 0.09 | 0 | NC | 0 | 0 | 83 | I | 1.3 | 0.06 |
| X79200 | *H. sapiens* mRNA for "SYT-SSX," synovial sarcoma translocation junction. /gb = X7920 | 423 | | −107 | MD | 1.3 | 0.09 | −54 | NC | 0 | 0 | −80 | D | 1.2 | 0.05 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| AC002115 | F25451_2 gene extracted from Human DNA from overlapping chromosome 19 cosm | 1130 | | 276 | I | 1.2 | 0.09 | 75 | NC | 0 | 0 | 38 | NC | 0 | 0 |
| D13146 | 2,3-cyclic-nucleotide 3'-phosphodiesterase gene extracted from Human "2,3-cyclic- | 5 | * | 28 | MI | -1.6 | 0.09 | 7 | NC | 0 | 0 | 18 | NC | 0 | 0 |
| G1728-HT173 | Non-Specific Cross Reacting Antigen "(Gb:D90277)," Alt. Splice Form 2 — "Also Repre | 510 | | 158 | I | 1.3 | 0.09 | 67 | NC | 0 | 0 | 55 | NC | 0 | 0 |
| HG846-HT846 | Cyclophilin-Related Protein | 263 | * | -77 | D | 1.4 | 0.09 | -49 | NC | 0 | 0 | 1 | NC | 0 | 0 |
| L31801 | Homo sapiens monocarboxylate transporter 1 (SLC16A1) "mRNA," complete cds | 34 | | -22 | D | -1.7 | 0.09 | -19 | NC | 0 | 0 | -19 | NC | 0 | 0 |
| M13450 | Human esterase D "mRNA," 3'end | 86 | | -32 | D | 1.6 | 0.09 | 19 | NC | 0 | 0 | -6 | NC | 0 | 0 |
| M35198 | Human integrin B-6 "mRNA," complete cds | 115 | * | 54 | I | 1.5 | 0.09 | 34 | NC | 0 | 0 | 8 | NC | 0 | 0 |
| M97388 | Human TATA binding protein-associated phosphoprotein (DR1) "mRNA," complete c | -4 | | 36 | | -1.6 | 0.09 | 20 | NC | 0 | 0 | 2 | NC | 0 | 0 |
| X64269 | H. sapiens gene MITF1 for mitochondrial transcription factor 1 | 84 | | -31 | MD | 1.6 | 0.09 | 20 | NC | -1.0 | 0 | -33 | NC | 0 | 0 |
| U44378 | Human homozygous deletion target in pancreatic carcinoma (DPC4) "mRNA," compl | 99 | | -35 | MD | 1.5 | 0.08 | -110 | D | -4.9 | 1.54 | -11 | NC | 0 | 0 |
| U47077 | Human DNA-dependent protein kinase catalytic subunit (DNA-PKcs) "mRNA," compl | 15 | | 19 | I | -1.7 | 0.08 | 62 | I | -3.8 | 0.81 | 1 | NC | 0 | 0 |
| M23613 | Human nucleophosmin "mRNA," complete cds | 52 | | -21 | D | 1.7 | 0.08 | 71 | | 2.4 | 0.37 | 1 | NC | 0 | 0 |
| D12775 | Human mRNA for erythrocyte-specific AMP "deaminase," complete cds — Also Repre | 1941 | | 365 | I | 1.2 | 0.08 | 749 | | 1.4 | 0.26 | -542 | NC | 0 | 0 |
| D50840 | Human mRNA for ceramide "glucosyltransferase," complete cds | 21 | | 15 | MI | 1.7 | 0.08 | 20 | I | 2 | 0.13 | 18 | NC | 0 | 0 |
| M16342 | Human nuclear ribonucleoprotein particle (hnRNP) C protein "mRNA," complete cds | 361 | | -94 | D | 1.4 | 0.08 | 111 | MI | 1.3 | 0.08 | -109 | NC | 0 | 0 |
| U38846 | Human stimulator of TAR RNA binding (SRB) "mRNA," complete cds | 788 | | 194 | I | 1.2 | 0.08 | 170 | I | 1.2 | 0.06 | -7 | NC | 0 | 0 |
| Y00264 | Human mRNA for amyloid A4 precursor of Alzheimer's disease | 1087 | | 243 | I | 1.2 | 0.08 | 160 | I | 1.1 | 0.04 | 168 | I | 1.2 | 0.04 |
| D10511 | H. sapiens erm "gene," exon "2,3,4,5," (and joined CDS) | 189 | | 70 | I | 1.4 | 0.08 | 43 | I | 1.2 | 0.03 | 60 | I | 1.3 | 0.06 |
| X96381 | Human mRNA for mitochondrial acetoacetyl-CoA thiolase | 115 | | -38 | D | 1.5 | 0.08 | 20 | NC | 0 | 0 | -62 | D | 2.1 | 0.28 |
| U58682 | Human ribosomal protein S28 "mRNA," complete cds | 163 | | 65 | I | 1.4 | 0.08 | -2 | NC | 0 | 0 | 82 | I | 1.5 | 0.12 |
| D86966 | Human mRNA for KIAA0211 "gene," complete cds | 2145 | | 375 | I | 1.2 | 0.08 | 145 | NC | 0 | 0 | 382 | I | 1.2 | 0.08 |
| D87017 | C7 segment gene extracted from Human (lambda) DNA for immunoglobin light chain | 107 | | -37 | D | 1.5 | 0.08 | -31 | NC | 0 | 0 | -16 | NC | 0 | 0 |
| M86752 | Human mRNA for transformation-sensitive protein (IEF SSP 3521) "mRNA," complete cds | 238 | * | 87 | I | 1.4 | 0.08 | 44 | NC | 0 | 0 | 59 | NC | 0 | 0 |
| U14394 | Human tissue inhibitor of metalloproteinases-3 "mRNA," complete cds | 827 | | -171 | D | 1.3 | 0.08 | -118 | NC | 0 | 0 | -152 | NC | 0 | 0 |
| X75861 | H. sapiens TEGT gene | 60 | * | 32 | I | 1.5 | 0.08 | 30 | NC | 0 | 0 | 27 | NC | 0 | 0 |
| X83218 | H. sapiens mRNA for ATP synthase | 1079 | | -214 | D | 1.2 | 0.08 | 2 | NC | 0 | 0 | -141 | NC | 0 | 0 |
| X89750 | H. sapiens mRNA for TGIF protein | 557 | | 155 | I | 1.3 | 0.08 | -52 | NC | 0 | 0 | 73 | NC | 0 | 0 |
| Y00757 | Human mRNA for polypeptide 7B2 | 146 | | 59 | I | 1.4 | 0.08 | -12 | NC | 0 | 0 | 77 | NC | 0 | 0 |
| | | 92 | | 45 | I | 1.5 | 0.08 | 18 | NC | 0 | 0 | -18 | NC | 0 | 0 |
| | | -4 | | 33 | MI | -1.5 | 0.07 | 117 | I | -5.6 | 1.86 | 21 | NC | 0 | 0 |
| | | 14 | | 18 | MI | -1.6 | 0.07 | 93 | MI | -5.4 | 1.56 | 16 | NC | 0 | 0 |
| D86956 | Human mRNA for KIAA0201 "gene," complete cds | 34 | | -14 | D | -1.7 | 0.07 | 97 | I | 3.9 | 1.04 | -8 | NC | 0 | 0 |
| U31383 | Human G protein gamma-10 subunit "mRNA," complete cds | 44 | | 24 | MI | 1.5 | 0.07 | 110 | I | 3.5 | 0.96 | 19 | NC | 0 | 0 |
| L10284 | Homo sapiens integral membrane "protein," "calnexin," (IP90) "mRNA," complete cds | 296 | | -73 | MD | 1.3 | 0.07 | 197 | I | 1.7 | 0.26 | -15 | NC | 0 | 0 |
| M58460 | Human 75-kD autoantigen (PM-Sc1) "mRNA," complete cds | 8 | | 22 | I | -1.5 | 0.07 | 29 | I | -1.8 | 0.13 | 5 | NC | 0 | 0 |
| U44103 | Human small GTP binding protein Rab9 "mRNA," complete cds. | 16 | | 26 | I | -1.6 | 0.07 | 19 | I | -1.7 | 0.09 | -1 | NC | 0 | 0 |
| Z22534 | H. sapiens ALK-2 mRNA | 48 | | -57 | MD | 1.5 | 0.07 | 20 | MI | 1.4 | 0.05 | 26 | NC | 0 | 0 |
| M81601 | Human transcription elongation factor (Sil) "mRNA," complete cds | 206 | | 74 | MI | 1.4 | 0.07 | 60 | NC | 0 | 0 | -65 | D | 1.5 | 0.09 |
| D14660 | Human mRNA for KIAA0104 "gene," complete cds | 211 | | -19 | D | 1.3 | 0.07 | -59 | NC | 0 | 0 | 66 | NC | 0 | 0 |
| D28888 | Human mRNA for KIAA0048 "gene," complete cds | 49 | | -20 | D | 1.6 | 0.07 | 3 | NC | 0 | 0 | -18 | NC | 0 | 0 |
| G2147-HT221 | Mucin "3," intestinal (Gb:M55405) | 56 | | 117 | MD | 1.6 | 0.07 | -3 | NC | 0 | 0 | -7 | NC | 0 | 0 |
| G3111-HT328 | Autoantigen (Gb:S67069) | 454 | | 117 | I | 1.3 | 0.07 | 4 | NC | 0 | 0 | 50 | NC | 0 | 0 |
| HG33-HT33 | Ribosomal Protein S4, X-Linked | 2697 | | 425 | I | 1.2 | 0.07 | 178 | NC | 0 | 0 | -340 | NC | 0 | 0 |
| L00058 | Human (GH) germline c-myc "proto-oncogene," 5' flank | 1777 | | 322 | MI | 1.2 | 0.07 | 296 | NC | 0 | 0 | 268 | NC | 0 | 0 |
| | | 94 | | -32 | D | 1.5 | 0.07 | 7 | NC | 0 | 0 | 18 | NC | 0 | 0 |

TABLE 4-continued

ISGs and IRGs identified from human fibrosarcoma cells incubated in IFN-α, IFN-β or IFN-γ

| GenBank Accession | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| U65928 | Human Jun activation domain binding protein "mRNA," complete cds | 173 | | 61 | I | 1.4 | 0.07 | −11 | NC | 0 | 0 | −49 | NC | 0 | 0 |
| X04327 | Human erythrocyte "2,3-bisphosphoglycerate" mutase mRNA EC 2.7.5.4 | 13 | * | 19 | MI | −1.6 | 0.07 | 28 | NC | 0 | 0 | 3 | NC | 0 | 0 |
| X53416 | Human mRNA for actin-binding protein (filamin) (ABP-280) | 1236 | | −210 | D | 1.2 | 0.07 | −222 | NC | 0 | 0 | 54 | NC | 0 | 0 |
| D31885 | Human mRNA for KIAA0069 "gene," partial cds | 214 | | 69 | MI | 1.2 | 0.06 | 164 | I | 1.8 | 0.28 | −20 | NC | 0 | 0 |
| Y00971 | Human mRNA for phosphoriobosyl pyrophosphate synthetase subunit II (EC 2.7.6.1) | 82 | | 33 | MI | 1.4 | 0.06 | 58 | I | 1.7 | 0.15 | 11 | NC | 0 | 0 |
| J04111 | Human c-jun proto oncogene "(JUN)," complete "cds," clone hCl-1 | 10 | * | 19 | I | −1.5 | 0.06 | 26 | I | −1.8 | 0.12 | 11 | NC | 0 | 0 |
| M37583 | Human histone (H2A.Z) "mRNA," complete cds | 1398 | | 233 | MI | 1.2 | 0.06 | 339 | I | 1.2 | 0.1 | 40 | NC | 0 | 0 |
| Z21507 | H. sapiens EF-1delta gene encoding human elongation factor-1-delta | 1261 | | 228 | I | 1.2 | 0.06 | 215 | I | 1.2 | 0.06 | 576 | I | 1.5 | 0.28 |
| X92720 | H. sapiens mRNA for phosphoenolpyruvate carboxykinase | 246 | | 74 | MI | 1.3 | 0.06 | 74 | I | 1.3 | 0.06 | 146 | I | 1.6 | 0.19 |
| X61587 | H. sapiens mRNA for rhoG GTPase | 314 | | 84 | MI | 1.2 | 0.06 | 48 | I | 1.2 | 0.02 | 164 | I | 1.5 | 0.17 |
| X90858 | H. sapiens mRNA for uridine phosphorylase | 216 | | 66 | I | 1.3 | 0.06 | −16 | NC | 0 | 0 | 164 | I | 1.8 | 0.27 |
| X85372 | H. sapiens mRNA for Sm protein F | 645 | | 134 | I | 1.3 | 0.06 | 16 | NC | 0 | 0 | 61 | I | 1.1 | 0.02 |
| L19783 | Human GPI-H "mRNA," complete cds | 10 | | 21 | I | −1.5 | 0.06 | 16 | NC | 0 | 0 | 12 | I | −1.1 | 0.01 |
| AB000468 | Human mRNA for zinc finger "protein," clone "RES4-26," complete cds | 182 | | −47 | D | 1.3 | 0.06 | −57 | NC | 0 | 0 | −23 | NC | 0 | 0 |
| D17400 | Human mRNA for 6-pyruvoyl-tetrahydropterin "synthase," complete cds | 146 | | −42 | D | 1.4 | 0.06 | 23 | NC | 0 | 0 | −47 | NC | 0 | 0 |
| D83767 | Human clone N9 Rep-8 "mRNA," complete cds | 32 | | −14 | D | −1.6 | 0.06 | −7 | NC | 0 | 0 | −19 | NC | 0 | 0 |
| G2855-HT299 | Heat Shock "Protein," 70 Kda (Gb:Y00371) | 1631 | | 255 | I | 1.2 | 0.06 | −16 | NC | 0 | 0 | −196 | NC | 0 | 0 |
| L11669 | Human tetracycline transporter-like protein "mRNA," complete cds | 135 | | −39 | MD | 1.4 | 0.06 | −21 | NC | 0 | 0 | 3 | NC | 0 | 0 |
| M57703 | Human melanin concentrating hormone (MCH) "mRNA," complete cds — Also Repres | 7 | * | 23 | I | −1.5 | 0.06 | 6 | NC | 0 | 0 | 4 | NC | 0 | 0 |
| S80562 | acidic calponin "human," "kidney," "mRNA," 1607 nt] | 184 | | 61 | I | 1.3 | 0.06 | 91 | NC | 0 | 0 | 21 | NC | 0 | 0 |
| U07418 | Human DNA mismatch repair (hmlh1) "mRNA," complete cds | 129 | | 45 | I | 1.4 | 0.06 | 72 | NC | 0 | 0 | 43 | NC | 0 | 0 |
| U28014 | Human cysteine protease (ICErel-II) "mRNA," complete cds | 105 | | 40 | MI | 1.3 | 0.06 | 62 | NC | 0 | 0 | 15 | NC | 0 | 0 |
| U59289 | Human H-cadherin "mRNA," complete cds | 23 | * | 14 | MI | 1.6 | 0.06 | 11 | NC | 0 | 0 | 10 | NC | 0 | 0 |
| X02317 | Human mRNA for Cu/Zn superoxide dismutase (SOD) | 1055 | | 206 | I | 1.2 | 0.06 | −48 | NC | 0 | 0 | −20 | NC | 0 | 0 |
| X74104 | H. sapiens mRNA for TRAP beta subunit | 1150 | | 208 | I | 1.2 | 0.06 | −87 | NC | 0 | 0 | 75 | NC | 0 | 0 |
| X82153 | H. sapiens mRNA for cathepsin O | 31 | | −18 | MD | −1.5 | 0.06 | 3 | NC | 0 | 0 | −7 | NC | 0 | 0 |
| X94754 | H. sapiens mRNA for yeast methionyl-tRNA synthetase homologue | 892 | | −159 | D | 1.2 | 0.06 | 81 | NC | 0 | 0 | 81 | NC | 0 | 0 |
| Z48570 | H. sapiens Spl7 gene | 13 | * | 19 | I | −1.6 | 0.06 | −8 | NC | 0 | 0 | 9 | NC | 0 | 0 |
| D90070 | Human ATL-derived PMA-responsive (APR) peptide mRNA — Also Represents: M572 | 4 | * | 23 | I | −1.4 | 0.05 | 65 | I | −3.5 | 0.71 | 38 | I | −2.1 | 0.21 |
| U83115 | Human non-lens beta gamma-crystallin like protein (AIM1) "mRNA," partial cds | 66 | | −20 | MD | 1.4 | 0.05 | 49 | I | 1.7 | 0.15 | −17 | NC | 0 | 0 |
| U25975 | Human serine kinase (hPAK65) "mRNA," complete cds | 53 | | −17 | MD | 1.5 | 0.05 | 30 | MI | 1.6 | 0.08 | −12 | NC | 0 | 0 |
| M16652 | Human pancreatic elastase IIA "mRNA," complete cds — Also Represents: M16653 | 483 | | −93 | MD | 1.2 | 0.05 | −111 | D | 1.3 | 0.07 | −66 | NC | 0 | 0 |
| X68242 | H. sapiens mRNA for Hin-1 | 30 | | −17 | D | 1.3 | 0.05 | −20 | MD | −1.5 | 0.06 | 102 | I | 1.6 | 0.15 |
| AB006781 | Homo sapiens mRNA for "galectin-4," complete cds. /gb = AB006781 /ntype = RNA — Al | 29 | | −19 | D | −1.5 | 0.05 | −25 | MD | −1.5 | 0.06 | 351 | MI | 1.2 | 0.1 |
| D87073 | Human mRNA for KIAA0236 "gene," complete cds | 28 | | −27 | D | −1.4 | 0.05 | −22 | D | −1.4 | 0.05 | 448 | I | 1.2 | 0.08 |
| U47105 | Human H10Se3 "mRNA," complete cds | 148 | | −38 | D | 1.3 | 0.05 | −29 | D | 1.2 | 0.03 | −38 | MD | −1.5 | 0.03 |
| Z18948 | H. sapiens mRNA for S100E calcium binding protein | 38 | | 18 | MI | 1.5 | 0.05 | −68 | NC | 0 | 0 | 72 | I | 1.5 | 0.08 |
| U50939 | Human amyloid precursor protein-binding protein 1 "mRNA," complete cds | 55 | | −18 | D | 1.5 | 0.05 | −1 | NC | 0 | 0 | 70 | I | 2.9 | 0.53 |
| M35296 | Human tyrosine kinase arg gene mRNA | 79 | | −23 | D | 1.4 | 0.05 | −10 | NC | 0 | 0 | −34 | NC | 2.6 | 0.3 |
| X13967 | Human mRNA for leukaemia inhibitory factor (LIF/HILDA) | 181 | | 51 | I | 1.3 | 0.05 | −3 | NC | 0 | 0 | −42 | NC | 2.1 | 0.23 |
| U94855 | Human translation initiation factor 3 47 kDa subunit "mRNA," complete cds | 1571 | | 224 | I | 1.1 | 0.05 | −137 | NC | 0 | 0 | 102 | I | 1.6 | 0.15 |
| D13748 | Human eukaryotic initiation factor 4AI | 2721 | | 355 | I | 1.1 | 0.05 | 233 | NC | 0 | 0 | 351 | MI | 1.2 | 0.1 |
| J00117 | Human chorionic gonadotropin (hcg) beta subunit "mRNA," complete cds | 232 | | −53 | D | 1.3 | 0.05 | −59 | NC | 0 | 0 | 448 | I | 1.2 | 0.08 |
| X87838 | H. sapiens mRNA for beta-catenin | 429 | | 97 | I | 1.2 | 0.05 | 99 | NC | 0 | 0 | −38 | MD | 1.2 | 0.03 |
| D25216 | Human mRNA for KIAA0014 "gene," complete cds | 381 | | −76 | MD | 1.2 | 0.05 | −112 | NC | 0 | 0 | −116 | NC | 0 | 0.03 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| D61380 | Human mRNA for DJ-1 "protein," complete cds | 1209 | | 193 | I | 1.2 | 0.05 | -25 | NC | 0 | 0 | -29 | NC | 0 | 0 |
| G1112-HT111 | Ras-Like Protein Tc4 | 1287 | | 199 | I | 1.2 | 0.05 | 112 | NC | 0 | 0 | 157 | NC | 0 | 0 |
| J02683 | Human ADP/ATP carrier protein "mRNA," complete cds — Also Represents: M57424 | 1731 | | 250 | I | 1.1 | 0.05 | 93 | NC | 0 | 0 | 128 | NC | 0 | 0 |
| J03040 | Human SPARC/osteonectin "mRNA," complete cds | 1037 | | -151 | D | 1.2 | 0.05 | 228 | NC | 0 | 0 | 17 | NC | 0 | 0 |
| L00352 | Human low density lipoprotein receptor gene | 143 | | -36 | D | 1.3 | 0.05 | 19 | NC | 0 | 0 | 16 | NC | 0 | 0 |
| M16447 | Human dihydropteridine reductase (hDHPR) "mRNA," complete cds | 74 | | -22 | I | 1.4 | 0.05 | -23 | NC | 0 | 0 | -16 | NC | 0 | 0 |
| U57877 | Human integral membrane protein CII-3 "mRNA," nuclear gene encoding mitochondr | 140 | | 46 | MI | 1.3 | 0.05 | -1 | NC | 0 | 0 | 40 | NC | 0 | 0 |
| U78027 | L44L gene (L44-like ribosomal protein) extracted from Human Bruton's tyrosine kinas | 2179 | | 290 | I | 1.1 | 0.05 | 196 | NC | 0 | 0 | -231 | NC | 0 | 0 |
| U90549 | Human non-histone chromosomal protein (NHC) "mRNA," complete cds | 277 | | 73 | I | 1.3 | 0.05 | -84 | NC | 0 | 0 | -14 | NC | 0 | 0 |
| X81788 | H. sapiens DS-1 mRNA | 192 | | 52 | I | 1.3 | 0.05 | 9 | NC | 0 | 0 | 15 | NC | 0 | 0 |
| Y07596 | H. sapiens mRNA for GP18 protein | -8 | * | 36 | MI | -1.4 | 0.05 | 27 | I | -1.0 | 0 | 26 | NC | 0 | 0 |
| Y11897 | H. sapiens Brx gene 3'UTR. /gb = Y11897 /ntype = RNA | 65 | * | 26 | I | 1.4 | 0.05 | -29 | NC | 0 | 0 | 15 | NC | 0 | 0 |
| U82311 | Human unknown protein "mRNA," partial cds. /gb = U82311 /ntype = RNA | 231 | | -44 | MD | 1.2 | 0.04 | -165 | MD | 3.5 | 1.17 | -31 | NC | -1.2 | 0.03 |
| U49837 | Human LIM protein MLP "mRNA," complete cds | -16 | * | 42 | I | -1.3 | 0.04 | 66 | I | -2.5 | 0.4 | 40 | I | -1.5 | 0.06 |
| U07802 | Human Tis11d "gene," complete cds | 10 | | 18 | I | -1.4 | 0.04 | 29 | I | -2.0 | 0.15 | 20 | I | 1.2 | 0.01 |
| S77576 | ERV9 reverse transcriptase homolog (clone RT18) "[human," multiple "sclerosis," bra | 41 | | -12 | MD | 1.4 | 0.04 | -21 | D | -2.1 | 0.1 | -7 | MD | 0 | 0 |
| U78556 | Human cisplatin resistance associated alpha protein (hCRA alpha) "mRNA," complet | 215 | | 50 | I | 1.2 | 0.04 | 89 | I | 1.4 | 0.08 | -20 | NC | 0 | 0 |
| M26708 | Human prothymosin alpha mRNA "(ProT-alpha)," complete cds — "Also Represents: N | 2208 | | 235 | I | 1.1 | 0.04 | 400 | I | 1.2 | 0.07 | -260 | NC | 1.3 | 0.04 |
| M62402 | Human insulin-like growth factor binding protein 6 (IGFBP6) "mRNA," complete cds | 259 | | -51 | D | 1.2 | 0.04 | -65 | D | 1.3 | 0.04 | -53 | D | 0 | 0 |
| S78187 | CDC25Hu2 = cdc25+ homolog "[human," "mRNA," 3118 nt] | 291 | | -58 | MD | 1.3 | 0.04 | -54 | MD | 1.2 | 0.03 | 7 | NC | 1.8 | 0.17 |
| X66785 | H. sapiens mRNA for transacylase (DBT) | 101 | | -24 | I | 1.3 | 0.04 | -23 | D | 1.3 | 0.03 | -46 | D | -1.0 | 0 |
| M27543 | Human guanine nucleotide-binding protein (Gf) alpha subunit "mRNA," complete cds | -15 | * | 41 | D | -1.3 | 0.04 | 40 | I | -1.2 | 0 | 24 | I | 1.7 | 0.1 |
| M63483 | Human major nuclear matrix protein mRNA | 70 | | -20 | D | 1.4 | 0.04 | 104 | NC | 0 | 0 | -28 | D | 1.4 | 0.09 |
| D14657 | Human mRNA for KIAA0101 "gene," complete cds | 248 | | -48 | D | 1.2 | 0.04 | 6 | D | 1 | 0 | -74 | D | 1.3 | 0.09 |
| U32944 | Human cytoplasmic dynein light chain 1 (hdlc1) "mRNA," complete cds | 731 | | 119 | MI | 1.3 | 0.04 | 131 | NC | 0 | 0 | 198 | MD | 1.5 | 0.06 |
| D83785 | Human mRNA for KIAA0200 "gene," complete cds | 70 | | -20 | MD | 1.4 | 0.04 | 2 | NC | 0 | 0 | -23 | D | -1.3 | 0.05 |
| M61199 | Human cleavage signal 1 protein "mRNA," complete cds | 27 | | -27 | D | -1.3 | 0.04 | 11 | NC | 0 | 0 | -34 | D | 1.2 | 0.05 |
| U51004 | Human putative protein kinase C inhibitor (PKCI-1) "mRNA," complete cds | 1056 | | 158 | I | 1.1 | 0.04 | -135 | D | 0 | 0 | 187 | D | -1.3 | 0.05 |
| U60060 | Human FEZ1 "mRNA," complete cds | 27 | * | -24 | D | 1.2 | 0.04 | -19 | NC | 0 | 0 | -33 | D | 1.2 | 0.04 |
| X70218 | H. sapiens mRNA for protein phosphatase X | 812 | | 135 | MI | 1.3 | 0.03 | -7 | NC | 0 | 0 | 137 | I | 1.2 | 0.03 |
| D25547 | Human mRNA for PIMT isozyme "I," complete cds | 100 | | 30 | I | 1.2 | 0.03 | -51 | NC | 0 | 0 | 24 | MI | 1.1 | 0.02 |
| X67698 | H. sapiens tissue specific mRNA | 454 | | 81 | MI | 1.2 | 0.04 | -156 | NC | 0 | 0 | 57 | I | | |
| | | -4 | * | 30 | I | -1.3 | 0.03 | 6 | NC | 0 | 0 | 3 | NC | 0 | 0 |
| D10495 | Human mRNA for protein kinase C delta-type | 108 | | -27 | D | 1.3 | 0.03 | -18 | NC | 0 | 0 | 3 | NC | 0 | 0 |
| D87461 | Human mRNA for KIAA0271 "gene," complete cds | 17 | | 12 | I | -1.4 | 0.04 | -16 | NC | 0 | 0 | -7 | NC | 0 | 0 |
| K02405 | Human MHC class II HLA-DC-3-beta gene "(DR3,3)" | 94 | | -22 | MD | 1.3 | 0.04 | -17 | NC | 0 | 0 | -24 | NC | 0 | 0 |
| M98343 | Homo sapiens amplaxin (EMS1) "mRNA," complete cds | 32 | | -10 | I | 1.5 | 0.04 | -57 | NC | 0 | 0 | -53 | NC | 0 | 0 |
| X13482 | Human mRNA for U2 snRNP-specific A' protein | 263 | | 63 | I | 1.2 | 0.04 | 8 | NC | 0 | 0 | 10 | NC | 0 | 0 |
| X64229 | H. sapiens dek mRNA | 28 | | -17 | D | -1.4 | 0.04 | 24 | NC | 0 | 0 | -10 | NC | 0 | 0 |
| X76770 | H. sapiens PAP mRNA | 137 | | -30 | MD | 1.3 | 0.04 | -40 | NC | 0 | 0 | -8 | NC | 0 | 0 |
| Z46629 | Homo sapiens SOX9 mRNA | 82 | * | 21 | I | 1.3 | 0.03 | 23 | I | 1.3 | 0.03 | 15 | I | 1.2 | 0.02 |
| L19437 | Human transaldolase mRNA containing transposable "element," complete cds | 365 | | -55 | D | 1.2 | 0.03 | -32 | NC | 1.1 | 0.01 | -24 | NC | 0 | 0 |
| Z70219 | H. sapiens mRNA for 5'UTR for unknown protein (clone ICRFp507C0696). /gb = Z702 | 33 | | 12 | MI | 1.4 | 0.03 | -5 | NC | 0 | 0 | 24 | MI | 1.7 | 0.1 |
| U61234 | Human tubulin-folding cofactor C "mRNA," complete cds | 67 | | 19 | I | 1.3 | 0.03 | -3 | NC | 0 | 0 | 32 | MI | 1.5 | 0.07 |
| L07541 | Human replication factor "C," 38-kDa subunit "mRNA," complete cds | 26 | | -19 | D | -1.3 | 0.03 | -2 | NC | 0 | 0 | -16 | D | -1.3 | 0.03 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| D49354 | Human mRNA for enhancer protein in hsp70 "gene," partial cds — "Also Represents: | 25 | | -27 | D | ~1.2 | 0.03 | -3 | NC | 0 | 0 | -14 | NC | 0 | 0 |
| L11708 | Human 17 beta hydroxysteroid dehydrogenase type 2 "mRNA," complete cds | 25 | * | -23 | D | ~1.3 | 0.03 | -7 | NC | 0 | 0 | -23 | NC | 0 | 0 |
| L19527 | Homo sapiens ribosomal protein L27 (RPL27) "mRNA," complete cds | 3541 | | 286 | I | 1.1 | 0.03 | -154 | NC | 0 | 0 | 246 | NC | 0 | 0 |
| M25756 | Human secretogranin II "gene," complete cds | 26 | * | -22 | D | ~1.3 | 0.03 | 13 | NC | 0 | 0 | -19 | NC | 0 | 0 |
| M26880 | Human ubiquitin "mRNA," complete cds | 997 | | 128 | MI | 1.1 | 0.03 | 110 | NC | 0 | 0 | -63 | NC | 0 | 0 |
| S54005 | thymosin beta-10 "[human], metastatic melanoma cell "line," "mRNA," 453 nl] — Also | 2124 | | 194 | MI | 1.1 | 0.03 | -8 | NC | 0 | 0 | -98 | NC | 0 | 0 |
| U07857 | Human 18 kDa Alu RNA binding protein "mRNA," complete cds | 346 | | 57 | MI | 1.2 | 0.03 | 46 | NC | 0 | 0 | -35 | NC | 0 | 0 |
| U16861 | Human inward rectifying potassium channel "mRNA," complete cds | 26 | * | -27 | D | ~1.3 | 0.03 | -25 | NC | 0 | 0 | -26 | NC | 0 | 0 |
| U25165 | Human fragile X mental retardation protein 1 homolog FXR1 "mRNA," complete cds | 33 | | -10 | MD | 1.4 | 0.03 | 47 | NC | 0 | 0 | -4 | NC | 0 | 0 |
| U85767 | Human myeloid progenitor inhibitory factor-1 MPIF-1 "mRNA," complete cds | -17 | | 41 | I | ~1.2 | 0.03 | 79 | NC | 0 | 0 | 35 | NC | 0 | 0 |
| X72841 | H. sapiens IEF 7442 mRNA | 292 | | 57 | I | 1.2 | 0.03 | -11 | NC | 0 | 0 | 6 | NC | 0 | 0 |
| X75308 | H. sapiens mRNA for collagenase 3 | 26 | * | -18 | MD | ~1.3 | 0.03 | -20 | NC | 0 | 0 | -18 | NC | 0 | 0 |
| Z80787 | H. sapiens H4/j gene | 26 | * | -20 | D | ~1.3 | 0.03 | -20 | NC | 0 | 0 | -7 | NC | 0 | 0 |
| X83416 | H. sapiens PrP "gene," exon 2 — "Also Represents: D00015_ma1, D00015" | 326 | | 41 | MI | 1.1 | 0.02 | 155 | I | 1.5 | 0.15 | -65 | I | 1.8 | 0.34 |
| D78577 | H. sapiens DNA for 14-3-3 protein eta chain — Also Represents: L20422 | 635 | | 60 | MI | 1.1 | 0.02 | 173 | I | 1.3 | 0.08 | -55 | D | 1.2 | 0.19 |
| L00389 | Human cytochrome P-450 4 gene | 113 | | -19 | MI | 1.1 | 0.02 | 36 | MI | 1.3 | 0.05 | -26 | NC | 1.5 | 0.08 |
| X98248 | H. sapiens mRNA for sortlin | 259 | | 34 | I | 1.1 | 0.02 | -17 | NC | 0 | 0 | 211 | I | ~1.3 | 0.03 |
| Z28407 | H. sapiens mRNA for ribosomal protein L8 | 7077 | | 303 | I | 1 | 0.02 | 264 | NC | 0 | 0 | 1496 | I | 1 | 0.01 |
| S82471 | SSX3 = Kruppet-associated box containing SSX gene "[human]," "testis," mRNA "Parti | 128 | | -18 | MD | 1.2 | 0.02 | 33 | NC | 0 | 0 | -41 | D | | |
| D83781 | Human mRNA for KIAA0197 "gene," complete cds | 7 | * | 18 | I | ~1.3 | 0.02 | 15 | NC | 0 | 0 | 19 | I | | |
| U49869 | Human mRNA for KIAA0071 "gene," partial cds | 5047 | | 241 | I | 1 | 0.02 | -1241 | NC | 0 | 0 | 205 | I | | |
| D31888 | Calmodulin Type I | 24 | * | -25 | D | ~1.2 | 0.02 | 13 | NC | 0 | 0 | -4 | NC | | |
| G1862-HT189 | Tyrosine Phosphatase "1," "Non-Receptor," Alt. Splice 3 — "Also Represents: HG3187 | 229 | | -31 | D | 1.2 | 0.02 | 97 | NC | 0 | 0 | -45 | NC | | |
| G3187-HT336 | Homo sapiens bone-derived growth factor (BPGF-1) "mRNA," complete cds | 23 | * | -30 | MD | ~1.1 | 0.02 | -18 | NC | 0 | 0 | -15 | NC | | |
| L42379 | Human cytoplasmic beta-actin "gene," complete cds — Also Represents: HSAC07/X0 | 242 | | -30 | MD | 1.1 | 0.02 | 39 | NC | 0 | 0 | 122 | NC | | |
| M10277 | Human laminin receptor (2H5 epitope) "mRNA," 5' end — "Also Represents: HG1773- | 5913 | | 284 | I | 1 | 0.02 | -300 | NC | 0 | 0 | 19 | NC | | |
| M14199 | Human alpha enolase "mRNA," complete cds — Also Represents: M55914 | 7808 | | 351 | MI | 1 | 0.02 | -1190 | NC | 0 | 0 | -842 | NC | | |
| M14328 | Human grancalcin "mRNA," complete cds | 4800 | | 317 | I | 1.1 | 0.02 | -278 | NC | 0 | 0 | 78 | NC | | |
| M81637 | Human 5-HT1D-type serotonin receptor "gene," complete cds | -9 | | 32 | I | ~1.2 | 0.02 | 2 | NC | 0 | 0 | 14 | NC | | |
| M89955 | Human aldehyde dehydrogenase ALDH7 "mRNA," complete cds | -17 | | 40 | MI | ~1.1 | 0.02 | 8 | NC | 0 | 0 | 19 | NC | | |
| U10868 | Human centromere protein-A (CENP-A) "mRNA," complete cds | 72 | | 16 | I | 1.2 | 0.02 | 5 | NC | 0 | 0 | 2 | NC | | |
| U14518 | Human mRNA for KIAA0118 "mRNA," complete cds | 63 | | -12 | D | 1.2 | 0.02 | 26 | NC | 0 | 0 | 5 | NC | | |
| U19261 | Human Epstein-Barr virus-induced protein "mRNA," complete cds | 46 | | 12 | I | 1.3 | 0.02 | -26 | NC | 0 | 0 | 2 | NC | | |
| U25433 | Human protein associated with tumorigenic conversion (CAIR1.3) "mRNA," complete | 0 | * | 24 | I | ~1.2 | 0.02 | 6 | NC | 0 | 0 | 10 | NC | | |
| U40992 | Human heat shock protein hsp40 homolog "mRNA," complete cds | -8 | | 31 | MI | ~1.1 | 0.02 | 30 | NC | 0 | 0 | 7 | NC | | |
| U41813 | Human class I homeoprotein (HOXA9) "mRNA," partial cds | 15 | | 10 | MI | 1.2 | 0.02 | 10 | NC | 0 | 0 | -1 | NC | | |
| U83598 | Human death domain receptor 3 soluble form (DDR3) "mRNA," partial cds — Also Rep | 89 | | -16 | MD | 1.2 | 0.02 | 44 | NC | 0 | 0 | 21 | NC | | |
| X52009 | H. sapiens alpha-1 strychnine binding subunit of inhibitory glycine receptor mRNA. — A | 25 | * | -12 | D | ~1.3 | 0.02 | -11 | NC | 0 | 0 | 19 | NC | | |
| U25789 | Human ribosomal protein L21 "mRNA," complete cds | 2072 | | 67 | MI | 1 | 0.01 | -20 | NC | 0 | 0 | -20 | NC | | |
| D42087 | Human mRNA for KIAA0118 "gene," partial cds | 55 | | 11 | I | 1.2 | 0.01 | -655 | D | 1.5 | 0.3 | -436 | NC | | |
| U02081 | Human guanine nucleotide regulatory protein (NET1) "mRNA," complete cds | 11 | | 12 | I | ~1.1 | 0.01 | 48 | I | 1.9 | 0.17 | -7 | NC | | |
| L10838 | Homo sapiens SR protein "family," pre-mRNA splicing factor (SRp20) "mRNA," comp | 531 | | -29 | MD | 1.1 | 0.01 | 27 | I | ~1.9 | 0.14 | 10 | NC | | |
| U50360 | Human "calcium," calmodulin-dependent protein kinase II gamma "mRNA," partial cd | -15 | | 36 | I | ~1.1 | 0.01 | 160 | I | 1.3 | 0.09 | -48 | NC | | |
| Z11559 | H. sapiens mRNA for iron regulatory factor | 109 | | 14 | I | 1.1 | 0.01 | 44 | NC | 0 | 0.08 | 13 | NC | 0 | 0.21 |
| X69978 | H. sapiens mRNA for XP-G factor | 47 | | 5 | D | 1.1 | 0.01 | 27 | NC | 0 | 0 | 85 | I | 1.8 | 0.21 |
| | | | | | | | | 14 | | | | 7 | D | 1.1 | 0.01 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| D21063 | Human mRNA for KIAA0030 "gene," partial cds | −7 | | 28 | I | −1.1 | 0.01 | 23 | MI | −1.0 | 0 | 26 | MI | −1.0 | 0 |
| G3254-HT343 | Phosphatidylinositol 3-Kinase "P110," Beta isoform | 382 | * | −33 | D | 1.1 | 0.01 | 70 | NC | 0 | 0 | 89 | NC | 0 | 0 |
| G3925-HT419 | Surfactant Protein Sp-A2 Delta — "Also Represents: M30838, M68519_ma1, HG3928- | 23 | | −17 | D | −1.1 | 0.01 | 7 | NC | 0 | 0 | −8 | NC | 0 | 0 |
| M29610 | Human glycophorin E "mRNA," complete cds — Also Represents: J02982 | −2 | * | 24 | I | −1.1 | 0.01 | 20 | MI | −1.0 | 0 | 10 | NC | 0 | 0 |
| M69238 | Human aryl hydrocarbon receptor nuclear translocator (ARNT) "mRNA," complete cd | 22 | | −22 | D | −1.1 | 0.01 | −6 | NC | 0 | 0 | −19 | NC | 0 | 0 |
| U38980 | Human PMS2 related (hPMSR6) "mRNA," complete cds | −26 | | 47 | MI | −1.1 | 0.01 | 36 | NC | 0 | 0 | 25 | NC | 0 | 0 |
| U58334 | Human "Bcl2," p53 binding protein Bbp/53BP2 (BBP/53BP2) "mRNA," complete cds | 152 | * | −20 | MD | 1.1 | 0.01 | 31 | NC | 0 | 0 | 16 | NC | 0 | 0 |
| U82467 | Human tub homolog (TUB) "mRNA," complete cds. | 49 | | 8 | D | 1.2 | 0.01 | 44 | NC | 0 | 0 | 17 | NC | 0 | 0 |
| X14767 | Human mRNA for GABA-A "receptor," beta 1 subunit | 21 | * | −39 | MD | −1.1 | 0.01 | −25 | NC | 0 | 0 | −19 | NC | 0 | 0 |
| X53777 | Human L23 mRNA for putative ribosomal protein | 24 | | 5 | I | 1 | 0.01 | 18 | NC | 0 | 0 | −11 | NC | 0 | 0 |
| X79201 | H. sapiens mRNA for SYT | 4719 | * | 210 | I | 1 | 0.01 | −632 | NC | 0 | 0 | −133 | MD | 1.1 | 0 |
| Y00787 | Human mRNA for MDNCF (monocyte-derived neutrophil chemotactic factor) — "Also | 24 | | −8 | D | −1.2 | 0.01 | 4 | NC | 0 | 0 | −2 | NC | 0 | 0 |
| U73499 | Human hapatic nuclear factor 1-alpha (TCF-1-alpha) "gene," promoter region and pa | 4 | | 17 | I | −1.1 | 0.01 | 15 | MI | −1.0 | 0 | −1 | NC | 0 | 0 |
| X16707 | Human fra-1 mRNA | 189 | | −68 | NC | 0 | 0 | −244 | MD | −9.4 | 4.5 | −35 | NC | 0 | 5.58 |
| M21388 | Human unproductively rearranged Ig mu-chain mRNA V-region (VD), 5′ end, clone m | 18 | | 25 | NC | 0 | 0 | 196 | I | −10.7 | 4.48 | 236 | I | −12.7 | 5.58 |
| D38293 | Human mRNA for clathrin-like "protein," complete cds | −7 | | 187 | NC | 0 | 0 | 200 | I | −9.7 | 4.17 | 258 | I | −12.5 | 5.78 |
| | | 28 | | −1 | NC | 0 | 0 | 218 | I | 8.9 | 4.05 | −13 | NC | 0 | 0 |
| | | 22 | | 43 | NC | 0 | 0 | 185 | MI | 9.2 | 3.86 | 51 | I | 3.3 | 0.58 |
| U50648 | Human interferon-inducible RNA-dependent protein kinase (Pkr) gene — "Also Repres | −36 | | 20 | NC | 0 | 0 | 207 | I | −8.5 | 3.8 | 43 | NC | 0 | 0 |
| X89416 | H. sapiens mRNA for protein phosphatase 5 | 39 | | 29 | NC | 0 | 0 | 233 | I | 7 | 3.36 | −6 | NC | 0 | 0 |
| Z78289 | H. sapiens mRNA (clone 1D2). /gb = Z78289 /ntype = DNA /annol = mRNA | 49 | | 54 | NC | 0 | 0 | 256 | I | 6.2 | 3.09 | 110 | MI | 3.3 | 0.84 |
| U22431 | Human hypoxia-inducible factor 1 alpha (HIF-1 alpha) "mRNA," complete cds — "Also | 182 | | −81 | NC | 0 | 0 | −158 | D | −5.4 | 3 | −31 | NC | 0 | 0 |
| Y09836 | H. sapiens mRNA for 3′UTR of unknown protein | 29 | | 4 | NC | 0 | 0 | 175 | I | 7.6 | 2.93 | 21 | NC | 0 | 0 |
| Z50194 | H. sapiens mRNA for PQ-rich protein | 11 | | −30 | NC | 0 | 0 | 139 | I | 7.1 | 2.75 | 24 | NC | 0 | 0 |
| G3543-HT373 | Insulin-Like Growth Factor 2 | 46 | | 57 | NC | 0 | 0 | 199 | I | 5.3 | 2.28 | 164 | I | 4.5 | 1.69 |
| U76010 | Human putative zinc transporter ZnT-3 (ZnT-3) "mRNA," complete cds. | 129 | | −37 | NC | 0 | 0 | −129 | D | −6.4 | 2.27 | −14 | NC | 0 | 0 |
| U88047 | Human DNA binding protein homolog (DRX) "mRNA," partial cds | 469 | | −179 | NC | 0 | 0 | −351 | D | 4 | 2.07 | −173 | I | 0 | 0.07 |
| U41766 | Human metalloprotease/disintegrin/cysteine-rich protein precursor (MDC9) "mRNA," | −40 | | 117 | NC | 0 | 0 | 147 | I | −5.4 | 1.97 | 146 | NC | 0 | 0 |
| | | 25 | | 5 | NC | 0 | 0 | 110 | I | 5.3 | 1.69 | −7 | NC | 0 | 0 |
| | | 10 | | 16 | NC | 0 | 0 | 100 | I | −5.5 | 1.67 | 10 | NC | 0 | 0 |
| X78817 | H. sapiens partial C1 mRNA | 206 | | −61 | NC | 0 | 0 | −160 | D | −5.0 | 1.65 | −31 | I | −1.4 | 0.12 |
| U41387 | Human Gu protein "mRNA," partial cds | −19 | | 33 | NC | 0 | 0 | 120 | I | 4.5 | 1.64 | 48 | NC | 0 | 0 |
| | | 53 | | 3 | NC | 0 | 0 | 173 | I | 4.3 | 1.6 | 4 | MI | 1.8 | 0.12 |
| X70649 | H. sapiens cl. 1042 mRNA of DEAD box protein family | 39 | | 89 | NC | 0 | 0 | 129 | I | 4.3 | 1.4 | 29 | NC | 0 | 0 |
| D79999 | Human mRNA for KIAA0177 "gene," partial cds | 49 | | 32 | NC | 0 | 0 | 150 | I | 4.1 | 1.38 | 1 | NC | 0 | 0 |
| U79291 | Human clone 23721 mRNA sequence | 32 | | −10 | NC | 0 | 0 | 109 | I | 4.4 | 1.33 | 11 | NC | 0 | 0 |
| J03473 | Human poly(ADP-ribose) synthetase "mRNA," complete cds | 16 | | −18 | NC | 0 | 0 | 82 | I | −4.9 | 1.3 | 4 | NC | 0 | 0.42 |
| U58046 | Human p167 "mRNA," complete cds — Also Represents: D50929 | 61 | | 69 | NC | 0 | 0 | 164 | I | 3.7 | 1.26 | 85 | I | 2.4 | 0 |
| U62437 | Human nicotinic acetylcholine receptor beta2 subunit "precursor," "mRNA," complete | 21 | | −4 | NC | 0 | 0 | 79 | I | 4.7 | 1.22 | −7 | NC | 0 | 0 |
| M94880 | Human MHC class I (HLA-A*8001) mRNA — "Also Similar To: M80469_ma1, M80468 | 78 | | −89 | NC | 0 | 0 | −107 | D | −3.9 | 1.1 | −58 | NC | 0 | 1.04 |
| L14076 | Human pre-mRNA splicing factor SRp75 "mRNA," complete cds | 127 | | 124 | NC | 0 | 0 | 241 | I | 2.9 | 1.02 | 244 | I | 2.9 | 0 |
| X07979 | Human mRNA for fibronectin receptor beta subunit | 31 | | 63 | NC | 0 | 0 | 90 | I | 3.9 | 1.02 | 46 | NC | 0 | 0.12 |
| D29640 | Human mRNA for KIAA0051 "gene," complete cds — Also Represents: L33075 | 682 | | −41 | NC | 0 | 0 | 790 | I | 2.2 | 1.01 | −184 | D | 1.4 | 0 |
| U12139 | Human alpha1(XI) collagen (COL11a1) "gene," 5′ region and exon 1 /gb = U12139 /nt | 26 | | 7 | NC | 0 | 0 | 77 | I | 4 | 0.97 | 11 | I | 0 | 0 |
| | | 66 | | −54 | NC | 0 | 0 | −136 | D | −3.3 | 0.95 | −54 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Un-treated In-tensity | B = A | IFN-a In-tensity | Incr Decr | Fold Change | Sig | IFN-b In-tensity | Incr Decr | Fold Change | Sig | IFN-g In-tensity | Incr Decr | Fold Change | Sig |
|---|---|---|---|---|---|---|---|---|---|---|---|---|---|---|---|
| S72008 | hCDC10 = CDC10 homolog "[human,"] fetal "lung," "mRNA," 2314 nt] | 43 | | −12 | NC | 0 | 0 | 106 | I | 3.5 | 0.92 | 0 | NC | 0 | 0 |
| G3214-HT339 | Metallopanstimulin 1 | 4442 | | −579 | NC | 0 | 0 | −1874 | D | 1.7 | 0.88 | −438 | D | 1.1 | 0.05 |
| L47276 | Homo sapiens (cell line HL-60) alpha topoisomerase truncated-form "mRNA," 3'UTR | 58 | | 1 | NC | 0 | 0 | 128 | I | 3.2 | 0.88 | −8 | NC | 0 | 0 |
| | | 7505 | | 221 | NC | 0 | 0 | 3946 | I | 1.5 | 0.86 | 1205 | NC | 0 | 0 |
| U05040 | Human FUSE binding protein "mRNA," complete cds | 60 | * | 24 | NC | 0 | 0 | 129 | I | 3.1 | 0.86 | 3 | NC | 0 | 0 |
| D79986 | Human mRNA for KIAA0164 "gene," complete cds | 4 | * | 25 | NC | 0 | 0 | 71 | I | −3.8 | 0.85 | 15 | NC | 0 | 0 |
| L13210 | Human Mac-2 binding protein "mRNA," complete cds | 463 | | 156 | NC | 0 | 0 | 526 | I | 2.1 | 0.81 | 483 | I | 2 | 0.7 |
| D16481 | Human mRNA for mitochondrial 3-ketoacyl-CoA thiolase beta-subunit of trifunctional | 45 | * | 41 | NC | 0 | 0 | 102 | I | 3.2 | 0.8 | 57 | I | 2.3 | 0.31 |
| M14660 | Human ISG-54K gene (interferon stimulated gene) encoding a 54 kDa protein | −62 | | 57 | I | −1.0 | 0 | 123 | I | −3.1 | 0.8 | 57 | I | −1.0 | 0 |
| Y07604 | H. sapiens mRNA for nucleoside-diphosphate kinase | 194 | | 20 | NC | 0 | 0 | 277 | I | 2.4 | 0.77 | 151 | I | 1.8 | 0.27 |
| M21259 | Human Alu repeats in the region 5' to the small nuclear ribonucleoprotein E gene | 102 | | 122 | NC | 0 | 0 | 176 | I | 2.7 | 0.77 | 91 | I | 1.9 | 0.25 |
| U81554 | Human CaM kinase II isoform "mRNA," complete cds. /gb = U81554 /ntype = RNA | 112 | | 52 | NC | 0 | 0 | 185 | I | 2.7 | 0.75 | 5 | NC | 0 | 0 |
| U70370 | Human hindIImb expressed homeobox protein backfoot (Bft) "mRNA," complete cds | −112 | * | 75 | MI | −1.0 | 0 | 166 | MI | −2.7 | 0.74 | 84 | I | −1.0 | 0 |
| Z25535 | H. sapiens mRNA for nuclear pore complex protein hnup153 | 22 | | 12 | NC | 0 | 0 | 60 | I | 3.7 | 0.74 | 26 | NC | 0 | 0 |
| Z48042 | H. sapiens mRNA encoding GPI-anchored protein p137 | 220 | | 89 | NC | 0 | 0 | 288 | I | 2.3 | 0.71 | 137 | I | 1.6 | 0.2 |
| | | 31 | | −6 | NC | −1.0 | 0 | 72 | I | 3.3 | 0.71 | 33 | I | 2.1 | 0.19 |
| X54326 | H. sapiens mRNA for glutaminyl-tRNA synthetase | 5559 | | −17 | NC | 0 | 0 | 2845 | MI | 1.5 | 0.71 | −620 | NC | 0 | 0 |
| X15187 | Human tra1 mRNA for human homologue of murine tumor rejection antigen gp96 | 49 | | −11 | NC | 0 | 0 | 100 | I | 3 | 0.71 | −5 | NC | 0 | 0 |
| X60036 | H. sapiens mRNA for mitochondrial phosphate carrier protein | 125 | | 3 | NC | 0 | 0 | 191 | I | 2.5 | 0.7 | −23 | NC | 0 | 0 |
| | | 3078 | | −156 | NC | 0 | 0 | −1270 | D | 1.7 | 0.7 | −96 | NC | 0 | 0 |
| | | 3 | * | 27 | NC | 0 | 0 | 65 | I | −3.4 | 0.69 | 28 | MI | −1.5 | 0.07 |
| | | 0 | * | 49 | NC | 0 | 0 | 67 | MI | −3.4 | 0.68 | 47 | MI | −2.4 | 0.3 |
| U61232 | Human tubulin-folding cofactor E "mRNA," complete cds | 69 | | −18 | NC | 0 | 0 | −59 | D | −3.5 | 0.68 | −18 | NC | 0 | 0 |
| U30894 | Human N-sulphoglucosamine sulphohydrolase "mRNA," complete cds | 71 | * | −32 | NC | 0 | 0 | −55 | D | −3.5 | 0.67 | −15 | NC | 0 | 0 |
| D63875 | Human mRNA for KIAA0155 "gene," complete cds | 14 | | −1 | NC | 0 | 0 | 55 | I | −3.5 | 0.66 | −96 | NC | 0 | 0 |
| M85164 | Homo sapiens SRF accessory protein 1B (SAP-1) "mRNA," complete cds | 11 | * | 9 | NC | 0 | 0 | 56 | I | −3.4 | 0.63 | 21 | I | −1.6 | 0.07 |
| U34605 | Human retinoic acid- and interferon-inducible 58K protein RI58 "mRNA," complete cd | 8 | | 8 | NC | 0 | 0 | 59 | I | −3.3 | 0.62 | 13 | NC | 0 | 0 |
| L08069 | Human heat shock "protein," E. coli DnaJ homologue "mRNA," complete cds | 168 | | 81 | NC | 0 | 0 | 218 | I | 2.3 | 0.61 | 15 | NC | 0 | 0 |
| X92396 | H. sapiens mRNA for novel gene in Xq28 region | 78 | * | 1 | NC | 0 | 0 | 126 | I | 2.6 | 0.6 | −7 | NC | 0 | 0 |
| X98260 | Human mRNA for M-phase "phosphoprotein," mpp11 | −9 | | 15 | NC | 0 | 0 | 70 | I | −3.1 | 0.6 | 2 | NC | 0 | 0 |
| M23161 | Human transposon-like element mRNA | 112 | | 16 | NC | 0 | 0 | 161 | I | 2.4 | 0.59 | −35 | NC | 0 | 0 |
| M28249 | Human very late antigen-2 (VLA-2)/collagen receptor alpha-2 subunit "mRNA," comp | 31 | | −3 | NC | 0 | 0 | 65 | I | 3.1 | 0.59 | −9 | NC | 0 | 0 |
| M82882 | Human cis-acting sequence | 2 | | 20 | NC | 0 | 0 | 61 | I | −3.1 | 0.59 | 7 | NC | 0 | 0 |
| X05276 | Human mRNA for fibroblast tropomyosin TM30 (pl) | 414 | | 38 | NC | 0 | 0 | 406 | I | 2 | 0.58 | −81 | NC | 0 | 0 |
| D13630 | Human mRNA for KIAA0005 "gene," complete cds | 199 | | 111 | NC | 0 | 0 | 238 | I | 2.2 | 0.58 | 41 | NC | 0 | 0 |
| L23959 | Homo sapiens E2F-related transcription factor (DP-1) "mRNA," complete cds | 33 | | −30 | NC | 0 | 0 | 67 | MI | 3 | 0.57 | −21 | NC | 0 | 0 |
| D16480 | Human mRNA for mitochobdrial enoyl-CoA hydratase/3-hydroxyacyl-CoA dehydroge | 92 | | 27 | NC | 0 | 0 | 136 | MI | 2.5 | 0.57 | 14 | NC | 0 | 0 |
| G2743-HT392 | Caldesmon "1," Alt. Splice "6," Non-Muscle — "Also Represents: HG2743-HT3927, M | 3 | | 6 | NC | 0 | 0 | 60 | I | −3.1 | 0.57 | 2 | NC | 0 | 0 |
| U45973 | Human phosphatidylinositol "(4,5)bisphosphate" 5-phosphatase homolog "mRNA," pa | 236 | | −58 | NC | 0 | 0 | −141 | D | 2.5 | 0.57 | −43 | NC | 0 | 0 |
| M20867 | Human glutamate dehydrogenase (GDH) "mRNA," complete cds — Also Represents: | 98 | | 85 | NC | 0 | 0 | 141 | I | 2.4 | 0.56 | 48 | NC | 0 | 0 |
| U78798 | Human TNF receptor associated factor 6 (TRAF6) "mRNA," complete cds. | 117 | | −72 | NC | 0 | 0 | −76 | D | 2.8 | 0.55 | −88 | NC | 0 | 0 |
| J04102 | Human erythroblastosis virus oncogene homolog 2 (ets-2) "mRNA," complete cds | 20 | | −6 | NC | 0 | 0 | 47 | MI | 3.3 | 0.55 | 14 | D | 4.1 | 1.08 |
| X60188 | Human ERK1 mRNA for protein serine/threonine kinase | 214 | | −88 | NC | 0 | 0 | −128 | D | 2.5 | 0.55 | −18 | NC | 0 | 0 |
| | | 10717 | | −1650 | NC | 0 | 0 | −3023 | D | 1.4 | 0.54 | −1322 | D | 1.1 | 0.11 |
| G3638-HT384 | Amyloid Beta (A4) Precursor "Protein," Alt. Splice "2," A4(751) — Also Represents: YO | 93 | | 47 | NC | 0 | 0 | 134 | I | 2.4 | 0.54 | 58 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| M77698 | *Homo sapiens* GLI-Krupple related protein (YY1) "mRNA," complete cds | 114 | | 36 | NC | 0 | 0 | 154 | I | 2.3 | 0.54 | 37 | NC | 0 | 0 |
| X96969 | *H. sapiens* mRNA for urea transporter | 62 | * | −11 | NC | 0 | 0 | −53 | D | −3.1 | 0.54 | −3 | NC | 0 | 0 |
| Z69915 | *H. sapiens* mRNA (clone ICRFp507L1876). /gb = Z69915 /ntype = RNA | 23 | * | 4 | NC | 0 | 0 | 50 | I | 3.2 | 0.54 | 5 | NC | 0 | 0 |
| AB001106 | Human mRNA for glia maturation "factor," complete cds | 6 | * | 9 | NC | 0 | 0 | 55 | I | −3.0 | 0.53 | 16 | NC | 0 | 0 |
| X62534 | *H. sapiens* HMg-2 mRNA — "Also Represents: Z17240, M83665_ma1" | 164 | | 29 | NC | 0 | 0 | 195 | I | 2.2 | 0.52 | −37 | NC | 0 | 0 |
| D38551 | Human mRNA for KIAA0078 "gene," complete cds | 35 | | 5 | NC | 0 | 0 | 66 | I | 2.8 | 0.51 | 8 | NC | 0 | 0 |
| D63477 | Human mRNA for KIAA0143 "gene," partial cds | 45 | | 15 | NC | 0 | 0 | 77 | I | 2.7 | 0.51 | −6 | NC | 0 | 0 |
| L06499 | *Homo sapiens* ribosomal protein L37a (RPL37A) "mRNA," complete cds | 9324 | | −1501 | NC | 0 | 0 | −2660 | D | 1.4 | 0.51 | −1592 | NC | 0 | 0 |
| U28811 | Human cysteine-rich fibroblast growth factor receptor (CFR-1) "mRNA," complete cds | 93 | | −36 | NC | 0 | 0 | −61 | D | 2.9 | 0.51 | −51 | NC | 0 | 0 |
| X55715 | Human Hums3 mRNA for 40S ribosomal protein s3 | 7796 | | −175 | NC | 0 | 0 | −2315 | MD | 1.4 | 0.51 | −838 | NC | 0 | 0 |
| Z15115 | *H. sapiens* TOP2 mRNA for DNA topoisomerase II (partial) | 41 | | −24 | NC | 0 | 0 | 71 | MI | 2.7 | 0.5 | −21 | D | −2.0 | 0.14 |
| U26312 | Human heterochromatin protein HP1Hs-gamma "mRNA," complete cds — Also Repre | 64 | | 4 | NC | 0 | 0 | 99 | MI | 2.5 | 0.5 | −19 | NC | 0 | 0 |
| | | −25 | | 21 | NC | 0 | 0 | 79 | I | −2.7 | 0.49 | 51 | I | −1.3 | 0.04 |
| X74039 | *H. sapiens* mRNA for urokinase plasminogen activator receptor | 22 | * | 30 | NC | 0 | 0 | 46 | MI | 3.1 | 0.49 | 27 | NC | 0 | 0 |
| D63861 | Human DNA for cyclophilin "40," complete cds — Also Represents: L11667 | 50 | | 22 | NC | 0 | 0 | 80 | I | 2.6 | 0.48 | 3 | NC | 0 | 0 |
| G2755-HT288 | T-Plastin | 64 | | 1 | NC | 0 | 0 | 95 | I | 2.5 | 0.48 | −34 | NC | 0 | 0 |
| X66363 | *H. sapiens* mRNA PCTAIRE-1 for serine/threonine protein kinase | 68 | * | 20 | NC | 0 | 0 | 99 | I | 2.4 | 0.47 | 46 | MI | 1.7 | 0.13 |
| U19252 | Human putative transmembrane protein "mRNA," complete cds — Also Represents: U | 11 | * | 13 | NC | 0 | 0 | 48 | I | −3.0 | 0.47 | 19 | NC | 0 | 0 |
| D23660 | Human mRNA for ribosomal "protein," complete cds | 5996 | | 79 | NC | 0 | 0 | −1804 | D | 1.4 | 0.46 | −1017 | NC | 0 | 0 |
| | | −17 | | 45 | NC | 0 | 0 | 70 | I | −2.6 | 0.45 | 58 | NC | 0 | 0 |
| G4557-HT496 | Small Nuclear Ribonucleoprotein "U1," 1snrp | −3 | * | 8 | NC | 0 | 0 | 58 | I | −2.8 | 0.45 | 11 | NC | 0 | 0 |
| J04088 | Human DNA topoisomerase II (top2) "mRNA," complete cds | 33 | * | 3 | NC | 0 | 0 | 59 | I | 2.7 | 0.45 | −2 | NC | 0 | 0 |
| M63896 | *Homo sapiens* transcriptional enhancer factor (TEF1) "DNA," complete CDS | 15 | | 7 | NC | 0 | 0 | 44 | I | −3.0 | 0.45 | −5 | NC | 0 | 0 |
| X01677 | Human liver mRNA for glyceraldehyde-3-phosphate dehydrogenase "(G3PD)," EC 1.2 | 9394 | | −1733 | NC | 0 | 0 | −2482 | D | 1.4 | 0.44 | −1164 | NC | 0 | 0 |
| X80200 | *H. sapiens* MLN62 mRNA | 302 | | 8 | NC | 0 | 0 | −160 | MD | 2.1 | 0.44 | −9 | NC | 0 | 0 |
| G4660-HT507 | Microtubule-Associated Protein 1b | 13 | * | 30 | NC | 0 | 0 | 45 | I | −2.9 | 0.43 | 25 | I | −1.9 | 0.13 |
| | | 17 | * | 7 | NC | 0 | 0 | 41 | I | −2.9 | 0.43 | 9 | NC | 0 | 0 |
| | | 1 | | 8 | NC | 0 | 0 | 53 | MI | −2.7 | 0.42 | 15 | NC | 0 | 0 |
| D21260 | Human mRNA for KIAA0034 "gene," complete cds | 79 | | −1 | NC | 0 | 0 | 103 | MI | 2.3 | 0.42 | 7 | NC | 0 | 0 |
| X84740 | *H. sapiens* mRNA for DNA ligase III | 90 | | −16 | NC | 0 | 0 | −56 | MD | 2.7 | 0.42 | 48 | NC | 0 | 0 |
| X15183 | Human mRNA for 90-kDa heat-shock protein | 1516 | | 196 | NC | 0 | 0 | 827 | I | 1.5 | 0.41 | −374 | D | 1.3 | 0.15 |
| L18960 | Human protein synthesis factor (eIF-4C) "mRNA," complete cds | 46 | | 19 | NC | 0 | 0 | 69 | I | 2.5 | 0.41 | 12 | NC | 0 | 0 |
| L14837 | Human tight junction (zonula occludens) protein ZO-1 "mRNA," complete cds | 29 | | −3 | NC | 0 | 0 | 49 | I | 2.5 | 0.4 | 18 | NC | 0 | 0 |
| L20298 | *Homo sapiens* transcription factor (CBFB) "mRNA," 3' end | 75 | | 9 | NC | 0 | 0 | 96 | I | 2.7 | 0.4 | 24 | NC | 0 | 0 |
| M13934 | RPS14 gene (ribosomal protein S14) extracted from Human ribosomal protein S14 "g | 5922 | | −708 | NC | 0 | 0 | −1680 | D | 2.3 | 0.4 | −219 | D | 1.3 | 0 |
| M87338 | Human replication factor "C," 40-kDa subunit (A1) "mRNA," complete cds | 86 | | −26 | NC | 0 | 0 | −53 | D | 2.6 | 0.4 | −20 | NC | 0 | 0 |
| L24804 | Human (p23) "mRNA," complete cds | 149 | | 41 | NC | 0 | 0 | 154 | I | 2 | 0.39 | 49 | NC | 0 | 0 |
| L36844 | *Homo sapiens* (clone p15INK4B/HA5) CDK inhibitory protein "mRNA," complete cds | 1 | * | 58 | NC | 0 | 0 | 51 | MI | −2.6 | 0.38 | 21 | NC | 0 | 0 |
| M33374 | Human cell adhesion protein (SQM1) "mRNA," complete cds | 192 | | 46 | NC | 0 | 0 | −105 | MD | 2.2 | 0.38 | 19 | NC | 0 | 0 |
| U37547 | Human IAP homolog B (MIHB) "mRNA," complete cds | 10 | | 21 | NC | 0 | 0 | 44 | I | −2.7 | 0.38 | 4 | NC | 0 | 0 |
| X59798 | Human PRAD1 mRNA for cyclin | 498 | | −118 | NC | 0 | 0 | 352 | I | 1.7 | 0.37 | −161 | D | 1.5 | 0.16 |
| M18000 | Human ribosomal protein S17 "gene," complete cds | 5362 | | −839 | NC | 0 | 0 | −1497 | D | 1.4 | 0.37 | −914 | D | 1.2 | 0.14 |
| J02621 | Human non-histone chromosomal protein HMG-14 "mRNA," complete cds — Also Rep | 262 | | 131 | NC | 0 | 0 | 225 | I | 1.9 | 0.37 | −1 | NC | 0 | 0 |
| U16307 | Human glioma pathogenesis-related protein (GliPR) "mRNA," complete cds | 12 | | 2 | NC | 0 | 0 | 42 | I | −2.7 | 0.37 | −5 | NC | 0 | 0 |
| X65488 | *H. sapiens* U21.1 mRNA | 234 | | −46 | NC | 0 | 0 | 205 | I | 1.9 | 0.37 | −25 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| X98411 | *H. sapiens* mRNA for myosin-IE | 137 | | -43 | NC | 0 | 0 | -78 | D | 2.3 | 0.37 | -31 | NC | 0 | 0 |
| D28476 | Human mRNA for KIAA0045 "gene," complete cds | 51 | | -23 | NC | 0 | 0 | 69 | I | 2.3 | 0.36 | -22 | MD | 1.7 | 0.1 |
| D87716 | Human mRNA for KIAA0007 "gene," partial cds — Also Represents: D26488 | 18 | * | -9 | NC | 0 | 0 | 37 | I | -2.8 | 0.36 | 2 | NC | 0 | 0 |
| M37190 | Human ras inhibitor "mRNA," 3' end | 39 | * | -15 | NC | 0 | 0 | 57 | MI | 2.5 | 0.36 | 1 | NC | 0 | 0 |
| S42303 | N-cadherin "[human," umbilical vein endothelial "cells," "mRNA," 4132 nt] | 48 | | 20 | NC | 0 | 0 | 65 | I | 2.4 | 0.35 | 39 | I | 1.8 | 0.15 |
| L09235 | Human vacuolar ATPase (isoform VA68) "mRNA," complete cds | 2 | | 10 | NC | 0 | 0 | 48 | I | -2.5 | 0.35 | 17 | NC | 0 | 0 |
| U15008 | Human SnRNP core protein Sm D2 "mRNA," complete cds | 3474 | | -245 | NC | 0 | 0 | -1045 | D | 1.4 | 0.35 | -504 | NC | 0 | 0 |
| U90551 | Human histone 2A-like protein (H2A/l) "mRNA," complete cds | 11 | * | 42 | NC | 0 | 0 | 41 | I | -2.6 | 0.35 | 17 | NC | 0 | 0 |
| AB006782 | *Homo sapiens* mRNA for galectin-9 "isoform," complete cds. /gb = AB006782 /ntype = | 134 | | 0 | NC | 0 | 0 | 134 | I | 2 | 0.34 | 22 | NC | 0 | 0 |
| G3748-HT401 | Basic Transcription "Factor," 44 Kda Subunit | 124 | | -14 | NC | 0 | 0 | 125 | I | 2 | 0.34 | -23 | NC | 0 | 0 |
| U13219 | Human forkhead protein FREAC-1 "mRNA," complete cds | 21 | * | -8 | NC | 0 | 0 | 36 | I | 2.7 | 0.34 | -4 | NC | 0 | 0 |
| M11058 | Human 3-hydroxy-3-methylglutaryl coenzyme A reductase "mRNA," complete cds | 23 | * | -9 | NC | 0 | 0 | 38 | I | 2.6 | 0.33 | -12 | NC | 0 | 0 |
| U32214 | Human caveolin-2 "mRNA," complete cds | 30 | | 1 | NC | 0 | 0 | 45 | I | 2.5 | 0.33 | -5 | NC | 0 | 0 |
| U60325 | Human DNA polymerase gamma "mRNA," nuclear gene encoding mitochondrial "pro | 94 | | -7 | NC | 0 | 0 | -54 | D | 2.3 | 0.32 | 9 | NC | 0 | 0 |
| U68019 | Human mad protein homolog (hMAD-3) "mRNA," complete cds | 160 | | 37 | NC | 0 | 0 | 144 | I | 1.9 | 0.32 | 28 | NC | 0 | 0 |
| X05908 | Human mRNA for lipocortin | 120 | | 7 | NC | 0 | 0 | 119 | I | 2 | 0.32 | -69 | NC | 0 | 0 |
| Z48512 | *H. sapiens* XG mRNA (clone PEP6) /gb = Z48512 /ntype = RNA | 52 | | -2 | NC | 0 | 0 | -39 | MD | -2.6 | 0.31 | 15 | NC | 0 | 0 |
| D13645 | Human mRNA for KIAA0020 "gene," complete cds | 16 | * | -15 | NC | 0 | 0 | 36 | MI | -2.6 | 0.31 | 8 | NC | 0 | 0 |
| M27436 | Human tissue factor "gene," complete "cds," with a Alu repetitive sequence in the 3' | 55 | | 16 | NC | 0 | 0 | 67 | I | 2.2 | 0.31 | -9 | NC | 0 | 0 |
| U10492 | Human Mox1 protein (MOX1) "mRNA," complete cds | 4 | * | 37 | NC | 0 | 0 | 45 | I | -2.4 | 0.31 | 26 | NC | 0 | 0 |
| U49070 | Human peptidyl-prolyl isomerase and essential mitotic regulator (PIN1) "mRNA," com | 245 | | -61 | NC | 0 | 0 | -120 | D | 2 | 0.31 | -19 | NC | 0 | 0 |
| U52100 | Human XMP "mRNA," complete cds | 93 | | -29 | NC | 0 | 0 | -53 | D | 2.3 | 0.31 | 8 | NC | 0 | 0 |
| X75091 | *H. sapiens* mRNA for HLA-DR associated protein II (PHAPII) — Also Represents: M93 | 161 | | 12 | NC | 0 | 0 | 143 | I | 1.9 | 0.31 | -25 | NC | 0 | 0 |
| Z48511 | *H. sapiens* XG mRNA (clone PEP11) | 51 | | -14 | NC | 0 | 0 | -39 | D | -2.5 | 0.31 | -17 | NC | 0 | 0 |
| | | 1 | * | 6 | NC | 0 | 0 | 47 | I | -2.4 | 0.3 | 4 | NC | 0 | 0 |
| U35835 | Human DNA-PK "mRNA," partial cds — Also Represents: U47077 | 42 | | -29 | NC | 0 | 0 | 54 | MI | 2.3 | 0.3 | -19 | NC | 0 | 0 |
| U82130 | Human tumor susceptibility protein (TSG101) "mRNA," complete cds | 108 | | 44 | NC | 0 | 0 | 105 | I | 2 | 0.3 | 3 | NC | 0 | 0 |
| X66503 | Human adenylosuccinate synthetase mRNA | 27 | * | -1 | NC | 0 | 0 | 39 | I | 2.5 | 0.3 | -6 | NC | 0 | 0 |
| Z18951 | *H. sapiens* mRNA for caveolin | 353 | | -69 | NC | 0 | 0 | 246 | I | 1.7 | 0.3 | -66 | NC | 0 | 0 |
| U90552 | Human butyrophilin (BTF5) "mRNA," complete cds — Also Represents: U97502_ma1 | 51 | | 50 | NC | 0 | 0 | 60 | MI | 2.2 | 0.29 | 63 | MI | 2.2 | 0.31 |
| D00723 | Human mRNA for hydrogen carrier "protein," a component of an enzyme "complex," | 12 | | 9 | NC | 0 | 0 | 37 | I | -2.5 | 0.29 | 10 | NC | 0 | 0 |
| HG884-HT884 | Oncogene "E6-Ap," Papillomavirus — Also Represents: U84404 | 11 | * | 16 | NC | 0 | 0 | 37 | I | -2.4 | 0.29 | 10 | NC | 0 | 0 |
| J03764 | "Human," plasminogen activator inhibitor-1 "gene," exons 2 to 9 | 928 | | 20 | NC | 0 | 0 | 471 | I | 1.5 | 0.29 | -23 | NC | 0 | 0 |
| M28215 | *Homo sapiens* GTP-binding protein (RAB5) "mRNA," complete cds | 8 | * | 7 | NC | 0 | 0 | 40 | MI | -2.4 | 0.29 | 14 | NC | 0 | 0 |
| U03272 | Human fibrillin-2 "mRNA," complete cds | 14 | | 7 | NC | 0 | 0 | 36 | I | -2.5 | 0.29 | 23 | NC | 0 | 0 |
| U73936 | Human Jagged 1 (HJ1) "mRNA," complete cds | 77 | | 37 | NC | 0 | 0 | 82 | I | 2.1 | 0.29 | 12 | NC | 0 | 0 |
| X16832 | Human mRNA for cathepsin H (EC 3.4.22.16) | 39 | * | -29 | NC | 0 | 0 | 50 | I | 2.3 | 0.29 | 42 | NC | 0 | 0 |
| M83667 | Human NF-IL6-beta protein "mRNA," complete cds — Also Represents: S63168_ma1 | 24 | * | 6 | NC | 0 | 0 | 35 | I | 2.5 | 0.28 | 84 | I | 4.5 | 1.19 |
| D38550 | Human mRNA for KIAA0075 "gene," partial cds | 17 | | -6 | NC | 0 | 0 | 33 | I | -2.5 | 0.28 | 14 | I | -1.6 | 0.06 |
| D44466 | Human mRNA for proteasome subunit "p112," complete cds | 8110 | | -377 | NC | 0 | 0 | 2128 | I | 1.3 | 0.28 | 1289 | NC | 0 | 0 |
| K03195 | Human (HepG2) glucose transporter gene "mRNA," complete cds | 237 | | -9 | NC | 0 | 0 | 179 | I | 1.8 | 0.28 | -64 | NC | 0 | 0 |
| S77356 | transcript ch21 = oligomycin sensitivity conferral protein osrp homolog "[human," "RF1 | 201 | | 160 | NC | 0 | 0 | 159 | MI | 1.8 | 0.28 | 159 | NC | 0 | 0 |
| U01157 | Human glucagon-like peptide-1 receptor mRNA with CA dinucleotide "repeat," compl | 241 | | 5 | NC | 0 | 0 | 180 | MI | 1.7 | 0.28 | 27 | NC | 0 | 0 |
| U78524 | Human Gu binding protein "mRNA," partial cds. | 21 | * | 5 | NC | 0 | 0 | 32 | MI | 2.5 | 0.28 | -8 | NC | 0 | 0 |
| | | 64 | | 9 | NC | 0 | 0 | 70 | I | 2.1 | 0.28 | 26 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| X70394 | *H. sapiens* OZF mRNA | 28 | | −8 | NC | 0 | 0 | 39 | I | 2.4 | 0.28 | −2 | NC | 0 | 0 |
| Z29083 | *H. sapiens* 5T4 gene for 5T4 Oncofetal antigen | 190 | | 58 | NC | 0 | 0 | 153 | I | 1.8 | 0.28 | 7 | NC | 0 | 0 |
| X96752 | *H. sapiens* mRNA for L-3-hydroxyacyl-CoA dehydrogenase | 17 | * | 14 | NC | 0 | 0 | 32 | I | −2.5 | 0.27 | 59 | I | −3.8 | 0.8 |
| U09953 | Human ribosomal protein L9 "mRNA," complete cds | 3077 | | 45 | NC | 0 | 0 | −843 | D | 1.4 | 0.27 | −822 | D | 1.4 | 0.26 |
| M11147 | Human ferritin L chain "mRNA," complete cds | 5140 | | −601 | NC | 0 | 0 | −1243 | D | 1.3 | 0.27 | −1145 | D | 1.3 | 0.23 |
| G4557-HT496 | Small Nuclear Ribonucleoprotein "U1," 1snrp | 0 | * | 8 | NC | 0 | 0 | 45 | I | −2.3 | 0.27 | −6 | NC | 0 | 0 |
| M83216 | Human aorta caldesmon "mRNA," complete cds — "Also Represents: HG2743-HT392 | 6 | * | −9 | NC | 0 | 0 | 41 | I | −2.3 | 0.27 | −3 | NC | 0 | 0 |
| S67070 | heat shock protein HSP72 homolog "[human," thyroid associated ophthalmopathy "pa | 43 | | −54 | NC | 0 | 0 | −62 | MD | −2.1 | 0.27 | −1 | NC | 0 | 0 |
| X00588 | Human mRNA for precursor of epidermal growth factor receptor | 14 | | −4 | NC | 0 | 0 | 34 | I | −2.4 | 0.27 | 4 | NC | 0 | 0 |
| X16560 | Human COX VIIc gene for subunit VIIc of cytochrome c oxidase (EC 1.9.3.1) | 1974 | | −3 | NC | 0 | 0 | −594 | MD | 1.4 | 0.26 | −495 | D | 1.3 | 0.18 |
| U14973 | Human ribosomal protein S29 "mRNA," complete cds | 5050 | | −470 | NC | 0 | 0 | −1211 | D | 1.3 | 0.26 | −971 | D | 1.2 | 0.17 |
| M26730 | Human mitochondrial ubiquinone-binding protein "gene," 5' flank with an LTR-like sec | 137 | | 40 | NC | 0 | 0 | 115 | MI | 1.8 | 0.26 | −50 | D | 1.6 | 0.11 |
| D83777 | Human mRNA for KIAA0193 "gene," complete cds | 82 | | −9 | NC | 0 | 0 | 80 | I | 2 | 0.26 | −21 | MD | 1.3 | 0.04 |
| M23254 | Human Ca2-activated neutral protease large subunit (CANP) "mRNA," complete cds | 791 | | 80 | NC | 0 | 0 | 394 | I | 1.5 | 0.26 | −44 | NC | 0 | 0 |
| M86400 | Human phospholipase A2 "mRNA," complete cds | 836 | | 93 | NC | 0 | 0 | 411 | I | 1.5 | 0.26 | 58 | NC | 0 | 0 |
| S79873 | h-lamp-2 = lysosome-associated membrane protein-2 {alternatively spliced} "[human," | 12 | | 12 | NC | 0 | 0 | 35 | I | −2.4 | 0.26 | 3 | NC | 0 | 0 |
| S82297 | beta 2-microglobulin {11bp deleted between nucleotides 98–99} "[human," colon canc | 704 | | 36 | NC | 0 | 0 | 362 | I | 1.5 | 0.26 | −59 | D | 1.5 | 0.16 |
| U33920 | Human clone lambda 5 semaphorin "mRNA," complete cds | −7 | | 17 | NC | 0 | 0 | 51 | MI | −2.2 | 0.26 | 5 | NC | 0 | 0 |
| U65579 | Human mitochondrial NADH dehydrogenase-ubiquinone Fe—S protein "8," 23 kDa su | 220 | | 35 | NC | 0 | 0 | −103 | MD | 1.9 | 0.26 | 99 | NC | 0 | 0 |
| U95740 | 362G6.2 gene extracted from Human chromosome 16p 13.1 BAC clone CIT987SK-36 | 4 | * | 22 | NC | 0 | 0 | 41 | MI | −2.3 | 0.26 | 16 | NC | 0 | 0 |
| D83004 | Human epidermoid carcinoma mRNA for ubliquitin-conjugating enzyme E2 similar to | 213 | | 130 | NC | 0 | 0 | 153 | I | 1.7 | 0.25 | 41 | MI | 1.2 | 0.03 |
| D87120 | Human cancellous bone osteoblast mRNA for "GS3786," complete cds | 13 | | −5 | NC | 0 | 0 | 34 | I | −2.3 | 0.25 | 1 | NC | 0 | 0 |
| D89377 | Human mRNA for "MSX-2," complete cds — Also Represents: X69295 Same Unigen | 48 | | 2 | NC | 0 | 0 | −31 | D | −2.4 | 0.25 | −8 | NC | 0 | 0 |
| M19961 | Human cytochrome c oxidase subunit Vb (coxVb) "mRNA," complete cds | 1036 | | 47 | NC | 0 | 0 | −350 | D | 1.5 | 0.25 | −91 | NC | 0 | 0 |
| M59830 | Human MHC class III HSP70-2 gene "(HLA)," complete cds | 100 | | 32 | NC | 0 | 0 | 90 | MI | 1.9 | 0.25 | 21 | NC | 0 | 0 |
| U77413 | Human O-linked GlcNAc transferase "mRNA," complete cds. /gb = U77413 /ntype = RN | 8 | * | −1 | NC | 0 | 0 | 38 | I | −2.3 | 0.24 | 0 | NC | 0 | 0 |
| X01060 | Human mRNA for transferrin receptor | 485 | | 94 | NC | 0 | 0 | 277 | I | 1.6 | 0.24 | 26 | NC | 0 | 0 |
| X62654 | ME491 gene extracted from *H. sapiens* gene for Me491/CD63 antigen | 1391 | | 131 | NC | 0 | 0 | −438 | D | 1.5 | 0.25 | 63 | NC | 0 | 0 |
| Z31690 | *H. sapiens* (HepG2) LAL mRNA for lysosomal acid lipase — "Also Represents: X76488 | 16 | | 1 | NC | 0 | 0 | 32 | I | −2.4 | 0.24 | −13 | NC | 0 | 0 |
| M63573 | Human secreted cyclophilin-like protein (SCYLP) "mRNA," complete cds | 2163 | | −384 | NC | 0 | 0 | −603 | D | 1.4 | 0.24 | −501 | D | 1.3 | 0.16 |
| X96924 | *H. sapiens* gene encoding mitochondrial citrate transport protein | 679 | | −140 | NC | 0 | 0 | −247 | MD | 1.6 | 0.24 | 217 | I | 1.3 | 0.11 |
| U00947 | Human clone C4E 3.2 (CAC)n(GTG)n repeat-containing mRNA — Also Represents: | 860 | | 83 | NC | 0 | 0 | 402 | I | 1.5 | 0.24 | 160 | I | 1.2 | 0.05 |
| | | 10469 | | −1403 | NC | 0 | 0 | −1969 | D | 1.2 | 0.24 | −1192 | D | 0 | 0 |
| HG429-HT429 | B-Cell Growth Factor 1 | 159 | | 26 | NC | 0 | 0 | 124 | I | 1.8 | 0.24 | −63 | NC | 0 | 0 |
| M25077 | Human SS-A/Re ribonucleoprotein autoantigen 60 kd subunit "mRNA," complete cds | −18 | * | 0 | NC | 0 | 0 | 59 | I | −2.0 | 0.23 | −1 | NC | 0 | 0 |
| S74728 | antiquitin = 26g turgor protein homolog "[human," "kidney," "mRNA," 1809 nt] | 67 | | −21 | NC | 0 | 0 | 67 | I | 2 | 0.24 | 1 | NC | 0 | 0 |
| U37426 | Human kinesin-like spindle protein HKSP (HKSP) "mRNA," complete cds | 14 | * | −18 | NC | 0 | 0 | 33 | I | −2.3 | 0.24 | −13 | NC | 0 | 0 |
| X14684 | Human mRNA for La protein C-terminal region — "Also Represents: X13697, M20328 | 65 | | 13 | NC | 0 | 0 | 64 | I | 2 | 0.24 | −41 | D | 1.3 | 0.11 |
| Z80777 | *H. sapiens* H2A/k gene | −6 | * | 24 | NC | 0 | 0 | 49 | I | −2.1 | 0.23 | 5 | NC | 0 | 0 |
| D14826 | Human mRNA for hCREM (cyclic AMP-responsive element modulator) type 2 "prote | 23 | * | 12 | NC | 0 | 0 | 31 | I | 2.3 | 0.23 | 19 | I | 1.8 | 0.11 |
| L29008 | Human L-iditol-2 dehydrogenase "mRNA," complete cds | 20 | * | 12 | NC | 0 | 0 | 28 | MI | −2.4 | 0.23 | 9 | NC | 0 | 0 |
| U40369 | Human spermidine/spermine N1-acetyltransferase (SSAT) "gene," complete cds | 139 | | 39 | NC | 0 | 0 | 108 | I | 1.8 | 0.23 | 49 | NC | 0 | 0 |
| U57341 | Human neurofilament triplet L protein "mRNA," partial cds. /gb = U57341 /ntype = cds | 21 | | 12 | NC | 0 | 0 | 29 | MI | 2.4 | 0.23 | 3 | NC | 0 | 0 |
| U76189 | Human EXTL3 "mRNA," partial cds. /gb = U76189 /ntype = RNA | 23 | | 20 | NC | 0 | 0 | 30 | I | 2.3 | 0.23 | 15 | NC | 0 | 0 |
| | | 15 | | −2 | NC | 0 | 0 | 31 | I | −2.3 | 0.23 | −5 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| M29064 | Human hnRNP B1 protein mRNA | 377 | | -77 | NC | 0 | 0 | 213 | I | 1.6 | 0.22 | -174 | D | 1.9 | 0.32 |
| G3936-HT420 | Interleukin 9 Receptor (GbS71404) | 45 | * | -15 | NC | 0 | 0 | -32 | MD | -2.2 | 0.22 | -39 | NC | 0 | 0 |
| L19161 | Human translation initiation factor eIF-2 gamma subunit "mRNA," complete cds | 56 | | 20 | NC | 0 | 0 | 55 | I | 2 | 0.22 | -2 | NC | 0 | 0 |
| M14113 | Human coagulation factor VIII:C "mRNA," complete cds | 11 | * | -22 | D | -1.0 | 0 | 33 | I | -2.2 | 0.22 | 5 | NC | 0 | 0 |
| S82024 | SCG10 = neuron-specific growth-associated protein/stathmin homolog "[human]," "emb | 12 | * | 8 | NC | 0 | 0 | 33 | I | -2.2 | 0.22 | -4 | NC | 0 | 0 |
| U67171 | Human selenoprotein W (selW) "mRNA," complete cds. /gb = U67171 /ntype = RNA | 586 | | 100 | NC | 0 | 0 | -213 | MD | 1.6 | 0.22 | -12 | NC | 0 | 0 |
| | | 7780 | | -799 | NC | 0 | 0 | -1472 | D | 1.2 | 0.21 | -223 | NC | 0 | 0 |
| D78361 | Human mRNA for ornithine decarboxylase "antizyme," ORF 1 and ORF 2 | 6151 | | -96 | NC | 0 | 0 | -1256 | D | 1.3 | 0.21 | -366 | NC | 0 | 0 |
| G2981-HT312 | "Epican," Alt. Splice 1 — "Also Represents: HG2981-HT3934, HG2981-HT3931, HG29 | 408 | | 113 | NC | 0 | 0 | 222 | I | 1.5 | 0.21 | 46 | NC | 0 | 0 |
| L27706 | Human chaperonin protein (Tcp20) gene complete cds | 163 | | 26 | NC | 0 | 0 | 114 | I | 1.7 | 0.21 | -58 | NC | 0 | 0 |
| M31520 | Human ribosomal protein S24 mRNA — Also Represents: HG3214-HT3391 | 73 | | -23 | NC | 0 | 0 | -38 | D | 2.1 | 0.21 | -25 | NC | 0 | 0 |
| M37197 | Human CCAAT-box-binding factor (CBF) "mRNA," complete cds | 21 | * | 0 | NC | 0 | 0 | 27 | I | 2.3 | 0.21 | -19 | NC | 0 | 0 |
| U09510 | Human glycyl-tRNA synthetase "mRNA," complete cds — Also Represents: U09587 | 445 | | 66 | NC | 0 | 0 | 234 | I | 1.5 | 0.21 | 12 | NC | 0 | 0 |
| U51990 | Human hPrp18 "mRNA," complete cds | -3 | | 12 | NC | 0 | 0 | 44 | I | -2.0 | 0.21 | 7 | NC | 0 | 0 |
| U78027 | L44L gene (L44-like ribosomal protein) extracted from Human Bruton's tyrosine kinas | 39 | * | -22 | NC | 0 | 0 | -56 | D | -2.0 | 0.21 | 6 | NC | 0 | 0 |
| U94832 | Human KH type splicing regulatory protein KSRP "mRNA," complete cds. | 336 | | 137 | NC | 0 | 0 | 193 | I | 1.6 | 0.21 | 85 | NC | 0 | 0 |
| Y08612 | H. sapiens mRNA for Nup88 protein | 105 | | 34 | NC | 0 | 0 | 85 | I | 1.8 | 0.21 | 23 | NC | 0 | 0 |
| D31767 | Human mRNA for KIAA0058 "gene," complete cds | 171 | | 65 | NC | 0 | 0 | 115 | I | 1.7 | 0.2 | 71 | MI | 1.4 | 0.09 |
| D13627 | Human mRNA for KIAA0002 "gene," complete cds | 277 | | 42 | NC | 0 | 0 | 162 | I | 1.6 | 0.2 | -86 | NC | 0 | 0 |
| D26018 | Human mRNA for KIAA0039 "gene," partial cds | 12 | * | 20 | NC | 0 | 0 | 31 | I | -2.1 | 0.2 | 11 | NC | 0 | 0 |
| D80005 | Human mRNA for KIAA0183 "gene," partial cds | 111 | | -11 | NC | 0 | 0 | 86 | I | 1.8 | 0.2 | 22 | NC | 0 | 0 |
| L05147 | Human dual specificity phosphatase tyrosine/serine "mRNA," complete cds | 54 | | -7 | NC | 0 | 0 | -29 | D | 2.2 | 0.2 | -15 | NC | 0 | 0 |
| L35546 | Homo sapiens gamma-glutamylcysteine synthetase light subunit "mRNA," complete | 150 | | 33 | NC | 0 | 0 | 107 | MI | 1.7 | 0.2 | 43 | NC | 0 | 0 |
| U06698 | Human neuronal kinesin heavy chain "mRNA," complete cds | 4 | * | 18 | NC | 0 | 0 | 38 | I | -2.1 | 0.2 | 15 | NC | 0 | 0 |
| X66899 | H. sapiens EWS mRNA | 438 | | -74 | NC | 0 | 0 | 228 | I | 1.5 | 0.2 | 61 | NC | 0 | 0 |
| Z70759 | H. sapiens mitochondrial 16S rRNA gene (partial). /gb = Z70759 /ntype = RNA | 6416 | | -979 | NC | 0 | 0 | 1445 | MI | 1.2 | 0.2 | -699 | NC | 0 | 0 |
| D31887 | Human mRNA for KIAA0062 "gene," partial cds | 270 | | 49 | NC | 0 | 0 | 156 | I | 1.6 | 0.19 | 45 | NC | 0 | 0 |
| G2815-HT402 | "Myosin," Light "Chain," "Alkali,," Smooth Muscle "(GbtU02629)," Smooth "Muscle," A | 4909 | | -209 | NC | 0 | 0 | -1007 | D | 1.3 | 0.19 | -815 | NC | 0 | 0 |
| L40357 | Homo sapiens thyroid receptor interactor (TRIP7) "mRNA," 3' end of cds | 8 | * | 13 | NC | 0 | 0 | 33 | I | 1.6 | 0.19 | 1 | NC | 0 | 0 |
| M15661 | Human ribosomal protein "mRNA," complete cds | 297 | | 100 | NC | 0 | 0 | 168 | I | -2.1 | 0.19 | 56 | NC | 0 | 0 |
| M31642 | Human hypoxanthine phosphoribosyltransferase (HPRT) "mRNA," complete cds | 9 | * | -18 | NC | 0 | 0 | 33 | I | 1.6 | 0.19 | -12 | NC | 0 | 0 |
| U21090 | Human DNA polymerase delta small subunit "mRNA," complete cds | 383 | | 57 | NC | 0 | 0 | -142 | D | 1.6 | 0.19 | 100 | MD | -1.0 | 0 |
| U28833 | Human Down syndrome critical region protein (DSCR1) "mRNA," complete cds | 12 | * | -2 | NC | 0 | 0 | 30 | I | -2.1 | 0.19 | 8 | NC | 0 | 0 |
| U29607 | Human methionine aminopeptidase "mRNA," complete cds | 3 | | 1 | NC | 0 | 0 | 38 | I | -2.0 | 0.19 | 5 | NC | 0 | 0 |
| U56637 | Human capping protein alpha subunit isoform 1 "mRNA," complete cds | 352 | | -102 | NC | 0 | 0 | 187 | I | 1.7 | 0.19 | -190 | NC | 0 | 0 |
| X51688 | Human mRNA for cyclin A | 121 | | 43 | NC | 0 | 0 | 88 | I | 1.5 | 0.19 | 7 | NC | 0 | 0 |
| Z49254 | H. sapiens L23-related mRNA | 451 | | 76 | NC | 0 | 0 | 212 | I | 1.5 | 0.18 | 212 | I | 1.5 | 0.18 |
| Z19554 | H. sapiens vimentin gene — Also Represents: M18895_cds2 Same Unigene Cluster a | 7150 | | -730 | NC | 0 | 0 | -1301 | D | 1.2 | 0.18 | -954 | MD | 1.2 | 0.11 |
| D86960 | Human mRNA for KIAA0205 "gene," complete cds | -3 | | 9 | NC | 0 | 0 | 42 | I | -2.0 | 0.18 | 27 | I | -1.2 | 0.02 |
| Y00636 | Human mRNA for lymphocyte function associated antigen-3 (LFA-3) | 10 | * | 11 | MI | -1.1 | 0 | 31 | I | -2.1 | 0.18 | 13 | I | -1.2 | 0.01 |
| D43951 | Human mRNA for KIAA0099 "gene," complete cds | 26 | * | 0 | NC | 0 | 0 | 29 | I | 2.1 | 0.18 | 2 | NC | 0 | 0 |
| D63878 | Human mRNA for KIAA0158 "gene," complete cds | 265 | | -38 | NC | 0 | 0 | 146 | I | 1.6 | 0.18 | -68 | NC | 0 | 0 |
| D64015 | Homo sapiens mRNA for T-cluster binding "protein," complete cds. /gb = D64105 /ntyp | 1 | | 11 | NC | 0 | 0 | 39 | I | -2.0 | 0.18 | 12 | NC | 0 | 0 |
| D78514 | Human mRNA for ubiquitin-conjugating "enzyme," complete cds | 23 | * | 22 | NC | 0 | 0 | 26 | I | 2.1 | 0.18 | 5 | NC | 0 | 0 |
| D86978 | Human mRNA for KIAA0225 "gene," partial cds | 85 | | 14 | NC | 0 | 0 | 66 | I | 1.8 | 0.18 | 39 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| L77886 | Human protein tyrosine phosphatase "mRNA," complete cds | 85 | | 0 | NC | 0 | 0 | 65 | I | 1.8 | 0.18 | -23 | NC | 0 | 0 |
| S82597 | Description: UDP-GalNAc:polypeptide N-acetylgalactosaminyltransferase gene extra | 0 | * | 9 | NC | 0 | 0 | 40 | I | ~2.0 | 0.18 | -1 | NC | 0 | 0 |
| X95384 | H. sapiens mRNA for unknown 14kDa protein | 11 | * | -14 | NC | 0 | 0 | 30 | I | ~2.1 | 0.18 | -6 | NC | 0 | 0 |
| D84361 | Human mRNA for p52 and p64 isoforms of "N-Shc," complete cds | 37 | | -39 | NC | 0 | 0 | -49 | D | ~1.8 | 0.17 | -54 | MD | ~1.8 | 0.18 |
| | | 7968 | | -1139 | NC | 0 | 0 | -1340 | D | 1.2 | 0.17 | -532 | NC | 0 | 0 |
| D86967 | Human mRNA for KIAA0212 "gene," complete cds | 50 | | -6 | NC | 0 | 0 | 44 | MI | 1.9 | 0.17 | 8 | NC | 0 | 0 |
| G3521-HT371 | Ras-Related Protein Rap1b | 81 | | 27 | NC | 0 | 0 | 62 | I | 1.8 | 0.17 | 7 | NC | 0 | 0 |
| K02268 | Human enkephalin B (enkB) "gene," 5' flank and | 13 | | 13 | NC | 0 | 0 | 28 | I | ~2.1 | 0.17 | 23 | NC | 0 | 0 |
| L03532 | Human M4 protein "mRNA," complete cds | 291 | | -35 | NC | 0 | 0 | 150 | I | 1.5 | 0.17 | -48 | NC | 0 | 0 |
| L05624 | Homo sapiens MAP kinase kinase "mRNA," complete cds — Also Represents: L11284 | 112 | | 14 | NC | 0 | 0 | 78 | I | 1.7 | 0.17 | -9 | NC | 0 | 0 |
| L09209 | Homo sapiens amyloid protein homologue "mRNA," complete cds — Also Represents: | 128 | | 22 | NC | 0 | 0 | 86 | MI | 1.7 | 0.17 | 55 | NC | 0 | 0 |
| L78440 | Homo sapiens STAT4 "mRNA," complete cds | 17 | * | 21 | NC | 0 | 0 | 25 | I | ~2.1 | 0.17 | 14 | NC | 0 | 0 |
| M19283 | Human cytoskeletal gamma-actin "gene," complete cds | 2495 | | -252 | NC | 0 | 0 | -582 | D | 1.3 | 0.17 | -305 | NC | 0 | 0 |
| U28749 | Human high-mobility group phosphoprotein isoform I-C (HMGIC) "mRNA," complete | 101 | | -51 | NC | 0 | 0 | 71 | I | 1.7 | 0.17 | -42 | NC | 0 | 0 |
| U73477 | Human acidic nuclear phosphoprotein pp32 "mRNA," complete cds — Also Represent | 41 | | 23 | NC | 0 | 0 | 37 | I | 1.9 | 0.17 | -27 | NC | 0 | 0 |
| U90913 | Human clone 23665 mRNA sequence | 366 | | 151 | NC | 0 | 0 | 178 | I | 1.5 | 0.17 | 134 | NC | 0 | 0 |
| X93499 | H. sapiens mRNA for RAB7 protein | 453 | | -35 | NC | 0 | 0 | 25 | I | 1.5 | 0.17 | -25 | NC | 0 | 0 |
| L35249 | Homo sapiens vacuolar H+-ATPase Mr "56,000" subunit (HO57) "mRNA," complete | 156 | | 106 | NC | 0 | 0 | 206 | I | 1.6 | 0.16 | 204 | I | 2.3 | 0.59 |
| D28423 | Human mRNA for pre-mRNA splicing factor "SRp20," 5'UTR (sequence from the 5'ca | 1179 | | -127 | NC | 0 | 0 | 95 | I | 1.3 | 0.16 | -429 | D | 1.6 | 0.31 |
| D26067 | Human mRNA for KIAA0033 "gene," complete cds | 19 | * | 10 | NC | 0 | 0 | 23 | I | ~2.1 | 0.16 | -3 | NC | 0 | 0 |
| G3076-HT323 | Heterogeneous Nuclear Ribonucleoprotein "K," Alt. Splice 1 — Also Represents: X727 | 702 | | 145 | NC | 0 | 0 | 277 | I | 1.4 | 0.16 | 8 | NC | 0 | 0 |
| J00139 | Human dihydroorotate reductase gene — Also Represents: HG2846-HT2983, J00146 | 46 | | 28 | NC | 0 | 0 | 41 | I | 1.9 | 0.16 | 33 | NC | 0 | 0 |
| L05188 | Homo sapiens small proline-rich protein 2 (SPRR2B) "gene," complete cds | 46 | | -11 | NC | 0 | 0 | -24 | D | 2.1 | 0.16 | -15 | NC | 0 | 0 |
| U24266 | Human pyrroline-5-carboxylate dehydrogenase (P5CDh) "mRNA," long "form," comp | 1 | * | 21 | NC | 0 | 0 | 37 | MI | ~1.9 | 0.16 | 19 | NC | 0 | 0 |
| U29091 | Human selenium-binding protein (hSBP) "mRNA," complete cds. /gb = U29091 /ntype | 36 | | -30 | NC | 0 | 0 | -50 | D | ~1.8 | 0.16 | -30 | NC | 0 | 0 |
| U90915 | Human clone 23600 cytochrome c oxidase subunit IV "mRNA," complete cds | 2579 | | -131 | NC | 0 | 0 | -561 | D | 1.3 | 0.16 | -309 | NC | 0 | 0 |
| X89430 | H. sapiens mRNA for methyl CpG binding protein 2 | 12 | * | 11 | NC | 0 | 0 | 29 | I | ~2.0 | 0.16 | -8 | NC | 0 | 0 |
| X94703 | H. sapiens rab28 mRNA | 6 | * | 1 | NC | 0 | 0 | 33 | I | ~1.9 | 0.16 | -19 | NC | 0 | 0 |
| D13413 | Human mRNA for tumor-associated 120 kDa nuclear protein "p120," partial cds(carb | 5323 | | -575 | NC | 0 | 0 | -937 | D | 1.2 | 0.15 | -1368 | D | 1.3 | 0.31 |
| J04173 | Homo sapiens phosphoglycerate mutase (PGAM-B) "mRNA," complete cds | 1250 | | 25 | NC | 0 | 0 | 390 | I | 1.3 | 0.15 | 409 | I | 1.3 | 0.16 |
| AF007875 | Homo sapiens dolichol monophosphate mannose synthase (DPM1) "mRNA," partial | 94 | | 1 | NC | 0 | 0 | 65 | MI | 1.7 | 0.15 | -45 | NC | 0 | 0 |
| D49489 | Human mRNA for protein disulfide isomerase-related protein "P5," complete cds | 265 | | 111 | NC | 0 | 0 | 135 | I | 1.5 | 0.15 | 43 | NC | 0 | 0 |
| G3075-HT323 | Focal Adhesion Kinase — Also Represents: L13616 | 25 | | -6 | NC | 0 | 0 | 25 | I | 2 | 0.15 | -10 | NC | 0 | 0 |
| L14856 | Human somatostatin receptor "gene," complete cds | 144 | | -42 | NC | 0 | 0 | -60 | MD | 1.7 | 0.15 | -35 | NC | 0 | 0 |
| M14636 | Human liver glycogen phosphorylase "mRNA," complete cds | 23 | | 6 | NC | 0 | 0 | 23 | I | 2 | 0.15 | 5 | NC | 0 | 0 |
| M31724 | Human phosphotyrosyl-protein phosphatase (PTP-1B) "mRNA," complete cds | 74 | | 5 | NC | 0 | 0 | 54 | MI | 1.7 | 0.15 | 34 | NC | 0 | 0 |
| M67468 | Human Fragile X mental retardation 1 FMR-1 "gene," 3' "end," clones BC72 and BC2 | 1 | * | 8 | NC | 0 | 0 | 36 | I | ~1.9 | 0.15 | -2 | NC | 0 | 0 |
| M69181 | Human nonmuscle myosin heavy chain-B (MYH10) mRNA, partial cds. | 80 | | -1 | NC | 0 | 0 | 57 | I | 1.7 | 0.15 | 18 | NC | 0 | 0 |
| U68494 | Human hbc647 mRNA sequence | 35 | | -2 | NC | 0 | 0 | 31 | I | 1.9 | 0.15 | -21 | NC | 0 | 0 |
| X00274 | Human gene for HLA-DR alpha heavy chain a class II antigen (immune response ge | 111 | | -27 | NC | 0 | 0 | -48 | D | 1.8 | 0.15 | 31 | NC | 0 | 0 |
| X97064 | H. sapiens mRNA for Sec23A "isoform," 2748bp | 12 | * | 1 | NC | 0 | 0 | 28 | I | ~2.0 | 0.15 | 3 | NC | 0 | 0 |
| L14754 | Human DNA-binding protein (SMBP2) "mRNA," complete cds | 3 | * | 31 | NC | 0 | 0 | 33 | MI | ~1.8 | 0.14 | 32 | I | 1.3 | 0.13 |
| D00762 | Human mRNA for proteasome subunit HC8 | 199 | | 42 | NC | 0 | 0 | 104 | I | 1.5 | 0.14 | -83 | NC | 0 | 0 |
| D28473 | Human T-lymphocyte mRNA for isoleucyl-tRNA "synthetase," complete cds — Also Re | 451 | | 110 | NC | 0 | 0 | 188 | I | 1.4 | 0.14 | 27 | NC | 0 | 0 |
| G2743-HT284 | Caldesmon "1," Alt. Splice "4," Non-Muscle — "Also Represents: HG2743-HT2843, HG | 24 | | -8 | NC | 0 | 0 | 23 | I | 2 | 0.14 | -13 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| M15796 | Human cyclin protein "gene," complete cds | 105 | | 14 | NC | 0 | 0 | 68 | I | 1.6 | 0.14 | 41 | NC | 0 | 0 |
| M86699 | Human kinase (TTK) "mRNA," complete cds | 3 | * | 2 | NC | 0 | 0 | 34 | MI | -1.8 | 0.14 | 2 | NC | 0 | 0 |
| M95787 | Human 22 kDa smooth muscle protein (SM22) "mRNA," complete cds | 321 | | -44 | NC | 0 | 0 | -110 | D | 1.5 | 0.14 | -73 | NC | 0 | 0 |
| U20530 | Human bone phosphoprotein spp-24 precursor "mRNA," complete cds. /gb = U20530 | 38 | * | 4 | NC | 0 | 0 | -31 | MD | -1.9 | 0.14 | -18 | NC | 0 | 0 |
| X12953 | Human rab2 "mRNA," YPT1-related and member of ras family | 109 | | -11 | NC | 0 | 0 | 67 | I | 1.6 | 0.14 | -24 | NC | 0 | 0 |
| Z47727 | H. sapiens mRNA for RNA polymerase II subunit | 193 | | -9 | NC | 0 | 0 | 103 | I | 1.5 | 0.13 | -38 | NC | 0 | 0 |
| U91297 | Human chromosome 12p15 BAC clone CIT987SK-99D8 complete sequence. /gb = U9 | 689 | | -127 | NC | 0 | 0 | 239 | I | 1.3 | 0.13 | -280 | D | 1.7 | 0.31 |
| M29536 | Human translational initiation factor 2 beta subunit (eIF-2-beta) "mRNA," complete cd | 369 | | -23 | NC | 0 | 0 | 151 | I | 1.4 | 0.13 | -166 | D | 1.8 | 0.3 |
| L49380 | Homo sapiens clone B4 transcription factor ZFM1 "mRNA," complete cds | 358 | | 68 | NC | 0 | 0 | 151 | I | 1.4 | 0.13 | 206 | I | 1.6 | 0.22 |
| L32976 | Human protein kinase (MLK-3) "mRNA," complete cds | 44 | * | 25 | NC | 0 | 0 | 34 | I | 1.8 | 0.13 | 35 | I | 1.8 | 0.14 |
| D26598 | Human mRNA for proteasome subunit "HsC10-II," complete cds | 1869 | | 90 | NC | 0 | 0 | -398 | D | 1.3 | 0.13 | 173 | NC | 0 | 0 |
| D89289 | Human mRNA for "N-Acetyl-beta-D-glucosaminide," complete cds | 42 | | -3 | NC | 0 | 0 | 34 | I | 1.8 | 0.13 | 3 | NC | 0 | 0 |
| L40392 | Homo sapiens (clone S164) "mRNA," 3' end of cds | 15 | * | 11 | NC | 0 | 0 | 23 | MI | -1.9 | 0.13 | -2 | NC | 0 | 0 |
| M37075 | Human embryonic/atrial myosin light chain (MLC-1-emb/A isoform) gene | 35 | | -26 | NC | 0 | 0 | -39 | D | -1.7 | 0.13 | -5 | NC | 0 | 0 |
| M86667 | H. sapiens NAP (nucleosome assembly protein) "mRNA," complete cds | 432 | | -75 | NC | 0 | 0 | 169 | I | 1.4 | 0.13 | -106 | NC | 0 | 0 |
| S79522 | ubiquitin carboxyl extension protein "[human,", "mRNA," 540 nt] | 2912 | | -257 | NC | 0 | 0 | -554 | D | 1.2 | 0.13 | -896 | NC | 0 | 0 |
| U15128 | Human "beta-1,2-N-acetylglucosaminyltransferase" II (MGAT2) "gene," complete cds | 50 | | -14 | NC | 0 | 0 | -24 | D | 1.9 | 0.13 | 2 | NC | 0 | 0 |
| U28963 | Human Gps2 (GPS2) "mRNA," complete cds | 197 | | -20 | NC | 0 | 0 | -72 | D | 1.6 | 0.13 | -6 | NC | 0 | 0 |
| U41668 | Human deoxyguanosine kinase "mRNA," complete cds | 239 | | -39 | NC | 0 | 0 | -83 | D | 1.5 | 0.13 | -33 | NC | 0 | 0 |
| U77718 | Human desmosome associated protein pinin "mRNA," complete cds | 20 | * | -26 | NC | 0 | 0 | 20 | I | -2.0 | 0.13 | -21 | NC | 0 | 0 |
| X70944 | H. sapiens mRNA for PTB-associated splicing factor — Also Represents: X16850 | 319 | | -38 | NC | 0 | 0 | 140 | I | 1.4 | 0.13 | 22 | NC | 0 | 0 |
| Y10571 | H. sapiens mRNA for dinG gene | 0 | | 14 | NC | 0 | 0 | 36 | I | -1.8 | 0.13 | 12 | NC | 0 | 0 |
| D63874 | Human mRNA for "HMG-1," complete cds | 711 | | -145 | NC | 0 | 0 | 236 | I | 1.3 | 0.12 | -323 | D | 1.8 | 0.43 |
| G1612-HT16 | Macmarcks | 273 | | 32 | NC | 0 | 0 | 118 | I | 1.4 | 0.12 | 204 | I | 1.7 | 0.3 |
| M84711 | Human v-fos transformation effector protein "(Fte-1)," mRNA complete cds | 4735 | | -403 | NC | 0 | 0 | -757 | D | 1.2 | 0.12 | -1075 | D | 1.3 | 0.23 |
| L37127 | Homo sapiens (clone mf.18) RNA polymerase II "mRNA," complete cds | 270 | | 62 | NC | 0 | 0 | 119 | I | 1.4 | 0.12 | 149 | MI | 1.6 | 0.18 |
| D85758 | Human mRNA for human protein homologous to DROER "protein," complete cds | 481 | | 38 | NC | 0 | 0 | 173 | I | 1.4 | 0.12 | 39 | MI | 1.1 | 0.01 |
| AB000449 | Human mRNA for "VRK1," complete cds | 13 | * | 42 | NC | 0 | 0 | 25 | I | -1.9 | 0.12 | -5 | NC | 0 | 0 |
| D29641 | Human mRNA for KIAA0052 "gene," partial cds | 30 | | 4 | NC | 0 | 0 | 25 | I | 1.8 | 0.12 | -11 | NC | 0 | 0 |
| D78129 | Human adult (34 year old) Male liver mRNA for squalene "epoxidase," partial cds. /gb | 56 | | 0 | NC | 0 | 0 | 38 | I | 1.7 | 0.12 | 5 | NC | 0 | 0 |
| G4518-HT492 | Transcription Factor BtfII Homolog (Gb:M90355) | 40 | | -17 | NC | 0 | 0 | 30 | I | 1.8 | 0.12 | 4 | NC | 0 | 0 |
| J00314 | Human beta-tubulin "gene," clone m40 | 460 | | -12 | NC | 0 | 0 | 170 | I | 1.8 | 0.12 | 74 | NC | 0 | 0 |
| L24774 | Homo sapiens "delta.3," delta2-CoA-isomerase "mRNA," 3' end — "Also Represents: Z | 217 | | 3 | NC | 0 | 0 | -74 | MI | 1.5 | 0.12 | -22 | NC | 0 | 0 |
| M93651 | Human set "gene," complete cds | 416 | | 59 | NC | 0 | 0 | 158 | I | 1.4 | 0.12 | -60 | NC | 0 | 0 |
| X07384 | Human mRNA for GLI protein | -10 | | -20 | NC | 0 | 0 | 43 | I | -1.7 | 0.12 | 24 | NC | 0 | 0 |
| X83703 | H. sapiens mRNA for cytokine inducible nuclear protein | 17 | * | 5 | NC | 0 | 0 | 21 | MI | -1.9 | 0.12 | -14 | NC | 0 | 0 |
| Y10511 | H. sapiens mRNA for CD176 protein. /gb = Y10511 /ntype = RNA | 34 | | -21 | NC | 0 | 0 | -36 | MD | -1.7 | 0.12 | -23 | NC | 0 | 0 |
| Z35085 | H. sapiens mRNA for unknown antigen — Also Represents: D86958 | 9 | * | 1 | NC | 0 | 0 | 27 | I | -1.8 | 0.12 | 4 | NC | 0 | 0 |
| X15341 | Human COX Via-L mRNA for cytochrome c oxidase liver-specific subunit Via (EC 1.9 | 2866 | | -55 | NC | 0 | 0 | -516 | MD | 1.2 | 0.11 | -556 | D | 1.2 | 0.13 |
| Y07755 | H. sapiens S100A2 "gene," exon "1," 2 and 3 | 1157 | | 70 | NC | 0 | 0 | -264 | D | 1.3 | 0.11 | 241 | I | 1.2 | 0.07 |
| Z50853 | H. sapiens mRNA for CLPP | 397 | | 3 | NC | 0 | 0 | 145 | I | 1.4 | 0.11 | 111 | I | 1.3 | 0.07 |
| D14678 | Human mRNA for kinesin-related "protein," partial cds | 7 | * | 26 | NC | 0 | 0 | 28 | I | -1.7 | 0.11 | 13 | NC | 0 | 0 |
| D14878 | Human mRNA for protein "D123," complete cds | 246 | | 24 | NC | 0 | 0 | 104 | I | 1.4 | 0.11 | -81 | NC | 0 | 0 |
| L33881 | Human protein kinase C iota "isoform," complete cds | 23 | | -2 | NC | 0 | 0 | 20 | I | 1.8 | 0.11 | -6 | NC | 0 | 0 |
| L40388 | Homo sapiens thyroid receptor interactor (TRIP15) "mRNA," 5' end of cds. /gb = L403 | -7 | | 18 | I | ~-1.0 | 0 | 39 | I | -1.6 | 0.11 | 2 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| L40397 | *Homo sapiens* (clone S311125) "mRNA," 3' end of cds | 441 | | 117 | NC | 0 | 0 | 158 | I | 1.4 | 0.11 | −23 | NC | 0 | 0 |
| L41939 | *Homo sapiens* (clone FBK III 11c) protein-tyrosine kinase (DRT) "mRNA," complete c | 65 | * | 30 | NC | 0 | 0 | 40 | MI | 1.6 | 0.11 | 20 | NC | 0 | 0 |
| M14123 | neutral protease large subunit from Human endogenous retrovirus HERV-K10. /gb = M | 35 | * | −22 | NC | 0 | 0 | −28 | D | −1.7 | 0.11 | 4 | NC | 0 | 0 |
| U09584 | Human PL6 protein (PL6) "mRNA," complete cds | 133 | | −26 | NC | 0 | 0 | −50 | MD | 1.6 | 0.11 | −16 | NC | 0 | 0 |
| X54941 | *H. sapiens* ckshs1 mRNA for Cks1 protein homologue | 814 | | 94 | NC | 0 | 0 | −198 | MD | 1.3 | 0.11 | 87 | NC | 0 | 0 |
| X58528 | Human PMP70 mRNA for a peroxisomal membrane protein — "Also Represents: M81 | 11 | * | 4 | NC | 0 | 0 | 25 | I | −1.8 | 0.11 | −5 | NC | 0 | 0 |
| Y13115 | *Homo sapiens* mRNA for serine/threonine protein kinase SAK | 43 | | 10 | NC | 0 | 0 | 31 | I | 1.7 | 0.11 | −14 | NC | 0 | 0 |
| Y00486 | adenine phosphoribosyltransferase (aprt) gene extracted from Human APRT gene to | 842 | | 10 | NC | 0 | 0 | 235 | MI | 1.3 | 0.1 | 246 | I | 1.3 | 0.11 |
| D38122 | Human mRNA for Fas "ligand," complete cds | 33 | | −16 | NC | 0 | 0 | −30 | D | −1.7 | 0.1 | −27 | D | −1.7 | 0.09 |
| D13435 | Human mRNA for PIG-F (phosphatidyl-inositol-glycan class "F)," complete cds | 25 | | 30 | NC | 0 | 0 | 19 | I | 1.8 | 0.1 | 14 | NC | 0 | 0 |
| D25274 | Human randomly sequenced mRNA | 733 | | −7 | NC | 0 | 0 | 210 | I | 1.3 | 0.1 | 68 | NC | 0 | 0 |
| D86979 | Human mRNA for KIAA0026 "gene," complete cds | 114 | | 23 | NC | 0 | 0 | 57 | I | 1.5 | 0.1 | −32 | NC | 0 | 0 |
| L10678 | Human profilin II "mRNA," complete cds | 588 | | 74 | NC | 0 | 0 | 184 | I | 1.3 | 0.1 | 135 | NC | 0 | 0 |
| M37755 | Human pregnancy-specific beta-1-glycoprotein gene PSGGA | 49 | | 2 | NC | 0 | 0 | 31 | I | 1.6 | 0.1 | 8 | NC | 0 | 0 |
| M86934 | Human GS1 (protein of unknown function) "mRNA," complete cds | 95 | | −8 | NC | 0 | 0 | −37 | D | 1.6 | 0.1 | −19 | NC | 0 | 0 |
| S78234 | nuc2 homolog "[human," "fibroblasts]," "3320 nt]" | 25 | | −3 | NC | 0 | 0 | 20 | MI | 1.8 | 0.1 | −13 | NC | 0 | 0 |
| X65633 | *H. sapiens* ACTH-R gene for adrenocorticotropic hormone receptor | −48 | | 31 | NC | 0 | 0 | 77 | I | −1.5 | 0.1 | 68 | MI | −1.0 | 0.29 |
| U46570 | Human tetratricopeptide repeat protein (tpr1) "mRNA," complete cds | 450 | | −144 | NC | 0 | 0 | −114 | D | 1.3 | 0.09 | −191 | D | 1.7 | 0.19 |
| D13315 | Human mRNA for lactoyl glutathion lyase | 504 | | 7 | NC | 0 | 0 | 155 | I | 1.3 | 0.09 | −176 | D | 1.5 | 0.09 |
| D12620 | Human mRNA for cytochrome P-450LTBV — Also Represents: U02388 | −10 | | 18 | NC | 0 | 0 | 41 | MI | −1.5 | 0.09 | 41 | I | −1.6 | 0.09 |
| Z93784 | *Homo sapiens* DNA sequence from PAC 398C22 on chromosome 22q11.2-qter. Con | 125 | | 43 | NC | 0 | 0 | 59 | MI | 1.5 | 0.09 | 56 | MI | 1.4 | 0.08 |
| L19183 | Human MAC30 "mRNA," 3' end | 35 | | 14 | NC | 0 | 0 | 24 | MI | 1.4 | 0.09 | 17 | I | 1.5 | 0.05 |
| D13643 | Human mRNA for KIAA0018 "gene," complete cds | 227 | | 64 | NC | 0 | 0 | 87 | I | 1.7 | 0.09 | 70 | NC | 0 | 0 |
| D86957 | Human mRNA for KIAA0202 "gene," partial cds | 31 | * | −18 | NC | 0 | 0 | 22 | I | 1.2 | 0.09 | 3 | NC | 0 | 0 |
| G3514-HT370 | Tropomyosin "Tm30nm," Cytoskeletal | 910 | | 119 | NC | 0 | 0 | 224 | I | 1.4 | 0.09 | −27 | NC | 0 | 0 |
| J04543 | Human synexin "mRNA," complete cds | 136 | | 15 | NC | 0 | 0 | 61 | I | 1.4 | 0.09 | −15 | NC | 0 | 0 |
| L08246 | Human myeloid cell differentiation protein (MCL1) mRNA | 210 | | −13 | NC | 0 | 0 | 85 | I | 1.4 | 0.09 | −6 | NC | 0 | 0 |
| L10338 | Human sodium channel beta-1 subunit (SCN1B) "mRNA," complete cds — "Also Repr | 117 | | −14 | NC | 0 | 0 | −40 | MD | 1.5 | 0.09 | −14 | NC | 0 | 0 |
| L13689 | Human microtubule-associated protein 1a (MAP1A) genomic sequence | 15 | * | −1 | NC | 0 | 0 | 20 | I | −1.7 | 0.09 | 20 | NC | 0 | 0 |
| L19779 | Human integrin-linked kinase (ILK) "mRNA," complete cds | 134 | | −4 | NC | 0 | 0 | 26 | MI | 1.4 | 0.09 | 6 | NC | 0 | 0 |
| M22632 | *Homo sapiens* histone H2A.2 "mRNA," complete cds | 517 | | 81 | NC | 0 | 0 | 60 | MI | 1.3 | 0.09 | 30 | NC | 0 | 0 |
| M76665 | Human mitochondrial aspartate aminotransferase "mRNA," complete cds | 48 | | 81 | NC | 0 | 0 | 157 | I | 1.3 | 0.09 | 59 | NC | 0 | 0 |
| M99439 | Human 11-beta-hydroxysteroid dehydrogenase (HSD11) gene | 26 | * | −2 | NC | 0 | 0 | −20 | D | 1.7 | 0.09 | −13 | NC | 0 | 0 |
| U04847 | Human transducin-like enhancer protein (TLE4) "mRNA," 3' end | 32 | | 2 | NC | 0 | 0 | 20 | MI | 1.8 | 0.09 | 2 | NC | 0 | 0 |
| U38175 | Human ini1 "mRNA," complete cds | 107 | | −19 | NC | 0 | 0 | −37 | D | −1.6 | 0.09 | −19 | NC | 0 | 0 |
| U38276 | Human HuR RNA binding protein (HuR) "mRNA," complete cds | 128 | | −34 | NC | 0 | 0 | −38 | MD | 1.6 | 0.09 | −2 | NC | 0 | 0 |
| U38291 | Human semaphorin III family homolog "mRNA," complete cds | 15 | * | −18 | NC | 0 | 0 | −43 | MD | 1.5 | 0.09 | −17 | NC | 0 | 0 |
| U40282 | Human clone 23773 mRNA sequence | 446 | | −56 | NC | 0 | 0 | 20 | I | −1.7 | 0.09 | 20 | NC | 0 | 0 |
| U90004 | *H. sapiens* ADE2H1 mRNA showing homologies to SAICAR synthetase and AIR carb | 217 | | −54 | NC | 0 | 0 | −114 | D | 1.3 | 0.09 | −49 | NC | 0 | 0 |
| X53793 | *H. sapiens* mRNA for ATP-citrate lyase | 334 | | 16 | NC | 0 | 0 | 83 | I | 1.4 | 0.09 | −50 | NC | 0 | 0 |
| X64330 | *H. sapiens* mRNA for p0071 protein | 828 | | 161 | NC | 0 | 0 | 112 | MI | 1.3 | 0.09 | 149 | NC | 0 | 0 |
| X80910 | *H. sapiens* mRNA for PPP1CB mRNA | 14 | | 0 | NC | 0 | 0 | −184 | D | 1.3 | 0.09 | −11 | NC | 0 | 0 |
| X81889 | *H. sapiens* mRNA for RNA helicase (Myc-regulated dead box protein) | 0 | | 10 | NC | 0 | 0 | 20 | I | −1.7 | 0.09 | 19 | NC | 0 | 0 |
| X98743 | *H. sapiens* mRNA for SRP1-like "protein," partial — Also Represents: AB002533 | 88 | | −28 | NC | 0 | 0 | 32 | I | −1.6 | 0.09 | −5 | NC | 0 | 0 |
| Y12393 | | 45 | | −10 | NC | 0 | 0 | 28 | MI | 1.6 | 0.09 | 1 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| Z24725 | *H. sapiens* mitogen inducible gene "mig-2," complete CDS | 170 | | 48 | NC | 0 | 0 | 72 | I | 1.4 | 0.09 | 52 | NC | 0 | 0.14 |
| Z48501 | *H. sapiens* mRNA for polyadenylate binding protein II. /gb = Z48501 /ntype = RNA — "Als | 1105 | | -192 | NC | 0 | 0 | 260 | I | 1.2 | 0.09 | -69 | NC | 0 | 0.13 |
| D14812 | Human mRNA for KIAA0026 "gene," complete cds | 695 | | -29 | NC | 0 | 0 | 183 | I | 1.3 | 0.08 | -199 | D | 1.4 | 0.14 |
| Y10659 | *H. sapiens* IL-13Ra mRNA | 10 | | 8 | NC | 0 | 0 | 23 | I | -1.7 | 0.08 | 27 | MI | -1.9 | 0.13 |
| L08132 | Human voltage-dependent anion channel isoform 1 (VDAC) "mRNA," complete cds | 581 | | 130 | NC | 0 | 0 | 161 | I | 1.3 | 0.08 | 159 | I | 1.3 | 0.08 |
| G3971-HT424 | Transcription Factor (Gb:L32162) | 14 | * | -17 | NC | 0 | 0 | 20 | MI | -1.7 | 0.08 | 13 | MI | -1.3 | 0.03 |
| U63825 | Human hepatitis delta antigen interacting protein A (dipA) "mRNA," complete cds | 413 | | -31 | NC | 0 | 0 | -100 | MD | 1.3 | 0.08 | 62 | MI | 1.2 | 0.03 |
| D11094 | Human mRNA for "MSS1," complete cds | 246 | | 95 | NC | 0 | 0 | 85 | MI | 1.3 | 0.08 | -40 | NC | 0 | 0 |
| D84294 | Human mRNA for "TPRDI," complete cds | 7 | * | -5 | NC | 0 | 0 | 25 | I | -1.6 | 0.08 | 3 | NC | 0 | 0 |
| HG662-HT662 | Epstein-Barr Virus Small Rna-Associated Protein | 622 | | 22 | NC | 0 | 0 | 159 | I | 1.3 | 0.08 | -101 | NC | 0 | 0 |
| L07493 | *Homo sapiens* replication protein A 14 kDa subunit (RPA) "mRNA," complete cds | 54 | | 4 | I | 1.1 | | 30 | I | 1.6 | 0.08 | 4 | I | 1.1 | 0 |
| L23808 | Human metalloproteinase (HME) "mRNA," complete cds | -10 | * | 9 | NC | 0 | 0 | 40 | I | -1.5 | 0.08 | 17 | I | -1.0 | 0 |
| M30496 | Human ubiquitin carboxyl-terminal hydrolase (PGP "9.5," UCH-L3) isozyme L3 "mRN | 102 | | -10 | NC | 0 | 0 | 46 | MI | 1.5 | 0.08 | -33 | NC | 0 | 0 |
| U24704 | Human antisecretory factor-1 "mRNA," complete cds | 376 | | -22 | NC | 0 | 0 | -95 | D | 1.5 | 0.08 | -42 | NC | 0 | 0 |
| U34252 | Human gamma-aminobutyraldehyde dehydrogenase "mRNA," complete cds | 173 | | -22 | NC | 0 | 0 | -54 | I | 1.5 | 0.08 | -23 | NC | 0 | 0 |
| U35451 | Human heterochromatin protein p25 "mRNA," complete cds | 58 | | -3 | NC | 0 | 0 | 30 | MI | 1.5 | 0.08 | -4 | NC | 0 | 0 |
| U42412 | Human 5'-AMP-activated protein "kinase," gamma-1 subunit "mRNA," complete cds | 256 | | -13 | NC | 0 | 0 | -70 | D | 1.4 | 0.08 | 21 | NC | 0 | 0 |
| U73704 | *Homo sapiens* 48 kDa FKBP-associated protein FAP48 "mRNA," complete cds | 17 | * | 1 | NC | 0 | 0 | 18 | I | -1.7 | 0.08 | -3 | NC | 0 | 0 |
| X04347 | Human liver mRNA fragment DNA binding protein UP1 homologue (C-terminus) — "Als | 1526 | | -43 | NC | 0 | 0 | 313 | I | 1.2 | 0.08 | -98 | NC | 0 | 0 |
| X05360 | Human CDC2 gene involved in cell cycle control | 69 | | 26 | NC | 0 | 0 | 35 | I | 1.5 | 0.08 | -13 | NC | 0 | 0 |
| X74987 | *H. sapiens* mRNA for 2'-5' oligoadenylate binding protein — Also Represents: X76388 | 7 | * | 21 | NC | 0 | 0 | 26 | MI | -1.6 | 0.08 | 3 | NC | 0 | 0 |
| X98482 | *H. sapiens* TNNT2 gene exon 11 /gb = X98482 /ntype = DNA /annot = mRNA | 1432 | | 105 | NC | 0 | 0 | 275 | I | 1.2 | 0.07 | 729 | I | 1.5 | 0.36 |
| AB004884 | Human mRNA for "PKU-alpha," partial cds. /gb = AB004884 /ntype = RNA | 62 | | -18 | NC | 0 | 0 | 30 | MI | 1.5 | 0.07 | -36 | D | 2.3 | 0.26 |
| | | 104 | | 49 | NC | 0 | 0 | 42 | MI | 1.4 | 0.07 | -6 | NC | 0 | 0 |
| D86550 | Human mRNA for serine/threonine protein "kinase," complete cds | 40 | * | -23 | NC | 0 | 0 | 21 | I | 1.5 | 0.07 | -5 | NC | 0 | 0 |
| D87466 | Human mRNA for KIAA0276 "gene," partial cds | 9 | * | 4 | NC | 0 | 0 | 23 | I | -1.6 | 0.07 | -2 | NC | 0 | 0 |
| G4716-HT515 | Guanosine 5'-Monophosphate Synthase | 401 | | -21 | NC | 0 | 0 | 115 | MI | 1.3 | 0.07 | -25 | NC | 0 | 0 |
| M19507 | Human myeloperoxidase "mRNA," complete cds | 30 | | -34 | NC | 0 | 0 | -33 | D | -1.5 | 0.07 | -22 | NC | 0 | 0 |
| S66793 | X-arrestin = S-antigen homolog "[human," "retina," "mRNA," 1314 nt] | 31 | | -25 | NC | 0 | 0 | -20 | D | -1.6 | 0.07 | -19 | NC | 0 | 0 |
| U03105 | Human B4-2 protein "mRNA," complete cds | 30 | | -2 | NC | 0 | 0 | -25 | D | -1.5 | 0.07 | -19 | NC | 0 | 0 |
| U15172 | Human Nip1 (NIP1) "mRNA," complete cds | 105 | | -13 | NC | 0 | 0 | -34 | MD | 1.5 | 0.07 | -8 | NC | 0 | 0 |
| U43077 | Human CDC37 homolog "mRNA," complete cds | 746 | | -79 | NC | 0 | 0 | -146 | D | 1.2 | 0.07 | -5 | NC | 0 | 0 |
| U46751 | Human phosphotyrosine independent ligand p62 for the Lck SH2 domain "mRNA," c | 2103 | | -350 | NC | 0 | 0 | -327 | D | 1.2 | 0.07 | -275 | D | 1.5 | 0.38 |
| X52022 | *H. sapiens* RNA for type VI collagen alpha3 chain | 1509 | | -247 | NC | 0 | 0 | 291 | I | 1.2 | 0.07 | -273 | NC | 0 | 0 |
| M64716 | Human ribosomal protein S25 "mRNA," complete cds | 3426 | | -580 | NC | 0 | 0 | -419 | D | 1.1 | 0.06 | -1074 | D | 1.5 | 0.24 |
| M91670 | Human ubiquitin carrier protein (E2-EPF) "mRNA," complete cds | 903 | | 213 | NC | 0 | 0 | 172 | I | 1.2 | 0.06 | 418 | I | 1.5 | 0.11 |
| U87459 | Human autoimmunogenic cancer/testis antigen NY-ESO-1 "mRNA," complete cds | 2224 | | -392 | NC | 0 | 0 | -306 | D | 1.2 | 0.06 | -413 | D | 1.2 | 0.07 |
| | | 8864 | | -200 | NC | 0 | 0 | 844 | I | 1.1 | 0.06 | 911 | I | 1.1 | |
| D43950 | Human mRNA for KIAA0098 "gene," partial cds | -14 | * | 34 | NC | 0 | 0 | 42 | I | -1.4 | 0.06 | 25 | NC | 0 | 0 |
| G4102-HT437 | N-Ethylmaleimide-Sensitive Factor | 124 | | 48 | NC | 0 | 0 | -37 | D | 1.2 | 0.06 | -11 | NC | 0 | 0 |
| | | 1091 | | 148 | NC | 0 | 0 | 203 | I | 1.6 | 0.06 | -29 | NC | 0 | 0 |
| J04988 | Human 90 kD heat shock protein "gene," complete cds | 32 | | -3 | NC | 0 | 0 | 18 | I | 1.2 | 0.06 | -5 | NC | 0 | 0 |
| J05106 | Human (clone pA3) protein disulfide isomerase related protein (ERp72) "mRNA," com | 2184 | | -335 | NC | 0 | 0 | 340 | I | 1.2 | 0.06 | -692 | D | -1.0 | 0 |
| | | 4 | | 20 | NC | 0 | 0 | 26 | I | -1.5 | 0.06 | 11 | I | | |

TABLE 4-continued

ISGs and IRGs identified from human fibrosarcoma cells incubated in IFN-α, IFN-β or IFN-γ

| GenBank Accession. | Entrez Definition — Afix Definition | B = A | Untreated Intensity | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| L05425 | Homo sapiens autoantigen "mRNA," complete cds | | 53 | −34 | NC | 0 | 0 | 24 | MI | 1.4 | 0.06 | −20 | NC | 0 | 0 |
| L24203 | Homo sapiens ataxia-telangiectasia group D-associated protein "mRNA," complete cds | * | −2 | 30 | NC | 0 | 0 | 31 | MI | −1.4 | 0.06 | 5 | NC | 0 | 0 |
| L42542 | Human RLIP76 protein "mRNA," complete cds | | 48 | −13 | NC | 0 | 0 | 23 | I | 1.5 | 0.06 | −18 | NC | 0 | 0 |
| L49229 | Homo sapiens retinoblastoma susceptibility protein (RB1) "gene," with a 3 bp deletion | * | 0 | 3 | NC | 0 | 0 | 29 | MI | −1.5 | 0.06 | −6 | NC | 0 | 0 |
| M74096 | Human long chain acyl-CoA dehydrogenase (ACADL) "mRNA," complete cds | * | −2 | 3 | NC | 0 | 0 | 31 | I | −1.4 | 0.06 | 6 | NC | 0 | 0 |
| S77763 | nuclear factor erythroid 2 isoform t = basic leucine zipper protein (alternatively "spliced | | 27 | −2 | NC | 0 | 0 | −42 | D | −1.4 | 0.06 | −16 | NC | 0 | 0 |
| U26424 | Human Ste20-like kinase (MST2) "mRNA," complete cds | | 8 | 2 | NC | 0 | 0 | 21 | I | −1.5 | 0.06 | 2 | NC | 0 | 0 |
| U45982 | Human G protein-coupled receptor GPR-9-6 "gene," complete cds | | 81 | −19 | NC | 0 | 0 | −25 | MD | 1.4 | 0.06 | −20 | NC | 0 | 0 |
| U50196 | Human adenosine kinase "mRNA," complete cds | | 98 | 12 | NC | 0 | 0 | 38 | MI | 1.4 | 0.06 | −27 | NC | 0 | 0 |
| U60205 | Human methyl sterol oxidase (ERG25) "mRNA," complete cds | | 29 | 8 | NC | 0 | 0 | −31 | D | −1.5 | 0.06 | 22 | NC | 0 | 0 |
| X66087 | H. sapiens a-myb mRNA | | 5 | 7 | NC | 0 | 0 | 24 | I | −1.4 | 0.06 | 1 | NC | 0 | 0 |
| X69962 | H. sapiens FMR-1 mRNA — "Also Represents: S65791, L29074__ma2, L29074__ma4, L | | 5 | −1 | NC | 0 | 0 | 25 | I | −1.5 | 0.06 | −1 | NC | 0 | 0 |
| X77794 | H. sapiens mRNA for cyclin G1 | | 143 | 33 | NC | 0 | 0 | 48 | I | 1.3 | 0.05 | −15 | NC | 0 | 0 |
| X99459 | H. sapiens mRNA for sigma 3B protein | | 226 | 50 | NC | 0 | 0 | 63 | MI | 1.3 | 0.05 | 126 | I | 1.6 | 0.17 |
| J03827 | Y box binding protein-1 (YB-1) mRNA | | 2530 | −366 | NC | 0 | 0 | 317 | I | 1.1 | 0.05 | −550 | D | 1.3 | 0.15 |
| U70439 | Human silver-stainable protein SSP29 "mRNA," complete cds — Also Represents: Y0 | | 1273 | −262 | NC | 0 | 0 | 201 | I | 1.2 | 0.05 | −271 | MD | 1.3 | 0.1 |
| D63851 | Human visinin-like peptide 1 homolog "mRNA," complete cds | | 61 | 11 | NC | 0 | 0 | 25 | I | 1.4 | 0.05 | 30 | I | 1.5 | 0.07 |
| U52101 | Human YMP "mRNA," complete cds | | 1093 | −65 | NC | 0 | 0 | −154 | D | 1.4 | 0.05 | 198 | I | 1.2 | 0.06 |
| U80012 | Human mRNA for KIAA0190 "gene," partial cds | | 106 | 21 | NC | 0 | 0 | 37 | I | 1.4 | 0.05 | 6 | NC | 0 | 0 |
| HG110-HT110 | Heterogeneous Nuclear Ribonucleoprotein A/B — Also Represents: U76713 | | 1109 | −1 | NC | 0 | 0 | 178 | I | 1.2 | 0.05 | −153 | NC | 0 | 0 |
| G2825-HT294 | Het Transforming Gene | | 111 | −14 | NC | 0 | 0 | 38 | I | 1.3 | 0.05 | 18 | NC | 0 | 0 |
| L05424 | CD44 gene (cell surface glycoprotein CD44) extracted from Human hyaluronate rece | | −2 | 4 | NC | 0 | 0 | 30 | I | −1.4 | 0.05 | −2 | NC | 0 | 0 |
| L36645 | Homo sapiens receptor protein-tyrosine kinase (HEK8) "mRNA," complete cds | | 13 | 11 | NC | 0 | 0 | 16 | MI | −1.5 | 0.05 | 1 | NC | 0 | 0 |
| S67970 | ZNF75 = KRAB zinc finger "human," lung "fibroblast," "mRNA," 1563 nt] | * | −2 | 5 | NC | 0 | 0 | 29 | I | −1.4 | 0.05 | −8 | NC | 0 | 0 |
| U14747 | Human visinin-like peptide 1 homolog "mRNA," complete cds | | −16 | 10 | NC | 0 | 0 | 42 | I | −1.3 | 0.05 | 16 | NC | 0 | 0 |
| U46025 | Human translation initiation factor eIF-3 p110 subunit "gene," complete cds | | 1477 | −171 | NC | 0 | 0 | 212 | I | 1.1 | 0.05 | 76 | NC | 0 | 0 |
| U47621 | Human nucleotar autoantigen No55 "mRNA," complete cds | | 207 | 9 | NC | 0 | 0 | −46 | D | 1.3 | 0.05 | −5 | NC | 0 | 0 |
| U53446 | Human mitogen-responsive phosphoprotein DOC-2 "mRNA," complete cds | | 51 | −26 | NC | 0 | 0 | −16 | D | 1.2 | 0.05 | −23 | NC | 0 | 0 |
| X03473 | Human gene for histone H1(0) | * | −7 | 22 | I | ~1.0 | 0 | 34 | I | 1.4 | 0.05 | 19 | NC | 0 | 0 |
| X87241 | H. sapiens mRNA for hFat protein | | 96 | −19 | NC | 0 | 0 | 24 | I | −1.4 | 0.05 | 41 | I | 1.4 | 0.35 |
| U79258 | Human clone 23732 "mRNA," partial cds. | * | 2 | 2 | NC | 0 | 0 | 24 | I | −1.3 | 0.04 | 49 | I | −2.5 | 0.12 |
| L08666 | Homo sapiens porin (por) "mRNA," complete cds and truncated cds | | 627 | 101 | NC | 0 | 0 | 110 | MI | 1.2 | 0.04 | 210 | I | 1.3 | 0.12 |
| S81914 | IEX-1 = radiation-inducible immediate-early gene "[human]," "placenta," mRNA "Partial | | 644 | 0 | NC | 0 | 0 | −104 | D | −1.3 | 0.04 | −131 | MD | 1.3 | 0.07 |
| Z23064 | H. sapiens mRNA gene for hnRNP G protein | | 267 | 42 | NC | 0 | 0 | 56 | I | 1.2 | 0.04 | 75 | MI | 1.3 | 0.06 |
| L13923 | Homo sapiens fibrillin "mRNA," complete cds | | 39 | 1 | NC | 0 | 0 | 16 | MI | 1.4 | 0.04 | 10 | MI | 1.3 | 0.02 |
| D16815 | Human mRNA for "EAR-1r," complete cds | | 0 | −4 | NC | 0 | 0 | 26 | I | −1.3 | 0.04 | 1 | NC | 0 | 0 |
| G1879-HT191 | Ras-Like Protein Tc10 | | 37 | −25 | NC | 0 | 0 | 16 | MI | 1.4 | 0.04 | −21 | NC | 0 | 0 |
| L11284 | Homosapiens ERK activator kinase (MEK1) mRNA | | 170 | 14 | NC | 0 | 0 | 41 | I | 1.2 | 0.04 | 45 | NC | 0 | 0 |
| L22009 | Human hnRNP H "mRNA," complete cds | | 212 | −90 | NC | 0 | 0 | 51 | I | 1.2 | 0.04 | −21 | NC | 0 | 0 |
| L32179 | Human arylacetamide deacetylase "mRNA," complete cds | | 26 | −5 | NC | 0 | 0 | −24 | D | −1.3 | 0.04 | −12 | NC | 0 | 0 |
| M61827 | Human leukosialin (CD43) "gene," complete cds — "Also Represents: J04168, J04536 | * | 81 | −7 | NC | 0 | 0 | −21 | D | 1.2 | 0.04 | −2 | NC | 0 | 0 |
| U03494 | Homo sapiens transcription factor LSF "mRNA," complete cds | | 27 | −12 | NC | 0 | 0 | −22 | MD | 1.4 | 0.04 | −17 | NC | 0 | 0 |
| U38845 | Human ARF-activated phosphatidylcholine-specific phospholipase D1a (hPLD1) "mR | | 25 | −31 | NC | 0 | 0 | −40 | D | −1.4 | 0.04 | −15 | NC | 0 | 0 |
| U78525 | Human eukaryotic translation initiation factor (eIF3) "mRNA," complete cds | | 736 | −66 | NC | 0 | 0 | 113 | I | −1.3 | 0.04 | −86 | NC | 0 | 0 |
| X02761 | Human mRNA for fibronectin (FN precursor) — Also Represents: HG3044-HT2527 | | 1142 | −177 | NC | 0 | 0 | 160 | I | 1.1 | 0.04 | −152 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Un-treated In-tensity | B = A | IFN-a In-tensity | Incr Decr | Fold Change | Sig | IFN-b In-tensity | Incr Decr | Fold Change | Sig | IFN-g In-tensity | Incr Decr | Fold Change | Sig |
|---|---|---|---|---|---|---|---|---|---|---|---|---|---|---|---|
| X80692 | H. sapiens ERK3 mRNA | 174 | | −62 | NC | 0 | 0 | 44 | I | 1.3 | 0.04 | −49 | NC | 0 | 0 |
| X93017 | H. sapiens nox2 gene (exon 2). /gb = X93017 /ntype = DNA /annot = exon | −10 | * | −1 | NC | 0 | 0 | 36 | I | −1.3 | 0.04 | 6 | NC | 0 | 0 |
| M92934 | Human connective tissue growth "factor," complete cds | 914 | | −174 | NC | 0 | 0 | −112 | D | 1.1 | 0.03 | −401 | D | 1.8 | 0.45 |
| X97335 | H. sapiens mRNA for kinase A anchor protein | 25 | * | 14 | NC | 0 | 0 | 10 | I | 1.4 | 0.03 | 32 | I | 2.3 | 0.23 |
| S58544 | 75 kda infertility-related sperm protein "[human,]" "testis," mRNA "Partial," 2427 nt] | 27 | | −11 | NC | 0 | 0 | −20 | D | −1.3 | 0.03 | −22 | D | −1.3 | 0.04 |
| AF002020 | Homo sapiens Niemann-Pick C disease protein (NPC1) mRNA, complete cds. /gb = | 119 | | −7 | NC | 0 | 0 | 27 | MI | 1.2 | 0.03 | 24 | NC | 0 | 0 |
| D42043 | Human mRNA for KIAA0084 "gene," partial cds | 202 | | 19 | NC | 0 | 0 | 41 | MI | 1.2 | 0.03 | 0 | NC | 0 | 0 |
| D87443 | Human mRNA for KIAA0254 "gene," complete cds | 34 | | −8 | NC | 0 | 0 | 12 | I | 1.3 | 0.03 | −13 | NC | 0 | 0 |
| M19645 | Human 78 kdalton glucose-regulated protein (GRP78) "gene," complete cds | 312 | | 10 | NC | 0 | 0 | 57 | MI | 1.2 | 0.03 | −32 | NC | 0 | 0 |
| U01038 | Human pLK "mRNA," complete cds | 562 | | −55 | NC | 0 | 0 | −78 | D | 1.4 | 0.03 | 28 | NC | 0 | 0 |
| U52827 | Human Crl-du-chat region "mRNA," clone NIBB11 | 23 | * | −1 | NC | 0 | 0 | 10 | I | −1.2 | 0.03 | −5 | NC | 0 | 0 |
| U63542 | Human putative FAP protein "mRNA," partial cds | 4 | * | 6 | NC | 0 | 0 | 22 | MI | −1.3 | 0.03 | −9 | NC | 0 | 0 |
| U78180 | Human sodium channel 2 (hBNaC2) "mRNA," alternatively "spliced," complete cds | −28 | | 20 | NC | 0 | 0 | 52 | MI | −1.3 | 0.03 | 9 | NC | 0 | 0 |
| U97018 | Homo sapiens echinoderm microtubule-associated protein homolog HuEMAP "mRNA | 1 | * | 22 | NC | 0 | 0 | 24 | MI | −1.3 | 0.03 | 31 | NC | 0 | 0 |
| X05409 | Human RNA for mitochondrial aldehyde dehydrogenase I ALDHT (EC 1.2.1.3) | 152 | | 23 | NC | 0 | 0 | 30 | I | −1.2 | 0.03 | −68 | NC | 0 | 0 |
| Y12856 | H. sapiens mRNA for AMP-activated protein kinase "alpha-1," partial. /gb = Y12856 /nt | 26 | | 9 | NC | 0 | 0 | 11 | I | 1.4 | 0.03 | 10 | NC | 0 | 0 |
| U13991 | Human TATA-binding protein associated factor 30 kDa subunit (tafII30) "mRNA," com | 419 | | 39 | NC | 0 | 0 | −51 | D | 1.1 | 0.02 | 208 | I | 1.5 | 0.19 |
| X79882 | H. sapiens lrp mRNA | 185 | | −22 | NC | 0 | 0 | 31 | I | 1.2 | 0.02 | 77 | MI | 1.4 | 0.09 |
| U35048 | Human TSC-22 protein "mRNA," complete cds | 138 | | 0 | NC | 0 | 0 | −20 | D | 1.2 | 0.02 | −23 | D | 1.2 | 0.02 |
| D79994 | Human mRNA for KIAA0172 "gene," partial cds | 6 | * | 12 | NC | 0 | 0 | 18 | I | −1.2 | 0.02 | 8 | NC | 0 | 0 |
| G1116-HT111 | Proliferating-Cell Nucleolar "Antigen," 120 Kda | 210 | | 11 | NC | 0 | 0 | 34 | I | 1.2 | 0.02 | 35 | NC | 0 | 0 |
| G3627-HT383 | Calcium "Channel," "Voltage-Gated," Beta 1 "Subunit," L "Type," Alt. Splice "2," Skel | −17 | | 33 | NC | 0 | 0 | 40 | MI | −1.2 | 0.02 | 26 | MI | −1.0 | 0 |
| L10910 | Homo sapiens splicing factor (CC1.3) "mRNA," complete cds | 10 | | 0 | NC | 0 | 0 | 15 | MI | −1.2 | 0.02 | −3 | NC | 0 | 0 |
| L36463 | Homo sapiens ras inhibitor (Rin1) "mRNA," complete cds — "Also Represents: HG | 23 | * | −24 | NC | 0 | 0 | −44 | MD | −1.2 | 0.02 | −31 | NC | 0 | 0 |
| M76125 | Human tyrosine kinase receptor (axl) "mRNA," complete cds — "Also Represents: HG | 80 | | 16 | NC | 0 | 0 | 19 | I | 1.2 | 0.02 | 14 | NC | 0 | 0 |
| U17033 | Human 180 kDa transmembrane PLA2 receptor "mRNA," complete cds | 1 | * | −11 | NC | 0 | 0 | 23 | I | −1.2 | 0.02 | 3 | NC | 0 | 0 |
| U17989 | Human nuclear autoantigen GS2NA "mRNA," complete cds | 2 | * | −6 | NC | 0 | 0 | 22 | I | −1.2 | 0.02 | 11 | NC | 0 | 0 |
| U20938 | Human lymphocyte dihydropyrimidine dehydrogenase "mRNA," complete cds. | 5 | * | 15 | NC | 0 | 0 | 20 | I | −1.2 | 0.02 | 5 | NC | 0 | 0 |
| U28488 | Human putative G protein-coupled receptor (AZ3B) "mRNA," complete cds — Also Re | −3 | | 23 | I | −1.0 | 0 | 27 | I | 1.1 | 0.02 | −2 | NC | 0 | 0 |
| U37690 | Human RNA polymerase II subunit (hsRPB10) "mRNA," complete cds | 1292 | | −37 | NC | 0 | 0 | −97 | D | 1.1 | 0.02 | 103 | NC | 0 | 0 |
| U46692 | Human cystatin B "gene," complete cds | 342 | | −33 | NC | 0 | 0 | −39 | MD | 1.2 | 0.02 | 1 | NC | 0 | 0 |
| U81006 | Human p76 "mRNA," complete cds | 133 | | −13 | NC | 0 | 0 | 24 | I | 1.1 | 0.02 | −34 | NC | 0 | 0 |
| U94831 | Human multispanning membrane protein "mRNA," complete cds. /gb = U94831 /ntype | 277 | | 32 | NC | 0 | 0 | 40 | I | 1.2 | 0.02 | 34 | NC | 0 | 0 |
| X74330 | H. sapiens mRNA for DNA primase (subunit p48) | 83 | | 14 | NC | 0 | 0 | 17 | I | 1.1 | 0.01 | −2 | NC | 0 | 0 |
| M76378 | Human cysteine-rich protein (CRP) gene | 1374 | | −33 | NC | 0 | 0 | −76 | D | −1.1 | 0.01 | 338 | I | 1.2 | 0.1 |
| D25538 | Human mRNA for KIAA0037 "gene," complete cds | −4 | * | 6 | NC | 0 | 0 | 26 | I | 1.1 | 0.01 | 15 | NC | 0 | 0 |
| D86968 | Human mRNA for KIAA0213 "gene," partial cds | 20 | | −21 | NC | 0 | 0 | 4 | D | 1.2 | 0.01 | 9 | I | −1.0 | 0 |
| D86969 | Human mRNA for KIAA0215 "gene," complete cds | 3 | * | 5 | NC | 0 | 0 | 19 | D | 1.2 | 0.01 | 7 | NC | 0 | 0 |
| D89501 | Human PBI "gene," complete cds | 21 | | −20 | D | −1.1 | 0 | −26 | D | −1.1 | 0.01 | −18 | NC | 0 | 0 |
| G2480-HT257 | Fmlp-Related Receptor I | 23 | | 6 | NC | 0 | 0 | −10 | D | −1.2 | 0.01 | 1 | NC | 0 | 0 |
| L06845 | Human cysteinyl-tRNA synthetase "mRNA," partial cds | 406 | | −69 | NC | 0 | 0 | −39 | I | 1.1 | 0.01 | 40 | I | 1.2 | 0 |
| L35035 | Homo sapiens ribose 5-phosphate isomerase (RPI) mRNA | 14 | | −2 | NC | 0 | 0 | 8 | I | 1.1 | 0.01 | 3 | I | −1.0 | 0 |
| L49173 | Human OCP2 "gene," partial cds. /gb = L49173 /ntype = DNA /annot = CDS | 8 | * | 21 | NC | 0 | 0 | 14 | D | −1.1 | 0.01 | 36 | NC | 0 | 0 |
| M55153 | Human transglutaminase (TGase) "mRNA," complete cds | 186 | | −60 | NC | 0 | 0 | −21 | D | −1.1 | 0.01 | −55 | NC | 0 | 0 |
| M96740 | Human NSCL-2 gene sequence | 0 | * | 7 | NC | 0 | 0 | 22 | I | −1.1 | 0.01 | 16 | NC | 0 | 0 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| S72869 | H4(D10S170) = putative cytoskeletal protein "[human,]" "thyroid," "mRNA," 3011 nt] | −12 | | 14 | NC | 0 | 0 | 34 | I | −1.1 | 0.01 | 26 | I | −1.0 | 0 |
| U06863 | Human follistatin-related protein precursor "mRNA," complete cds | 79 | * | −10 | NC | 0 | 0 | 10 | MI | 1.1 | 0.01 | −25 | NC | 0 | 0 |
| U31342 | Human nucleobindin gene | 96 | * | 6 | NC | 0 | 0 | 11 | MD | −1.1 | 0.01 | 50 | NC | 0 | 0 |
| U33052 | Human "lipid-activated," protein kinase PRK2 "mRNA," complete cds — Also Represe | −10 | | 19 | NC | 0 | 0 | 32 | I | 1.1 | 0.01 | 14 | NC | 0 | 0 |
| U70322 | Human transportin (TRN) "mRNA," complete cds. | 121 | | −34 | NC | 0 | 0 | 18 | I | 1.2 | 0.01 | −62 | NC | 0 | 0 |
| X16416 | Human c-abl mRNA encoding p150 protein | 426 | | −13 | NC | 0 | 0 | −31 | I | 1.1 | 0.01 | −15 | NC | 0 | 0 |
| X16901 | Human mRNA for RAP30 subunit of transcription initiation factor RAP30/74 | 7 | * | 4 | I | ~1.0 | 0 | 15 | I | −1.1 | 0.01 | 15 | NC | 0 | 0 |
| X79781 | H. sapiens ray mRNA | 81 | | −10 | NC | 0 | 0 | 7 | MI | 1.1 | 0.01 | −10 | NC | 0 | 0 |
| Z24459 | exon2A from H. sapiens MTCP1 "gene," exons 2A to 7 (and joined mRNA). /gb = Z244 | 22 | | −23 | NC | 0 | 0 | −27 | D | −1.1 | 0.01 | −17 | MD | −5.5 | 1.67 |
| X17025 | Human homolog of yeast IPP isomerase | 109 | | −54 | NC | 0 | 0 | 38 | NC | 0 | 0 | −101 | I | 2.4 | 1.63 |
| X59892 | H. sapiens mRNA for IFN-inducible gamma2 protein | 874 | | 76 | NC | 0 | 0 | −65 | NC | 0 | 0 | 1242 | I | 1.9 | 1.43 |
| X15940 | Human mRNA for ribosomal protein L31 | 5905 | | −904 | NC | 0 | 0 | 153 | NC | 0 | 0 | −2823 | D | −4.3 | 1.18 |
| M24283 | Human major group rhinovirus receptor (HRV) "mRNA," complete cds | −8 | | 4 | NC | 0 | 0 | −6 | NC | 0 | 0 | 94 | I | 3.7 | 1.18 |
| X85237 | H. sapiens mRNA for splicing factor SF3a120 | 52 | * | −3 | NC | 0 | 0 | 50 | NC | 0 | 0 | 141 | I | 3.8 | 1.02 |
| U31628 | H. sapiens mRNA for interleukin-15 receptor alpha chain precursor (IL15RA) "mRNA," complete cds | 36 | | 51 | NC | 0 | 0 | 76 | NC | 0 | 0 | 100 | I | 3.3 | 0.95 |
| X84213 | H. sapiens BAK mRNA for BCl-2 homologue — "Also Represents: U16811, U23765" | 57 | | 20 | NC | 0 | 0 | 25 | NC | 0 | 0 | 132 | MI | 2.9 | 0.93 |
| M37435 | Human macrophage-specific colony-stimulating factor (CSF-1) "mRNA," complete cd | 103 | | 56 | NC | 0 | 0 | 94 | NC | 0 | 0 | 197 | I | 2.3 | 0.84 |
| G3494-HT368 | Nuclear Factor Ni-116 | 352 | | 39 | NC | 0 | 0 | 92 | NC | 0 | 0 | 441 | I | 3.4 | 0.84 |
| M15841 | Human U2 small nuclear RNA-associated B" antigen "mRNA," complete mRNA. | 129 | | −26 | NC | 0 | 0 | −9 | NC | 0 | 0 | −92 | D | −3.9 | 0.84 |
| Z31695 | H. sapiens mRNA for 43 kDa inositol polyphosphate 5-phosphatase. | 79 | | −42 | NC | 0 | 0 | −29 | NC | 0 | 0 | −61 | MD | 1.5 | 0.76 |
| X56932 | H. sapiens mRNA for 23 kD highly basic protein | 11210 | | −2597 | NC | 0 | 0 | −2411 | NC | 0 | 0 | −3671 | D | 2.3 | 0.75 |
| M58286 | Homo sapiens tumor necrosis factor receptor "mRNA," complete cds — "Also Represe | 255 | | 102 | NC | 0 | 0 | 59 | NC | 0 | 0 | 330 | I | 3.5 | 0.71 |
| X97748 | H. sapiens PTX3 gene promotor region. /gb = X97748 /ntype = DNA /annot = mRNA — Als | 90 | | −26 | NC | 0 | 0 | 17 | NC | 0 | 0 | −64 | I | 3 | 0.71 |
| Z35278 | H. sapiens PEBP2aC1 acute myeloid leukaemia mRNA | 55 | | 18 | NC | 0 | 0 | 26 | NC | 0 | 0 | 108 | I | 3 | 0.64 |
| L40379 | Homo sapiens thyroid receptor interactor (TRIP10) "mRNA," 3' end of cds | 45 | | −2 | NC | 0 | 0 | 27 | NC | 0 | 0 | 88 | I | 3.1 | 0.6 |
| U18009 | Human chromosome 17q21 mRNA clone LF113 | 30 | * | 34 | NC | 0 | 0 | 22 | NC | 0 | 0 | 64 | MI | 3 | 0.6 |
| U85011 | Human preferentially expressed antigen of melanoma (PRAME) "mRNA," complete cds | 37 | * | 35 | NC | 0 | 0 | 30 | NC | 0 | 0 | 74 | I | 1.7 | 0.57 |
| L09604 | Homo sapiens differentiation-dependent A4 protein "mRNA," complete cds | 1021 | | 129 | NC | 0 | 0 | 157 | NC | 0 | 0 | 752 | MD | −3.0 | 0.53 |
| L33243 | Homo sapiens polycystic kidney disease 1 protein (PKD1) "mRNA," complete cds | 60 | | −28 | NC | 0 | 0 | −23 | NC | 0 | 0 | −57 | I | 1.8 | 0.53 |
| M75126 | Homo sapiens hexokinase 1 (HK1) "mRNA," complete cds | 548 | | 150 | NC | 0 | 0 | 272 | NC | 0 | 0 | 464 | MI | 2.8 | 0.53 |
| U30521 | Human P311 HUM -3.1 "mRNA," complete cds | 46 | | 23 | NC | 0 | 0 | 13 | NC | 0 | 0 | 80 | I | 2 | 0.53 |
| Z14093 | H. sapiens mRNA for branched chain decarboxylase alpha subunit | −51 | | 77 | NC | 0 | 0 | 40 | NC | 0 | 0 | 102 | MI | −2.5 | 0.51 |
| X95735 | H. sapiens mRNA for zyxin 2 | 752 | | 11 | NC | 0 | 0 | −6 | NC | 0 | 0 | 560 | I | 1.7 | 0.5 |
| D38073 | Human mRNA for hRIf beta subunit (p102 "protein)," complete cds | 143 | | 36 | NC | 0 | 0 | 148 | NC | 0 | 0 | 169 | MI | 2.2 | 0.48 |
| L29277 | Homo sapiens DNA-binding protein (APRF) "mRNA," complete cds | 52 | | 39 | NC | 0 | 0 | 37 | NC | 0 | 0 | 83 | I | 2.6 | 0.48 |
| X90978 | H. sapiens mRNA for an acute myeloid leukaemia protein (1793bp) | 40 | | 32 | NC | 0 | 0 | 21 | NC | 0 | 0 | 68 | I | 2.7 | 0.46 |
| X97058 | H. sapiens mRNA for P2Y6 receptor | 5 | | 42 | NC | 0 | 0 | 18 | NC | 0 | 0 | 52 | I | −2.9 | 0.46 |
| D14530 | Human homolog of yeast ribosomal protein "S28," complete cds | 3768 | | −302 | NC | 0 | 0 | −687 | NC | 0 | 0 | −1242 | D | 1.5 | 0.45 |
| L20010 | Human HCF1 gene related mRNA sequence | 176 | | −25 | NC | 0 | 0 | 31 | NC | 0 | 0 | 189 | I | 2.1 | 0.45 |
| J00220 | IGHA1 gene extracted from Human Ig germline H-chain G-E-A region A: gamma-3 5' | −13 | | 32 | NC | 0 | 0 | 18 | NC | 0 | 0 | 66 | MI | −2.6 | 0.44 |
| M15205 | Human thymidine kinase "gene," complete "cds," with clustered Alu repeats in the int | 275 | | 101 | NC | 0 | 0 | 37 | NC | 0 | 0 | 249 | I | 1.9 | 0.42 |
| U58681 | Human neurogenic basic-helix-loop-helix protein (NeuroD2) "gene," complete cds. | 56 | | −47 | NC | 0 | 0 | −34 | NC | 0 | 0 | −45 | D | −2.8 | 0.41 |
| X86779 | H. sapiens mRNA for FAST kinase | 171 | | 67 | NC | 0 | 0 | 70 | NC | 0 | 0 | 173 | I | 2 | 0.4 |
| U18934 | Human receptor tyrosine kinase (DTK) "mRNA," complete cds | 145 | | 139 | NC | 0 | 0 | 106 | NC | 0 | 0 | 151 | I | 2 | 0.39 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| X14787 | Human mRNA for thrombospondin | 303 | | −44 | NC | 0 | 0 | −140 | NC | 0 | 0 | −154 | D | 2 | 0.39 |
| L17131 | Human high mobility group protein (HMG-I(Y)) gene exons "1-8," complete cds | 1474 | | −78 | NC | 0 | 0 | 120 | NC | 0 | 0 | 754 | D | 1.5 | 0.37 |
| X13546 | put. HMG-17 protein gene extracted from Human HMG-17 gene for non-histone chro | 2008 | | −98 | NC | 0 | 0 | 20 | NC | 0 | 0 | −700 | I | 1.5 | 0.37 |
| X74301 | H. sapiens mRNA for MHC class II transactivator — Also Represents: U18259 | −1 | * | 4 | NC | 0 | 0 | −4 | NC | 0 | 0 | 52 | D | −2.6 | 0.37 |
| X86691 | H. sapiens mRNA for 218kD MI-2 protein | 268 | | −84 | NC | 0 | 0 | 41 | NC | 0 | 0 | −136 | D | 2 | 0.36 |
| X77584 | H. sapiens mRNA for ATL-derived factor/thiredoxin | 1704 | | −216 | NC | 0 | 0 | −229 | NC | 0 | 0 | −605 | D | 1.6 | 0.35 |
| G4704-HT514 | Glial Growth Factor 2 | 54 | | −23 | NC | 0 | 0 | −8 | NC | 0 | 0 | −39 | D | −2.7 | 0.35 |
| G3364-HT354 | Ribosomal Protein L37 | 5500 | | −873 | NC | 0 | 0 | −764 | NC | 0 | 0 | −1433 | D | 1.4 | 0.33 |
| K03515 | Human neuroleukin "mRNA," complete cds | 613 | | 56 | NC | 0 | 0 | 92 | NC | 0 | 0 | 385 | D | 1.6 | 0.33 |
| U85265 | Human down syndrome critical region 1 (DSCR1) "gene," alternative exon 1 /gb = U85 | −23 | * | 18 | NC | 0 | 0 | 26 | I | −1.0 | 0 | 68 | I | −2.3 | 0.33 |
| L38941 | Homo sapiens ribosomal protein L34 (RPL34) "mRNA," complete cds | 3050 | | −391 | NC | 0 | 0 | −288 | NC | 0 | 0 | −910 | D | 1.4 | 0.32 |
| X16064 | Human mRNA for translationally controlled tumor protein | 4023 | | −647 | NC | 0 | 0 | −443 | NC | 0 | 0 | −1128 | D | 1.4 | 0.32 |
| X73460 | H. sapiens mRNA for ribosomal protein L3 | 6926 | | −1365 | NC | 0 | 0 | −1676 | NC | 0 | 0 | −1679 | D | 1.3 | 0.32 |
| M80335 | Homo sapiens protein kinase A catalytic subunit "mRNA," 3′ end | 44 | | 26 | NC | 0 | 0 | 21 | NC | 0 | 0 | 57 | D | 2.3 | 0.31 |
| X51345 | Human jun-B mRNA for JUN-B protein | 89 | | −22 | NC | 0 | 0 | −1 | NC | 0 | 0 | −51 | D | 2.3 | 0.3 |
| G4319-HT458 | Ribosomal Protein L5 | 187 | | 27 | NC | 0 | 0 | 6 | NC | 0 | 0 | 155 | I | 1.8 | 0.3 |
| J05614 | Human proliferating cell nuclear antigen (PCNA) "gene," promoter region. /gb = J05614 | 2621 | | 6 | NC | 0 | 0 | 22 | NC | 0 | 0 | −772 | D | 1.4 | 0.29 |
| M23294 | Human beta-hexosaminidase beta-subunit (HEXB) gene | 630 | | −125 | NC | 0 | 0 | 87 | NC | 0 | 0 | −253 | D | 1.7 | 0.28 |
| G2274-HT237 | Rna Polymerase "II," 14.5 Kda Subunit | 130 | | −36 | NC | 0 | 0 | 8 | NC | 0 | 0 | −68 | MD | 2.1 | 0.28 |
| L76200 | Human mRNA for HHR23A "protein," complete cds | 314 | | 94 | NC | 0 | 0 | 50 | NC | 0 | 0 | 210 | I | 1.7 | 0.27 |
| M88458 | Human guanylate kinase (GUK1) "mRNA," complete cds | 700 | | 91 | NC | 0 | 0 | 3 | NC | 0 | 0 | 376 | I | 1.5 | 0.27 |
| G1869-HT190 | Human ELP-1 mRNA sequence | 197 | | 85 | NC | 0 | 0 | 142 | NC | 0 | 0 | 152 | I | 1.8 | 0.27 |
| G2036-HT209 | Male Enhanced Antigen | 369 | | 84 | NC | 0 | 0 | 101 | NC | 0 | 0 | 233 | I | 1.6 | 0.26 |
| M95809 | Stimulatory Gdp/Gip Exchange Protein For C-Ki-Ras P21 and Smg P21 | 34 | | 49 | NC | 0 | 0 | 47 | NC | 0 | 0 | 43 | D | 2.3 | 0.26 |
| U37022 | Human basic transcription factor 62kD subunit "(BTF2)," complete cds | 76 | | −5 | NC | 0 | 0 | 13 | NC | 0 | 0 | −43 | D | 2.3 | 0.26 |
| U60276 | Human cyclin-dependent kinase 4 (CDK4) "gene," complete cds | 585 | | 143 | NC | 0 | 0 | 26 | NC | 0 | 0 | 325 | I | 1.6 | 0.26 |
| D21235 | Human hASNA-I "mRNA," complete cds | 126 | | 32 | NC | 0 | 0 | −104 | NC | 0 | 0 | 109 | MI | 1.9 | 0.26 |
| M37245 | Human mRNA for HHR23A "protein," complete cds | 301 | | 65 | NC | 0 | 0 | 82 | NC | 0 | 0 | 194 | I | 1.6 | 0.25 |
| U07424 | Human Ig superfamily cytotoxic T-lymphocyte-associated protein (CTLA-4) gene | 67 | | −40 | NC | 0 | 0 | −7 | NC | 0 | 0 | −38 | MD | 2.3 | 0.25 |
| U25182 | Human putative tRNA synthetase-like protein "mRNA," complete cds | 851 | | 103 | NC | 0 | 0 | 51 | NC | 0 | 0 | 405 | I | 1.5 | 0.25 |
| X04500 | Human antioxidant enzyme AOE37-2 "mRNA," complete cds | 141 | | 74 | NC | 0 | 0 | 9 | NC | 0 | 0 | 116 | MI | 1.8 | 0.25 |
| X17042 | Human gene for prointerleukin 1 beta | 482 | | 121 | NC | 0 | 0 | 26 | NC | 0 | 0 | −192 | D | 1.7 | 0.25 |
| Z35093 | Human mRNA for hematopoetic proteoglycan core protein | 751 | | 82 | NC | 0 | 0 | −190 | NC | 0 | 0 | −274 | D | 1.6 | 0.25 |
| D21853 | H. sapiens mRNA for SURF-1 | 432 | | 99 | NC | 0 | 0 | 5 | NC | 0 | 0 | 253 | I | 1.6 | 0.24 |
| J02902 | Human mRNA for KIAA0111 "gene," complete cds | 448 | | 100 | NC | 0 | 0 | 120 | NC | 0 | 0 | 255 | I | 1.6 | 0.24 |
| J04823 | Human protein phosphatase 2A regulatory subunit alpha-isotype (alpha-PR65) "mRN | 344 | | 47 | NC | 0 | 0 | 103 | NC | 0 | 0 | 211 | I | 1.6 | 0.24 |
| L76191 | Human cytochrome c oxidase subunit VIII (COX8) "mRNA," complete cds | 1696 | | 55 | NC | 0 | 0 | 174 | NC | 0 | 0 | 653 | I | 1.4 | 0.24 |
| M22898 | Homo sapiens interleukin-1 receptor-associated kinase (IRAK) "mRNA," complete cd | 998 | | 43 | NC | 0 | 0 | 21 | NC | 0 | 0 | 451 | I | 1.5 | 0.24 |
| Z49989 | Human phosphoprotein p53 gene | 47 | | 33 | NC | 0 | 0 | 18 | NC | 0 | 0 | 51 | I | 2.1 | 0.24 |
| U24169 | H. sapiens mRNA for smoothelin | 153 | * | 16 | NC | 0 | 0 | 32 | NC | 0 | 0 | 119 | MI | 1.8 | 0.24 |
| | Human JTV-1 (JTV-1) "mRNA," complete cds | 292 | | 94 | NC | 0 | 0 | 64 | NC | 0 | 0 | 184 | I | 1.6 | 0.23 |
| D79205 | Human mRNA for ribosomal protein "L39," complete cds | 4000 | | 471 | NC | 0 | 0 | 585 | NC | 0 | 0 | 1112 | I | 1.3 | 0.22 |
| J03592 | Human ADP/ATP translocase "mRNA," 3′ end, clone pHAT8 | 3136 | | −198 | NC | 0 | 0 | −467 | NC | 0 | 0 | −767 | D | 1.3 | 0.22 |
| M81695 | H. sapiens leukocyte adhesion glycoprotein "p150,95" "mRNA," complete cds — Also R | 2289 | * | 255 | NC | 0 | 0 | 234 | NC | 0 | 0 | 763 | I | 1.3 | 0.22 |
| | | 14 | | 17 | NC | 0 | 0 | 21 | NC | 0 | 0 | 31 | I | −2.3 | 0.22 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| S65738 | actin depolymerizing factor "[human,]" fetal "brain," "mRNA," 1452 nt] | 850 | | -3 | NC | 0 | 0 | 142 | NC | 0 | 0 | -282 | D | 1.5 | 0.22 |
| Z12830 | H. sapiens mRNA for SSR alpha subunit | 39 | | 27 | NC | 0 | 0 | 26 | NC | 0 | 0 | 43 | MI | 2.1 | 0.22 |
| U14603 | Human protein-tyrosine phosphatase (HU-PP-1) "mRNA," partial sequence | 279 | | -71 | NC | 0 | 0 | 37 | NC | 0 | 0 | -116 | D | 1.7 | 0.21 |
| X64364 | H. sapiens mRNA for M6 antigen | 645 | | 220 | NC | 0 | 0 | 79 | NC | 0 | 0 | 305 | I | 1.5 | 0.21 |
| Z37986 | H. sapiens mRNA for phenylalkylamine binding protein | 402 | | 104 | NC | 0 | 0 | -9 | NC | 0 | 0 | 216 | I | 1.5 | 0.21 |
| G4318-HT458 | Lim-Domain Transcription Factor Lim-1 — Also Represents: U14755 | 56 | * | -24 | NC | 0 | 0 | -7 | NC | 0 | 0 | -30 | D | 2.2 | 0.2 |
| J03589 | Human ubiquitin-like protein (GdX) "gene," complete cds | 65 | | 20 | NC | 0 | 0 | 25 | NC | 0 | 0 | 59 | MI | 1.9 | 0.2 |
| L16842 | Human ubiquinol cytochrome-c reductase core I protein "mRNA," complete cds | 1010 | | 18 | NC | 0 | 0 | -4 | NC | 0 | 0 | 404 | I | 1.4 | 0.2 |
| L25080 | Human GTP-binding protein (rhoA) "mRNA," complete cds | 1151 | | 121 | NC | 0 | 0 | 49 | NC | 0 | 0 | 442 | I | 1.4 | 0.2 |
| M34338 | Human spermidine synthase "mRNA," complete cds — Also Represents: M64231_ma | 802 | | 100 | NC | 0 | 0 | 24 | NC | 0 | 0 | 343 | I | 1.4 | 0.2 |
| M94046 | Human zinc finger protein (MAZ) mRNA | 583 | | 30 | NC | 0 | 0 | -34 | NC | 0 | 0 | 278 | I | 1.5 | 0.2 |
| U77846 | Human elastin "gene," partial cds and partial 3'UTR — "Also Represents: HG2994-HT | 13 | * | 30 | NC | 0 | 0 | 32 | NC | 0 | 0 | 31 | I | -2.2 | 0.2 |
| G4638-HT505 | Spliceosomal Protein Sap 49 | 289 | | 36 | NC | 0 | 0 | 114 | NC | 0 | 0 | 165 | I | 1.6 | 0.19 |
| L19871 | Human activating transcription factor 3 (ATF3) "mRNA," complete cds | 16 | | 3 | NC | 0 | 0 | 4 | NC | 0 | 0 | 28 | I | -2.2 | 0.19 |
| M16279 | Human MIC2 "mRNA," complete cds | 437 | | 54 | NC | 0 | 0 | 31 | NC | 0 | 0 | 218 | I | 1.5 | 0.19 |
| U16031 | Human transcription factor IL-4 Stat "mRNA," complete cds | 29 | * | 16 | NC | 0 | 0 | 15 | NC | 0 | 0 | 32 | MI | 2.1 | 0.19 |
| U30255 | Human phosphogluconate dehydrogenase (hPGDH) "gene," complete cds | 264 | | 74 | NC | 0 | 0 | 79 | NC | 0 | 0 | 151 | I | 1.6 | 0.19 |
| U52112 | RbP gene (renin-binding protein) extracted from Human Xq28 genomic DNA in the re | 88 | | -46 | NC | 0 | 0 | -37 | NC | 0 | 0 | -44 | MD | 2 | 0.19 |
| U57099 | Human APEG-1 "mRNA," complete cds | 15 | * | 18 | NC | 0 | 0 | 12 | NC | 0 | 0 | 28 | I | 2 | 0.19 |
| U66469 | Human cell growth regulator CGR19 "mRNA," complete cds | 75 | | -14 | NC | 0 | 0 | -31 | NC | 0 | 0 | -38 | D | -2.2 | 0.19 |
| X67951 | H. sapiens mRNA for proliferation-associated gene (pag) | 2638 | | -138 | NC | 0 | 0 | -74 | NC | 0 | 0 | -636 | D | 1.3 | 0.19 |
| Z46632 | H. sapiens HSPDE4C1 gene for "3',5'-cyclic" AMP phosphodiesterase | 14 | * | 31 | NC | 0 | 0 | 39 | NC | 0 | 0 | 29 | MD | -2.1 | 0.19 |
| D00017 | Human lipocortin II mRNA | 3431 | | -148 | NC | 0 | 0 | -249 | NC | 0 | 0 | -757 | D | 1.3 | 0.18 |
| L21936 | Human succinate dehydrogenase flavoprotein subunit (SDH) "mRNA," complete cds | 282 | | 62 | NC | 0 | 0 | 85 | NC | 0 | 0 | 157 | I | 1.6 | 0.18 |
| U28386 | Human nuclear localization sequence receptor hSRP1 alpha "mRNA," complete cds | 296 | | 135 | NC | 0 | 0 | 145 | NC | 0 | 0 | 163 | I | 1.5 | 0.18 |
| X03342 | Human mRNA for ribosomal protein L32 | 7474 | | -365 | NC | 0 | 0 | -304 | NC | 0 | 0 | -1339 | D | 1.2 | 0.18 |
| D13641 | Human mRNA for KIAA0016 "gene," complete cds | 217 | | -15 | NC | 0 | 0 | 101 | NC | 0 | 0 | -86 | D | 1.7 | 0.17 |
| J04182 | Homo sapiens lysosomal membrane glycoprotein-1 (LAMP1) "mRNA," complete cds | 572 | | 60 | NC | 0 | 0 | 16 | NC | 0 | 0 | 243 | I | 1.4 | 0.17 |
| M92843 | H. sapiens zinc finger transcriptional regulator "mRNA," complete cds — "Also Represe | 26 | | 15 | NC | 0 | 0 | 12 | NC | 0 | 0 | 28 | MI | 2.1 | 0.17 |
| U57342 | Human myelodysplasia/myeloid leukemia factor 2 (MLF2) "mRNA," complete cds | 612 | | 56 | NC | 0 | 0 | 150 | NC | 0 | 0 | 260 | I | 1.4 | 0.17 |
| U79257 | Human clone 23932 mRNA sequence | 1 | * | 11 | NC | 0 | 0 | -11 | NC | 0 | 0 | 38 | I | -1.9 | 0.17 |
| X69391 | H. sapiens mRNA for ribosomal protein L6 | 4078 | | 42 | NC | 0 | 0 | -768 | NC | 0 | 0 | -825 | D | 1.3 | 0.17 |
| Y09022 | H. sapiens mRNA for Not56-like protein | 440 | | 28 | NC | 0 | 0 | 34 | NC | 0 | 0 | 208 | I | 1.5 | 0.17 |
| D85433 | Human MURR1 "mRNA," sequence. /gb = D85433 /ntype = RNA | 35 | * | 3 | NC | 0 | 0 | 15 | NC | 0 | 0 | 32 | I | 1.9 | 0.16 |
| J04031 | Human methylenetetrahydrofolate dehydrogenase-methenyltetrahydrofolate cyclohy | 137 | | 34 | NC | 0 | 0 | 46 | NC | 0 | 0 | 85 | I | 1.6 | 0.16 |
| L26339 | Human autoantigen "mRNA," complete cds | 67 | | 2 | NC | 0 | 0 | 0 | NC | 0 | 0 | 53 | D | 1.8 | 0.16 |
| M96995 | Homo sapiens epidermal growth factor receptor-binding protein GRB2 (EGFRBP-GR | 286 | | -40 | NC | 0 | 0 | -51 | NC | 0 | 0 | -106 | D | 1.6 | 0.16 |
| U96113 | Homo sapiens Nedd-4-like ubiquitin-protein ligase WWP1 "mRNA," partial cds. /gb = U | 67 | | -35 | NC | 0 | 0 | -38 | NC | 0 | 0 | -32 | MD | 1.9 | 0.16 |
| U06956 | Human HALPHA44 gene for "alpha-tubulin," exons 3-Jan | 723 | | 97 | NC | 0 | 0 | -41 | NC | 0 | 0 | 278 | I | 1.4 | 0.16 |
| X13293 | Human mRNA for B-myb gene | 173 | * | 41 | NC | 0 | 0 | 15 | NC | 0 | 0 | 101 | MI | 1.6 | 0.16 |
| X01420 | H. sapiens mRNA for hHKb1 protein | 3070 | | -530 | NC | 0 | 0 | 995 | NC | 0 | 0 | -651 | D | 1.3 | 0.16 |
| X95586 | H. sapiens mRNA MB1 gene | 1294 | | 116 | NC | 0 | 0 | -95 | NC | 0 | 0 | 418 | I | 1.3 | 0.16 |
| Z49105 | H. sapiens HO21 mRNA | 346 | | -76 | NC | 0 | 0 | -24 | NC | 0 | 0 | -122 | MD | -1.9 | 0.16 |
| D13720 | H. sapiens mRNA for "LYK," complete cds — Also Represents: L10717 | 7 | * | 15 | NC | 0 | 0 | 22 | NC | 0 | 0 | 31 | I | 1.5 | 0.15 |
| L09260 | Human (chromosome 3p25) membrane protein mRNA | 268 | | 96 | NC | 0 | 0 | 26 | NC | 0 | 0 | 165 | I | 1.4 | 0.15 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| U03735 | Human MAGE-3 antigen (MAGE-3) "gene," complete cds | 731 | | −157 | NC | 0 | 0 | 9 | NC | 0 | 0 | −214 | D | 1.4 | 0.15 |
| U12595 | Human tumor necrosis factor type 1 receptor associated protein (TRAP1) "mRNA," p | 349 | | 65 | NC | 0 | 0 | −28 | NC | 0 | 0 | 162 | I | 1.5 | 0.15 |
| U18300 | Human damage-specific DNA binding protein p48 subunit (DDB2) "mRNA," complete | 128 | | 31 | NC | 0 | 0 | 35 | NC | 0 | 0 | 81 | I | 1.6 | 0.15 |
| U28686 | Human putative RNA binding protein RNPL "mRNA," complete cds | 137 | | 116 | NC | 0 | 0 | 112 | NC | 0 | 0 | 83 | I | 1.6 | 0.15 |
| U83461 | Human putative copper uptake protein (hCTR2) "mRNA," complete cds. /gb = U83461 | 34 | * | 16 | NC | 0 | 0 | 3 | NC | 0 | 0 | 31 | I | 1.9 | 0.15 |
| X59434 | Human rohu mRNA for rhodanese | 121 | * | 12 | NC | 0 | 0 | 4 | NC | 0 | 0 | 77 | I | 1.6 | 0.15 |
| X76057 | H. sapiens PMI1 mRNA for phosphomannose isomerase | 81 | | 6 | 1 | 1.1 | 0 | 55 | NC | 0 | 0 | 58 | I | 1.7 | 0.15 |
| | | 36 | * | −35 | NC | 0 | 0 | −44 | NC | 0 | 0 | −41 | D | −1.8 | 0.14 |
| K02574 | Human purine nucleoside phosphorylase (PNP) "mRNA," complete cds | 437 | | 99 | NC | 0 | 0 | 38 | NC | 0 | 0 | 181 | I | 1.4 | 0.14 |
| L11285 | Homosapiens ERK activator kinase (MEK2) mRNA | 330 | | 38 | NC | 0 | 0 | 22 | NC | 0 | 0 | 150 | MI | 1.5 | 0.14 |
| M19483 | Human ATP synthase beta subunit gene | 1639 | | 107 | NC | 0 | 0 | 93 | NC | 0 | 0 | 461 | I | 1.3 | 0.14 |
| S81003 | L-UBC = ubiquitin conjugating enzyme "[human," odontogenic "keratocysts," mRNA "R | 344 | | 96 | NC | 0 | 0 | 122 | NC | 0 | 0 | 156 | MI | 1.5 | 0.14 |
| U01923 | Human BTK region clone ftp-3 mRNA | 38 | | −17 | NC | 0 | 0 | 3 | NC | 0 | 0 | −28 | D | −1.9 | 0.14 |
| U52427 | Human RNA polymerase II seventh subunit (rpb-7) "gene," complete cds. | 308 | | 96 | NC | 0 | 0 | 4 | NC | 0 | 0 | 142 | MI | 1.5 | 0.14 |
| U58048 | Human metallopeptidase PRSM1 "mRNA," complete cds | 170 | | 26 | NC | 0 | 0 | 29 | NC | 0 | 0 | 92 | MI | 1.5 | 0.14 |
| X78338 | Synthetic adenovirus transformed human retina cell "line," MRP mRNA | 39 | | 13 | NC | 0 | 0 | 18 | NC | 0 | 0 | 33 | MI | 1.8 | 0.14 |
| X98261 | H. sapiens mRNA for M-phase "phosphoprotein," mpp5 | 107 | * | 11 | NC | 0 | 0 | −49 | NC | 0 | 0 | 67 | MI | 1.6 | 0.14 |
| Y11681 | Homo sapiens mRNA for mitochondrial ribosomal protein S12. /gb = Y11681 /ntype = R | 704 | | 21 | NC | 0 | 0 | 57 | NC | 0 | 0 | 250 | I | 1.4 | 0.14 |
| Z37166 | H. sapiens BAT1 mRNA for nuclear RNA helicase (DEAD family) | 1427 | | −91 | NC | 0 | 0 | −80 | NC | 0 | 0 | 409 | I | 1.3 | 0.14 |
| D16105 | Human nucleotide-binding protein "mRNA," complete cds | 218 | | 37 | NC | 0 | 0 | −77 | NC | 0 | 0 | 105 | MI | 1.5 | 0.13 |
| G1804-HT182 | Ornithine Aminotransferase-Like 3 | 28 | | −12 | NC | 0 | 0 | 5 | NC | 0 | 0 | 26 | MI | 1.9 | 0.13 |
| J04809 | Human cytosolic adenylate kinase (AK1) "gene," complete cds | 35 | * | 36 | NC | 0 | 0 | 29 | NC | 0 | 0 | 29 | MI | 1.8 | 0.13 |
| M16750 | Human plim-1 oncogene "mRNA," complete cds — "Also Represents: M27903, M2477 | 10 | * | 2 | NC | 0 | 0 | 26 | NC | 0 | 0 | 27 | I | −1.9 | 0.13 |
| U01833 | Human vacuolar H+ ATPase proton channel subunit "mRNA," complete cds | 80 | | 8 | NC | 0 | 0 | 4 | NC | 0 | 0 | 52 | MI | 1.7 | 0.13 |
| X56468 | Human mRNA for 14.3.3 "protein," a protein kinase regulator | 1773 | | −18 | NC | 0 | 0 | −490 | NC | 0 | 0 | −387 | D | 1.3 | 0.13 |
| D25539 | Human mRNA for KIAA0040 "gene," complete cds | 37 | * | −36 | NC | 0 | 0 | −7 | NC | 0 | 0 | −24 | MD | −1.9 | 0.12 |
| D86965 | Human mRNA for KIAA0210 "gene," complete cds | 115 | | −11 | NC | 0 | 0 | −9 | NC | 0 | 0 | −45 | MD | 1.6 | 0.12 |
| G1614-HT161 | Protein Phosphatase "1," Alpha Catalytic Subunit | 738 | | 144 | NC | 0 | 0 | 47 | NC | 0 | 0 | 240 | I | 1.3 | 0.12 |
| G2999-HT475 | Thyroid "Peroxidase," Alt. Splice 2 — Also Represents: M25715 | 36 | | −14 | NC | 0 | 0 | −23 | NC | 0 | 0 | −25 | D | −1.8 | 0.12 |
| G3991-HT426 | Cpg-Enriched "Dna," Clone E18 | 398 | | 146 | NC | 0 | 0 | 148 | NC | 0 | 0 | 152 | I | 1.4 | 0.12 |
| J04444 | Human cytochrome c-1 "gene," complete cds | 1004 | | 45 | NC | 0 | 0 | −61 | NC | 0 | 0 | 291 | MI | 1.3 | 0.12 |
| L08096 | Human CD27 ligand mRNA, complete cds. — Also Represents: HG903-HT903 | 97 | | 46 | NC | 0 | 0 | 47 | NC | 0 | 0 | 59 | MI | 1.6 | 0.12 |
| M61832 | Human S-adenosylhomocysteine hydrolase (AHCY) "mRNA," complete cds — Also Re | 573 | | 89 | NC | 0 | 0 | 60 | NC | 0 | 0 | 201 | I | 1.4 | 0.12 |
| M62762 | Human vacuolar H+ ATPase proton channel subunit "mRNA," complete cds | 771 | | 88 | NC | 0 | 0 | 111 | NC | 0 | 0 | 246 | I | 1.3 | 0.12 |
| U39412 | Human platelet alpha SNAP "mRNA," complete cds | 55 | | 31 | NC | 0 | 0 | 19 | NC | 0 | 0 | 38 | I | 1.7 | 0.12 |
| U51586 | Human slah binding protein 1 (SlahBP1) "mRNA," partial cds. | 491 | | 105 | NC | 0 | 0 | 13 | NC | 0 | 0 | 175 | I | 1.4 | 0.12 |
| X15729 | Human mRNA for nuclear p68 protein — Also Represents: X52104 | 480 | | −23 | NC | 0 | 0 | 141 | NC | 0 | 0 | −140 | D | 1.4 | 0.12 |
| X53002 | Human mRNA for integrin beta-5 subunit — Also Represents: J05633 | 462 | | −131 | NC | 0 | 0 | −12 | NC | 0 | 0 | −136 | D | 1.4 | 0.12 |
| X53331 | Human mRNA for matrix Gla protein | 78 | | 39 | NC | 0 | 0 | −38 | NC | 0 | 0 | 50 | MI | 1.6 | 0.12 |
| X81003 | H. sapiens HCG V mRNA | 302 | | 61 | NC | 0 | 0 | −56 | NC | 0 | 0 | 130 | I | 1.4 | 0.12 |
| Z17227 | H. sapiens mRNA for transmembrane receptor protein | 46 | * | 19 | NC | 0 | 0 | 7 | NC | 0 | 0 | 34 | MI | 1.7 | 0.12 |
| Z36714 | H. sapiens mRNA for cyclin F | 129 | | 4 | NC | 0 | 0 | −36 | NC | 0 | 0 | 72 | MI | 1.6 | 0.12 |
| AC002115 | F25451_2 gene extracted from Human DNA from overlapping chromosome 19 cosm | 99 | | −22 | NC | 0 | 0 | −22 | NC | 0 | 0 | −39 | MD | 1.7 | 0.11 |
| D21851 | Human mRNA for KIAA0028 "gene," partial cds | 30 | | 11 | NC | 0 | 0 | 4 | NC | 0 | 0 | 24 | I | 1.8 | 0.11 |
| G3039-HT320 | Adp-Ribosylation-Like Factor | 418 | | 20 | NC | 0 | 0 | −214 | NC | 0 | 0 | 151 | I | 1.4 | 0.11 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| J04794 | Human aldehyde reductase "mRNA," complete cds | 319 | | 55 | NC | 0 | 0 | −7 | NC | 0 | 0 | 129 | MI | 1.4 | 0.11 |
| L38935 | Homo sapiens GT212 mRNA | 39 | * | −8 | NC | 0 | 0 | 17 | NC | 0 | 0 | −19 | D | 1.9 | 0.11 |
| M28213 | Homo sapiens GTP-binding protein (RAB2) "mRNA," complete cds — Also Represents | 117 | | −5 | NC | 0 | 0 | 52 | NC | 0 | 0 | −45 | D | 1.6 | 0.11 |
| M64098 | Human high density lipoprotein binding protein (HBP) "mRNA," complete cds | 299 | | −128 | NC | 0 | 0 | −6 | NC | 0 | 0 | −93 | MD | 1.5 | 0.11 |
| U10117 | Human endothelial-monocyte activating polypeptide II "mRNA," complete cds | 76 | | 2 | NC | 0 | 0 | 1 | NC | 0 | 0 | −32 | D | 1.7 | 0.11 |
| U59877 | Human low-Mr GTP-binding protein (RAB31) "mRNA," complete cds — Also Represen | 159 | | −43 | NC | 0 | 0 | 58 | NC | 0 | 0 | −57 | MD | 1.6 | 0.11 |
| U91985 | Human DNA fragmentation factor-45 "mRNA," complete cds | 114 | * | 15 | NC | 0 | 0 | 35 | NC | 0 | 0 | 61 | I | 1.5 | 0.11 |
| X13839 | Human mRNA for vascular smooth muscle alpha-actin | 208 | | 36 | NC | 0 | 0 | 17 | NC | 0 | 0 | 95 | MI | 1.5 | 0.11 |
| AF009368 | Homo sapiens Luman "mRNA," complete cds. /gb = AF009368 /ntype = RNA | 198 | | 55 | NC | 0 | 0 | −2 | NC | 0 | 0 | 85 | MI | 1.4 | 0.1 |
| D21261 | Human mRNA for KIAA0120 "gene," complete cds | 2203 | | −128 | NC | 0 | 0 | −2 | NC | 0 | 0 | 454 | I | 1.2 | 0.1 |
| D78275 | Human mRNA for proteasome subunit "p42," complete cds | 131 | | 54 | NC | 0 | 0 | 78 | NC | 0 | 0 | −46 | MD | 1.5 | 0.1 |
| L16464 | Human ETS oncogene (PEP1) "mRNA," complete cds | 34 | | −6 | NC | 0 | 0 | −5 | NC | 0 | 0 | −26 | MD | −1.7 | 0.1 |
| M25164 | Human thyrotropin beta subunit gene | 20 | | 25 | NC | 0 | 0 | 36 | NC | 0 | 0 | 18 | MI | 1.9 | 0.1 |
| U12897 | Human non-translated mRNA sequence | 35 | | −20 | NC | 0 | 0 | −15 | NC | 0 | 0 | −22 | D | −1.7 | 0.1 |
| X74331 | H. sapiens mRNA for DNA primase (subunit p58) | 62 | | 47 | NC | 0 | 0 | 7 | NC | 0 | 0 | 38 | MI | 1.6 | 0.1 |
| X96698 | H. sapiens mRNA for D1075-like gene | 118 | | 10 | NC | 0 | 0 | −10 | NC | 0 | 0 | 60 | I | 1.5 | 0.1 |
| D64142 | Human mRNA for histone "Hix," complete cds | 646 | | 137 | NC | 0 | 0 | 75 | NC | 0 | 0 | 184 | I | 1.3 | 0.09 |
| HG415-HT415 | "Lectin," "Galactoside-Binding," "Soluble," 2 | 23 | * | 4 | NC | 0 | 0 | 3 | NC | 0 | 0 | 18 | I | 1.8 | 0.09 |
| J03779 | Human common acute lymphoblastic leukemia antigen (CALLA) "mRNA," complete c | 99 | | −26 | NC | 0 | 0 | 6 | NC | 0 | 0 | −36 | D | 1.6 | 0.09 |
| L02326 | Homo sapiens (clone Hu lambda-17) lambda-like "gene," complete cds | 30 | * | 27 | NC | 0 | 0 | 3 | NC | 0 | 0 | −51 | D | −1.5 | 0.09 |
| L33842 | Homo sapiens (clone FFE-7) type II inosine monophosphate dehydrogenase (IMPDH | 1773 | | −212 | NC | 0 | 0 | −274 | NC | 0 | 0 | 375 | I | 1.2 | 0.09 |
| L43631 | Homo sapiens scaffold attachment factor (SAF-B) "gene," partial cds | 116 | | 8 | NC | 0 | 0 | 73 | NC | 0 | 0 | 56 | I | 1.5 | 0.09 |
| M31013 | Human nonmuscle myosin heavy chain (NMHC) "mRNA," 3' end | 652 | | −106 | NC | 0 | 0 | 119 | NC | 0 | 0 | 184 | I | 1.3 | 0.09 |
| M93650 | Human paired box gene (PAX6) "homologue," complete cds | 82 | | −29 | NC | 0 | 0 | −4 | NC | 0 | 0 | −30 | MD | 1.6 | 0.09 |
| S75463 | P43 = mitochondrial elongation factor homolog "[human," "liver," "mRNA," 1644 nt] | 1529 | | 47 | NC | 0 | 0 | −214 | NC | 0 | 0 | 321 | I | 1.2 | 0.09 |
| X69550 | H. sapiens mRNA for rho GDP-dissociated inhibitor 1 | 977 | | 66 | NC | 0 | 0 | 130 | NC | 0 | 0 | 237 | I | 1.2 | 0.09 |
| X75535 | H. sapiens mRNA for PxF protein | 50 | | 19 | NC | 0 | 0 | −8 | NC | 0 | 0 | 31 | I | 1.6 | 0.09 |
| X82554 | H. sapiens SPHAR gene for cyclin-related protein | 33 | * | −17 | NC | 0 | 0 | −15 | NC | 0 | 0 | −25 | MD | −1.7 | 0.09 |
| Y00815 | Human mRNA for LCA-homolog, LAR protein (leukocyte antigen related) | 204 | | 6 | NC | 0 | 0 | −25 | NC | 0 | 0 | 84 | I | 1.4 | 0.09 |
| Y08613 | H. sapiens alternative 3' UTR of Nup88 mRNA. /gb = Y08613 /ntype = RNA | −7 | * | 54 | NC | 0 | 0 | 24 | NC | 0 | 0 | 38 | MI | −1.6 | 0.09 |
| D50914 | Human mRNA for KIAA0124 "gene," partial cds | 332 | | −2 | NC | 0 | 0 | 26 | NC | 0 | 0 | 108 | MI | 1.5 | 0.08 |
| D55654 | Human mRNA for cytosolic malate "dehydrogenase," complete cds | 490 | | 31 | NC | 0 | 0 | 65 | NC | 0 | 0 | −117 | MD | 1.3 | 0.08 |
| G2279-HT237 | Triosephosphate isomerase | 3121 | | 149 | NC | 0 | 0 | −172 | NC | 0 | 0 | 490 | I | 1.2 | 0.08 |
| L34587 | Homo sapiens RNA polymerase II elongation factor "SIII," p15 subunit "mRNA," com | 704 | | 77 | NC | 0 | 0 | 101 | NC | 0 | 0 | 173 | I | 1.2 | 0.08 |
| L49054 | Homo sapiens t(3;5)(q25.1;p34) fusion gene NPM-MLF1 mRNA, complete cds. | 4 | | 3 | NC | 0 | 0 | 17 | NC | 0 | 0 | 28 | I | −1.6 | 0.08 |
| M64676 | Human K+ channel subunit "gene," complete cds | 31 | | −25 | NC | 0 | 0 | −25 | NC | 0 | 0 | −30 | MD | −1.5 | 0.08 |
| S67325 | propionyl CoA carboxylase beta subunit "[human," "liver," "placenta," "HL1008," "mR | 86 | | 64 | NC | 0 | 0 | 0 | NC | 0 | 0 | 42 | MI | 1.5 | 0.08 |
| U25435 | H. sapiens alternative 3' UTR of Nup88 mRNA. /gb = Y08613 /ntype = RNA | 42 | | 1 | NC | 0 | 0 | 17 | NC | 0 | 0 | 24 | MI | 1.6 | 0.08 |
| U26914 | Human transcriptional repressor (CTCF) "mRNA," complete cds | 31 | | −19 | NC | 0 | 0 | −31 | NC | 0 | 0 | −34 | D | −1.5 | 0.08 |
| Y07829 | Human ras-responsive element binding protein (RREB-1) "mRNA," complete cds | −90 | * | 62 | NC | 0 | 0 | 106 | I | −1.0 | 0 | 116 | I | −1.3 | 0.08 |
| Z56281 | exon A2 from H. sapiens gene encoding RING finger protein. /gb = Y07829 /ntype = DN | 134 | | 4 | NC | 0 | 0 | −25 | NC | 0 | 0 | 56 | I | 1.4 | 0.08 |
| | H. sapiens mRNA for interferon regulatory factor 3 | 5063 | | 37 | NC | 0 | 0 | −18 | NC | 0 | 0 | 634 | I | 1.1 | 0.07 |
| D11428 | Human mRNA for PMP-22(PAS-II/SR13/Gras-3) of peripheral "myelin," complete cds | 88 | | −15 | NC | 0 | 0 | 20 | NC | 0 | 0 | −29 | MD | 1.5 | 0.07 |
| D13118 | Human mRNA for ATP synthase subunit c encoded by P1 gene | 746 | | 72 | NC | 0 | 0 | −90 | NC | 0 | 0 | 169 | I | 1.2 | 0.07 |
| D28589 | Human mRNA "(KIAA0167)," partial sequence. /gb = D28589 /ntype = RNA | 428 | | −59 | NC | 0 | 0 | −70 | NC | 0 | 0 | −101 | MD | 1.3 | 0.07 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| D29012 | Human mRNA for proteasome subunit "Y," complete cds | 1016 | | 89 | NC | 0 | 0 | −118 | NC | 0 | 0 | 205 | I | 1.2 | 0.07 |
| D82061 | Human B-cell mRNA for a member of the short-chain alcohol dehydrogenase "family | 86 | | 18 | NC | 0 | 0 | −3 | NC | 0 | 0 | 38 | I | 1.4 | 0.07 |
| L37792 | Human syntaxin 1A "mRNA," complete cds | 75 | | 8 | NC | 0 | 0 | −7 | NC | 0 | 0 | 36 | MI | 1.5 | 0.07 |
| M15182 | Human beta-glucuronidase "mRNA," complete cds | 101 | | −21 | NC | 0 | 0 | 20 | NC | 0 | 0 | 41 | MI | 1.4 | 0.07 |
| M24485 | Homo sapiens (clone pHGST-pl) glutathione S-transferase pl (GSTP1) "gene," comp | 1295 | | 14 | NC | 0 | 0 | −55 | NC | 0 | 0 | 244 | I | 1.2 | 0.07 |
| M29610 | Human glycophorin E "mRNA," complete cds — Also Represents: J02982 | 8 | * | 11 | NC | 0 | 0 | 5 | NC | 0 | 0 | 22 | I | 1.4 | 0.07 |
| U49436 | Human translation initiation factor 5 (eIF5) "mRNA," complete cds | 106 | | 42 | NC | 0 | 0 | −15 | NC | 0 | 0 | 46 | I | 1.4 | 0.07 |
| U59831 | Human transcription "factor," forkhead related activator 4 (FREAC-4) "gene," comple | 446 | | −7 | NC | 0 | 0 | 37 | NC | 0 | 0 | −98 | D | 1.3 | 0.07 |
| U60269 | putative envelope protein, orf similar to env of Type A and Type B retroviruses and to | 40 | * | 1 | NC | 0 | 0 | 5 | NC | 0 | 0 | 21 | I | 1.5 | 0.07 |
| U62325 | Human FE65-like protein (hFE65L) "mRNA," partial cds | 33 | | 4 | NC | 0 | 0 | −12 | NC | 0 | 0 | −17 | MD | −1.7 | 0.07 |
| X12876 | Human mRNA fragment for cytokeratin 18. — "Also Represents: M24842, M26326" | 663 | | 45 | NC | 0 | 0 | −58 | NC | 0 | 0 | 165 | I | 1.2 | 0.07 |
| X59417 | H. sapiens PROS-27 mRNA | 1741 | | −216 | NC | 0 | 0 | −284 | NC | 0 | 0 | 306 | I | 1.2 | 0.07 |
| Z29505 | H. sapiens mRNA for nucleic acid binding protein sub2.3 | 986 | | −33 | NC | 0 | 0 | −197 | NC | 0 | 0 | 218 | I | 1.2 | 0.06 |
| D50912 | Human mRNA for KIAA0122 "gene," partial cds | 64 | | −13 | NC | 0 | 0 | 15 | NC | 0 | 0 | 29 | MI | 1.5 | 0.06 |
| D63390 | Human mRNA for acetylhydrolase IB "beta-subunit," complete cds | 38 | | −17 | NC | 0 | 0 | −17 | NC | 0 | 0 | −15 | MD | 1.6 | 0.06 |
| D79983 | Human mRNA for KIAA0161 "gene," complete cds | 4 | * | 31 | NC | 0 | 0 | 22 | NC | 0 | 0 | 26 | I | −1.5 | 0.06 |
| HG36-HT410 | Polymyositis/Scleroderma (Pm-Scl) Autoantigen, Alt. Splice 2 — Also Represents: M58 | 95 | | 19 | NC | 0 | 0 | 27 | NC | 0 | 0 | −29 | MD | 1.4 | 0.06 |
| M23197 | Human differentiation antigen (CD33) "mRNA," complete cds | 90 | | 23 | NC | 0 | 0 | 4 | NC | 0 | 0 | 35 | I | 1.4 | 0.06 |
| M31303 | Human oncoprotein 18 (Op18) "gene," complete cds | 330 | | 9 | NC | 0 | 0 | 65 | NC | 0 | 0 | −74 | D | 1.3 | 0.06 |
| U16812 | Human Bak-2 "gene," complete cds — "Also Represents: U16811, U23765, X84213" | 66 | * | −16 | NC | 0 | 0 | −9 | NC | 0 | 0 | 28 | MI | 1.4 | 0.06 |
| U80184 | Homo sapiens FLII "gene," complete cds | 147 | | 66 | NC | 0 | 0 | 42 | NC | 0 | 0 | 49 | I | 1.3 | 0.06 |
| X05323 | Human MRC OX-2 gene signal sequence | 30 | * | −9 | NC | 0 | 0 | −13 | NC | 0 | 0 | −25 | MD | −1.5 | 0.06 |
| X68560 | H. sapiens SPR-2 mRNA for GT box binding protein | 32 | | −7 | NC | 0 | 0 | 14 | NC | 0 | 0 | −15 | D | −1.6 | 0.06 |
| X96484 | H. sapiens mRNA for DGCR6 protein | 224 | | 15 | NC | 0 | 0 | −26 | NC | 0 | 0 | 70 | I | 1.3 | 0.06 |
| X98801 | H. sapiens mRNA for dynactin | 234 | | −45 | NC | 0 | 0 | −65 | NC | 0 | 0 | 67 | I | 1.3 | 0.06 |
| Y07566 | H. sapiens mRNA for RIT protein | 16 | | 14 | NC | 0 | 0 | 14 | NC | 0 | 0 | 16 | MI | −1.6 | 0.06 |
| Y08999 | H. sapiens mRNA for Sop2p-like protein | 820 | | 7 | NC | 0 | 0 | 48 | NC | 0 | 0 | 159 | I | 1.2 | 0.06 |
| AF006041 | Homo sapiens Fas-binding protein (DAXX) "mRNA," partial cds. /gb = AF006041 /ntyp | 173 | | 13 | NC | 0 | 0 | 46 | NC | 0 | 0 | 51 | I | 1.3 | 0.05 |
| D00596 | Human thymidylate syntase (EC 2.1.1.45) "gene," complete cds | 592 | | 58 | NC | 0 | 0 | 41 | NC | 0 | 0 | 120 | I | 1.2 | 0.05 |
| D13636 | Human mRNA for KIAA0011 "gene," complete cds | 121 | | 5 | NC | 0 | 0 | 3 | NC | 0 | 0 | 39 | MI | 1.3 | 0.05 |
| D14710 | Human mRNA for ATP synthase alpha "subunit," complete cds | 1915 | | −21 | NC | 0 | 0 | −38 | NC | 0 | 0 | −255 | MD | 1.2 | 0.05 |
| D43642 | Human YL-1 mRNA for YL-1 protein (nuclear protein with DNA-binding "ability)," com | 303 | | −10 | NC | 0 | 0 | −35 | NC | 0 | 0 | 79 | I | 1.3 | 0.05 |
| G3107-HT328 | Plasma Membrane Calcium Pump Hpmca2a — Also Represents: U15688 | 34 | * | −1 | NC | 0 | 0 | −9 | NC | 0 | 0 | −12 | MD | 1.6 | 0.05 |
| M14483 | PTMA gene extracted from Human prothymosin alpha "mRNA," complete cds — "Also | 2251 | | 54 | NC | 0 | 0 | 567 | NC | 0 | 0 | −262 | D | 1.1 | 0.05 |
| M81757 | H. sapiens S19 ribosomal protein "mRNA," complete cds | 6279 | | 647 | NC | 0 | 0 | −9 | NC | 0 | 0 | 608 | I | 1.1 | 0.05 |
| U60115 | Human skeletal muscle LIM-protein SLIM1 "mRNA," complete cds | 79 | | 13 | NC | 0 | 0 | 44 | NC | 0 | 0 | 29 | MI | 1.4 | 0.05 |
| X13973 | Human mRNA for ribonuclease/angiogenin inhibitor (RAI) | 528 | | 53 | NC | 0 | 0 | −102 | NC | 0 | 0 | 108 | I | 1.2 | 0.05 |
| X59766 | H. sapiens mRNA for Zn-alpha2-glycoprotein | −46 | * | 73 | NC | 0 | 0 | 60 | NC | 0 | 0 | 71 | I | −1.2 | 0.05 |
| X69836 | H. sapiens mRNA sequence (15q11-13) | 45 | | 9 | NC | 0 | 0 | −5 | NC | 0 | 0 | 21 | MI | 1.5 | 0.05 |
| X80230 | H. sapiens mRNA (clone C-2k) mRNA for serine/threonine protein kinase | 287 | | 36 | NC | 0 | 0 | −84 | NC | 0 | 0 | 69 | MI | 1.2 | 0.05 |
| X82207 | H. sapiens mRNA for beta-centractin (PC3) | 106 | | −23 | NC | 0 | 0 | −19 | NC | 0 | 0 | 38 | I | 1.4 | 0.05 |
| X89399 | H. sapiens mRNA for "ins(1,3,4,5)P4-binding" protein — Also Represents: L20688 | 50 | | 0 | NC | 0 | 0 | 11 | NC | 0 | 0 | 23 | I | 1.5 | 0.05 |
| Y10376 | H. sapiens mRNA for seryl-tRNA synthetase | 720 | | −7 | NC | 0 | 0 | −69 | NC | 0 | 0 | 131 | MI | 1.2 | 0.05 |
| Y10376 | H. sapiens mRNA for SIRP-beta1 | 113 | * | 1 | NC | 0 | 0 | −38 | NC | 0 | 0 | 37 | MI | 1.3 | 0.05 |
| | | 7358 | | −700 | NC | 0 | 0 | 917 | NC | 0 | 0 | 562 | I | 1.1 | 0.04 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| AJ001421 | *Homo sapiens* mRNA for Rer1 protein. /gb = AJ001421 /ntype = RNA | 446 | | 70 | NC | 0 | 0 | 85 | NC | 0 | 0 | 87 | MI | 1.2 | 0.04 |
| D31764 | Human mRNA for KIAA0064 "gene," complete cds | 332 | | 10 | NC | 0 | 0 | -14 | NC | 0 | 0 | 69 | MI | 1.2 | 0.04 |
| J02645 | Human translational initiation factor "(eIF-2)," alpha subunit "mRNA," complete cds | 346 | | -12 | NC | 0 | 0 | 146 | NC | 0 | 0 | 70 | MI | 1.2 | 0.04 |
| L37936 | Human nuclear-encoded mitochondrial elongation factor Ts (EF-Ts) "mRNA," 3' end | 205 | | 9 | NC | 0 | 0 | 47 | NC | 0 | 0 | 48 | MI | 1.2 | 0.04 |
| M13792 | Human adenosine deaminase (ADA) "gene," complete cds | 135 | | 69 | NC | 0 | 0 | -2 | NC | 0 | 0 | 38 | MI | 1.3 | 0.04 |
| M60483 | protein phosphatase-2A catalytic subunit-alpha gene extracted from Human protein p | 109 | | 0 | NC | 0 | 0 | 20 | NC | 0 | 0 | -26 | MD | 1.3 | 0.04 |
| M65254 | Protein phosphatase 2A 65 kDa regulatory subunit-beta "mRNA," complete cds | 47 | | -3 | NC | 0 | 0 | 14 | NC | 0 | 0 | -14 | MD | 1.4 | 0.04 |
| M69197 | HPR from Human haptoglobin and haptoglobin-related protein (HP and HPR) "genes | 11 | * | 22 | NC | 0 | 0 | 5 | NC | 0 | 0 | 17 | I | -1.4 | 0.04 |
| M84332 | Human ADP-ribosylation factor 1 gene | 1308 | | 138 | NC | 0 | 0 | 62 | NC | 0 | 0 | 163 | I | 1.1 | 0.04 |
| U23143 | Human mitochondrial serine hydroxymethyltransferase "gene," nuclear encoded mito | 316 | | 33 | NC | 0 | 0 | -4 | NC | 0 | 0 | 70 | MI | 1.2 | 0.04 |
| U25988 | Human pregnancy-specific glycoprotein 13 (PSG13) "mRNA," complete cds | 280 | * | 13 | NC | 0 | 0 | 5 | I | 1 | 0 | 62 | MI | 1.2 | 0.04 |
| U43944 | Human breast cancer cytosolic NADP(+)-dependent malic enzyme "mRNA," partial c | 66 | | 12 | NC | 0 | 0 | 25 | NC | 0 | 0 | -19 | D | 1.4 | 0.04 |
| X78565 | *H. sapiens* mRNA for "tenascin-C," 7560bp | 41 | * | -24 | NC | 0 | 0 | -4 | NC | 0 | 0 | 16 | I | 1.4 | 0.04 |
| AF001548 | 815A9.1 gene (myosin heavy chain) extracted from *Homo sapiens* chromosome 16 B | -5 | * | -14 | NC | 0 | 0 | -5 | NC | 0 | 0 | 30 | I | -1.3 | 0.03 |
| | | 8301 | | -487 | NC | 0 | 0 | 1056 | NC | 0 | 0 | 489 | I | 1.1 | 0.03 |
| D15049 | Human mRNA for protein tyrosine phosphatase | 26 | | -23 | NC | 0 | 0 | -15 | NC | 0 | 0 | -24 | MD | 1.2 | 0.03 |
| G3415-HT359 | Poliovirus Receptor | 224 | | -23 | NC | 0 | 0 | 22 | NC | 0 | 0 | 46 | MI | 1.2 | 0.03 |
| G4606-HT501 | "Centractin," Alpha | 174 | | -28 | NC | 0 | 0 | 16 | NC | 0 | 0 | 35 | MI | 1.2 | 0.03 |
| G4747-HT519 | Nadh-Ubiquinone "Oxidoreductase," 51 Kda Subunit | 149 | | -16 | NC | 0 | 0 | 25 | NC | 0 | 0 | 35 | MI | 1.2 | 0.03 |
| J03027 | | 8 | * | 13 | NC | 0 | 0 | 4 | NC | 0 | 0 | 18 | I | -1.3 | 0.03 |
| L15189 | *Homo sapiens* mitochondrial HSP75 mRNA, complete cds. — Also Represents: L1106 | 204 | | 17 | NC | 0 | 0 | 109 | NC | 0 | 0 | -37 | D | 1.2 | 0.03 |
| L36529 | Human (clone N5-4) protein p84 "mRNA," complete cds | 25 | * | -13 | NC | 0 | 0 | -8 | NC | 0 | 0 | -22 | MD | -1.2 | 0.03 |
| M14219 | Human chondroitin/dermatan sulfate proteoglycan (PG40) core protein "mRNA," com | 6 | * | -7 | NC | 0 | 0 | 37 | NC | 0 | 0 | 19 | I | -1.3 | 0.03 |
| S67156 | ASP = aspartoacylase "[human," "kidney," "mRNA," 1435 nt] | 27 | * | -7 | NC | 0 | 0 | -7 | NC | 0 | 0 | -9 | MD | -1.4 | 0.03 |
| U09646 | Human camitine palmitoyltransferase II precursor (CPT1) gene | 1 | * | 1 | NC | 0 | 0 | 10 | NC | 0 | 0 | 24 | MI | 1.3 | 0.03 |
| U33936 | Human adenosine kinase "mRNA," complete cds. /gb = U33936 /ntype = RNA — Also Re | 100 | | 6 | NC | 0 | 0 | 16 | NC | 0 | 0 | -23 | MD | 1.3 | 0.03 |
| U81556 | Human hypothetical protein A4 "mRNA," complete cds | 340 | | -26 | NC | 0 | 0 | -138 | NC | 0 | 0 | 64 | MI | 1.2 | 0.03 |
| U89505 | Human Hlark "mRNA," complete cds. | 511 | | -6 | NC | 0 | 0 | -114 | NC | 0 | 0 | 71 | MI | 1.1 | 0.03 |
| U92436 | Human mutated in multiple advanced cancers protein (MMAC1) "mRNA," complete c | -4 | * | 18 | NC | 0 | 0 | 13 | NC | 0 | 0 | 29 | I | -1.3 | 0.03 |
| X06614 | Human mRNA for receptor of retinoic acid | 119 | | 18 | NC | 0 | 0 | -65 | NC | 0 | 0 | 28 | MI | 1.2 | 0.03 |
| X62535 | *H. sapiens* mRNA for diacylglycerol kinase | 174 | | -5 | NC | 0 | 0 | -32 | NC | 0 | 0 | 36 | MI | 1.2 | 0.03 |
| X64643 | *H. sapiens* c6.1A mRNA | 25 | | -26 | NC | 0 | 0 | -10 | NC | 0 | 0 | -25 | MD | -1.2 | 0.03 |
| X69654 | *H. sapiens* mRNA for ribosomal protein S26 | 3581 | | 28 | NC | 0 | 0 | -544 | NC | 0 | 0 | 314 | I | 1.1 | 0.03 |
| X74570 | *H. sapiens* mRNA for Gal-beta(1-3/1-4)GlcNAc alpha-2,3-sialyltransferase | 93 | | -47 | NC | 0 | 0 | 11 | NC | 0 | 0 | 25 | MI | 1.3 | 0.03 |
| X83572 | *H. sapiens* ARSD mRNA | 104 | | -54 | NC | 0 | 0 | -78 | NC | 0 | 0 | 25 | MI | 1.2 | 0.03 |
| X94910 | *H. sapiens* mRNA for ERp31 protein | 318 | | -81 | NC | 0 | 0 | 52 | NC | 0 | 0 | 53 | MI | 1.2 | 0.03 |
| X99975 | *H. sapiens* mRNA for hRTR/hGCNF protein | -1 | | 10 | NC | 0 | 0 | 23 | NC | 0 | 0 | 27 | I | -1.3 | 0.03 |
| Y08991 | *H. sapiens* mRNA for adaptor protein p150 | 55 | | 0 | NC | 0 | 0 | 18 | NC | 0 | 0 | 18 | I | 1.3 | 0.03 |
| | | 24 | | -2 | NC | 0 | 0 | -5 | NC | 0 | 0 | -20 | D | 1.2 | 0.02 |
| D16562 | Human mRNA for ATP synthase gamma-subunit "(L-type)," complete cds | 628 | | 89 | NC | 0 | 0 | 265 | NC | 0 | 0 | -56 | MD | 1.1 | 0.02 |
| D38145 | Human mRNA for prostacyclin "synthase," complete cds | 24 | | -13 | NC | 0 | 0 | -16 | NC | 0 | 0 | -28 | MD | -1.2 | 0.02 |

TABLE 4-continued

ISGs and IRGs identified from human fibrosarcoma cells incubated in IFN-α, IFN-β or IFN-γ

| GenBank Accession. | Entrez Definition — Afix Definition | Untreated Intensity | B = A | IFN-a Intensity | Incr Decr | Fold Change | Sig | IFN-b Intensity | Incr Decr | Fold Change | Sig | IFN-g Intensity | Incr Decr | Fold Change | Sig |
|---|---|---|---|---|---|---|---|---|---|---|---|---|---|---|---|
| D56495 | Human mRNA for Reg-related sequence derived peptide-2 | 26 | | 12 | NC | 0 | 0 | 10 | NC | 0 | 0 | −11 | D | −1.3 | 0.02 |
| L16991 | Human thymidylate kinase (CDC8) "mRNA," complete cds | 254 | | 30 | NC | 0 | 0 | −2 | NC | 0 | 0 | 40 | I | 1.2 | 0.02 |
| M14676 | Human src-like kinase (slk) "mRNA," complete cds | 128 | | −22 | NC | 0 | 0 | −22 | NC | 0 | 0 | −21 | MD | 1.2 | 0.02 |
| M33680 | Human 26-kDa cell surface protein TAPA-1 "mRNA," complete cds | 1959 | | −64 | NC | 0 | 0 | 79 | NC | 0 | 0 | 159 | I | 1.1 | 0.02 |
| M59371 | Human protein tyrosine kinase "mRNA," complete cds | 191 | | 23 | NC | 0 | 0 | 8 | NC | 0 | 0 | 32 | I | 1.2 | 0.02 |
| M93143 | Human plasminogen-like protein (PLGL) "mRNA," complete cds. | 13 | * | −5 | NC | 0 | 0 | −5 | NC | 0 | 0 | 12 | MI | −1.2 | 0.02 |
| U14575 | Human (ard-1) "mRNA," complete cds | 49 | | 11 | NC | 0 | 0 | 0 | NC | 0 | 0 | 11 | MI | 1.2 | 0.02 |
| U86529 | Human glutathione transferase Zeta 1 (GSTZ1) "mRNA," complete cds. /gb = U86529 | 347 | | 34 | NC | 0 | 0 | −61 | NC | 0 | 0 | 49 | MI | 1.1 | 0.02 |
| U88898 | Human endogenous retroviral H protease/integrase-derived ORF1 "mRNA," complete | 97 | * | −28 | NC | 0 | 0 | −13 | NC | 0 | 0 | 21 | MI | 1.2 | 0.02 |
| X99699 | H. sapiens mRNA for XIAP associated factor-1 | 65 | * | −26 | NC | 0 | 0 | −57 | NC | 0 | 0 | 16 | I | 1.3 | 0.02 |
| L00137 | GHRF gene (growth hormone releasing factor) extracted from Human growth hormon | 4 | * | −8 | NC | 0 | 0 | 17 | NC | 0 | 0 | 18 | MI | −1.1 | 0.01 |
| M59807 | Human NK4 "mRNA," complete cds | 234 | | −57 | NC | 0 | 0 | −16 | NC | 0 | 0 | 16 | MI | 1.1 | 0.01 |
| S46622 | calcineurin A catalytic subunit "[human,"] "testis," "mRNA," 2134 nt] | 23 | * | −1 | NC | 0 | 0 | 8 | NC | 0 | 0 | −17 | MD | −1.1 | 0.01 |
| U02019 | Human AU-rich element RNA-binding protein AUF1 "mRNA," complete cds | 22 | * | −1 | NC | 0 | 0 | 0 | NC | 0 | 0 | −22 | MD | −1.1 | 0.01 |
| U17886 | Human succinate dehydrogenase iron-protein subunit (sdhB) gene | 337 | | 42 | NC | 0 | 0 | 19 | NC | 0 | 0 | 34 | MI | 1.1 | 0.01 |
| U37251 | Human KRAB zinc finger protein (ZNF177) "mRNA," splicing "variant," complete cds | 22 | * | −20 | NC | 0 | 0 | 4 | NC | 0 | 0 | −25 | D | −1.1 | 0.01 |
| U45975 | Human phosphatidylinositol "(4,5)bisphosphate" 5-phosphatase homolog "mRNA," pa | 137 | | 23 | NC | 0 | 0 | 12 | NC | 0 | 0 | 14 | D | 1.1 | 0.01 |
| U74612 | Human hepatocyte nuclear factor-3/fork head homolog 11A (HFH-11A) mRNA compl | 326 | | 0 | MI | 1 | 0 | −22 | NC | 0 | 0 | 19 | MI | 1.1 | 0.01 |
| X85134 | H. sapiens RBQ-3 mRNA | 22 | | 3 | NC | 0 | 0 | −9 | NC | 0 | 0 | −26 | D | −1.1 | 0.01 |
| Z68747 | H. sapiens mRNA for imogen 38 /gb = Z68747 /ntype = RNA | 22 | * | −2 | NC | 0 | 0 | 37 | NC | 0 | 0 | −22 | D | −1.1 | 0.01 |
| AB000114 | Human mRNA for "osteomodulin," complete cds | 12 | | 22 | NC | 0 | 0 | −8 | NC | 0 | 0 | −35 | D | −1.0 | 0 |

TABLE 5

ISGs and IRGs identified from mouse embryonic fibroblast incubated
in the presence or absence of IFN-αBBDB Database: GenBank accession numbers
Diff, difference
I = those genes that were induced or upregulated by the treatment (ISGs)
D = those genes that were repressed or downregulated by the treatment (IRGs)
Fold C, fold change
Sig, significance factor

| Accession | Description | | intensity | Change | Dif | B | Fold C | Sig |
|---|---|---|---|---|---|---|---|---|
| X56602 | Mus musculus mRNA interferon-induced 15-KDa protein | gene | 2655 | 2499 | I | | 17 | 22.12 |
| L32974 | "Mouse interferon-inducible protein homologue mRNA, complete cds" | gene | 1829 | 1699 | I | | 14 | 16.11 |
| U73037 | "Mus musculus interferon regulatory factor 7(mirf7) mRNA, complete cds" | gene | 890 | 844 | I | | 19.4 | 13.81 |
| X98519 | M. musculus mRNA for interleukin 11 receptor | gene | 52 | -868 | D | | 17.8 | 13.37 |
| M86829 | "Mus musculus (crg-2) mRNA, complete cds" | gene | 624 | 599 | I | | 24.6 | 13.15 |
| AA153021 | mq67e05.r1 Soares 2NbMT Mus musculus cDNA clone 583808 5' similar to gb:M55543 | est | 528 | 515 | I | * | ~26.4 | 12.6 |
| U15636 | "Mus musculus GTP binding protein (GTP2) mRNA, complete cds" | gene | 476 | 464 | I | * | ~23.8 | 11.39 |
| L32973 | "Mouse thymidylate kinase homologue mRNA, complete cds" | gene | 328 | 309 | I | * | ~16.4 | 7.57 |
| U19119 | "Mus musculus G-protein-like LRG-47 mRNA, complete cds" | gene | 400 | 367 | I | | 12.2 | 6.78 |
| U06924 | "Mus musculus signal transducer and activator of transcription (Stat1) mRNA, complete cds" | gene | 461 | 420 | I | | 11.1 | 6.76 |
| M63620 | "Mus musculus predicted GTP binding protein (IRG-47) mRNA, complete cds" | gene | 265 | 255 | I | * | ~13.3 | 5.98 |
| U34815 | "Mouse monokine induced by gamma interferon (MIG) mRNA, complete cds" | gene | 260 | 245 | I | * | ~13.0 | 5.78 |
| U46637 | "Mus musculus thymic shared antigen-1 (TSA-1) gene, complete cds" | gene | 1717 | 1371 | I | | 5 | 5.53 |
| U22031 | "Mus musculus 20S proteasome subunit Lmp7 (Lmp7d allele) mRNA, complete cds" | gene | 382 | 340 | I | | 9 | 5.14 |
| U15635 | "Mus musculus IFN-gamma induced (Mg11) mRNA, complete cds" | gene | 380 | 331 | I | | 7.7 | 4.36 |
| AA013783 | mh13a03.r1 Soares mouse placenta 4NbNMF13.5 14.5 Mus musculus cDNA clone 4423 | est | 250 | 223 | I | * | 9.5 | 4.34 |
| U44731 | "Mus musculus putative purine nucleotide binding protein mRNA, complete cds" | gene | 241 | 211 | I | | 8.1 | 3.65 |
| X56548 | M. musculus Np-b mRNA for purine-nucleoside phosphorylase | gene | 833 | 641 | I | | 4.3 | 3.16 |
| L16894 | "Mus musculus Cyclophilin C (CyCPA) mRNA, complete cds" | gene | 765 | 586 | I | | 1.3 | 2.96 |
| L04262 | "Mus musculus(clones p10a-[1.5n, 1.7]b and pG4-14) lysyl oxidase gene, exon 7 and cd | gene | 278 | -788 | D | | 3.8 | 2.93 |
| M21117 | "Mouse interferon-onduced Mx1 protein gene conferring selective resistance to influenza | gene | 152 | 450 | I | | ~7.6 | 2.9 |
| U60328 | "Mus musculus proteasome activator PA28 alpha subunit mRNA, complete cds" | gene | 366 | 293 | I | | 5.1 | 2.61 |
| X75129 | "M. musculus (129/Sv) gene for xanthing dehydrogenase, exon 1" | gene | 188 | 159 | I | * | 6.5 | 2.55 |
| W13646 | ma93f05.r1 Soares mouse p3NMF19.5 Mus musculus cDNA clone 318273 5' similar to | est | 140 | 127 | I | | ~7.0 | 2.46 |
| W13646 | ma93f05.r1 Soares mouse p3NMF19.5 Mus musculus cDNA clone 318273 5' similar to | est | 136 | 122 | I | | ~6.8 | 2.34 |
| U33626 | "Mus musculus PML isoform 1 (Pml) mRNA, complete cds" | gene | 163 | 137 | I | | 6.2 | 2.24 |
| X52574 | Mouse mRNA from Mov10 locus | gene | 164 | 136 | I | * | 6 | 2.15 |
| L39123 | "Mus musculus apolipoprotein D (apoD) mRNA, complete cds" | gene | 530 | 322 | I | | 4 | 1.98 |
| D21207 | "Mouse mRNA for peripheral-type benzodiazepine receptor, complete cds" | gene | 657 | 468 | I | | 3.5 | 1.93 |
| U43085 | "Mus musculus glucocorticoid-attenuated response gene 39 (GARG-39) mRNA, complete cds" | gene | 115 | 109 | I | * | ~5.8 | 1.85 |
| AA165782 | mt74e04.r1 Soares mouse lymph node NbMLN Mus musculus cDNA clone 635646-5' s | est | 402 | 291 | I | | 3.6 | 1.63 |
| U43084 | "Mus musculus glucocorticoid-attenuated response gene 16 (GARG-39) mRNA, complete | est | 107 | 96 | I | | ~5.3 | 1.58 |
| M44537 | "Mus musculus HAM1 gene, complete cds" | gene | 151 | 120 | I | | 4.9 | 1.58 |
| U60329 | "Mus musculus proteasome activator PA28 beta subunit mRNA, complete cds" | gene | 403 | 287 | I | | 3.5 | 1.52 |
| W76686 | me81f08.r1 Soares mouse embryo NbME13.5 14.5 Mus musculus cDNA clone 401991 | est | 235 | 177 | I | | 4.1 | 1.51 |
| X04653 | Mouse mRNA fro Ly-6 alloantigen (Ly-6E.1) | gene | 2057 | 1175 | I | | 2.3 | 1.47 |
| M31419 | "Mus musculus 204 interferon-activatable protein mRNA, complete cds" | gene | 116 | 92 | I | | 4.9 | 1.4 |
| AA013830 | mh04h06.r1 Soares mouse placenta 4NbMP13.5 14.5 Mus musculus cDNA clone 441 | est | 99 | 84 | I | * | ~4.9 | 1.34 |
| AA002528 | mg54a04.r1 Soares mouse embryo NbME13.5 14.5 Mus musculus cDNA clone 427566 | est | 571 | 374 | I | * | 2.9 | 1.27 |
| U02298 | "Mus musculus NIH 3T3 chemokine rantes (Scya5) gene, complete cds" | gene | 117 | 91 | I | | 4.6 | 1.27 |
| U65313 | "Mus musculus ras-GTPase-activating SH3-domain binding protei(l (G3BP) gene, complete | gene | 128 | 99I | I | 4.4 | 1.27 | 1.27 |

TABLE 5-continued

ISGs and IRGs identified from mouse embryonic fibroblast incubated
in the presence or absence of IFN-αBBDB

| | | | | | | | |
|---|---|---|---|---|---|---|---|
| U46690 | "Mus musculus ATP-dependent RNA helicase mRNA, partial cds" | gene | 178 | 133 | I | 3.9 | 1.23 |
| D44464 | "Mouse mRNA for uridine phosphorylase, complete cds" | gene | 96 | 75 | I | * | 1.14 |
| X70058 | M. musculus cytokine gene | gene | 2114 | 1107 | I | | 1.12 |
| L38847 | "Mus musculus hepatoma transmembrane kinase ligand (HTK ligand) mRNA, complete gene | gene | 26 | −81 | D | 4.1 | 1.02 |
| AA060167 | mj72h03.r1 Soares mouse p3NMF19.5 Mus musculus cDNA clone 481685 5' similar to | est | 96 | 73 | I | 4.2 | 1.02 |
| D76440 | "Mouse gene for necdin, complete cds and promoter sequence" | gene | 387 | 251 | I | 2.8 | 1.01 |
| AA059700 | mj77g08.r1 Soares mouse p3NMF19.5 Mus musculus cDNA clone 482174 5' similar to | est. | 1306 | 1107 | I | 2.2 | 1 |
| M86736 | "Mouse acrogranin mRNA, complete cds" | gene | 652 | 390 | I | 2.5 | 0.97 |
| X07699 | Mouse nucleolin gene | gene | 106 | −200 | D | | 2.9 | 0.93 |
| AA072961 | "mm80b02.r1 Stratagene mouse embryonic carcinoma RA (#937318) Mus musculus cD | est | 80 | 72 | I | * | −4.0 | 0.92 |
| X51397 | Murine MyD88 mRNA induced by interleukin-6 | gene | 194 | 133 | I | | 3.2 | 0.91 |
| AA106166 | mm18d01.r1 Stratagene mouse diaphragm (#937303) Mus musculus cDNA clone 5218 | est | 165 | 116 | I | | 3.3 | 0.9 |
| L10244 | "Mouse spermidine/spermine N1-acetyltransferase (SSAT) mRNA, complete cds" | gene | 384 | 241 | I | | 2.7 | 0.89 |
| AA034714 | "mi55h03.r1 Soares mouse embryo NbME13.5 14.5 Mus musculus cDNA clone 467477 | est | 911 | −892 | D | | 2 | 0.88 |
| W41883 | mc64g08.r1 Soares mouse embryo NbME13.5 14.5 Mus musculus cDNA clone 35334 | est | 1394 | 718 | I | | 2.1 | 0.87 |
| D13664 | Mouse mRNA for osteoblast specific factor 2 (OSF-2) | gene | 234 | −338 | D | | 2.4 | 0.87 |
| M21050 | "Mouse lysozyme M gene, exon 4" | gene | 421 | −513 | D | | 2.2 | 0.87 |
| M73748 | "Mouse OTS-8 mRNA, complete cds" | gene | 568 | 331 | I | | 2.4 | 0.83 |
| X58251 | MouseCOL1A2 mRNA for pro-alpha-2(I) collagen | gene | 7702 | 2811 | I | | 1.6 | 0.81 |
| L11613 | "Mus musculus proteasome (imp2) gene, complete mRNA" | gene | 72 | 75 | I | * | −3.6 | 0.81 |
| M63658 | "M. musculus G protein, beta-subunit mRNA, complete cds" | gene | 129 | 90 | I | | 3.4 | 0.8 |
| M33960 | "Mouse plasminogen activator inhibitor (PAI-1) mRNA, complete cds" | ge..ne | 2684 | 1191 | I | | 1.8 | 0.79 |
| U08020 | "Mus musculus FVB/N collagen pro-alpha-1 type I chain mRNA, complete cds" | 1936 | 914 | I | | 1.9 | 0.79 |
| AA170444 | ms90f10.r1 Soares mouse 3NbMS Mus musculus cDNA clone 618859 5' similar to SW | 150 | 102 | I | | 3.1 | 0.77 |
| AA087943 | mn94h06.r1 Soares mouse lung 937302 Mus musculus cDNA clone 551771 5' sim | est | 602 | 338 | I | | 2.3 | 0.75 |
| U51992 | "Mus musculus interferon stimulated gene factor gamma mRNA, complete cds" | gene | 74 | 56 | I | | −3.7 | 0.74 |
| W13646 | ma93f05.r1 Soares mouse p3NMF1,9.5 Mus musculus cDNA clone 318273 5' similar to | est | 3002 | 1253 | I | | 1.7 | 0.71 |
| M57890 | "Mouse factorB mRNA, complete cds" | gene | 130 | 89 | I | | 3.1 | 0.7 |
| M21065 | "Mouse interferon regulatory factor 1 mRNA, complete cds" | est | 112 | 78 | I | | 3.2 | 0.7 |
| L04961 | Mouse nuclear-localized inactive X-specific transcript (Xist) mRNA | gene | 13 | −56 | MJ | | −3.5 | 0.66 |
| X14425 | Mouse mRNA for profilin | gene | 557 | 305 | D | | 2.2 | 0.66 |
| D49382 | "Mouse Nedd5 mRNA for DIFF6- orCDC3,10,11,12-like protein with GTPase-motif" | est | 114 | −172 | D | MJ | 2.5 | 0.65 |
| U02997 | "Mus musculus 129 cryptdin-2 (Defcr2) gene, exon 2 and complete cds" | gene | 150 | 97 | I | MJ * | 2.8 | 0.62 |
| D28599 | "Mouse mRNA for proteoglycan, PG-M" | gene | 68 | −113 | D | | 2.7 | 0.6 |
| M55154 | "Mouse transglutaminase (TGase) mRNA, complete cds" | gene | 68 | 48 | I | | 3.4 | 0.59 |
| M26270 | "mouse stearoyl-CoA desaturase (SCD2) mRNA, complete cds" | gene | 191 | −231 | D | | 2.2 | 0.58 |
| X51703 | Mouse mRNA for ubiquitin | gene | 7705 | 2388 | I | | 1.4 | 0.56 |
| Y00516 | Mouse mRNA for aldolase A | gene | 3042 | 1149 | I | | 1.8 | 0.55 |
| U59463 | "Mus musculus ICH-3 mRNA, complete cds" | gene | 86 | 58 | I | | 3.1 | 0.55 |
| AA068780 | mm64g04.r1 Stratagene mouse embryonic carcinoma (#937317) Mus musculus cDNA | est | 63 | 50 | i | | −3.1 | 0.53 |
| W45807 | mc80a10.r1 Soares mouse embryo NbNMF13.5 14.5 Mus musculus cDNA clone 354810 | est | 63 | 46 | MJ * | −3.2 | 0.5i | 0.51 |
| U29152 | "Mus musculus aldose reductase mRNA, complete cds" | gene | 675 | 328 | I | | 1.9 | 0.5 |
| U60087 | "Mus musculus TAP2 (TAP2-d) mRNA, complete cds" | gene | 61 | 50 | J | * | −3.0 | 0.49 |
| D88793 | "Mouse mRNA for cystein rich protein-1, complete cds" | gene | 337 | 181 | i | | 2.2 | 0.48 |
| U27838 | "Mus musculus glycosyl-phosphatidyl-inositol-anchored protein homolog mRNA, compl | gene | 83 | −95 | D | | 2.5 | 0.48 |
| AA117100 | mo60a10.r1 Stratagene mouse Tcell 937311 Mus musculus cDNA clone 557946 5' sim | est | 196 | −211 | D | | 2.1 | 0.48 |
| U77630 | "Mus musculus adrenomedullin precursor mRNA, complete cds" | gene | 182 | 97 | MJ | | 2.5 | 0.48 |
| X77952 | M. musculus (CDI) endoglin mRNA | gene | 61 | 44 | I | | −3.1 | 0.47 |
| AA118758 | mp59h02.r1 Soares 2NbMT Mus musculus cDNA clone 573555 5' similar to gb:X54326 | est | 37 | −64 | D | | 2.7 | 0.47 | 0.47 |
| W82026 | me96a05.r1 Soares mouse embryo NbME13.5 14.5 Mus musculus cDNA clone 403376 | est | 294 | 159 | I | | 2.2 | 0.46 |

TABLE 5-continued

ISGs and IRGs identified from mouse embryonic fibroblast incubated in the presence or absence of IFN-αβBDB

| Accession | Description | Type | Val1 | Val2 | Col | Val3 | Val4 |
|---|---|---|---|---|---|---|---|
| X75313 | M. musculus (C57BL/6) GB-like mRNA | gene | 7224 | 2071 | I | 1.4 | 0.46 |
| U14172 | "Mus musculus p162 protein mRNA, complete cds" | gene | 28 | −51 | D | 2.9 | 0.46 |
| W29730 | mc09c09.r1 Soares mouse p3NMF19.5 Mus musculus cDNA clone 348016 5' similar to | est | 292 | 158 | I | 2.2 | 0.46 |
| M58691 | "Mouse growth factor-inducible protein mRNA, complete cds" | gene | 72 | 47 | MI | 2.9 | 0.45 |
| J05186 | "Mouse protein disulfide isomerase-related protein (ERp72)mRNA, complete cds" | gene | 575 | 276 | I | 1.9 | 0.45 |
| AA097287 | mk16h10.r1 Sbares mouse p3NMF19.5 Mus musculus cDNA clone A93123 5' similar to | est | 155 | 91 | MI | 2.4 | 0.43 |
| X63535 | M. musculus ufo mRNA | gene | 564 | 264 | J | 1.9 | 0.42 |
| M91458 | "Mus musculus sterol-carrier protein X mRNA, complete cds" | gene | 58 | −82 | D | 2.4 | 0.41 |
| X80638 | M. musculus rhoC mRNA | gene | 804 | 350 | I | 1.8 | 0.41 |
| U50712 | "Mus musculus monocyte chemoattractant protein-5 precursor(MCP-5) mRNA, comple | gene | 57 | 42 | I | ~2.9 | 0.41 |
| U27455 | "Mus musculus serine palmitoyltransferase LCB2 subunit mRNA, complete cds" | gene | 110 | 66 | I | 2.5 | 0.41 |
| AA114648 | mm04b0S.r1 Beddington mouse embryonic region Mus musculus cDNA clone 536913 5 | est | 83 | 52 | I | 2.7 | 0.41 |
| AA033424 | m136h07.r1 Soares mouse embryo NbMF13.5 14.5 Mus musculus cDNA clone 465589 | est | 20 | −38 | D | 2.9 | 0.4 |
| W36586 | mb86c07.r1 Soares mouse p3NMF19.5 Mus musculus cbNA clone 336300 5' similar to | est | 43 | −65 | D | 2.5 | 0.4 |
| D38379 | Mouse mRNA for pyrubate kinase M | gene | 2164 | 748 | I | 1.5 | 0.38 |
| W85270 | mf42d05.r1 Soares mouse embryo NbME13.5 14.5 Mus musculus cDNA clone 407721 | est | 507 | 233 | I | 1.9 | 0.38 |
| D87903 | "Mouse mRNA for ARF6, complete cds" | gene | 122 | 70 | I | 2.4 | 0.37 |
| AA140026 | mq39h04.r1 Barstead MPLRB1 Mus musculus cDNA clone 581143 5' similar to TR:G92 | est | 24 | −41 | ME | 2.7 | 0.37 |
| L14677 | "Mus musculus Epoc-1 mRNA, complete cds" | gene | 54 | 40 | I | ~2.7 | 0.36 |
| Z49085 | M. musculus mRNA for mouse developmental kinase 2 (MDK2) | gene | 399 | 188 | I | 1.9 | 0.36 |
| AA080704 | mj63b03.d Soares mouse P3NMF19.5 Mus musculus cDNA clone 480749 5' similar to | est | 436 | 203 | I | 1.9 | 0.36 |
| U58884 | "Mus musculus SH3-containing protein SH3P7 mRNA, complete cds similar to Human | gene | 125 | 72 | MI | 2.3 | 0.36 |
| M38196 | "Mouse serine threonine tyrosine kinase (STY) mRNA, complete cds" | gene | 73 | 45MI | * | 0.36 | |
| M38381 | "Mus musculus palmytoylated protein p55 mRNA, complete cds" | gene | 13 | −40 | D | 2.6 | 0.35 |
| L15429 | "Mus musculus L6 antigen mRNA, complete cds" | gene | 825 | 336 | I | 1.7 | 0.35 |
| AA170104 | ms49a04.r1 Life Tech mouse embryo 13.5dpc 10688014 Mus musculus cDNA clone 6 | est | 54 | 38 | I | ~2.7 | 0.35 |
| M60474 | "Mouse myristoylated alanine-rich C-kinase substrate (MARCKS) mRNA, complete cds" | gene | 128 | −128 | D | 20.35 | |
| AA034714 | mi55h03.r1 Soares mouse embryo NbME13.5 14.5 Mus musculus cDNA clone 467477 | est | 1807 | −829 | D | 1.5 | 0.34 |
| AA034874 | mi53a02.r1 Soares mouse embryo NbME13.5 14.5 Mus musculus cDNA clone 467210 | est | 55 | 34 | I | 2.7 | 0.34 |
| U38981 | "Mus musculus uterine mRNA, complete cds" | gene | 13 | −40 | D | ~2.6 | 0.34 |
| X81582 | M. musculus mRNA for insulin-like growth factor binding protein-4 | gene | 371 | 174 | I | 1.9 | 0.34 |
| M19681 | "Mouse platelet-derived growth factor-inducible protein (JE) gene, complete cds" | gene | 1798 | 618 | I | 1.5 | 0.34 |
| W36757 | mb94b01.r1 Soares mouse p3NMF19.5 Mus musculus cDNA clone 337033 5' similar to | est | 235 | −194 | D | 1.8 | 0.33 |
| X16319 | Mouse mRNA for 54K subunit of signal recognition particle | gene | 33 | −47 | D | 2.4 | 0.32 |
| D63902 | "Mouse mRNA for estrogen-responsive finger protein, complete cds" | gene | 72 | 43 | MI | 2.5 | 0.32 |
| D10727 | "Mouse mRNA for NDPP-1 protein, complete cds" | gene | 19 | −34 | MD | * | 2.7 | 0.32 |
| L09104 | "Mouse tissue factor (mtf) mRNA, complete cds" | gene | 389 | 174 | I | 1.8 | 0.32 |
| M22479 | "Mus musculus glucose phosphate isomerase mRNA, 3' end" | gene | 650 | −387 | D | 1.6 | 0.31 |
| U78085 | "Mus. musculus ribosomal protein S5 mRNA, complete cds" | gene | 2491 | 767 | I | 1.4 | 0.31 |
| J04179 | "Mouse chromatin nonhistone high mobility group protein (HGM-I(Y), complete cds" | gene | 355 | 162 | I | 1.8 | 0.31 |
| X99572 | M. musculus mRNA for new member of PDGFNEGT family of growth factors | gene | 111 | 61 | MI | 2.2 | 0.3 |
| AA107455 | mp08f02.r1 Life Tech mouse embryo 8. 5dpc 1066401.9 Mus musculus cDNA clone 568 | est | 122 | 65 | I | 2.2 | 0.29 |
| M21285 | "Mouse stearoyl-CoA desaturase gene, exon 6" | gene | 117 | −110 | D | 1.9 | 0.29 |
| M28071 | "Mouse tissue factor (mtf) mRNA, complete cds" | gene | 134 | 71 | MI | 2.1 | 0.29 |
| U25633 | "Mus musculus tumor-associated membrane protein (TMP) mRNA, complete cds" | gene | 551 | 227 | I | 1.7 | 0.29 |
| AA103356 | mo18e02.r1 Life Tech mouse embryo 13 5dpc 10666014 Mus musculus cDNA clone 55 | est | 137 | 72 | MI | 2.1 | 0.29 |
| Z03970 | M. musculus (Balb/C) TIMP-3 gene for metalloproteinase-3 tissue inhibitor | gene | 118 | −108 | D | 1.9 | 0.28 |
| U69488 | Mouse mRNA for cytotoxic T-cell membrane glycoprotein Ly-3 340 flank | est | 105 | 56 | MI | 2.2 | 0.27 |
| X07997 | M. musculus viral envelope like protein (G7e) gene, complete cds | gene | 121 | −108 | D | 1.9 | 0.27 |
| X07295 | M. musculus mitochondrial malate dehydrogenase gene 5' flank and exon 1 (and joined( | gene | 290 | −201 | D | 0.27 | 1.7 |

TABLE 5-continued

ISGs and IRGs identified from mouse embryonic fibroblast incubated in the presence or absence of IFN-αBBDB

| Accession | Description | Type | Col1 | Col2 | Col3 | Col4 | Col5 |
|---|---|---|---|---|---|---|---|
| X75313 | M. musculus (C57BL/6) GB-like mRNA | gene | 4600 | 1132 | I | 1.3 | 0.26 |
| AA118729 | mp57g08.r1 Soares mouse 2NbMT Mus musculus cDNA clone 573374 5' similar to SW:TRAM | est | 63 | 36 | I | 2.3 | 0.26 |
| L19932 | "Mouse (beta ig-h3) mRNA, complete cds" | gene | 140 | 71 | I | 2 | 0.26 |
| D86232 | "House mouse; Musculus domesticus mRNA for Ly-6C variant, complete cds" | gene | 128 | 66 | MI | 2.1 | 0.26 |
| AA089117 | mt57e07.r1 Stratagene mouse testis (#937308) Mus. musculus cDNA clone 516132 5' s | est | 13 | −35 | D | −2.4 | 0.26 |
| M57999 | "Mouse transcription factor NF-kappa-B DNA binding subunit mRNA, complete cds" | gene | 41 | −48 | D | 2.2 | 0.25 |
| AA034714 | "mi55h03.r1 Soares mouse embryo NbME13.5 14.5 Mus musculus cDNA clone 467477 | est | 567 | −308 | D | 1.5 | 0.25 |
| X61172 | Mouse mRNA for alpha-mannosidase II | gene | 73 | −71 | D | 2 | 0.25 |
| X65128 | M. musculus gas1 mRNA | gene | 582 | 223 | I | 1.6 | 0.25 |
| AA105621 | "rnn68b06.r1 Stratagene mouse macrophage (#937306) Mus musculus cDNA clone 53 | est | 666 | 249 | I | 1.6 | 0.25 |
| W99875 | "mg28d12.r1 Soares mouse embryo NbME13.5 14.5 Mus musculus cDNA clone 42491 | est | 460 | 183 | I | 1.7 | 0.24 |
| X65582 | M. musculus mRNA for alpha-2 collagen VI | gene | 521 | 201 | I | 1.8 | 0.24 |
| W08610 | mb46d04.r1 Soares mouse embryo p3NMF19.5 Mus musculus cDNA clone 332455 5' similar to | est | 218 | 98 | I | 1.8 | 0.24 |
| D83784 | "Mouse mRNA for MIDA1, complete cds" | gene | 19 | −28 | D | −2.4 | 0.23 |
| X63162 | M. musculus mRNA for transin-1 | gene | 850 | 292 | I | 1.5 | 0.23 |
| X65553 | M. musculus mRNA for poly(A) binding protein | gene | 622 | 229 | I | 1.6 | 0.23 |
| AA106783 | mm91d10.r1 Stratagene mouse embryonic carcinomaRA (#937318) Mus musculus cDN | est | 188 | 86 | I | 1.9 | 023 |
| AA107807 | "mp04g03.r1 Life Tech mouse embryo 8 5dpc 10664019 Mus musculus cDNA clone 56 | est | 498 | 190 | I | 1.6 | 0.23 |
| U79523 | "Mus musculus peptidylglycine alpha-amidating monooxygenase (PAM) mRNA, comple | gene | 48 | 32 | MI | * | 0.23 |
| VV65178 | md78h05.r1 Soares mouse embryo NbME13.5 14.5 Mus musculus cDNA clone 374553 | est | 52 | −52 | D | ~2.3 | 0.22 |
| AA003431 | "mg49a11.r1 Soares mouse embryo NbME13.5 14.5 Mus musculus cDNA clone 42710 | est | 675 | 235 | I | 2 | 0.22 |
| X82786 | M. musculus mRNA for Ki-67 | gene | 13 | −32 | D | 1.5 | 0.22 |
| W15003 | mb25b12.r1 Soares mousep 3NMF19.5 Mus musculus cDNA clone 330431 5' similar to | est | 47 | 27 | MI | ~2.3 | 0.22 |
| X53929 | M. musculus mRNA for PGII (decorin) | gene | 1023 | 326 | I | ~2.3 | 0.22 |
| X65026 | M. musculus mRNA for GTP-binding protein | gene | 117 | 58 | MI | 1.5 | 0.22 |
| AA117980 | mn06b05.r1 Beddington mouse embryonic region Mus musculus cDNA clone 537105 5 | est | 190 | 86 | MI | 2 | 0.22 |
| D21252 | "Mouse mRNA for OSF-3, complete cds" | gene | 1139 | 358 | I | 1.8 | 0.22 |
| W15873 | "mb55b12.r1 Soares mouse p3NMF19.5 Mus musculus CDNA clone 333311 5' similar to | est | 184 | −124 | D | 1.5 | 0.21 |
| L25126 | "Mus musculus RNA helicase mRNA, complete cds" | gene | 27 | −33 | D | 1.7 | 0.21 |
| L27990 | "Mus musculus Ro protein mRNA, complete cds" | gene | 49 | 28 | MI | 2.2 | 0.21 |
| U38940 | "Mus musculus asparagine synthetase mRNA, complete cds" | gene | 417 | 181 | I | 2.3 | 0.21 |
| X16151 | Mouse mRNA for early T-lymphocyte activation 1 protein (ETa-1) | gene | 828 | −355 | D | 1.6 | 0.2 |
| X92665 | M. musculus mRNA for ubiquitin-conjugating enzyme UbcM3 | gene | 144 | 66 | I | 1.4 | 0.2 |
| X59728 | M. musculus mRNA for gas5 growth arrest specific protein | gene | 277 | −161 | D | 1.9 | 0.2 |
| U34259 | "Mus musculus Goigi 4-transmembrane spanning transporter MTP mRNA, complete cd | gene | 413 | 155 | I | 1.8 | 0.2 |
| X80478 | M. musculus AEBP1 mRNA | gene | 807 | 2561 | I | 1.6 | 0.2 |
| W99235 | mf60c03.r1 Soares mouse embryo NbME13.5 14.5 Mus musculus cDNA clone 418660 | est | 45 | 25 | MI | ~2.2 | 0.19 |
| U42386 | "Mus musculus fibroblast growth factor inducible gene 14 (FIN14) mRNA, complete cds | est | 34 | −35 | D | 2 | 0.19 |
| W13875 | "mb36g03.r1 Soares mouse embryo p3NMF19.5 Mus musculus cDNA clone 331540 5' similar to | est | 433 | 156 | I | 1.6 | 0.19 |
| M28723 | "Mus musculus housekeeping-type protein (MERS) mRNA, complete cds" | gene | 30 | −33 | D | 2.1 | 0.19 |
| M77174 | "Mus musculus perlecan mRNA, complete cds" | gene | 58 | −51 | ME | 1.9 | 0.18 |
| J03776 | "Mouse down regulatory protein (rpt-1r) of interleukin 2 receptor mRNA, complete cds" | gene | 42 | 29 | I | ~2.1 | 0.18 |
| W41883 | "mc64g08.r1 Soares mouse embryo NbME13.5 14.5 Mus musculus cDNA clone 35334 | est | 1106 | 317 | I | 1.4 | 0.18 |
| L38611 | "Mouse mRNA for protein synthesis initiation factor 4A (elf-4A) gene, exons 10 and 11, cor | gene | 543 | 183 | I | 1.5 | 0.18 |
| D10578 | Mouse mRNA for ubiquitin activating enzyme E1 | gene | 442 | 157 | I | 1.5 | 0.18 |
| AA036265 | "rni72g03.r1 Soares mouse embryo NbME13.5 14.5 Mus musculus CDNA clone 469108 | est | 64 | 32 | I | 2 | 0.18 |
| Y00309 | Mouse LDH-A gene for lactate dehydrogenase-A | gene | 2240 | 547 | 1 | 1.5 .0.19 1.30.18 | |
| M65255 | "Mouse hydrophilic protein (KE2 wt) mRNA, complete cds" | gene | 76 | −61 | ME | 1.8 | 0.18 |
| M15525 | "Mouse laminin B1 mRNA, complete cds" | gene | 128 | −89 | D | 1.7 | 0.18 |
| L20315 | "Mus musculus MP81 gene and mRNA1 3' end" | gene | 42 | 26 | MI | ~2.1 | 0.17 |

TABLE 5-continued

ISGs and IRGs identified from mouse embryonic fibroblast incubated
in the presence or absence of IFN-αBBDB

| | | | | | | | |
|---|---|---|---|---|---|---|---|
| D10061 | Mouse mRNA for DNA topoisomerase 1 | gene | 40 | −37 | D | 1.9 | 0.17 |
| AA000813 | mg3Sh10.r1 Soares mouse embryo NbME13.5 14.5 Mus musculus cDNA clone 425827 | est | 155 | 67 | MI | 1.8 | 0.17 |
| AA002605 | mg44g07.r1 Soares mouse embryo NbME13.5 14.5 Mus musculus cDNA clone 426684 | est | 168 | 70 | MI | 1.7 | 0.17 |
| AA028877 | mh90g10.r1 Soares mouse placenta 4NbMP13.5 14.5 Mus musculus cDNA clone 4582 | est | 143 | 62 | I | 1.8 | 0.17 |
| X01756 | Mouse cytochrome c gene (MCI) | gene | 529 | 175 | I | 1.5 | 0.17 |
| U19825 | "Mus musculus macrophage migration inhibitory factor (Mif) gene, complete cds" | gene | 889 | 281 | MI | 1.4 | 0.17 |
| M31131 | "Mouse neural cadherin (N-cadherin) mRNA, complete cds" | gene | 35 | −34 | I | 2 | 0.17 |
| AA036574 | "mi69e05.r1 Soares mouse embryo NbME13.5 14.5 Mus musculus cDNA clone 468800 | est | 39 | −36 | D | 1.9 | 0.16 |
| U27267 | "Mus musculus LPS-induced C-X-C chemokine LIX precursor, mRNA, complete cds" | gene | 562 | −236 | D | 1.4 | 0.16 |
| W29420 | 99mb99a01.r1 Soares mouse p3NMF19.5Mus musculus cDNA clone 337512 5′ similar to | est | 2150 | 502 | I | 1.3 | 0.16 |
| AA034646 | mh17d07.r1 Soares mouse placenta 4NbMP13.5 14.5 Mus musculus cDNA clone 34427 | est | 37 | 41 | D | ~1.9 | 0.16 |
| X81323 | M. musculus mRNA for tripeptidyl peptidase II | gene | 48 | −41 | D | 1.9 | 0.18 |
| AA064066 | mj62d04.r1 Soares mouse p3NMF19.5 Mus musculus cDNA clone 480679 5′ similar to | est | 1116 | 301 | I | 1.4 | 0.16 |
| U43208 | "Mus musculus phosphatidylethanolamine binding protein mRNA, complete cds" | gene | 1027 | 285 | MI | 1.4 | 0.16 |
| AA118546 | mn09c06.r1 Beddington mouse embryonic region Mus musculus cDNA clone 537418 5 | est | 173 | 71 | I | 1.7 | 0.16 |
| AA003383 | mg49d05.r1 Soares mouse embryo NbME13.5 14.5 Mus musculus cDNA clone 427113 | est | 50 | 25 | MI | 2 | 0.18 |
| M81477 | "Mouse cytoplasmic phosphotyrosine phosphatase mRNA, complete cds" | gene | 28 | −28 | D | 2 | 0.18 |
| AA103457 | mo24g05.r1 Life Tech mouse embryo 13 5dpc 10S6014 Mus musculus CDNA clone 55 | est | 71 | 34 | MI | 1.9 | 0.18 |
| J04596 | "Mouse platelet-derived growth factor-inducible KC protein mRNA, complete cds" | gene | 118 | −78 | D | 1.6 | 0.15 |
| U13262 | "Mus musculus myelin gene expression factor (MEF-2) mRNA, partial cds" | gene | 15 | −25 | D | ~2.0 | 0.15 |
| L42293 | "Mus musculus acyl-coenzyme A:cholesterol acyltransferase (ACACT) mRNA, complet | gene | 179 | 70 | MI | 1.6 | 0.15 |
| M032948 | mi24a02.r1 Soares mouse embryo NbME13.5 14.5 Mus musculus cDNA clone 464426 | gene | 105 | 46 | D | 1.8 | 0.15 |
| X66473 | M. musculus mRNA for (pro)collagenase | gene | 115 | 50 | MI | 1.9 | 0.15 |
| AA144469 | mr16c09/r1 Soares mouse 3NbMS Mus musculus cDNA clone 597618 5′ similar to gb:X | est | 69 | 32 | I | 1.3 | 0.15 |
| W18308 | "mb68h11.r1 Soares mouse p3NMF19.5 Mus musculus cDNA clone 334629 5′ similar to | est | 2126 | 478 | D | 1.9 | 0.14 |
| W47719 | | est | 57 | 27 | MI | 1.5 | 0.14 |
| X14194 | Mouse mRNA for entactin | gene | 178 | −95 | ME | | 1.80.14 |
| AA119078 | "mp65d05.r1 Soares mouse 2NbMT Mus musculus cDNA clone 574089 5′ similar to | gb:X5874C | 144 | 106 | 48 | | 0.14 |
| W42234 | mc37a06.r1 Soares mouse p3NMF19.5 Mus musculus cDNA clone 350674 5′ similar to | est | 687 | 58 | MI | 1.7 | 0.14 |
| Y00094 | Mouse mRNA for ras-related YPT1 protein | gene | 88 | 195 | I | 1.4 | 0.14 |
| U76832 | "Mus musculus plasma membrane protein syntaxin-4 mRNA, complete cds" | gene | 223 | 39 | MI | 1.8 | 0.14 |
| W33440 | mc15d01.r1 Soares mouse p3NMF19.5 Mus musculus cDNA clone 348577 5′ similar to | est | 271 | 81 | MI 1.8 | 0.14 | 0.14 |
| M12347 | "Mus musculus skeletal alpha-actin gene, complete cds" | gene | 605 | 96 | MI | 1.5 | 0.14 |
| X16834 | Mouse mRNA for Mac-2 antigen | gene | 372 | 221 | I | 1.4 | 0.14 |
| D88729 | "Mouse mRNA for topoisomerase-inhibitor suppressed, complete cds" | gene | 1745 | −184 | D | 1.4 | 0.14 |
| J02870 | "Mouse laminin receptor mRNA, complete cds" | gene | 84 | −477 | D | 1.3 | 0.14 |
| X72910 | M. musculus Cd24a gene | gene | 110 | −57 | ME | 1.9 | 0.13 |
| M29015 | "Mouse ribosomal protein L7 (rpL7) gene, complete cds" | est | 34 | −67 | D * | 1.6 | 0.13 |
| W51271 | | gene | 25 | −29 | D | 1.9 | 0.13 |
| M88489 | "Mouse thymidine kinase gene1 complete cds" | gene | 38 | −23 | D | 1.8 | 0.13 |
| L37092 | "Mus musculus cyclin-dependent kinase homologue (P130PITSL) mRNA1 complete cds" | gene | 74 | −31 | D | 1.7 | 0.13 |
| U11073 | "Mus musculus Balb/angiotensin II receptor type 2 gene, exon 3 and complete cds" | est | 275 | −50 | ME | 1.5 | 0.13 |
| W71543 | "me39c09.r1 Soares mouse embryo NbME13.5 14.5 Mus musculus cDNA clone 38987 | | | 126 | ME | | 0.13 |
| L41154 | "Mus musculus SM22 alpha mRNA, complete cds" | gene | 35 | 2020 | 427 | | 1.30.13 |
| D49949 | "Mouse mRNA for IGIF precursor polypeptide, complete cds" | gene | 57 | 37 | I | ~1.7 | 0.13 |
| U37353 | "Mus musculus protein phosphatase 2A B′alpha3 regulatory subunit mRNA1 partial cds" | gene | 94 | 27 | 1 * | 1.9 | 0.13 |
| U20372 | "Mus musculus voltage-dependent calcium channel beta-3 subunit (CCHB3) mRNA, co | gene | 17 | 40 | MI | 1.7 | 0.13 |
| D30782 | Mouse mRNA for epiregulin, complete cds" | gene | 147 | −22 | D | ~1.9 | 0.13 |
| X56123 | Mouse mRNA for talin | est | 517 | 57 | I | 1.6 | 0.13 |
| W83337 | mf25h11.r1 Soares mouse embryo NbME.13.5 14.5 Mus musculus cDNA clone 406149 | | | 155 | | 1.4 | 0.13 |

TABLE 5-continued

ISGs and IRGs identified from mouse embryonic fibroblast incubated in the presence or absence of IFN-αBBDB

| ID | Description | Type | Val1 | Val2 | Val3 | Val4 | Val5 |
|---|---|---|---|---|---|---|---|
| W17644 | mb76b03.r1 Soares mouse p3NMF19.5 Mus musculus cDNA clone 335309 5' similar to | est | 1124 | 270 | I | 1.3 | 0.13 |
| AA009014 | mg97b12.r1 Soares mouse embryo NbME13.5 14.5 Mus musculus cDNA clone 440927 | est | 29 | -24 | D | 1.8 | 0.12 |
| X53753 | Mouse mRNA for nonmuscle tropomyosin 5 | gene | 796 | 205 | I | 1.3 | 0.12 |
| U49112 | "Mus musculus calcium-binding protein ALG-2 (ALG-257) mRNA, complete cds" | gene | 196 | 70 | MI | 1.6 | 0.12 |
| X53584 | "Mouse mRNA for HSP60 protein (clones 3T3-71 -9, and -M1)" | gene | 413 | -156 | D | 1.4 | 0.12 |
| X15052 | Mouse mRNA for3'-end of NCAM-140 and NCAM-180 isoforms | gene | 42 | -32 | D | 1.8 | 0.12 |
| X573371 | M. musculus CDNAp14 mRNA | gene | 706 | 184 | I | 1.4 | 0.12 |
| AA089264 | mo59d06.r1 Stratagene mouse Tcell 937311 Mus musculus cDNA clone 557867 5' sim | est | 831 | 212 | I | 1.3 | 0.12 |
| W13461 | mb34g09.r1 Soares mouse p3NMF19.5 Mus muscularis cDNA clone 331360 5' similar to | est | 187 | -89 | ME | 1.5 | 0.12 |
| U58494 | "Mus musculus melanoma cell-derived intracisternal A-particle mRNA, gag gene, comp | gene | 86 | -52 | D | 1.6 | 0.12 |
| AA164143 | mq84c11.r1 Stratagene mouse melanoma (#937312) Mus musculus cDNA clone 58542 | est | 36 | 28 | I | ~1.8 | 0.12 |
| W13502 | ma85a03.r1 Soares mouse p3NMF19.5 Mus musculus cDNA clone 317452 5' similar to | est | 836 | 212 | I | 1.3 | 0.12 |
| W51109 | | est | 43 | -31 | D | 1.7 | 0.11 |
| X62622 | "M. musculus TIMP-2 mRNA for tissue inhibitor of metalloproteinases, Type 2" | gene | 75 | 31 | I | 1.7 | 0.11 |
| M32309 | "Mouse zinc finger protein (Zfx) mRNA, complete cds, clone pDP1119" | gene | 5 | -29 | D | ~1.7 | 0.11 |
| L35556 | "Mus musculus Int-6 mRNA, complete cds" | gene | 355 | -139 | ME | 1.4 | 0.11 |
| D14571 | "Mouse mRNA for PEBP2b2 protein, complete cds" | gene | 111 | 61 | D | 1.6 | 0.11 |
| X61940 | Mouse mRNA for a growth factor-inducible immediate early gene (3CH134) | gene | 104 | 41 | MI | 1.6 | 0.11 |
| D87663 | "House mouse; Musculus domesticus mRNA for 14-3-3 epsilon, complete cds" | gene | 702 | 181 | I | 1.3 | 0.11 |
| X95580 | M. musculus mRNA for hypoxia-inducible factor I alpha | gene | 60 | 39 | ME | 1.6 | 0.11 |
| J02623 | "Mouse cytosolic aspartate aminotransferase isoenzyme mRNA, complete cds, clone pr | gene | 63 | 27 | I | 1.7 | 0.11 |
| W46016 | mc77h12.r1 Soares mouse embryo NbME13.5 14.5 Mus musculus cDNA clone 354575 | est | 33 | 30 | I | ~1.7 | 0.11 |
| AA110896 | mp62a09.r1 Soares mouse embryo 2NbMT Mus musculus cDNA clone 573784 5' similar to SW:EPIP | est | 185 | 61 | I | 1.5 | 0.11 |
| AA008043 | mg68e02.r1 Soares mouse embryo NbME13.5 14.5 Mus musculus cDNA clone 43817C | gene | 87 | -48 | D | 1.6 | 0.1 |
| D18432 | "Mouse murine CD83 mRNA for murine homologue of CD63/ME491, complete cds" | gene | 1439 | -334 | D | 1.2 | 0.1 |
| D50411 | "Mouse mRNA for metrin alpha, complete cds" | gene | 7 | -27 | D | 1.7 | 0.1 |
| Z72000 | M. musculus BTG3 mRNA | gene | 219 | 701 | D | 0.1 | 1.5 |
| U41785 | "Mus musculus metalloprotease/disintegrin/cysteine rich protein precursor (MDC9) cDN | gene | 69 | -41 | I | 1.6 | 0.1 |
| Z31555 | M. musculus (129/Sv) Ccte mRNA for CCT (chaperonin containing TCP-1) epsilon subu | gene | 699 | 167 | MI | 1.3 | 0.1 |
| AA168350 | ms30c06.r1 Stratagene mouse skin (#937313) Mus musculus cDNA clone 608458 5' si | est | 47 | 21 | I | 1.8 | 0.1 |
| AA008136 | mg68g11.r1 Soares mouse embryo NbME13.5 14.5 Mus musculus cDNA clone 438212 | est | 967 | 218 | D | 1.3 | 0.1 |
| M18194 | Mouse fibronectin (FN) mRNA | gene | 1024 | -266 | D | 1.5 | 0.1 |
| M20658 | "Mouse interleukin-1 receptor mRNA, complete cds" | gene | 148 | -70 | D | 1.5 | 0.1 |
| W33838 | mc55c11.r1 Soares mouse embryo NbME13.5 14.5 Mus musculus cDNA clone 352438 | est | 48 | -31 | D | 1.6 | 0.1 |
| M25244 | "Mouse pre-B cell P2B/LAMP-1 mRNA, complete cds" | gene | 1098 | -283 | D | 1.3 | 0.1 |
| M82831 | "Mus musculus macrophage metalloelastase mRNA, complete cds" | gene | 5 | -29 | D | 1.7 | 0.1 |
| M84607 | "Mus musculus PDGF-alpha-receptor (PDGF-alpha-R) mRNA, complete cds" | gene | 194 | -82 | D | 1.4 | 1.4 | 0.09 |
| M15668 | Mus musculus X chromosome-linked phosphoglycerate kinase (pgk-1) mRNA, comple | est | 1254 | 254 | I | 1.3 | 0.09 |
| AA059517 | mj61c11.r1 Soares mouse embryo NbME13.5 14.5 Mus musculus cDNA clone 480596 | est | 14 | -20 | D | ~1.7 | 0.09 | 0.09 |
| M76727 | "Mouse pyruvate dehydrogenase (pdha-1) mRNA, complete cds" | gene | 68 | -37 | D | 1.5 | 0.09 |
| U28138 | "Mus musculus dishevelled-1 protein (Dvl1) gene, complete cds" | gene | 39 | -25 | D | 1.6 | 0.09 |
| W98059 | mg07e08.r1 Soares mouse embryo NbME13.5 14.5 Mus musculus cDNA clone 423110 | est | 9 | -24 | D | ~1.7 | 0.09 | 0.09 |
| AA016858 | mh35f03.r1 Soares mouse placenta 4NbMP13.5 14.5 Mus musculus cDNA clone 4445( | est | 71 | 27 | MI | 1.6 | 0.09 |
| X55316 | M. musculus mRNA for CAAT-box DNA binding protein subunit B (NF-YB) (partial) | est | 38 | -25 | ME | 1.7 | 0.09 |
| X70847 | "Mus musculus vascular adhesion cell molecule-1 (VCAM1) gene, exon 10" | gene | 328 | 90 | MI | 1.4 | 0.09 |
| L22355 | Mouse mRNA for adenine nucleotide translocase | gene | 216 | 67 | MI | 1.5 | 0.09 |
| D78188 | Mouse mRNA for SCID complementing gene 2 | gene | 178 | -71 | D | 1.4 | 0.08 |
| D78647 | "Mouse mRNA for phospholipase A2, complete cds" | est | 168 | 50 | I | 1.4 | 0.08 |
| W17411 | mb58c09.r1 Soares mouse p3NMF19.5 Mus musculus cDNA clone 3336.18 5' s | est | 1137 | 218 | I | 1.2 | 0.08 |
| X66084 | M. musculus Pgp mRNA for CD44 (clone M4) | gene | 65 | 24 | MI | 1.6 | 0.08 |

TABLE 5-continued

ISGs and IRGs identified from mouse embryonic fibroblast incubated
in the presence or absence of IFN-αBBDB

| | Description | Type | Col4 | Col5 | Col6 | Col7 | Col8 | Col9 |
|---|---|---|---|---|---|---|---|---|
| W34756 | "mc32g09.r1 Soares mouse p3NMF19.5 Mus musculus cDNA clone 350272 5' similar to | est | 27 | −19 | D | | 1.7 | 0.08 |
| M60847 | "Mouse lipoprotein lipase (LPL) gene, exon 10" | gene | 197 | −720 | I | 1.4 | 0.08 | 0.07 |
| M91380 | "Mus musculus TGF-beta-inducible protein (TSC-36) mRNA, complete cds" | gene | 962 | 182 | I | | 1.2 | 0.07 |
| AA114576 | mo63h09.r1 Stratagene mouse heart (#937316) Mus musculus cDNA clone 558305 5' s | est | 84 | 28 | | | 1.5 | 0.07 |
| D000613 | Mouse mRNA for matrix Gla protein (MGP) | gene | 1778 | 2781 | | 1.2 | 0.07 | 0.07 |
| AA119191 | mp60h03.r1 Soares 2NbMT Mus musculus cDNA clone 573653 5' similar to TR:G1017 | est | 248 | −81 | ME | | 1.3 | 0.07 |
| W41722 | mc67b11.r1 Soares mouse embryo NbME13.5 14.5 Mus musculus cDNA clone 353585 | est | 123 | −52 | ME | | 1.4 | 0.07 |
| W62091 | md84h04.r1 Soares mouse embryo NbME13.5 14.5 Mus musculus cDNA clone 375127 | est | 136 | −49 | ME | | 1.4 | 0.06 |
| U33840 | "Mus musculus TRAF-related protein (TRAFarrin) mRNA, complete cds" | gene | 1 | −28 | D | | ~1.5 | 0.06 |
| W29434 | mb99f07.r1 Soares mouse p3NMF19.5 Mus musculus cDNA clone 337573 5' similar to | est | 1188 | 198 | I | | 1.2 | 0.06 |
| M74227 | "Mouse cyclophilin C (cyp C) mRNA, complete cds" | gene | 187 | −59 | D | | 1.3 | 0.06 |
| X16705 | Mouse mRNA for lamin B | gene | 24 | −15 | D | | 1.6 | 0.06 |
| L22472 | Mouse Bax alpha mRNA, complete cds | gene | 249 | −66 | M | | 1.3 | 0.05 |
| X04663 | Mouse mRNA for beta-tubulin (isotype Mbeta 5) | gene | 1181 | −190 | D | | 1.2 | 0.05 |
| AA003990 | mg30c04.r1 Soares mouse embryo NbME13.5 14.5 Mus musculus cDNA clone 439302 | gene | 59 | −25 D | D | 1.4 | 0.05 | 0.05 |
| Y00769 | Murine mRNA for integrin beta subunit | est | 813 | −155 | I | | 1.2 | 0.05 |
| AA104459 | mo55a03.r1 Life Tech mouse embryo 8 5dpc 10664019 Mus musculus cDNA clone 557 | est | 34 | 12 | | | 1.5 | 0.05 |
| AA109714 | mp49e12.r1 Barstead MPLRBI Mus musculus CDNA clone 572590 45' similar to SW:SK | est | 91 | 27 | | | 1.4 | 0.05 |
| L25069 | "Mouse catalase mRNA, complete cds" | gene | 90 | −34 | D | | 1.4 | 0.05 |
| AA144240 | mr78c07.r1 Stratagene mouse heart (#937316) Mus musculus cDNAclone 603564 5's | est | 32 | −16 | MI | | 1.5 | 0.05 |
| M21332 | "Mouse MHC class III RD gene (H2-d and H2Sk haplotypes), complete cds" | gene | 51 | −22 | D | | 1.4 | 0.05 |
| X04017 | Mouse mRNA for cysteine-rich glycoprotein SPARC | gene | 1909 | −232 D | | 1.1 | 0.04 | 0.04 |
| D45210 | "Mouse mRNA for zinc finger protein, complete cds" | gene | 5 | −22 | MD | * | ~1.3 | 0.04 |
| L29454 | "Mouse fibrillin (Fbn-1) mRNA, complete cds" | gene | 284 | −62 | MI | | 1.2 | 0.04 |
| U13053 | Mus musculus Ras-like protein (kir) mRNA, complete cds" | est | 28 | 17 | I | * | ~1.4 | 0.04 |
| AA103933 | mo43h05.r1 Life Tech mouse embryo 15 5dpc 10667012 Mus musculus cDNA clone 55 | est | 27 | 24 | I | * | ~1.4 | 0.04 |
| D12907 | "Mouse gene for 47-kDa heat shock protein(H8P47), exon 6" | gene | 1386 | 169 | MI | | 1.1 | 0.04 |
| L01640 | Mus musculus D-type GI cyclin catalytic subunit (P8K-J3/CDK4) mRNA1 complete cds | gene | 397 | −79 | MI | | 1.2 | 0.04 |
| M64086 | "Mouse spl2 proteinase inhibitor (spi2/eb4) mRNA, complete cds" | gene | 148 | 31 | MI | | 1.3 | 0.03 |
| M98035 | Mus musculus guanine nucleotide exchange factor delta subunit (JGR1) mRNA, comp | gene | 59 | −17 | D | | 1.3 | 0.03 |
| AA038511 | mi85h01.r1 Soares mouse p3NMF19.5 Mus musculus cDNA clone 473425 5' similar to | est | 412 | −73 | ML | | 1.2 | 0.03 |
| W77701 | "me81b01.r1 Soares mouse embryo NbME13.5 14.5 Mus musculus cDNA clone 40192 | est | 12 | −14 | D | ~1.3 | 0.03 | 0.03 |
| AA009169 | "mh01g11.r1 Soares mouse embryo NbME13.5 14.5 Mus musculus cDNA clone 44128 | est | 62 | −19 | MI | | 1.3 | 0.03 |
| AA146282 | "mr06e08.r1 Soares mouse 3NbMS Mus musculus cDNA clone 596678 5' similar to gb: | est | 26 | 21 | I | * | ~1.3 | 0.03 |
| M57891 | "Mouse complement component C2 mRNA, complete cds" | gene | 27 | 16 | I | | ~1.3 | 0.03 |
| W29424 | mb99b02.r1 Soares mouse p3NMF19.5 Mus musculus cDNA clone 33751 5 5' similar to | est | 191 | −42 | MI | | 1.2 | 0.03 |
| W65084 | me01e06.ri Soares mouse eembryo NbME13.5 14.5 Mus musculus cDNA clone 386242 | est | 24 | 29 | MI | * | ~1.2 | 0.0Q3 |
| W62646 | md82a07.r1 Soares mouse embryo NbME13.5 14.5 Mus musculus CDNA clone 37486 | est | 25 | −8 | D | | 1.3 | 0.02 |
| U07159 | Mus musculus medium chain acyl-CoA dehydrogenase mRNA, complete cds" | gene | 29 | −9M( | MI | 1.3 | 0.02 | 0.02 |
| L21973 | "Mus musculus E2F1 mRNA, complete cds" | gene | 30 | −8 | MI | | 1.3 | 0.02 |
| U05809 | "Mus musculus LAF1 transketolase mRNA, complete cds" | gene | 142 | 22 | MI | | 1.20.02 | |
| W34915 | mc60c11.r1 Soares mouse embryo NbME13.5 14.5 Mus musculus cDNA clone 352916 | est | 69 | −16 | D | | 1.2 | 0.02 |
| M81342 | "BALB/c fibroblast growth factor receptor 3 (mFR3) mRNA, complete cds" | gene | 4 | −21 | D | | ~1.2 | 0.02 |
| U37413 | "Mus musculus guanine nucleotide-binding protein (GnaI1) gene, exon 3-7,and comple | gene | 136 | −14 | MD | | 1.1 | 0.01 |

TABLE 6

ISGs and IRGs identified from mouse embryonic fibroblast incubated in the presence or absence of IFN-αBBDB, in the presence or absence of encephalomyocarditis virus Sample (1) untreated cells,
Sample (2) cells treated for 16 h with 10,000 units per ml of IFN-αBBDB,
Sample (3) cells treated for 16 h with 10,000 units per ml of IFN-αBBDB followed by infection with encephalomyocarditis virus at a multiplicity of infection of 10 plaque forming units per cell for an additional 6 h.
Database: GenBank accession numbers
1 vs 2, control vs interferon
1 vs 3, control vs. interferon plus virus.
2 vs 3, interferon vs interferon plus virus
Diff. difference
I = those genes that were induced or upregulated by the treatment
D = those genes that were repressed or downregulated by the treatment
Fold C, fold change
Sig. significance factor

RNL +/+ - IFN/EMCV

| Database | EntrezDefinition | Seq | C | R | Dif | 1 vs 2 ||||| 1 vs 3 ||||| 2 vs 3 |||
|---|---|---|---|---|---|---|---|---|---|---|---|---|---|---|---|---|---|---|
| | | | | | | B | Fold C | Sig | Di | B | Fold C | Sig | Dif | B | Fold C | Sig |
| X56602 | Mus musculus mRNA Interferon-induced 15-KDa protein | gene | B | N | I | * | ~165. | 57.7 | I | * | ~120. | 45.56 | D | | 1.4 | 0.4 |
| U73037 | "Mus musculus interferon regulatory factor 7 (mirf7) mRN | gene | C | N | I | * | ~117. | 44.7 | I | * | ~105. | 41.26 | NC | | 0 | 0 |
| L32974 | "Mouse interferon-inducible protein homologue mRNA, co | gene | D | N | I | * | 44.3 | 25.6 | I | * | 59.4 | 32.9 | I | | 1.3 | 0.3 |
| L16894 | "Mus musculus Cyclophilin C (CyCAP) mRNA, complete cd | gene | D | N | I | * | 8.1 | 15.9 | I | * | 13.9 | 11.72 | D | | 1.3 | 0.2 |
| U22031 | "Mus musculus 20S proteasome subunit Lmp7 (Lmp7d all | gene | A | N | I | * | ~33.2 | 15.7 | I | * | ~23.4 | 11.11 | D | | 1.4 | 0.2 |
| U06924 | "Mus musculus signal transducer and activator of transcri | gene | C | N | I | * | ~31.5 | 15.3 | I | * | ~24.8 | 12.16 | D | | 1.3 | 0.1 |
| X04653 | Mouse mRNA for Ly-6 alloantigen (Ly-6E.1) | geneD | N | I | | 8.1 | 12.3 | I | 6.6 | 8.95 | D | | 1.2 | 0.2 | | | |
| U15636 | "Mus musculus GTP binding protein (GTP2) mRNA, compl | gene | A | N | I | * | ~21.5 | 10.3 | I | * | ~31.4 | 14.96 | MI | | 1.5 | 0.2 |
| M86829 | "Mus musculus (crg-2) mRNA, complete cds" | gene | A | N | I | * | ~19.9 | 9.46 | I | * | ~53.4 | 23.9 | I | | 2.7 | 2.1 |
| U19119 | "Mus musculus G-protein-like LRG-47 mRNA, complete cd | gene | B | N | I | * | 17.7 | 8.9 | I | * | ~20.2 | 10.29 | NC | | 0 | 0 |
| L04262 | "Mus musculus (clones p10a-[1.5n, 1.7]b and pG4-14])ysy | gene | D | N | I | I | 11.1 | 8.27 | I | * | 13.2 | 10.28 | NC | | 0 | 0 |
| AA059700 | mj77g08.r1 Soares mouse p3NMF19.5 Mus musculus cDNA | est | D | N | I | * | 5.1 | 8.12 | I | | 5 | 7.85 | NC | | 0 | 0 |
| L39223 | "Mus musculus apolipoprotein D (apoD) mRNA, complete | gene | A | N | I | * | ~16.7 | 7.94 | I | * | ~7.3 | 2.74 | D | | 2.3 | 0.8 |
| M27034 | "Mouse MHC class 1 D-region cell surface antigen (D2d) g | gene | D | N | I | * | 11.2 | 7.51 | MI | * | 9.7 | 6.13 | NC | | 0 | 0 |
| M55637 | "Mus musculus HAM1 gene, complete cds" | gene | D | N | I | * | 7.3 | 7.3 | I | * | 13.3 | 5.94 | NC | | 0 | 0 |
| M19681 | "Mouse platelet-derived growth factor-inducible protein (J | gene | D | N | I | * | ~15.8 | 7.04 | I | * | 11.1 | 9.51 | I | | 1.2 | 0.1 |
| U44731 | "Mus musculus putative purine nucleotide binding protein | gene | B | N | I | * | 8.9 | 6.15 | I | * | ~13.2 | 6.08 | NC | | 0 | 0 |
| U27838 | "Mus musculus glycosyl-phosphatidyl-inositol-anchored p | gene | A | N | I | * | ~13.3 | 5.99 | I | * | ~12.7 | 5.65 | NC | | 0 | 0 |
| AA013783 | mh13a03.r1 Soares mouse placenta 4NbMP13.5 14.5 Mus | est | D | N | I | * | ~13.3 | 5.78 | I | * | 9 | 3.55 | D | | 1.4 | 0.2 |
| L32973 | "Mouse thymidylate kinase homologue mRNA, complete c | gene | A | N | I | * | ~12.8 | 5.75 | I | * | ~39.7 | 18.53 | I | | 3.1 | 2.5 |
| U47737 | "Mus musculus thymic shared antigen-1 (TSA-1) gene, cc | gene | D | N | I | * | 3.5 | 5.64 | I | | 3.2 | 4.55 | NC | | 0 | 0 |
| X14194 | Mouse mRNA for entactin | | gene | A | N | 5.61 | I | 8.8 | 5.35 | I | | 6.8 | 3.75 | D | 1.30.1 | | |
| D13664 | Mouse mRNA for osteoblast specific factor 2 (OSF-2) | gene | D | N | I | * | 8.8 | 5.01 | I | * | 7.5 | 4.21 | D | | 1.20.1 | |
| X61172 | Mouse mRNA for alpha-mannosidase II | gene | B | N | I | * | 1.1 | 4.74 | I | * | 10.1 | 4.48 | NC | | 0 | 0 |
| X95580 | M. musculus mRNA for hypoxia-inducible factor I alpha | gene | C | N | I | * | ~11.1 | 4.64 | I | * | ~11.9 | 5.21 | NC | | 0 | 0 |
| X07699 | Mouse nucleolin gene | gene | B | N | I | * | 8.9 | | I | * | 11.9 | 6.9 | I | | 1.3 | 0.1 |

TABLE 6-continued

ISGs and IRGs identified from mouse embryonic fibroblast incubated
in the presence or absence of IFN-αBBDB in the presence or absence of
encephalomyocarditis virus

| Accession | Description | Type | | | | | | | | | | |
|---|---|---|---|---|---|---|---|---|---|---|---|---|
| U15635 | "Mus musculus IFN-gamma induced (Mg11) mRNA, compl | gene | A | N | | I | ~10.5 | 4.39 | I | ~13.8 | NC | 0 | 0 |
| Y00769 | Murine mRNA for integrin beta subunit | gene | A | N | | I | 4.5 | 4.31 | I | 4.6 | 4.37 | NC | 0 | 0 |
| D14571 | "Mouse mRNA for PEBP2b2 protein, complete cds" | gene | A | N | | I | 10.2 | 4.24 | I | 11.6 | 5.02 | NC | 0 | 0.4 |
| D78188 | Mouse mRNA for SCID complementing gene 2 | gene | A | N | | I | 9.3 | 4.2 | I | 15.8 | 8.27 | I | 1.7 | 0.1 |
| Z30970 | M. musculus (Balb/C) TIMP-3 gene for metalloproteinase-3 | gene | A | N | * | I | 8.6 | 3.95 | * | 11.9 | 6.14 | I | 1.4 | 2.7 |
| U43084 | "Mus musculus glucocorticoid-attenuated response gene 1 | gene | C | N | * | I | ~9.5 | 3.91 | * | ~33.5 | 15.85 | I | 3.5 | 0 |
| D63902 | "Mouse mRNA for estrogen-responsive finger protein, com | gene | C | N | * | I | ~8.6 | 3.78 | * | ~10.3 | 4.74 | NC | 0 | 0 |
| W55140 | | est | A | Y | | I | 7.9 | 3.77 | I | 8.9 | 4.52 | NC | 0 | 0.3 |
| X16151 | Mouse mRNA for early T-lymphocyte activation 1 protein | gene | A | N | | I | 4.4 | 3.75 | I | 6.1 | 6.79 | I | 1.4 | 0 |
| X56548 | M. musculus Np-b mRNA for purine-nucleoside phosphoryla | gene | A | N | | I | 4.9 | 3.43 | I | 4.5 | 2.91 | NC | 0 | 0 |
| L38847 | "Mus musculus hepatoma transmembrane kinase ligand (I- | gene | A | N | * | I | ~8.7 | 3.43 | * | ~5.9 | 1.9 | MC | 1.5 | 0.1 |
| U16162 | "Mus musculus prolyl 4-hydroxylase alpha(I)-subunit mRNA | gene | A | N | | I | 4.1 | 2.98 | I | 2.4 | 0.77 | D | 1.7 | 0.6 |
| D49382 | "Mouse Ned5 mRNA for DIFF6- or CDC3,10,11,12-like p | gene | A | N | | I | 5.4 | 2.97I | 6.3 | 3.84NC | | | | |
| U65313 | Mus musculus ras-GTPase-activating SH3-domain binding | gene | C | N | | I | 2.96 | 1 | 7.1 | 3.39 | NC | 0 | 0 |
| D90225 | Mouse mRNA for OSF-1 | gene | C | N | | I | 4.3 | 2.87 | I | 3.2 | 1.5 | D | 1.3 | 0.2 |
| X64070 | M. musculus gene for cation-dependent mannose-6-phosp | gene | D | N | * | I | ~7.8 | 2.84 | * | ~9.1 | 3.57 | NC | 0 | 0 |
| M60474 | "Mouse myristoylated alanine-rich C-kinase substrate (MAF | gene | D | N | | I | 4.6 | 2.81 | I | 3.1. | 1.13 | D | 1.5 | 0.3 |
| U60329 | "Mus musculus proteasome activator PA28 beta subunit r | gene | C | N | | I | 3.9 | 2.79 | 3.8 | 2.58 | NC | 0 | 0 |
| M33212 | "Mouse nucleolar protein NC38 mRNA, complete cds" | gene | A | N | | I | 3.9 | 2.78I | 4.7 | 3.96 | I | 0.1 | 1.2 |
| M91380 | "Mus musculus TGF-beta-inducible protein (TSC-36) mRN | gene | A | N | | I | 4 | 2.78 | I | 3.9 | 2.63 | NC | 0 | 0 |
| M26071 | "Mouse tissue factor (mf) mRNA, complete cds" | gene | A | N | * | I | 6.8 | 2.74 | * | 8.5 | 3.88 | NC | 0 | 0 |
| M63630 | "Mus musculus predicted GTP binding protein (IRG-47) mf | gene | D | N | * | I | ~7.2 | 2.74 | * | ~7.5 | 2.92 | NC | 0 | 0 |
| U63323 | "Mus musculus translation initiation factor (EIf4g2) mRNA | gene | C | N | | I | 4 | 2.73 | I | 4.2 | 3.01 | NC | 0 | 0 |
| AA162233 | mn44h04.r1 Beddington mouse embryonic region Mus mu | est | C | N | * | I | ~7.4 | 2.67 | * | ~8.4 | 3.23 | NC | 0 | 0 |
| D13003 | "Mouse mRNA for reticulocabin, complete cds" | gene | C | N | | I | 5.2 | 2.67 | I | 4.6 | 2.13 | NC | 0 | 0 |
| U12763 | "Mus musculus OX40 ligand (ox401) mRNA, complete cds" | gene | D | N | D | * | ~7.0 | 2.65 | I | ~7.0 | 2.62 | NC | 0 | 0 |
| U16740 | "Mus musculus capping protein alpha 1 subunit mRNA, pa | gene | A | N | | I | 5.1 | 2.56 | I | 5.7 | 3.11 | NC | 0 | 0 |
| W66636 | me22g10.r1 Soares mouse embryo NbMEI3.5 14.5 Mus | est | C | N | * | I | 6.9 | 2.55 | * | 10.2 | 4.56 | I | 1.5 | 0.2 |
| M88242 | Mouse glucocorticoid-regulated inflammatory prostaglandin | gene | D | N | | I | ~7.0 | 2.51 | I | ~39.0 | 18.23 | I | 5.6 | 7.2 |
| X70058 | M. musculus cytokine gene | gene | A | N | | I | 3.6 | 2.48 | I | 5.1 | 5.17 | I | 1.4 | 0.4 |
| X70296 | M. musculus PN-1 mRNA for protease-nexin 1 | gene | B | N | | I | 4.3 | 2.43 | I | 3.1 | 1.22 | D | 1.4 | 0.1 |
| U33626 | "Mus musculus PML isoform 1 (Pm1) mRNA, complete cds | gene | B | N | * | I | 5.1 | 2.43 | * | ~5.8 | 0.93 | D | 1.6 | 0.2 |
| U60328 | "Mus musculus proteasome activator PA2B alpha subunit | gene | C | N | | I | 3.7 | 2.42 | I | 3.2 | 1.87 | NC | 0 | 0 |
| AA022526 | mg54a04.r1 Soares mouse embryo NbMEI3.5 14.5 Mus m | est | B | N | | I | 3.4 | 2.42 | I | 3.3 | 1.26 | D | 1.3 | 0.2 |
| X16319 | Mouse mRNA for 54K subunit of signal recognition particle | gene | C | N | * | I | ~6.7 | 2.4 | * | ~14.4 | 6.74 | I | 2.2 | 0.6 |
| X89650 | M. musculus mRNA for Rab7 protein | gene | B | N | | I | 4.6 | 2.4 | I | 4.6 | 2.36 | NC | 0 | 0 |
| W63809 | "md84a12.r1 Soares mouse embryo NbMEI3.5 1.4.5 Mus | est | D | N | | I | 5.9 | 2.4 | I | 5.6 | 2.17 | I | 1.7 | 0.4 |
| M21285 | "Mouse stearoyl-CoA desaturase gene, exon 6" | gene | A | N | | I | 3.9 | 2.39 | I | 2.3 | 0.67 | D | | |
| X56304 | Mouse mRNA for tenascin | gene | C | N | MD | I | 3.2 | 2.38I | 3.1 | 2.3 | NC | 0 | |
| D85414 | "House mouse; Musculus domesticus embryo neural precu | est | A | N | | I | 4.4 | 2.33 | I | 3.8 | 1.72 | NC | 0 | 0 |
| U20532 | "Mus musculus p45NF-E2 related factor 2 (Nrf 2) mRNA, | gene | C | N | * | I | ~6.8 | 2.32 | * | ~5.8 | 1.77 | NC | 0 | 0 |
| M33960 | "Mouse plasminogen activator inhibitor (PAI-1) mRNA, co | gene | A | N | | I | 2.6 | 2.3 | I | 5.4 | 11.64 | I | 2.1 | 2.6 |
| X59990 | M. musculus alpha-catenin gene for alpha-catenin | gene | A | N | | I | 4 | 2.24 | I | 3.7 | 1.86 | NC | 0 | 0 |
| U37720 | "Mus musculus CDC42 mRNA, complete cds" | gene | A | N | | I | 3.9 | 2.23 | I | 3.9 | 2.13 | NC | 0 | 0 |
| L02526 | "Mouse protein kinase (MEK) mRNA, complete cds | gene | D | N | | I | 4.2 | 2.23 | I | 3.5 | 1.5 | I | 2.2 | 0.6 |
| AA030569 | m126g10.r1 Soares mouse embryo NbMEI3.5 14.5 Mus n | est | B | N | | I | ~6.6 | 2.17 | I | 0 | 0 | NC | 0 | 0 |
| AA072961 | "nnn80b02.r1 Stratagene mouse embryonic carcinomaRA | est | C | N | * | I | ~6.3 | 2.16 | * | ~5.2 | 1.54 | NC | * | 0 |
| M87276 | Mouse thrombospondin 1 mRNA, complete cds | gene | A | N | | I | 3.3 | 2.14 | I | 4.9 | 4.91 | I | 1.5 | 0.4 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | |
|---|---|---|---|---|---|---|---|---|---|---|---|---|
| D17666 | "Mousese gene for mitochondrial stress-70 protein (PBP74/" | gene | D | N | I | 3.8 | 2.13 | | 3.5 | 1.77 | NC | 0 | 0 |
| M86736 | "Mouse acrogranin mRNA, complete cds" | gene | D | N | I | 3.2 | 2.1 | | 2.6 | 1.19 | D | 1.2 | 0.1 |
| L02918 | "Mouse procollagen type V alpha 2 (Col5a-2) mRNA, com" | gene | D | N | I | 2.06 | 1 | 2.1 | 1 | D | | 0.2 | |
| L20276 | "Mouse biglycan (Bgn) mRNA, complete cds" | gene | A | N | I | 2.1 | 2.01 | | 1.8 | 1.03 | D | 1.2 | 0.2 |
| M22479 | "Mouse tropomyosin isoform 2 mRNA; complete cds" | gene | A | N | I | 2.8 | 1.99 | | 3 | 2.42 | NC | 1.2 | 0.1 |
| U35142 | "Mus musculus retinoblastoma-binding protein (mRbAp46" | gene | A | N | I | 3.7 | 1.97 | | 3.1 | 1.25 | D | 1.2 | 0.1 |
| X52574 | Mouse mRNA from Mov10 locus | gene | B | N | I | 4.6 | 1.95 | | 3 | 0.76 | D | 1.5 | 0.2 |
| U14172 | "Mus musculus p162 protein mRNA, complete cds" | gene | B | N | I | 6 | 1.93 | * | 7.3 | 2.64 | MI | 1.2 | 0 |
| X80937 | M. musculus mRNA for RIP1 protein | gene | B | N | MI | ~5.9 | 1.86 | * | 1.71 | 1.87 | 0 | 0 | |
| U27830 | "Mus musculus mSTI1 mRNA, complete cds" | gene | A | N | I | 2.8 | 1.84 | ~5.7 | 2.8 | 2.01 | NC | 0 | 0 |
| AA138777 | "mq40g12.r1 Barstead MPLRB1 Mus musculus cDNA clon" | est | D | N | I | 3.7 | 1.82 | | 3.9 | 1.14 | NC | 0 | 0 |
| L12447 | "Mus musculus insulin-like growth factor binding protein 5" | gene | A | N | I | 3.3 | 1.82 | | 2.7 | 0.74 | NC | 0.3 | 0 |
| M36332 | "Mus musculus insulin-like growth factor II (IGF-II) gene, exons 5" | gene | B | N | I | 2.8 | 1.82 | | 2.1 | NC | 1.4 | 0 | 0.2 |
| L18888 | "Mus musculus calnexin mRNA, complete cds" | gene | C | N | I | 1.8 | I | 4.6 | 1.47 | I | 0 | 0 | 0.5 |
| M21065 | "Mouse interferon regulatory factor 1 mRNA, complete cc" | gene | D | N | * | 1.79 | I | ~11.3 | 5 | I | 2 | 0.6 | 0 |
| L07918 | "Mus musculus GDP-dissociation inhibitor mRNA, preferen" | gene | A | N | I | 3.5 | 1.79 | * | 3.3 | 1.47 | NC | 0 | 0 |
| W90364 | "Mouse (clone PMCAT) beta-catenin mRNA, complete cds" | gene | D | N | I | ~5.7 | 1.78 | * | ~3.9 | 0.86 | NC | 0 | 0 |
| W51428 | | est | A | Y | I | ~5.8 | 1.77 | | ~5.7 | 1.73 | NC | 0 | 0 |
| A038626 | | est | B | N | MI | 4.3 | 1.73 | * | 3.3 | 0.94 | NC | 0 | 0 |
| U37413 | "m193b07.r1 Soares mouse p3NMF19.5 Mus musculus cD" | est | A | N | I | 4.1 | 1.72 | | 4.5 | 2.09 | NC | 1.4 | 0.2 |
| M21952 | "Mus musculus guanine nucleotide-binding protein (Gnal1" | gene | D | N | I | 3.9 | 1.71 | | 5.7 | 3.47 | I | 1.8 | 0.5 |
| U03283 | "Mouse macrophage colony-stimulating factor (4 kb) mR" | gene | D | N | I | 4 | 1.7 | | 6.9 | 4.81 | I | 0 | 0 |
| U79550 | "Mus musculus C3H cytochrome P450 (Cyp1b1) mRNA, c" | gene | C | N | I | 5 | 1.65 | | 4.6 | 1.42 | NC | 0 | 0 |
| U69488 | "Mus musculus Slug zinc finger protein (Slugh) mRNA, co" | gene | C | N | I | 3.9 | 1.63 | | 3 | 0.91 | NC | 0 | 0 |
| J03776 | "Mus musculus viral envelope like protein (G7e) gene, cor" | gene | A | N | I | ~5.4 | 1.63 | * | ~3.5 | 0.71 | D | 1.5 | 0.7 |
| W62326 | "Mouse down regulatory protein (rpt-1r) of interleukin 2 r" | est | A | N | I | ~5.4 | 1.62 | * | 2 | 0.15 | NC | 2.6 | 0 |
| X60672 | M. musculus mRNA for radixin | gene | C | N | I | ~5.5 | 1.61 | * | ~8.8 | 3.39 | NC | 0 | 0 |
| X81323 | M. musculus mRNA for tripeptidyl peptidase II | gene | B | N | I | ~5.2 | 1.56 | * | ~5.6 | 1.73 | NC | 1.3 | 0.1 |
| X43844 | "Mus musculus cyclin D3 gene, complete cds" | gene | D | N | I | 3.5 | 1.55 | | 2.6 | 0.79 | D | 0 | 0 |
| X13605 | Murine mRNA for replacement variant histone H3.3 | gene | D | N | I | 3.2 | 1.64 | | 3.7 | 2.35 | NC | 0 | 0 |
| J04179 | "Mouse chromatin nonhistone high mobility group protein" | gene | D | N | I | 3 | 1.54 | | 3.5 | 2.29 | NC | 1.3 | 0.1 |
| AA00813 | "6mg68g11.r1 Soares mouse embryo NbME13.5 14.5 Mus" | est | B | N | I | 2.6 | 1.53 | | 3.1 | 2.39 | NC | 0 | 0.4 |
| AA060167 | "mj72h03.r1 Soares mouse p3NMF19.5 Mus musculus cDNA" | est | B | N | NC | ~5.2 | 1.53 | * | 0 | 0 | D | 2.2 | 0 |
| M31131 | "Mouse neural cadherin (N-cadherin) mRNA, complete cds" | gene | C | N | I | ~5.4 | 1.52 | | ~6.4 | 2.08 | NC | 0 | 0 |
| AA118062 | "mm07h01.r1 Beddington mouse embryonic region Mus mus" | est | C | N | I | 3.7 | 1.52 | | 3.2 | 1.14 | D | 0 | 0 |
| M73696 | "Murine Givr-1 mRNA, complete cds" | est | A | N | I | 4.1 | 1.51 | | 5.9 | 3.1 | I | 1.5 | 0.2 |
| AA003876 | "mg79c01.r1 Soares mouse embryo NbME13.5 14.5 Mus r" | est | D | N | I | 4.7 | 1.51 | * | 2.5 | 0.35 | NC | 0 | 0 |
| X53584 | "Mouse mRNA for HSP60 protein (clones 3T3-7, -9, and-" | gene | B | N | I | 2.8 | 1.49 | | 3 | 1.67 | NC | 0 | 0 |
| U51992 | "Mus musculus interferon stimulated gene factor 3 gamma" | gene | B | N | I | ~5.2 | 1.48 | * | ~3.5 | 0.63 | NC | 0 | 0 |
| D85904 | "Mouse mRNA for apg-2, complete cds" | gene | C | N | I | 3.7 | 1.47 | | 5 | 2.68 | I | 1.3 | 0.1 |
| W97102 | "mf61h08.r1 Soares mouse embryo NbME13.5 14.5 Mus m" | est | D | N | I | ~5.1 | 1.47 | * | ~6.7 | 2.32 | NC | 0 | 0 |
| M94087 | "M. musculus mAIF4 (mTR67) mRNA, complete cds" | gene | A | N | I | 2.1 | 1.47 | | 1.9 | 1.05 | NC | 0 | 0 |
| U34883 | "Mus musculus ATP sulfurylase/APS kinase mRNA, comple" | gene | A | N | I | 1.47 | I | 3.2 | 0.76 | D | 1.3 | 0.1 | |
| L40406 | "Mus musculus heat shock protein (hsp-E71) mRNA, comp" | gene | B | N | I | 3.2 | 1.47 | | 1.5 | 0.13 | D | 2.1 | 0.7 |
| D21297 | "Mouse mRNA for peripheral-type benzodiazepine recepto" | gene | C | N | I | 2.5 | 1.46 | | 2.1 | 0.88 | NC | 0 | 0 |
| X56045 | Mouse mRNA (clone lambda-19) for hypothetical protein | gene | A | N | I | 2.9 | 1.45 | | 3.1 | 1.74 | NC | 1.3 | 0.1 |
| X17459 | Mouse mRNA for J kappa RS-binding protein | gene | B | N | I | 4.7 | 1.45 | | 4.2 | 1.14 | NC | 0 | 0 |
| AA048974 | mj50d06.r1 Soares mouse embryo NbME13.5 14.5 Mus n | esy | B | N | NC | ~5.0 | 1.45 | * | 0 | 0 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | | |
|---|---|---|---|---|---|---|---|---|---|---|---|---|---|
| J05287 | "Mouse lysosoma; membrane glycoprotein (LAMP2) mRN | gene | D | N | I | * | 4.6 | 14.2 | I | * | 3.5 | 0.79 | MC | 1.3 | 0.1 | 0 |
| D42048 | "Mouse mRNA for sqalene epoxidase, complete cds" | gene | B | N | I | | 3.2 | 1.42 | NC | | 0 | 0 | D | 3.4 | 2 | 0.2 |
| W82720 | mf07g03.r1 Soares mouse p3NMF19.5 Mus musculus cDNA | est | A | N | I | | | 3.6 | 1.41 | I | | 3.7 | 1.47 | NC | 0 | 0 |
| L35556 | "Mus musculus Int-6 mRNA, complete cds" | gene | B | N | I | | | 3.1 | 1.39 | I | | 4.3 | 2.94 | I | 1.4 | 0 |
| X80508 | M. musculus YAP65 mRNA | gene | D | N | I | | | 3.4 | 1.39 | I | | 3.2 | 1.18 | NC | 0 | 0 |
| AA163272 | mn27b12.r1 Soares mouse 3NbMS Mus musculus cDNA c | est | A | N | I | | | 3.8 | 1.37 | I | | 3.2 | 0.96 | I | 0.96 | 0 |
| U20326 | "Mus musculus cellular nucleic acid binding protein mRNA | gene | A | N | I | * | | 2.9 | 1.37 | I | | 3.4 | 1.88 | NC | 0 | 0 |
| D28599 | "Mouse mRNA for proteoglycan, PG-M" | gene | A | N | I | | | 5 | 1.36 | I | | 5.7 | 1.75 | NC | 0 | 0 |
| X61232 | Mouse mRNA for carboxypeptidase H | gene | C | N | I | | | 3.5 | 1.36 | NC | | 0 | 0 | NC | 0 | 0 |
| D26089 | "Mouse mRNA for mcdc21 protein, complete cds" | gene | A | N | I | | | 4.1 | 1.35 | I | | 5.1 | 2.09 | I | 1.4 | 0 |
| L09104 | "Mus musculus glucose phosphate isomerase mRNA, 3' er | gene | A | N | I | * | | 2.5 | 1.35 | I | | 1.7 | 0.35 | D | 0.4 | 0.4 |
| X14425 | Mouse mRNA for profilin | gene | C | N | D | | | 1.9 | 1.34 | I | | 2.2 | 2.06 | NC | 0 | 0 |
| M97635 | M. musculus helix-loop-helix transcription factor sequence | gene | C | N | I | | 4.6 | 1.29 | I | 5.1 | 1.62 | NC | 0 | 0 |
| AA097203 | mm35h09.r1 Stratagene mouse skin (#97313) Mus musc | est | C | N | I | * | * | -4.1 | 1.28 | I | * | -3.4 | 0.9 | NC | 0 | 0 |
| D42124 | "Mouse mRNA for MafK1 complete cds" | gene | A | N | I | | | 4.5 | 1.27 | I | | 6.1 | 2.28 | NC | 0 | 0 |
| AA165782 | mt74e04.r1 Soares mouse lymph node NbMLN Mus musculus | est | D | N | I | | | 3.4 | 1.27 | I | | 3.3 | 1.14 | NC | 0 | 0 |
| M13227 | Mouse enkephalin mRNA | gene | A | N | I | | | 4.6 | 1.27 | I | | 3.5 | 0.72 | NC | 0 | 0.2 |
| L07803 | "Mouse thrombospondin 2 (THBS2) mRNA, complete cds" | gene | A | N | I | * | | 2.6 | 1.27 | I | | 1.9 | 0.49 | D | 1.4 | 0 |
| L11613 | "Mus musculus proteasome (Imp2) gene, complete mRNA | gene | C | N | I | * | | -4.3 | 1.26 | I | | -3.5 | 0.86 | NC | 0 | 0 |
| AA118758 | mp59n02.r1 Soares 2NbMT Mus musculus cDNA clone 573 | est | D | N | I | | | 4.3 | 1.25 | I | | 4.8 | 1.59 | NC | 0 | 0 |
| W10645 | ma39f12.r1 Soares mouse P3NMF19.5 Mus musculus cD | est | D | N | I | * | | -4.8 | 1.25 | NC | | 0 | 0 | NC | 0 | 0.3 |
| DB6729 | "Mouse mRNA for topoisomerase-inhibitor suppressed, co | gene | A | N | I | | | 2.8 | 1.24 | I | | 3.9 | 2.81 | I | 1.4 | 0 |
| W71889 | "meA6b06.r1 Soares mouse embryo NbME13.5 14.5 Musr | est | C | N | I | | | 2.9 | 1.23 | I | | 2.7 | 1 | NC | 0 | 0 |
| D86726 | "Mouse mRNA for mMIS5, complete cds" | gene | D | N | I | * | | 2.8 | 1.22 | I | | 2.6 | 1.03 | NC | 0 | 0 |
| AA016858 | mh35f03.r1 Soares mouse placenta 4NbMP.13.5 14.5 Mus | est | B | N | I | | | -4.6 | 1.22 | I | | -3.0 | 0.48 | MC | 1.5 | 0.1 |
| X77952 | M. musculus (CD1) endoglin mRNA | gene | D | N | I | | | -4.7 | 1.21 | I | | -4.6 | 1.19 | NC | 0 | 0 |
| AA145371 | mr10o08.r1 Soares mouse 3NbMS Mus musculus cDNA clo | est | D | N | I | | | 4.1 | 1.21 | I | | 3.9 | 1.05 | NC | 0 | 0 |
| X92665 | M. musculus mRNA for ubiquitin-conjugating enzyme UbcM | gene | B | N | MI | | 4 | 1.2 | I | 3.5 | 0.92 | NC | 0 | 0.9 |
| L29454 | "Mouse fibrillin (Fbn-1) mRNA, complete cds" | gene | A | N | I | | | 2.6 | 1.2 | I | | 1.3 | 0.07 | D | 2 | 0. |
| U70622 | "Mus musculus lysophosphatidic acid receptor (vzg-1) mR | gene | A | N | I | * | | -4.5 | 1.19 | I | * | -4.8 | 1.33 | NC | 0 | 0 |
| D10061 | Mouse mRNA for DNA topoisomerase I | gene | A | N | I | * | | -4.4 | 1.18 | I | * | -7.1 | 2.63 | NC | 0 | 0 |
| X53753 | Mouse mRNA for nonmuscle tropomyosin 5 | gene | A | N | I | 2.3 | 1.18 | I | 2 | 0.76 | NC | 0 | 0 |
| U46690 | "Mus musculus ATP-dependent RNA helicase mRNA, partia | gene | C | N | I | | | 2.7 | 1.18 | I | | 2.1 | 0.51 | D | 1.3 | 0.1 |
| D78645 | "Mouse mRNA for 78 kDa glucose-regulated protein, com | gene | D | N | I | | | 2.5 | 1.17 | I | | 2.7 | 1.44 | NC | 0 | 0 |
| X16857 | Mouse mRNA f4HSP86 heat-shock protein | gene | D | N | I | | | 3.4 | 1.16 | I | | 5.4 | 3 | I | 1.6 | 0.3 |
| U25633 | "Mus musculus tumor-associated membrane protein (TMP | gene | C | N | I | | | 2.3 | 1.15 | I | | 2.9 | 2.11 | NC | 0 | 0 |
| U41765 | "Mus musculus metalloprotease/disintegrin/cysteine rich | gene | B | N | I | | * | -4.4 | 1.14 | I | | -4.9 | 1.39 | NC | 0 | 0 |
| AA038511 | m185h01.r1 Soares mouse p3NMF19.5 Mus musculus cDNA | est | C | N | I | | | 2.2 | 1.14 | I | | 1.9 | 0.69 | NC | 0 | 0 |
| AA123463 | mm23e03.r1 Eddington mouse embryonic region Mus mu | est | D | N | I | | | 2.4 | 1.13 | I | | 2.9 | 1.89 | NC | 0 | 0 |
| M62867 | "Mouse Y box transcription factor (MSY-1) mRNA, comple | gene | A | N | I | | | 2.1 | 1.11 | I | | 3 | 3.23 | D | 1.3 | 0.4 |
| X58196 | M. musculus H19 mRNA | gene | A | N | I | | | 1.9 | 1.11 | I | | 1.4 | 0.29 | NC | 0 | 0 |
| U10406 | "Mus musculus capping protein beta-subunit isoform 1 mF | gene | A | N | I | | 2.2 | 1.1 | I | 2.4 | 1.35 | NC | 0 | 0 |
| AA002277 | mg42b03.r1 Soares mouse embryo NbME13.5 14.5 Mus | est | B | N | I | | | 3.3 | 1.1 | I | | 3 | 0.87 | NC | 0 | 0 |
| AA139989 | mq95e05.r1 Stratagene mouse heart (#97316) MuS musc | est | A | N | I | | * | 3.9 | 1.1 | I | * | 3.1 | 0.63 | NC | 0 | 0 |
| Z37110 | M. musculus mRNA for cyclin G | gene | B | N | I | | | 4 | 1.09 | I | | 5.5 | 2.02 | NC | 0 | 0 |
| J05185 | "Mouse protein disulfide isomerase (ERP59) mRNA, compL | gene | A | N | I | | 2 | 1.09 | I | 2 | 1.06 | NC | 0 | 0 |
| M86390 | Mus domesticus moesin mRNA, 3' end" | est | D | N | I | | | 4 | 1.08 | I | | 4.9 | 1.64 | NC | 0 | 0 |
| Z31553 | "M. musculus (129/Sv) Cctb mRNA for CCT (chaperonin co | gene | B | N | I | | | 2.3 | 1.08 | I | | 2.3 | 1.07 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | |
|---|---|---|---|---|---|---|---|---|---|---|---|
| U75680 | "Mus musculus histone stem-loop binding protein (SLBP) | gene | C | N | * | -4.3 | 1.08 | I | -3.6 | 0.72 | D | 0 | 0 |
| U77630 | "Mus musculus adrenomedullin precursor mRNA, complete | gene | C | N | | 3.1 | 1.08 | NC | 0 | 0 | NC | 4 | 2.3 |
| X99915 | "M. musculus HMGI-C gene, exon 1, and joined CDS" | gene | B | N | | 3.2 | 1.06 | I | 4.8 | 2.64 | I | 1.5 | 0.2 |
| M13685 | "Mouse prion protein (PrP) mRNA, complete cds" | gene | A | N | | 2.9 | 1.06 | I | 3.5 | 1.67 | MI | 1.2 | 0.1 |
| M64640 | "Mouse Mov-34 36 kD protein gene, exon 7" | gene | B | N | | 2.9 | 1.04 | I | 3 | 1.19 | NC | 0 | 0 |
| X63100 | M. musculus mRNA for connexin45 | gene | B | N | * | -4.3 | 1.04 | I | -4.1 | 0.92 | NC | 0 | 0 |
| X58876 | Murine mdm2 mRNA for mdm2 protein | gene | B | N | * | -4.3 | 1.03 | I | * | -4.2 | 1.03 | NC | 0 |
| M75122 | "Mouse acid beta-galactosidase (GLB-1) gene, exon 16" | gene | D | N | | 4.1 | 1.01 | I | -2.8 | 0.38 | NC | 0 | 0 |
| M91458 | "Mus musculus sterol-carrier protein X mRNA, complete c | gene | A | N | | 4.1 | 1 | I | 4.5 | 1.24 | NC | 0 | 0 |
| J03880 | "Mouse UDP-galactose:N-acetylglucosamine galactosyltrar | gene | D | N | * | 3.8 | 1 | I | 3.5 | 0.85 | NC | 0 | 0 |
| AA111149 | "mp10e11.r1 Life Tech mouse embryo 8 5dpc 10664019 | est | C | N | | 2.2 | 1 | NC | 2.1 | 0.79 | NC | 0 | 0 |
| L25069 | "M. musculus mRNA for poly(C)-binding protein, splice vari | gene | A | N | | 2.4 | 0.99 | NC | 0 | 0 | D | 1.6 | 0.4 |
| W18503 | "mb88b08.r1 Soares mouse p3NMF19.5 Mus musculus cD | est | D | N | | 3.7 | 0.99 | I | 3.4 | 0.8 | NC | 0 | 0 |
| M70641 | "Mouse FISP-12 protein (fisp-12) gene, complete cds" | gene | D | N | | 3.1 | 0.99 | I | 2.4 | 0.48 | D | 1.3 | 0.1 |
| W48519 | | gene | D | N | | 2.2 | 0.98 | Y | 3.7 | 3.84 | I | 1.7 | 0.9 |
| | | | | | | est | A | * | -4.1 | 0.98 | * | ~6.12.05 NC | |
| AA003323 | mg51g09.r1 Soares mouse embryo NbME13.5 14.5 Mus m | est | A | N | | 2.5 | 0.98 | I | 1.9 | 0.36 | D | 1.4 | 0.2 |
| AA153032 | "nr17e03.r1 Soares mouse 3NbMS Mus musculus cDNA | est | D | N | D | -4.0 | 0.97 | D | -4.0 | 0.97 | NC | 0 | 0 |
| Z25524 | "M. musculus integrin associated protein mRNA, complete | gene | D | N | | -4.2 | 0.97 | I | -3.0 | 0.44 | NC | 1.4 | 0.1 |
| D12713 | "Mouse DNA for MSEC66, complete cds" | gene | C | N | * | 4 | 0.96 | I | 4 | 0.96 | NC | 0 | 0 |
| X81058 | M. musculus tex261 mRNA | est | A | N | * | 3.2 | 0.96 | I | 2.9 | 0.76 | NC | 0 | 0 |
| AA110543 | m196e01.r1 Stratagene mouse embryo kidney (#937315) Mus musc | est | D | N | | 2.9 | 0.95 | I | 3.2 | 1.17 | NC | 1.3 | 0.3 |
| W20828 | mb91g06.r1 Soares mouse p3NMF19.5 Mus musculus cDN | est | D | N | D | 1.9 | 0.95 | D | 1.4 | 0.32 | I | | |
| L13968 | "Mouse delta/YY1/NF-EI/UCRBP transcription factor exor | gene | D | N | | -4.1 | 0.93 | I | -4.0 | 0.91 | NC | 1.3 | 0.1 |
| M58566 | "Mouse TJS11 primary response gene, complete cds" | gene | A | N | | 3.4 | 0.93 | MI | 2.6 | 0.49 | MC | 1.3 | 0 |
| U05245 | "Mus musculus BALB/c invasion inducing protein (Tiam-1) | gene | C | N | * | -3.8 | 0.92 | NC | 0 | 0 | NC | 0 | 0 |
| Z11997 | M. musculus mRNA for non-histone chromosomal high-mo | est | C | N | | -4.1 | 0.9 | I | -3.1 | 0.48 | NC | 0 | 0 |
| U40375 | "Mus musculus Supt6h mRNA, complete cds" | gene | A | N | | 3.9 | 0.89 | I | 2.7 | 0.38 | NC | 1.5 | 0.2 |
| L42293 | "Mus musculus acyl-coenzyme A:cholesterol acyltransfera" | gene | A | N | * | 3 | 0.88 | I | 4.5 | 2.14 | I | 0 | 0 |
| W62742 | md71c06.r1 Soares mouse embryo NbME13.5.14.5 Mus mL | est | A | N | * | 3.6 | 0.88 | I | 4.8 | 1.65 | NC | | |
| D86232 | "House mouse; Musculus domesticus mRNA for Ly-6C var | gene | D | N | * | 3.4 | 0.88 | I | 3.2 | 0.75 | D | | |
| L29441 | "Mus musculus mRNA, complete cds" | est | A | * | 2.7 | 0.88 | | 0.41 | D | | 1.3 | | |
| W98349 | mg13a01.r1 Soares mouse embryo NbME13.5 14.5, Mus r | gene | A | N | * | 3.7 | 0.88 | I | 0 | 0 | NC | 0.1 | |
| Z17804 | M. musculus p120 gene | gene | B | N | MI | -3.9 | 0.88 | NC | 0 | 0 | D | 1.7 | 0.2 |
| AA003022 | mg39h11.r1 Soares mouse embryo NbME13.5 14.5 Mus mu | est | D | N | * | 3.7 | 0.87 | I | 3.7 | 0.87 | NC | 0 | 0 |
| M63114 | "Mouse surfeit locus surfeit 4 protein mRNA, complete cd | gene | A | N | | 2.4 | 0.86 | I | 3 | 1.53 | I | 1.2 | 0.1 |
| AA038437 | m185f02.r1 Soares mouse p3NMF19.5 Mus musculus cDNA | est | D | N | * | 2.7 | 0.86 | I | 2.4 | 0.64 | NC | 0 | 0 |
| J00424 | "Mouse interferon-beta; 12S fraction mRNA, 3' end" | gene | B | N | | 3.9 | 0.86 | I | 3 | 0.46 | NC | 0 | 0 |
| AA015026 | mh26103.r1 Soares mouse placenta 4NbMP13.5 14.5 Mus | gene | A | N | * | 4 | 0.86 | I | 0 | 0 | NC | 0 | 0 |
| X57024 | Murine GLUD mRNA for glutamate dehydrogenase | gene | B | N | | 3 | 0.85 | I | 3.6 | 1.25 | NC | 0 | 0 |
| X59379 | Mouse mRNA for amyloid beta precursor (protease nexin 1 | gene | B | N | | 2.4 | 0.85 | I | 2.6 | 0.99 | D | 1.7 | 0 |
| W14540 | mb24c01.r1 Soares mouse p3NMF19.5.Mus musculus cD" | est | D | N | * | -3.9 | 0.85 | NC | 0 | 0 | MC | * | 3.8 | 1.3 |
| U20086 | "Mus. domesticus nuclear binding factor NF2d9 mRNA, co | gene | A | N | * | -3.8 | 0.84 | I | -3.4 | 0.66 | NC | 0 | O |
| X63535 | M. musculus ufo mRNA | gene | B | N | | 2.2 | 0.84 | I | 2 | 0.64 | NC | 1.4 | 0.1 |
| U79716 | Mus musculus ajuba (Ajuba) mRNA, complete cds | gene | C | N | | 2.9 | 0.84 | I | 0 | 0 | NC | 0 | 0 |
| X59728 | M. musculus mRNA for gas5 growth arrest specific protein | gene | B | N | | 2.8 | 0.83 | I | 3.3 | 1.21 | NC | 0 | 0 |
| AA124715 | mq81h11.r1 Stratagene mouse melanoma (#937312) Mus m | est | C | N | | 2.1 | 0.83 | I | 1.9 | 0.62 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | |
|---|---|---|---|---|---|---|---|---|---|---|---|---|
| U18869 | "Mus musculus mitogen-responsive 96 kDa phosphoprotei | gene | C | N | | 3.5 | 0.83 | I | 3 | 0.59 | NC | 0 | 0 |
| X90875 | M. musculus mRNA for FXR1 protein | gene | B | N | * | −3.7 | 0.82 | I | −5.8 | 1.88 | NC | 0 | 0 |
| J03484 | "Mouse laminin B2 chain mRNA, complete cds" | gene | D | N | | 3.1 | 0.81 | I | 2.6 | 0.5 | NC | 0 | 0 |
| X66032 | M. musculus mRNA for cyclin B2 | est | A | N | * | 3.1 | 0.81 | I | 2.5 | 0.47 | NC | 0 | 0 |
| X80686 | M. musculus mRNA for C5 component of protease | gene | D | N | | −3.6 | 0.8 | I | −4.2 | 1.08 | NC | 0 | 0 |
| AA144078 | mq53g12.r1 Soares 2NbMT Mus musculus cDNA clone 58 | gene | D | N | D | 2 | 0.8 | D | 1.6 | 0.37 | MI | 1.2 | 0.1 |
| M72414 | "Mouse microtubule-associated protein 4 (MAP4) mRNA | est | A | N | | 3.9 | 0.8 | I | 0 | 0 | MC | 1.9 | 0.3 |
| XS9520 | "Mouse CCK gene for cholecystokinin, exon 1" | gene | A | N | | 3 | 0.79 | I | 0 | 0 | MC | 1.5 | 0.2 |
| Y00094 | Mouse mRNA for ras-related YPT1 protein | gene | B | N | | 2.5 | 0.78 | I | 3.8 | 2.09 | I | 1.5 | 0.3 |
| M32745 | "mouse transforming growth factor beta-3 mRNA, comple | gene | A | N | | 2.2 | 0.78 | I | 2.7 | 1.42 | NC | 0 | 0 |
| D87663 | "House mouse; Musculus domesticus mRNA for 14-3-3 ep | gene | B | N | | 2.6 | 0.77 | I | 1.6 | 0.17 | D | 1.6 | 0.2 |
| U53456 | "Mus musculus protein phosphatase 1cgamma (PP1cgamr | gene | C | N | | 2 | 0.77 | I | 2.2 | 0.92 | NC | 0 | 0 |
| AA103538 | "mo40h06.r1 Life Tech mouse embryo 15 5dpc 10667012 | est | C | N | * | 2.4 | 0.77 | NC | 2.5 | 0.79 | NC | 0 | 0 |
| M95200 | "Mouse vascular endothelial growth factor mRNA, comple | gene | A | N | | 3.7 | 0.77 | I | 0 | 0 | NC | 0 | 0.5 |
| X83577 | M. musculus mRNA for K-glypican | gene | B | N | * | 3.1 | 0.76 | I | 3.7 | 1.17 | NC | 0 | 0.1 |
| AA072911 | mm72h12.r1 Stratagene mouse macrophage (#937306) M | est | C | N | | 3.1 | 0.76 | I | 2.3 | 0.33 | NC | 0 | 0 |
| U14648 | "Mus musculus putative myelin regulatory factor 1 mRNA | gene | C | N | * | 3.4 | 0.75 | I | 4.1 | 1.13 | NC | 0 | 0 |
| L22030 | "Mus musculus HIC-5 mRNA, complete cds" | gene | D | N | | 2.6 | 0.75 | I | 2.7 | 0.88 | NC | 0 | 0 |
| L22482 | "Mouse D-type cyclin (CYL2) mRNA, complete cds" | gene | A | N | 2.1 | 0.75 | I | 0.82 | NC | | 0 | | |
| M83749 | "Mus musculus NGFI-A binding protein 2 (NAB2) mRNA, c | gene | D | N | | 2.4 | 0.75 | I | 2.4 | 0.8 | NC | 0 | 0 |
| U47543 | "Mus musculus interferon-induced Mx1 protein gene conferring s | gene | C | N | MI | 3 | 0.75 | I | 2.3 | 0.38 | NC | 0 | 0 |
| M211T7 | mg45a11.r1 Soares mouse embryo NbME13.5 14.5 Mus r | est | A | N | * | 3.7 | 0.74 | I | 7.8 | 2.97 | I | 2.1 | 0.5 |
| AA002759 | | est | B | N | | 2.6 | 0.74 | I | 3.3 | 1.43 | I | 1.3 | 0.1 |
| W55556 | | gene | A | Y | | −3.1 | 0.74 | I | −3.3 | 0.81 | NC | 0 | 0 |
| U07617 | "Mus musculus Grb2 adaptor protein (grb2) mRNA, comp | gene | B | N | * | 3.6 | 0.74 | I | 0.58 | NC | | 0 | |
| AA032596 | mi29e04.r1 Soares mouse embryo NbME13.5 14.5 Mus m | est | B | N | | 2.6 | 0.74 | I | 2 | 0.35 | NC | 0 | 0 |
| L12030 | "Mus musculus cytokine (SDF-1-beta) mRNA, complete cc | gene | B | N | | 2.5 | 0.74 | I | 1.7 | 0.2 | D | 1.5 | 0.2 |
| X52046 | M. musculus COL3A1 gene for collagen alpha-I | gene | B | N | | 1.7 | 0.74 | I | 1.3 | 0.15 | D | 1.3 | 0.3 |
| X78709 | M. musculus NRF1 mRNA | gene | B | N | | 2.8 | 0.74 | I | 0 | 0 | D | 1.7 | 0.3 |
| X52101 | Mouse mRNA for a 25kDa nuclearprotein found in murine | gene | B | N | * | 3 | 0.74 | NC | 0 | 0 | NC | 0 | 0 |
| U37353 | "Mus musculus proteinphosphatase 2A B'alpha3 reguato | gene | B | N | | −3.7 | 0.73 | I | −5.1 | 1.41 | MI | 1.4 | 0.1 |
| L22355 | "Mus musculus vascular adhesion cell molecule-1 (VCAM1 | gene | D | N | * | 3.1 | 0.73 | I | 3.1 | 0.73 | NC | 0 | 2 |
| AA153021 | mq67e05.r1 Soares 2NbMT Mus musculus cDNA clone 583 | est | D | N | * | −3.3 | 0.72 | I | −11.9 | 5.46 | I | 3.6 | 0.1 |
| W21013 | mb80g05.r1 Soares mouse p3NMF19.5 Mus musculus cD | est | B | N | | 1.8 | 0.72 | I | 2 | 0.92 | MI | 0 | |
| W08454 | mb50o.10.r1 Soares mouse p3N.MF19.5 Mus musculus cD | est | C | N | D | 2.5 | 0.72 | I | 1.9 | 0.31 | D | 1.3 | 0.1 |
| U16163 | "Mus musculus prolyl 4-hydroxylase alpha(II)-subunit mRN | gene | A | N | 2.3 | 0.72 | NC | | D | | 1.7 | | |
| Y07836 | M. musculus mRNA for basic-helix-loop-helix protein | gene | C | N | * | −3.7 | 0.71 | I | −4.6 | 1.27 | NC | 0 | 0 |
| W55283 | | est | A | Y | | −3.4 | 0.71 | NC | 2.1 | 0.27 | MI | 1.4 | 0.1 |
| L00681 | "Mus musculus Unp mRNA, complete cds" | gene | A | N | | 2.9 | 0.71 | I | 0 | 0 | * | 0 | 0 |
| W90947 | mf82f08.r1 Soares mouse embryo NbME13.5 14.5 Mus mu | est | A | N | MI | −3.5 | 0.71 | NC | * | NC | | 0 | |
| X51397 | Murine MyD88 mRNA induced by interleukin-6 | gene | B | N | 3.1 | I | * | 5.1 | 1.98 | I | | | |
| D90151 | "Mouse mRNA for CArG-binding factor-A, complete cds" | gene | D | N | | 0.7 | 0.7 | I | 2.3 | 1.29 | NC | 0 | 0 |
| D38379 | Mouse mRNA for pyruvate kinase M | gene | A | N | | 1.9 | 0.7 | I | 1.4 | 0.39 | NC | 0 | 0 |
| J03520 | "Mouse tissue plasminogenactivator mRNA, complete cd | gene | A | N | 3 | 1.6 | 0.7 | I | 2.4 | | | | |
| M69260 | "Mouse lipocortin I gene, exon 13" | | geneD | N I | 1.9 0.69 | 0.7 | I | 2.83 | 0.36 I | 1.6 | 0.8 | | |
| U06670 | "Mus musculus very low densitylipoprotein receptor mRN | | geneA N 3.4 0.69 I | 1.8 | 0.1 D | 1.9 | 0.3 | | | | | | |

TABLE 6-continued

ISGs and IRGs identified from mouse embryonic fibroblast incubated in the presence or absence of IFN-αBBDB in the presence or absence of encephalomyocarditis virus

| | | | | | | | | | | | | |
|---|---|---|---|---|---|---|---|---|---|---|---|---|
| D87901 | "Mouse mRNA for ARF4, complete cds" | gene | C | N | I | 1.9 | 0.68 | I | 2.2 | 1.06 | NC | | 0 |
| AA058163 | mj59c08.r1 Soares mouse embryo NbME13.5 14.5 Mus rr | est | B | N | D | 1.6 | 0.68 | 0 | 1.7 | 0.87 | NC | 0 | 0 |
| Z14044 | M. musculus mRNA for valosin-containing protein | gene | B | N | | 2.4 | I | | 2.5 | 0.73 | | 0 | 0 |
| W11011 | ma47a11.r1 Soares mouse p3NMF19.5 Mus musculus cD | est | C | N | | 0.68 | 0.68 | * | -3.3 | 0.65 | NC | 0 | 0 |
| X74438 | M. musculus PTP35 mRNA | gene | A | N | * | -3.4 | 0.68 | * | 2.9 | 0.56 | NC | 0 | 0 |
| M74753 | "Mouse myosin heavy chain mRNA, 3' flank" | gene | B | N | * | 3.2 | 0.68 | * | 0 | 0 | NC | * | 0 |
| X64414 | M. musculus mRNA for low density lipoprotein receptor | gene | A | N | | -3.6 | 0.68 | | 0 | 0 | D | 3 | 1.5 |
| D50086 | "Mouse mRNA for neuropilin, complete cds" | bene | B | N | | 2.4 | 0.67 | I | 5.4 | 1.91 | NC | 0 | 0 |
| X14432 | Mouse mRNA for thrombomodulin | gene | B | N | | 3.3 | 0.67 | I | 4.1 | 1.58 | NC | 0 | 0 |
| U17162 | "Mus musculus bcl-2 binding protein BAG-1 m NA, comp | gene | A | N | I | 2.8 | | | | | 0 | 0 | 0 |
| U42383 | "Mus musculus fibroblast growth factor inducible gene 13 | gene | A | N | | 0.67 | I | 2.7 | 0.82 | NC | 0 | 0 | 0 |
| AA114648 | mm04b05.r1 Beddington mouse embryonic region Mus mu | est | C | N | | 2.3 | 0.67 | | 2.2 | 0.63 | NC | 0 | 0 |
| U28138 | "Mus musculus dishevelled-1 proten (Dvl1) gene, compe | gene | C | N | * | 2.8 | 0.67 | * | 2.6 | 0.57 | D | 2 | 0 |
| M72394 | "Mus musculus calcium-dependent phospholipid binding protein ( | gene | A | N | | 3.1 | 0.66 | NC | | | I | 0.3 | 0.1 |
| AA048304 | mj28a07.r1 Soares mouse embryo NbME13.5 14.5 Mus mu | est | B | N | | 2.8 | 0.66 | | 3.5 | 1.13 | * | 1.2 | 0 |
| M73329 | "Mouse phospholipase C-alpha (PLC-alpha) mRNA, comple | gene | A | N | | 3 | 0.66 | | 3.1 | 0.71 | | 0 | 0 |
| M28723 | "Mus musculus housekeeping-tupe protein (MER5) mRNA, | gene | A | N | | 2 | 0.65 | | 1.8 | 0.44 | | 0 | 0 |
| L36314 | "Mus musculus GDP dissociation inhibitor beta mRNA, con | gene | D | N | * | 3 | 0.64 | | 2.4 | 0.36 | MC | 1.2 | 0.1 |
| L27453 | "Mus musculus PBX1B mRNA, complete cds" | gene | B | N | | 2.1 | 0.64 | | 2.3 | 0.84 | NC | 0 | 0 |
| M32486 | "Mouse 19.5 mRNA, complete cds" | gene | C | N | * | 3.4 | 0.64 | | 3.2 | 0.55 | NC | 0 | 0 |
| U39302 | "Mus musculus 26S proteasome subunit 4 ATPase mRNA | gene | D | N | | 3.1 | 0.63 | | 2.5 | 0.39 | I | 1.3 | 0.1 |
| AA002621 | mg55f02.r1 Soares mouse embryo NbME13.5 14.5 Mus mu | est | C | N | | 2.3 | 0.63 | | 3 | 1.28 | | 0 | 0 |
| M18186 | "Mduse 84 kD heatshock protein mRNA, complete cds" | gene | B | N | | 1.7 | 0.63 | | 1.7 | 0.62 | NC | 0 | 0 |
| L22143 | "Mouse insulin-like growth factor II/cation independent m | gene | D | N | * | 1.7 | 0.63 | | 1.6 | 0.48 | NC | 0 | 0 |
| AA023796 | mh65e02.r1 Soares mouse placenta 4NbMP13.5 14.5 Mu | est | A | N | | 2.7 | 0.62 | 1.6 | 0.1 | D | | 1.7 | 0.2 |
| W33838 | mc55c11.r1 Soares mouse embryo NbME13.5 14.5 Mus mu | est | B | N | * | 2.9 | 0.62 | * | 4.2 | 1.42 | MI | 1.4 | 0.1 |
| AA104459 | mo55a03.r1 Life Tech mouse embryo 8 5dpc 10664019 Mu | est | C | N | I | 2.8 | I | 3.3 | 0.9 | | | 0 | 0 |
| J02652 | "Mouse malate NADP oxidoreductase mRNA, complete cds" | gene | D | N | 2.6 | 0.62 | 2.8 | 0.78 | NC | | 0 | | 0 |
| X60203 | M. musculus mRNA for FK506-binding protein | gene | B | N | * | -3.3 | 0.62 | * | -3.6 | 0.72 | NC | 0 | 0 |
| W37000 | "mb65311.r1 Soares mouse p3NMF19.5 Mus musculus c[ | est | A | N | | 2 | 0.62 | | 2 | 0.7 | NC | 0 | 0 |
| U43921 | "Mus. musculus ubi-d4 mRNA, complete cds" | gene | A | N | * | 1.7 | 0.62 | | 1.7 | 0.67 | NC | 0 | 0 |
| X80478 | M. musculus AEBP1 mRNA | gene | B | N | * | 2.6 | 0.61 | * | 1.8 | 0.18 | NC | 0 | 0 |
| AA059527 | mj61f10.r1 Soares mouse embryo NbME13.5 14.5 Mus mus | est | A | N | L | 1.9 | 0.61 | | 1.3 | 0.11 | D | 1.4 | 0.3 |
| U11274 | "Mus musculus clone pmuAUF1-3 RNA-binding protein AU | gene | A | N | * | -3.3 | 0.62 | * | 0 | 0 | NC | 0 | 0 |
| W96831 | mf96i07.r1 Soares mouse embryo NbME13.5 14.5 Mus mi | est | A | N | | 3.1 | 0.61 | I | 4.9 | 1.68 | NC | 0 | 0 |
| L20294 | "Mus musculus GTP-binding protein (mSara) homologue rr | gene | D | N | 2.4 | 0.61 | 2.7 | 0.87 | NC | | 0 | | 0 |
| L21707 | "Mus musculus receptor tyrosine kinase (MRK) mRNA, cor | gene | D | N | * | 2.3 | 0.61 | * | 2.4 | 0.69 | NC | 0 | 0 |
| X92664 | M. musculus mRNA for ubiquitin-conjugating enzyme UbcM | gene | B | N | * | 3.2 | 0.61 | * | 3 | 0.52 | NC | 0 | 0 |
| X15052 | Mouse mRNA for 3'-end of NCAM-140 and NCAM-180 iso | gene | B | N | | 2.9 | 0.61 | | 2.5 | 0.43 | NC | 0 | 0 |
| W70905 | me23c05.r1 Soares mouse embryo NbME13.5 14.5 Mus r | est | D | N | * | 3.2 | 0.61 | * | 2.7 | 0.39 | NC | 0 | 0 |
| W6489T | md9gb10.r1 Soares mouse embryo NbME13.5 14.5Mus rr | est | A | N | | 2.7 | 0.61 | | 2.2 | 0.36 | NC | 0 | 0 |
| U27455 | "Mus musculus serine palmitoyltransferase LCB2 subunit r | est | C | N | | 2.5 | 0.61 | | 2.1 | 0.34 | NC | 0 | 0 |
| AA047939 | "mj23e01.r1 Soares mouse embryo NbME13.5 14.5 Mus.. r | est | B | N | I | 2.8 | I | 2 | 2.2 | 0.31 | 0 | | 0 |
| X53476 | Mouse mRNA for non-histone chromosomal protein HMG-1 gene | B | N | 1.8 | 0.61 | 0.6 | 0.8 | NC | | 0 | | 0 | 0 |
| M57999 | "Mouse transcription factor NF-kappa-B DNA binding subu | gene | A | N | I | 2.6 | 0.6 | I | 2.1 | 0.32 | D | 1.2 | 0.2 |
| Y00516 | Mouse mRNA for aldolase A | gene | A | N | | 1.5 | 0.6 | | 1.3 | 0.19 | NC | * 0 | 0 |
| W74874 | | est | A | Y | MI | -3.1 | 0.6 | MI | 0 | 0 | NC | 0 | 0 |
| W29420 | "mb99a01.r1 Soares mousep3NMF19.5 Mus musculus cD | est | B | N | D | 1.5 | 0.59 | D | 1.9 | 1.41 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | | |
|---|---|---|---|---|---|---|---|---|---|---|---|---|---|
| M26251 | "Mouse mRNA encoding vimentin, complete cds" | gene | A | N | | 1.5 | 0.59 | I | 1.6 | 0.85 | NC | | 0 |
| X79233 | M. musculus EWS mRNA | gene | B | N | | 2.4 | 0.59 | I | 0.79 | NC | 0 | 0 | 0 |
| L39879 | "Mus musculus ferritin L-subunit gene exons 1–4, complet | gene | D | N | | 1.7 | 0.59 | I | 1.5 | 0.31 | NC | 0 | 0 |
| AA058163 | mj59c08.r1 Soares mouse embryo NbMF13.5 14.5.Mus m | est | B | N | D | 1.6 | 0.59 | MC | 1.3 | 0.24 | NC | 1.3 | 0.2 |
| D31717 | "Mouse MARlib mRNA for ribophorin, complete cds" | gene | C | N | | 1.8 | 0.59 | MI | 1.4 | 0.17 | D | 0.1 | 0.1 |
| W41762 | mc65g02.r1 Soares mouse embryo NbMF13.5 14.5 Mus m | est | D | N | * | 2.9 | 0.58 | I | 3.8 | 1.08 | I | 1.3 | 1.4 |
| X80232 | M. musculus mRNA for SIG41 | gene | C | N | | 2.9 | 0.58 | I | 3.7 | 1.03 | MI | 1.3 | 0.1 |
| X75313 | M. musculus (C57B/6) GB-like mRNA | gene | B | N | D | 1.4 | 0.57 | D | 1.4 | 0.52 | NC | 2.1 | 1.4 |
| M26270 | "Mouse stearoyl-CoA desaturase (SCD2) mRNA, complete | gene | A | N | I | 1.8 | 0.57 | NC | 0 | 0 | D | 1.7 | 1 |
| X53333 | Mouse mRNA for triosephosphate isomerase (EC 5.3.1.1) | gene | A | N | I | 1.6 | 0.57 | NC | 0 | 0 | D | 1.4 | 0.1 |
| L47480 | "Mus musculus BMPA gene, complete | gene | A | N | * | ~3.2 | 0.56 | NC | 0 | 0.6 | MC | 0 | |
| X75014 | M. musculus Phox2 mRNA for homeodomain protein | gene | C | N | D | ~3.2 | 0.56 | D | ~3.2 | 0.41 | NC | 0 | |
| U58205 | Mus musculus Btk locus, alpha-D-galactosidase A (Ags), | gene | A | N | * | 2.9 | I | I | 2.6 | I | | 0.5 | |
| U31758 | "Mus musculus transcriptional regulator RPD3 homdlog mf | gene | C | N | I | 0.55 | 0.55 | 6 | 2.61 | 0.85 | NC | 2.1 | |
| U78103 | Mus musculus embryonic ectoderm development protein ( | gene | C | N | | 3 | 0.55 | I | 3.7 | 0.84 | NC | 0 | 0 |
| AA058163 | mj59c08.r1 Soares mouse embryo NbMF13.5 14.5 Mus m | est | B | N | D | 1.6 | 0.55 | D | 1.7 | 0.55 | NC | 1.3 | 0 |
| W29456 | mc03e02.r1 Soares mouse p3NMF19.5 Mus muscuus cDNA | est | D | N | * | 2.5 | 0.55 | I | 2.5 | 0.44 | NC | 0 | 0.2 |
| D21252 | Mouse mRNA for OSF-3, complete cds" | gene | C | N | | 1.6 | 0.55 | I | 1.5 | 0.42 | NC | 0 | 0 |
| AA103356 | mo18e02.r1 Life Tech mouse embryo 13 5dpc 10666014 | est | A | N | | 2.1 | 0.55 | I | 1.9 | 0.39 | NC | 0 | 0.1 |
| U70662 | "Mouse epithelial zinc-finger protein EZF (Zie) mRNA,com | gene | A | N | | 2.9 | 0.55 | I | 2.5 | 0.15 | D | 1.3 | 0 |
| U25708 | "Mus musculus CD98 heavy chain mRNA, complete cds" | gene | B | N | | 1.9 | 0.55 | I | 1.4 | 0 | D | 0 | 0.2 |
| D31898 | "Mus musculus mRNA for protein tyrosine phosphatase, PTPBR7" | gene | C | N | MD | 2.9 | 0.55 | NC | 0 | 0 | NC | 0 | 0 |
| M15668 | "Mus musculus X chromosome-linked phosphoglycerate ki | gene | A | N | | 1.6 | 0.55 | NC | 0 | 0 | NC | 0 | 0.1 |
| U35249 | Mus musculus CDK-activating kinase assembly factor p3 | gene | B | N | | 3.1 | 0.54 | I | 4.6 | 1.32 | I | 1.5 | 0 |
| AA033153 | m137c08.r1 Soares mouse embryo NbMF13.5 14.5 Mus mu | est | A | N | | 2.9 | 0.54 | I | 2.8 | 0.53 | NC | 0 | 0.2 |
| U35141 | "Mus musculus retinoblastoma-binding protein (mRbAp48) | gene | B | N | | 1.9 | 0.54 | I | 1.6 | 0.29 | NC | 0 | 0 |
| W50167 | | est | A | Y | * | ~3.2 | 0.54 | NC | 0 | 0 | MC | 0.1 | 0.2 |
| AA120387 | mn46h09.r1 Beddington mouse embryonic region Mus mus | est | A | N | * | ~3.2 | 0.54 | NC | 0 | 0 | MC | 1.4 | 0.6 |
| M64404 | Mus domesticus interleukin 1 receptor antagonist (IL-1RA | gene | C | N | | 2.4 | 0.54 | NC | 0 | 0 | D | 1.6 | |
| U44426 | "Mus musculus D52 (mD52) mRNA, complete cds" | gene | C | N | I | 2.6/0.51 | I | | 4.4 | I | | | 0.2 |
| X54149 | "Mouse mRNA for MyD118, a myeloid differentiation prime | gene | B | N | ~3.1 | 0.53 | I | ~3.9 | 0.84 | NC | | | |
| U26259 | "Mus musculus C2-H2 zinc finger protein mRNA, complete | gene | B | N | * | 2.8 | 0.53 | MI | 3.4 | 0.81 | I | 1.7 | 0.2 |
| D14340 | "Mouse mRNA for ZO-1, complete cds" | gene | A | N | | 3 | 0.53 | I | 3.1 | 0.57 | NC | 0 | 0 |
| M77174 | "Mouse periecan mRNA, complete cds" | gene | D | N | * | ~3.0 | 0.53 | I | ~3.1 | 0.56 | NC | 0 | 0 |
| M64292 | "Mouse T1521 gene, complete cds" | gene | A | N | | 2.3 | 0.52 | I | 1.6 | 0.15 | NC | 0 0 | |
| W10377 | mb665a02.r1 Soares mouse p3NMF19.5 Mus musculus cD | est | B | N | * | 2.9 | 0.52 | I | 3 | 0.58 | NC | 0 | 0.2 |
| W65920 | "me09e10.r1 Soares mouse embryo NbMF13.5 14.5 Mus | est | A | N | | 1.9 | 0.52 | I | 1.4 | 0.14 | D | 1.4 | 0.6 |
| X67644 | M. musculus gly96 mRNA | gene | B | N | | 1.8 | 0.52 | NC | 0 | 0 | D | 1.7 | |
| Z46757 | M. musculus mRNA for high mobility group2 pr0tein | gene | B | N | MI | 2.6/0.51 | I | I | 1.78 | I | | 0.3 | 0.2 |
| W98592 | mg22g03.r1 Soares mouse embryo NbMF13.5 14.5 Mus r | est | B | N | MD | 2.4 | 0.51 | MD | ~4.0 | 3.8 | 1.66 | I | 1.6 |
| AA023287 | mh70h01.r1 Soares mouse placenta 4NbMF13.5 14.5 Mus | est | D | N | * | 3 | 0.51 | * | ~4.0 | 0.89 | NC | | |
| M36084 | "Mouse dytosolid malate dehydrogenase (cMDHase) gene, | gene | D | N | * | ~3.1 | 0.51 | I | 0.88 | NC | | | |
| U43900 | "Mouse mRNA signal transducing adaptor molecule STAM | gene | A | N | | 2.2 | 0.51 | I | 2.6 | 0.83 | NC | 0 | 0 |
| D67015 | "Mouse mRNA for scg, complete cds" | gene | C | N | | 3.1 | 0.51 | I | 3.7 | 0.77 | NC | 0 | 0 |
| W17644 | mb76b03.r1 Soares mouse p3NMF19.5 Mus musculus cD | est | D | N | | 2.4 | 0.51 | I | 2.5 | 0.62 | NC | 0 | 0 |
| X76653 | M. musculus mRNA for ARP-1 | gene | C | N | | 1.7 | 0.51 | I | 1.6 | 0.36 | NC | 0 | 0.2 |
| L42115 | Mus musculus insulin-activated amino acid transporter m | gene | C | N | | ~3.0 | 0.51 | I | ~2.5 | 0.34 | MD | 1.2 | 0 |
| X95351 | M. musculus mRNA for pMELK protein | gene | C | N | | 2.9 | I | 1.9 | 2 | 0.28 | 0.18 | NC | 0 |

TABLE 6-continued

ISGs and IRGs identified from mouse embryonic fibroblast incubated in the presence or absence of IFN-αBBDB in the presence or absence of encephalomyocarditis virus

| Accession | Description | Type | | | | | | | | | | |
|---|---|---|---|---|---|---|---|---|---|---|---|---|
| L75822 | "Mus musculus follistatin-like protein mRNA, complete | gene | B | N | | | 1.6 | 0.51 | | 1.3 | | | 0.2 |
| J03236 | "Mouse (M. musculus) jun-B mRNA, complete cds" | gene | D | N | * | | 3.1 | 0.5 | * | 7.7 | 2.85 | 1 | 2.4 | 0.8 |
| AA048650 | mj33b02.r1 Soares mouse embryo NbME13.5 14.5 Mus mu | est | B | N | I | | ~3.1 | 0.5 | I | ~3.8 | 0.79 | NC | 0 | 0 |
| U19891 | "Mus musculus putative CCAAT binding factor 1. (mCBF) | gene | C | N | I | * | 3 | 0.5 | I | 3.5 | 0.72 | NC | 0 | 0 |
| X13586 | "Murine mRNA for 2,3-bisphosphoglycerate mutase (BPGN | gene | B | N | I | * | ~3.0 | 0.5 | I | ~3.3 | 0.6 | NC | 0 | 0 |
| X55126 | M. musculus Zfp-29 gene for zinc finger protein | gene | B | N | D | | ~3.0 | 0.5 | D | ~3.0 | 0.5 | NC | 0 | 0 |
| W83187 | mf09b08.r1 Soares mouse p3NMF19.5 Mus musculus cDNA | est | B | N | I | | 2.6 | 0.5 | I | 2.3 | 0.38 | NC | 0 | 0 |
| D87903 | "Mouse mRNA for ARF6, complete cds" | gene | C | N | I | | 2 | 0.49 | I | 2.2 | 0.67 | NC | 0 | 0 |
| U18797 | "Mus musculus MHC class 1 antigen H-2M3 (H-2M3) mRN | gene | B | N | I | * | ~3.0 | 0.49 | I | ~3.2 | 0.56 | NC | 0 | 0 |
| AA036265 | "mi72g03.r1 Soares mouse embryo NbME13.5 14.5 Mus mu | est | B | N | MI | | 2.5 | 0.49 | I | 2.3 | 0.38 | NC | 0 | 0 |
| D12907 | "Mouse gene for 47-kDa heat shock protein(HSP47), exon | gene | D | N | I | | 1.6 | 0.49 | I | 1.4 | 0.28 | NC | 0 | 0 |
| J04953 | "Mouse gelsolin gene, complete cds" | gene | D | N | I | | 1.8 | 0.49 | NC | 0 | 0 | D | 1.3 | 0.2 |
| X01023 | Mouse normal c-myc gene and translocated homologue fr | gene | D | N | I | | 2.5 | 0.48 | I | 3.7 | 1.29 | I | 1.5 | 0.1 |
| X65627 | M. musculus mRNA TN for p68 RNA helicase | gene B | N | I | 2.2 | 2.2 | 0.48 | 1 | 1.28 | I | | 1.4 | | |
| X87817 | M. musculus mRNk for Ulip protein | gene | B | N | I | | I | 0.48 | I | 2.3 | 0.54 | NC | 0.2 | 0 |
| M65255 | "Mouse hydrophilic protein(KE2 wt) mRNA, complete cds | gene | D | N | I | 2.4 | 2.2 | I | 2.3 | 0.44 | NC | 0 | 0 |
| M19960 | "Mouse cAMP-dependent protein kinase alpha subunit gen | gene | A | N | I | | 0.48 | I | 3.2 | 1.7 | 0.18 | MC | 1.3 | 0.1 |
| W13586 | "ma93a02.r1 Soares mouse P3NMF19.5 Mus.musculus cDN | est | A | N | MD | | 3 | 0.48 | I | 2.3 | 0 | MI | * | 1.4 | 0 |
| U16216 | "Mus musculus uroporphyrinogen III synthase (UROS) mRN | gene | A | N | I | 2.9 | 0.48 | NC | 0 | 0 | NC | * | 0 |
| AA139469 | mr82e09.r1 Stratagene mouse heart(#937316) Mus musc | est | D | N | I | * | ~3.0 | 0.47 | I | ~3.9 | 0.86 | NC | * | 0 |
| AA118546 | mm09c06.r1 Beddington mouse embryonic region Mus mus | est | C | N | I | | 2 | 0.47 | I | 2.4 | 0.83 | NC | 0 | 0 |
| W44201 | mc74b05.r1 Soares mouse embryo NbME13.5 14.5 Mus m | est | A | N | I | | 2.6 | 0.47 | * | 3 | 0.7 | NC | 1.3 | 0 |
| AA068057 | mm26b03.r1 Stratagene mouse skin (#937313) Mus musc | est | C | N | I | | 2.3 | 0.47 | I | 2.6 | 0.64 | NC | 1.4 | 0 |
| AA167947 | "ns21d05.r1 Stratagene mouse skin (#937313) Mus musc | est | D | N | I | * | ~3.1 | 0.47 | * | ~3.4 | 0.61 | NC | 0 | 0 |
| W29669 | mc05f11.r1 Soares mouse p3NMF19.5 Mus musculus cDNA | est | D | N | I | * | 2.8 | 0.47 | I | 2.6 | 0.39 | NC | 0 | 0 |
| W14823 | mb35d10.r1 Soares mouse p3NMF19.5 Mus musculus cDNA | est | D | N | I | | 2.5 | 0.47 | * | 2.1 | 0.27 | NC | 0 | 0 |
| AA000813 | mg35h10.r1 Soares mouse embryo NbME13.5 14.5 Mus mu | est | B | N | I | | 2.1 | 0.47 | I | 1.6 | 0.14 | D | 1.4 | 0.1 |
| AA116282 | mq05f12.r1 Soares mouse 2NbMT Mus musculus cDNA clone 5 | est | C | N | MI | * | 2.7 | 0.47NC | * | 0 | 0 | * | 0 | |
| W62960 | "md86g09.r1 Soares mouse embryo NbME13.5 14.5 Mus r | est | A | N | MI | | 2.3 | 0.47 | NC | 0 | 0 | NC | 0 | 0 |
| M34815 | "Mouse monokine induced by gamma interferon (MIG) mR | gene | D | N | I | * | ~2.9 | 0.46 | I | ~6.1 | 2.03 | I | 2.1 | 0.5 |
| M32490 | "Mouse Cyr61 mRNA, complete cds" | gene | D | N | | | 2 | 0.46 | I | * | 3.1 | 1.74 | I | 1.60.4 |
| AA118739 | mp54b08.r1 Soares mouse 2NbMT Mus musculus cDNA clone 5 | est | D | N | | 1.8 | 2.4 | I | 2.9 | 0.82MI | | 1.2 | |
| U73200 | "Mus musculus p116Rip mRNA, complete cds" | gene C | N | I | * | 0.46 | 1 | 0.5NC | | 0 | 0 | | |
| X83601 | M. musculus PTX3 mRNA | gene | C | N | | * | 2.5 | 0.46 | I | 2.2 | 0.32 | NC | 0 | 0 |
| AA142800 | "mq64e01.r1 Soares 2NbMT Mus musculus cDNA clone 58 | est | C | N | I | | 2.1 | 0.46 | I | 1.8 | 0.28 | NC | 0 | 0 |
| D55720 | "Mouse mRNA for nuclear pore-targeting complex, comple | gene | A | N | I | | 2.1 | 0.46 | I | 1.7 | 0.22 | MI | 1.2 | 0.1 |
| U14103 | "Mus musculus RGL protein mRNA, complete cds" | gene | A | N | | | * | ~2.7 | 0.46 | NC | 0 | 0 | OMI | 1.8 | 0.2 |
| W82881 | "mf22b12.r1 Soares mouse embryo NbME13.5 14.5 Mus m | est | B | N | I | | 2.4 | 0.46 | I | 2.2 | 0.98 | D | 1.3 | 0.1 |
| D88793 | Mouse mRNA for cystein rich protein-1, complete cds | est | C | N | | | 1.7 | 0.45 | I | 2.9 | 0.72 | I | 1.20.1 | |
| W17549 | "mb74a01.r1 Soares mouse p3NMF19.5 Mus musculus c | est | B | N | I | * | 2.4 | 0.45 | I | 1.7 | 0.28 | NC | 0 | 0 |
| U29152 | "Mus musculus at dose reductase mRNA, complete cds" | gene | A | N | I | | 1.9 | 0.45 | * | | | D | ~6.0 | 3.2 |
| W15722 | mb53b04.r1 Soares mouse p3NMF19.5 Mus musculus cb | est | A | N | | | ~2.9 | 0.45 | NC | | | D | 0 | 0 |
| U48363 | "Mus musculus transcription at activator alpha-NAC (Naca) | gene | B | N | I | | 1.7 | 0.44 | I | 1.9 | 0.72 | NC | 0 | 0 |
| W77613 | me68d10.r1 Soares mouse embryo NbME13.5 14.5 Mus r | est | D | N | I | | 2.4 | 0.44 | I | 2.5 | 0.49 | NC | 0 | 0 |
| M29464 | "Mouse platelet-derived growth factor A chain (PDGFA) m | gene | A | N | I | | 2.4 | 0.44 | I | 2.5 | 0.48 | NC | 0 | 0 |
| AA087332 | mm95e11.r1 Stratagene mouse lung 937302 Mus muscull | est | C | N | I | | 2.6 | 0.44 | I | 2.5 | 0.42 | NC | 0 | 0 |
| W33440 | mc15d01.r1 Soares mouse p3NMF19.5 Mus musculus cbN | est | C | N | I | | 1.9 | 0.44 | I | 1.6 | 0.23 | NC | 0 | 0 |
| W33721 | mc54h12.r1 Soares mouse embryo NbME13.5 14.5 Mus m | est | D | N | I | | 1.5 | 0.44 | I | 1.3 | 0.16 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | |
|---|---|---|---|---|---|---|---|---|---|---|---|---|
| L31398 | "Mus musculus dynamin (UDnm) mRNA, complete cds" | gene | A | N | * | 2.2 | 0.44 | NC | * | 0 | 0 | 0 |
| U27462 | "Mus musculus BS4 peptide RNA, complete cds" | gene | A | N | I | ~2.9 | 0.44 | NC | * | 0 | 1.9 | 0.2 |
| U28789 | "Mus musculus p53-associated cellular protein PACT mRN" | gene | C | N | I | 2.9 | 0.44 | NC | * | 0 | 0 | 0 |
| U43085 | "Mus musculus glucocorticoid-attenuated response" | gene | gene | C | Z | * | ~2.6 | 0.43 | I | * | ~12.4 | 5.75 | I | 0 | 4.72.7 |
| AA039109 | "mi99d11.r1 Soares mouse embryo NbME13.5 14.5 Mus m" | est | D | N | * | 2.1 | 0.43 | I | 2.9 | 1.1 | I | 1.4 | 0.2 |
| U22015 | "Mus musculus retinoid X receptor interacting protein (RIF" | gene | A | N | * | ~2.7 | 0.43 | I | *~3.3 | 0.68 | NC | 0 | 0 |
| AA039104 | "mi99c09.r1 Soares mouse embryo NbME13.5 14.5 Mus mI" | est | B | N | * | ~3.0 | 0.43 | I | *~3.2 | 0.54 | NC | 0 | 0 |
| AA119078 | "mp65d05.r1 Soares 2NbMT Mus musculus cDNA clone 5" | est | B | N | * | 2.5 | 0.43 | NC | 2.4 | 0.42 | NC | 0 | 0 |
| U20636 | "Mus musculus cyclin F mRNA, alternatively spliced form," | gene | A | N | * | ~2.8 | 0.43 | NC | * 0 | 0 | MI | 3.1 | 0.7 |
| W33415 | "mc52c10.r1 Soares mouse embryo NbME13.5 14.5 Mus m" | est | D | N | * | 2.7 | 0.43 | I | 0 | 0 | D | 1.6 | 0.2 |
| AA161979 | "ms25g12.r1 Stratagene mouse skin (#937313) Mus muscu" | est | C | N | * | ~2.7 | 0.42 | I | *~5.3 | 1.63 | NC | 0 | 0 |
| U42386 | "Mus musculus fibroblast growth factor inducible gene 14" | gene | C | N | I | 2.9 | 0.421 | 4.8 ..1.3 ..1.70.2 | I | | | | |
| D00925 | Mouse mRNA for transcription factor S-II-related protein | gene | D | N | * | ~2.9 | 0.42 | I | *~3.9 | 0.84 | NC | 0 | 0 |
| AA162093 | mn45d08.r1 Beddington mouse embryonic region Mus mu | est | C | N | * | 2.9 | 0.42 | I | * 3.6 | 0.72 | NC | 0 | 0 |
| U21960 | "Mus musculus calcium modulating cyclophilin ligand (CA" | gene | B | N | * | 2.5 | 0.42 | I | * 3 | 0.67 | NC | 1.9 | 0.4 |
| Z31554 | M. musculus (129/Sv) Cctd mRNA for CCT (chaperonin co | gene | B | N | * | 1.8 | 0.42 | I | 2 | 0.58 | NC | 0 | 0 |
| L31958 | "Mus musculus (clone pMAT1) mRNA, complete cds" | gene | A | N | I | 0.42 | I | 2 | 0.38 | NC | NC | 0 | 0 |
| D38077 | "Mouse gene for APEX nuclease, complete cds" | gene | B | N | 2 | 2.1 | 0.42 | I | 2 | 0.36 | NC | 0 | |
| X12507 | Mouse eIF-4AII mRNA for protein synthesis initiation facto | gene | B | N | * | 2.2 | 0.42 | I | 1.80.25 | NC | NC | 0 | |
| AA108822 | mp39h01.r1 Barstead MPLRB1 Mus musculus cDNA clone 5 | est | A | N | * | ~2.8 | 0.42 | NC | 1.1 | 0.01 | D | 1.9 | 0.4 |
| AA107471 | m196g10.r1 Stratagene mouse kidney (#937315) Mus musc | est | D | N | * | 2.4 | 0.42 | NC | * 0 | 0 | NC | 0 | 0 |
| X52102 | M. musculus p16K gene for 16 kDa protein | gene | B | N | | 0.42 | I | 0 | 0 | NC | 0 | 0 | |
| D78641 | "Mouse mRNA for membrane glycoprotein, complete cds"gene | C | Z | I | 0.42 | NC | 0 | NC | NC | 0 | 0 | | |
| M16465 | "Mouse calpactin I light chain (p11) mRNA, complete cds" | gene | D | N | 2.3 | 1.6 | 0.42 | NC | 0 | NC | 0 | 0 | 0 |
| M63725 | "Mouse binding protein for T-cell receptor (TCR-ATF1) mF" | gene | A | N | MD | ~2.9 | 0.41 | I | *~3.1 | 0.48 | NC | 0 | 0 |
| U43512 | "Mus musculus dystroglycan (Dag1) mRNA, partial cds" | gene | C | N | * | 2.1 | 0.41 | I | 1.6 | 0.13 | NC | 0 | 0 |
| M34476 | "Mouse retinoic acid receptor gamma (mRAR-gamma-A) n | gene | A | N | * | ~2.9 | 0.42 | I | 0 | 0 | NC | 0 | 01.1 0 |
| AA051486 | mg55d01.r1 Soares mouse embryo NbME 13.5 14.5 Mus mu | est | B | N | * | 1.9 | 0.4 | I | 2.6 | 1.09 | I | 1.4 | 0.2 |
| L16846 | "Mouse BTG1 mRNA, complete cds" | gene | D | N | | 2.6 | 0.4 | I | 3.1 | 0.67 | NC | 0 | 0 |
| AA089187 | mi85h02.r1 Stratagene mouse kidney (#937315) Mus mu | est | A | N | * | 2.4 | 0.4 | I | 2.5 | 0.46 | NC | 0 | 0 |
| W70629 | me19e04.r1 Soares mouse embryo NbME13.5 14.5 Mus mu | est | A | N | * | ~2.8 | 0.4 | I | *~3.0 | 0.46 | NC | 0 | 0 |
| U29396 | "Mus musculus annexin V (Anx5) mRNA, complete cds" | gene | A | N | * | 1.7 | 0.4 | I | 1.6 | 0.31 | NC | 1.4 | 0.1 |
| AA117064 | mn29e08.r1 Beddington mouse embryonic region Mus mus | est | C | N | | 2.7 | 0.4 | I | 2 | 0.16 | D | 1.4 | 0.1 |
| L08757 | "mi09f07.r1 Soares mouse macrophage p3NMF19.5 Mus musculus cDNA | est | B | N | * | 2.3 | 0.4 | I | 1.7 | 0.14 | D | 0 | 0 |
| M25244 | "Mouse pre-B cell P2B/LAMP-1 mRNA,complete cds" | gene | A | N | | 1.6 | 0.4 | I | 1.3 | 0.13 | NC | 1.2 | 0.3 |
| L18880 | "Mouse vinculin mRNA, complete cds" | gene | A | N | * | ~2.8 | 0.4 | MI | *~1.8 | 0.12 | D | 1.6 | 0.4 |
| X53824 | Mouse X16 mRNA | gene | B N | 2.2 | NC | NC | 0 | ONC | 0 | D | 0 | 1.5 | 0.1 |
| M87539 | "Mouse cellular retinoic acid binding protein type II (CRAB" | gene | D | N | I | ~2.6 | 0.4 | NC | 0 | 0 | D | ~7.1 | 2.8 |
| M23384 | "Mouse glucose transporter 1 mRNA, complete cds" | gene D | N | 1.9 | 0.4 | NC | 0 | D | 1.7 | 0.5 | | | |
| M57999 | "Mouse transcription factor NF-kappa-B DNA binding subu" | gene | A | N | * | 2.7 | 0.39 | I | 3.1 | 0.57 | NC | 0 | 0 |
| AA072252 | "mm69d07.r1 Stratagene mouse macrophage (#937306) M" | est | C | N | * | 2.5 | 0.39 | I | 2 | 0.19 | NC | 0 | 0 |
| AA027667 | "mi09f07.r1 Soares mouse macrophage p3NMF19.5 Mus musculus cDNA | est | B | N | * | 2.9 | 0.39 | NC | 0 | 0 | NC | 0 | 0 |
| U08020 | "Mus musculus FVB/N collagen pro-alpha-1 type 1 chain m | gene | A | N | | 1.4 | 0.39 | NC | 0 | 0 | D | 1.2 | 0.3 |
| M84324 | "Mus musculus type IV collagenase mRNA, complete cds" | gene | D | N | | 1.9 | 0.39 | MI | 1.3 | 0 | D | 1.6 | 0.4 |
| U70210 | "Mus musculus TR2L mRNA, complete cds" | gene | C | N | * | 2.5 | 0.38 | I | 2.7 | 0.47 | D | 0 | 0 |
| U08110 | Mus musculus RNA1 homolog (Fug1) mRNA, complete cd | gene | B | N | * | 2.2 | 0.38 | I | *~2.3 | 0.42 | NC | 0 | 0 |
| AA144601 | mr68g02.r1 Stratagene mouse testis (#937308) Mus muscu | est | D | N | | 2.5 | 0.38 | I | *~2.6 | 0.4 | NC | 0 | 0 |

TABLE 6-continued

ISGs and IRGs identified from mouse embryonic fibroblast incubated in the presence or absence of IFN-αBBDB in the presence or absence of encephalomyocarditis virus

| Accession | Description | Type | | | | | | | | | | |
|---|---|---|---|---|---|---|---|---|---|---|---|---|
| AA050551 | mj20e07.r1 Soares mouse embryo NbME13.5 14.5 Mus mu | est | D | N | I | * | ~2.7 | 0.38 | I | ~2.6 | 0.34 | NC | 0 | 0 |
| AA020620 | mh63a06.r1 Soares mouse placenta 4NbMR13.5 14.5 Mus m | est | B | N | I | * | ~2.8 | 0.38 | I | ~2.5 | 0.28 | NC | 0 | 0 |
| AA155371 | mn43f12.r1 Beddington mouse embryonic region Mus mu | est | A | N | I | * | 2.5 | 0.38 | I | 1.6 | 0.08 | D | 1.5 | 0.1 |
| Z72000 | M. musculus BTG3 mRNA | gene | B | N | I | | 1.9 | 0.37 | I | 2.7 | 1.05 | I | 1.4 | 0.2 |
| X52875 | Mouse homeobox gene S8 mRNA | gene | D | N | MI | | 2.2 | 0.37 | * | 2.8 | 0.76 | MI | 1.3 | 0.1 |
| AA145181 | "ms04d10.r1 Stratagene mouse skin (#937313) Mus musc | est | D | N | I | * | 2.6 | 0.37 | * | 3.3 | 0.68 | NC | 0 | 0 |
| W85250 | mf49e09.r1 Soares mouse embryo NbME13.5 14.5 Mus mu | est | D | N | I | * | ~2.8 | 0.37 | * | ~3.3 | 0.55 | NC | 0 | 0 |
| X51829 | Mouse myeloid differentiation primary response mRNA en | gene | B | N I | * | 2.5 | 0.37 | I | 0.44 | NC | 0 | | | |
| D28492 | Mouse mRNA for Nedd2 protein, complete cds" | gene | A | N | I | | 2.6 | 0.37 | 2.7 | 2.6 | 0.37 | NC | 0 | |
| AA008737 | mg98e04.r1 Soares mouse embryo NbME13.5 14.5 Mus r | est | B | N | I* | ~2.7 | 0.37 | * | ~2.2 | 0.21 | D | 0 | |
| W82026 | me96a05.r1 Soares mouse embryo NbME13.5 14.5 Mus mu | est | A | N | I | | 1.9 | 0.37 | I | 1.5 | 0.16 | D | 1.2 | 0.1 |
| W97055 | "mg07h12.r1 Soares mouse embryo NbME13.5 14.5 Mus | est | A | N | I | | 2 | 0.37 | MI | 0 | 0 | D | 2.5 | 0.9 |
| UD6119 | "Mus musculus cathepsin H prepropeptide (ctsH) mRNA, | gene | A | N | MI | | 2.6 | 0.37 | NC | 0 | 0 | NC | 0 | 0 |
| X69657 | M. musculus (clone W13) WRS mRNA for tryptophan–tRN/ | gene | B | N | I | * | 2.2 | 0.37 | 0 | D | 1.6 | 0.2 | | |
| AA163305 | mr92g12.r1 Stratagene mouse embryonic carcinoma (#937 | est | B | N | I | * | 2.6 | 0.36 | I | 3.7 | 0.9 | NC | 0 | 0 |
| XD1756 | Mouse cytochrome c gene (MC1) | gene | B | N | I | | 2 | 0.36 | I | 2.6 | 0.88 | I | 1.3 | 0.1 |
| AA051500 | mL53d10.r1 Soares mouse embryo NbME13.5 14.5 Mus m | est | C | N | I | | 1.8 | 0.36 | I | 2 | 0.56 | NC | 0 | 0 |
| U55861 | "Mus musculus RNA binding protein TIAR mRNA, complet | gene | B | N | I | | 2.2 | 0.36 | MI | 2.3 | 0.42 | NC | 0 | 0 |
| U66620 | "Mus musculus SWI/SNF complex 60 kDa subunit (BAF60 | gene | A | N | I | * | ~2.7 | 0.36 | I | ~2.6 | 0.3 | NC | 0 | 0 |
| W13502 | ma85a03.r1 Soares mouse p3NMF19.5 Mus musculus cDN | est | D | N | I | | 1.5 | 0.36 | I | 1.4 | 0.24 | NC | 0 | 0 |
| X64837 | M. musculus Oat mRNA for ornithine aminotransferase | gene | B | N | I | | 1.9 | 0.36 | D | 1.7 | 0.22 | D | 1.1 | 0 |
| D16141 | "Mouse mgl-1 mRNA for CRF, complete cds" | gene B | N | I | 2 | 0.36 | I | 0.36 | 1.6 | 0.14 NC | 0 | | | |
| M57891 | "Mouse complement component C2 mRNA, complete cds" | gene | B | N | I | | ~2.4 | 0.36 | I | ~1.6 | 0.1 | NC | 0 | 0 |
| M12600 | "Mouse androgen regulated gene RP2, complete cds, with | gene | A | N | I | * | 2.6 | 0.36 | NC | 0 | 0 | NC | 0 | 0 |
| M34141 | "Mouse prostaglandin endoperoxide (PGG/H) mRNA, comp | gene | C | N | I | | 2.2 | 0.35 | I | 2.8 | 0.73 | NC | 0 | 0 |
| U10119 | "Mus musculus SKD1 protein mRNA, complete cds" | gene | A | N | I | * | ~2.6 | 0.35 | * | ~2.9 | 0.45 | NC | 0 | 0 |
| D50367 | "House mouse; Musculus domesticus mRNA for KAP3B, c | gene | C | N | I | | ~2.7 | 0.35 | I | ~3.0 | 0.44 | NC | 0 | 0 |
| AA061989 | mj83a01.r1 Soares mouse p3NMF19.5 Mus musculus cDN | est | D | N | MD | | 2.7 | 0.35 | D | ~2.9 | 0.4 | NC | 0 | 0 |
| W30116 | "mc26h02.r1 Soares mouse p3NMF19.5 Mus musculus cDN | est | B | N | I | | 2.1 | 0.35 | I | 2.2 | 0.39 | NC | 0 | 0 |
| U43076 | "Mus musculus cdc37 homolog mRNA, complete cds" | gene | D | N | I | | 1.6 | 0.35I | | 1.6 | NC | 0 | | |
| W11011 | ma47a11.r1 Soares mouse p3NMF19.5 Mus musculus ,cD | est | C | N | I | * | 2.1 | 0.35 | MI | * | 2.1 | 0.34 | NC | 0 | 0 |
| M12379 | Mouse Thy-1.2 glycoprotein gene, complete cds | gene | A | N | I | | 1.6 | 0.35 | I | * | 1.6 | 0.33 | NC | 0 | 0 |
| L37092 | "Mus musculus cyclin-dependent kinase homologue (p130 | gene | A | N | I | * | 2.4 | 0.35 | I | * | 2.2 | 0.28 | NC | 0 | 0 |
| X7D887 | M. musculus mRNA for p59 immunophilin | gene A | gene | N | 1 | 1.7 | 0.35 | 1.7 | 0.35 | MI | 1.3 | 1.4 | 0.11 | 1.30.1 |
| W08392 | "mb43c10.r1 Stratagene mouse p3NMF19.5 Mus musculus | est | C | N | I | | 1.7 | 0.35 | I | 1.3 | 0.1 | D | 1.3 | 0.1 |
| AAD31158 | mi47e11.r1 Soares mouse embryd NbME13.5 14.5 Mus m | est | B | N | I | * | 1.6 | 0.34I | 2 | 0.82 | I | 1.2 | 0.1 | |
| D13695 | "Mouse mRNA for ST2L protein, complete cds" | gene | D | N | I | | ~2.60.34 | | ~3.40.67 | I | 1.3 | 0.1 | | |
| AA166088 | ms24c05.r1 Stratagene mouse 3NbMS Mus musculus cDNA clo | est | D | N | I | | 2.5 | 0.34 | I | 3.1 | 0.58 | NC | 0 | 0 |
| AA168959 | "mr31d03.r1 Soares mouse 3NbMS Mus musculus cDNA clo | est | C | N | I | | 2.6 | 0.34 | I | 3.2 | 0.56 | NC | 0 | 0 |
| Z67745 | "M. musculus mRNA for phosphatase 2A catalytic subunit, | gene | B | N | I | | 1.9 | 0.34 | I | 2.2 | 0.54 | NC | 0 | 0 |
| L33726 | "Mouse fascin mRNA, complete cds" | gene | A | N | I | | 1.8 | 0.34 | I | 1.9 | 0.43 | NC | 0 | 0 |
| M96163 | "Mus musculus (clone 2) serum inducible kinase (SNK) mF | gene | A | N | I | | 2 | 0.34 | MI | 2 | 0.29 | NC | 0 | 0 |
| AA050852 | mj20d12.r1 Soares mouse embryo NbME13.5 14.5 Mus m | est | D | N | I | | 1.7 | 0.34 | I | 1.6 | 0.23 | NC | 0.1 | 0 |
| M33760 | "Mouse FGF receptor mRNA, complete cds" | est | D | N | I | | 2 | 0.34 | I | 1.8 | 0.23 | NC | 0 | 0 |
| X07997 | Mouse mRNA for cytotoxic T-cell membrane glycoprotein | gene | A | N | I | | 2 | 0.34 | I | 1.5 | 0.1 | D | 1.3 | 0.1 | 0.1 |
| J04036 | M. musculus (clone p70ZN8) band 3-related protein mF | gene | A | N | I | * | 2 | 0.34 | NC | 0 | 0 | NC | 2 | 0 |
| X67083 | M. musculus chop-10 mRNA | gene | B | N | I | | 1.8 | 0.34 | NC | 0 | 0 | D | 0.6 | 0 |

TABLE 6-continued

ISGs and IRGs identified from mouse embryonic fibroblast incubated in the presence or absence of IFN-αBBDB in the presence or absence of encephalomyocarditis virus

| Accession | Description | Type | C1 | C2 | C3 | C4 | C5 | C6 | C7 | C8 | C9 | C10 | C11 |
|---|---|---|---|---|---|---|---|---|---|---|---|---|---|
| AA153519 | ms61g12.r1 Stratagene mouse embryonic carcinoma (#93 | est | A | N | I | 2.4 | 0.33 | I | 4.1 | 1.26 | NC | 0 | 0 |
| X79003 | M. musculus mRNA for integrin alpha 5 subunit | gene | B | N | I | 1.9 | 0.33 | I | 2.3 | 0.62 | NC | 0 | 0 |
| M76727 | M.musculus mRNA for cyclin A | gene | A | N | I | 2.1 | 0.33 | I | 2.2 | 0.43 | NC | 0 | 0 |
| Z26580 | M.musculus mRNA for cyclin A | gene | B | N | MI | 2.3 | 0.33 | I | 2.3 | 0.35 | NC | 0 | 0 |
| X84692 | M. musculus 5pnr mRNA for RNA binding protein | gene | C | N | D | −2.6 | 0.33 | D | −2.6 | 0.33 | NC | * | 0 |
| Z37164 | "M. musculus Cctq mRNA encoding cytosolic chaperone c | gene | B | N | I | 1.8 | 0.33 | I | 1.8 | 0.32 | NC | 0 | 0 |
| M84607 | "Mus musculus PDGF-alpha-receptor (PDGF-alpha-R) mRN | gene | D | N | I | 2.4 | 0.33 | I | 2.3 | 0.32 | NC | 0 | 0 |
| U76832 | "Mus musculus plasma membrane protein syntaxin-4 mRN | gene | C | N | I | 2.1 | 0.33 | I | 1.9 | 0.26 | NC | 0 | 0 |
| D10475 | Mouse mRNA for epimorphin | gene | A | N | I | 2.1 | 0.33 | I | 1.8 | 0.23 | NC | 0 | 0 |
| M18194 | Mouse fibronectin (FN) mRNA | gene | D | N | I | 1.5 | 0.33I | * | 0.1 | 0.2 | NC | 0 | 0 |
| W41501 | mc43d41.r1 Soares mousse p3NMF19.5 Mus musculus cD | est | A | N | I | 1.9 | 0.33 | NC | 0 | 0 | D | 1.3 | 0.1 |
| D29016 | Mouse mRNA for squalene synthase | gene | A | N | I | 1.7 | 0.33 | NC | 0 | 0 | D | 2.2 | 1.1 |
| W13425 | mb33h06.r1 Soares mouse p3NMF19.5 Mus musculus cDNA | est | B | N | I | 1.9 | 0.33 | NC | 0 | 0 | D | 1.7 | 0.4 |
| X96639 | M. musculus mRNA for protein responsible for hereditary n | gene | B N | I | 1.9 | 0.32 | I | 2.6 | 0.93 | I | 1.4 | 0.2 | |
| U49112 | "Mus musculus calcium-binding protein ALG-2 (ALG-257) gene | B | N | I | 2 | 0.32 | I | 2.1 | 0.42 | NC | 0 | * | 0 |
| Z46663 | M. musculus DNA for growth hormone gene and promoter | gene | D | N | I | 2.3 | 0.32 | MI | * | 2.5 | 0.38 | MC | 0 | * |
| D76446 | "Mouse mRNA for TAK1 (TGF-beta-activated kinase), corr | gene | C | N | I | −2.5 | 0.32 | I | * | −2.4 | 0.29 | NC | 0 | 0 |
| W11954 | "ma79e11.r1 Soares mouse p3NMF19.5 Mus musculus cDN | est | D | N | I | 2 | 0.32 | I | * | 2 | 0.17 | NC | 0 | 0 |
| AA154451 | mq47f04.r1 Soares mouse 2NbMT Mus musculus cDNA clone 58 | est | B | N | I | 2.4 | 0.32 | I | * | 1.9 | 0.16 | NC | 0 | 0.2 |
| W63876 | md64b01.r1 Soares mouse embryo NbME13.5 14.5 Mus m | est | A | N | I | 2.2 | 0.32 | NC | 0 | 0 | MC | 1.7 | 0 |
| U22394 | "Mus musculus mSin3A (sin3A) mRNA, complete cds" | gene | A | N | I | 2.5 | 0.32 | I | * | 0 | 0 | NC | 0 | 0 |
| AA003458 | "mg58h04.r1 Soares mouse embryo NbME13.5 14.5 Mus mu | est | B | N | I | 2 | 0.32 | NC | 0 | 0 | NC | 0 | 0 |
| U51112 | "Mus musculus Na+/H+ exchanger (NHE-1) mRNA, compl | gene | C | N | I | 2.2 | 0.32 | NC | 0 | 0 | NC | 0 | 0 |
| U38196 | "Mus musculus palmytoylated protein p55 mRNA, comple | gene | B | N | I | 2.3 | 0.32 | NC | 0 | 0 | NC | 0 | 0 |
| W20990 | mb89f11.r1 Soares mouse p3NMF19.5 Mus musculus cD | est | D | N | I | 2.2 | 0.32 | NC | 0 | 0 | NC | 0 | 0 |
| W41899 | mc64g01.r1 Soares mouse embryo NbME13.5 14.5 Mus mu | est | D | N | D | 1.8 | 0.32 | NC | 0 | 0 | NC | 0 | 0.4 |
| X72910 | M. musculus Cd24a gene | gene | D | N | I | 2.2 | 0.31 | I | 3.8 | 1.35 | I | 1.7 | 0 |
| U13262 | "Mus musculus myelin gene expression factor (MEF-2) mF | gene | A | N | I | −2.4 | 0.31 | I | −3.2 | 0.59 | NC | 0 | 0 |
| AA152884 | mr14e04.r1 Soares mouse 3NbMS Mus musculus cDNA cl | est | D | N | I | 2.3 | 0.31 | I | 2.7 | 0.51 | I | 1.2 | 0 |
| D14636 | "Mouse mRNA for PEBP2a1 protein, complete cds" | gene | B | N | I | −2.5 | 0.31 | I | * | −3.0 | 0.5 | NC | 0 | 0 |
| U52945 | "Mus musculus tumor susceptibility protein TSG101 (tsg1 | gene | C | N | I | 1.9 | 0.31 | NC | 0 | 0 | NC | 0 | 0 |
| X14926 | Mouse mRNA for calreticulin | gene | D | N | I | 1.9 | 0.31 | I | 1.9 | 0.43 | NC | 0 | 0 |
| AA067362 | mm39b05.r1 Stratagene mouse melanoma (#937312) MU | est | A | Y | MI | 1.9 | 0.31 | I | * | 1.9 | 0.37 | NC | 0 | 0 |
| D88315 | "Mouse mRNA for tetracycline transporter-like protein, co | gene | C | N | I | 2.2 | 0.31 | I | * | 2.2 | 0.34 | NC | 0 | 0 |
| L07037 | "Mus musculus (clone E31.1 in pGEM7ZI(+)) N-acetylgluc | gene | D | N | I | 2.5 | 0.31 | I | * | 2.4 | 0.25 | NC | 0 | 0 |
| M62766 | "Mouse HMG-CoA reductase mRNA1 3' end" | | gene D | N | I | 2.1 | 0.31 | I | 1.7 | 0.14 | NC | 0 | 0 |
| X13135 | Murine mRNA fragment for fatty acid synthase (EC 2.3.1 | gene | B | N | Z | * | 2.4 | 0.31 | I | * | 1.5 | I | 1.7 | 0 |
| U03378 | "Mus musculus acute phase response factor (APRF) mRN | gene | D | N | I | 1.8 | 0.31 | NC | 0 | 0 | 0.06 | NC | 0 | 0 |
| J03928 | "Mouse CD1 phosphofructokinase (PFK) mRNA, complete | gene | C | N | I | 1.8 | 0.31 | NC | 0 | 0 | D | * | 1.9 | 0.5 |
| W84260 | mf45b08.r1 Soares mouse embryo NbME13.5 14.5 Mus m | est | A | N | MI | 1.6 | 0.31 | NC | 0 | 0 | D | 0 | 0 |
| W51433 | Mouse mRNA for ASF | est | A | Y | I | −2.5 | 0.3 | I | * | −3.9 | 0.87 | NC | 0 | 1.1 |
| X66091 | M. musculus ASF mRNA | gene | B | N | I | 2.3 | 0.3 | I | * | 3.4 | 0.85 | NC | 0 | 0 |
| L36611 | "Mus musculus protein synthesis initiation factor 4A (elf-4 | gene | B | N | I | −2.5 | 0.3 | I | 3.8 | 0.81 | NC | 0 | 0 |
| AA032948 | m124a02.r1 Soares mouse embryo NbME13.5 14.5 Mus m | est | B | N | I | 1.5 | 0.3 | I | 1.8 | 0.62 | NC | 0 | 0 |
| U69270 | Mus musculus nuclear LiM interactor (NLI) mRNA, compl | (gene | C | N | I | 2 | 0.3 | I | 2.6 | 0.62 | NC | 0 | 0 |
| AA097292 | "mk16h08.r1 Soares mouse p3NMF19.5 Mus musculus c | est | A | N | MI | 2.1 | 0.3 | I | 2.6 | 0.59 | NC | 0 | 0 |
| AA111494 | mo51c06.r1 Life Tech mouse embryo 10 5dpc 10665016 M | est | C | N | D | 1.5 | 0.3 | D | 1.7 | 0.46 | NC | 0 | 0 |
| AA030635 | "mi11hp9.r1 Soares mouse p3NMF19.5 Mus musculus cDN | est | B | N | I | −2.5 | 0.3 | I | * | 2.5 | 0.31 | NC | 0 | 0 |
| | | | | | D | −2.3 | 0.3 | D | −2.3 | 0.26 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | |
|---|---|---|---|---|---|---|---|---|---|---|---|---|
| U16741 | "Mus musculus capping protein alpha 2 subunit mRNA, c | gene | A | N | I | | 2.1 | 0.3 | | | 0 | 0 |
| U25844 | "Mus musculus serine proteinase inhibitor (SPI1) mRNA, c | gene | A | N | I | | 1.7 | 0.3 | I | | 0 | 0 |
| W35058 | mc35g06.r1 Soares mouse p3NMF19.5 Mus musculus cD | est | B | N | I | | 1.7 | 0.3 | NC | 1.8 | 0.5 | |
| X99572 | M. musculus mRNA for new member of PDGF/VEGT family | gene | C | N | I | | 2.1 | 0.3 | NC | 0 | 1.3 | 0.4 |
| Y00309 | Mouse LDH-A gene for lactate dehydrogenase-A | gene | C | N | I | 0 | 1.3 | 0.3 NC | | | | |
| AA008095 | my71h12.r1 Soares mouse embryo bME13.5 14.5 Mus | est | D | N | I | | ~2.6 | 0.3 | NC | D | 0 | 0.4 |
| J04115 | "Mouse c-jun protein oncogene mRNA, complete cds" | gene | D | N | I | * | ~2.3 | 0.29 | I | NC | 2.6 | 0.8 |
| U19854 | "Mus musculus ubiquitinating enzyme E2-20K mRNA ,com | gene | B | N | I | * | ~2.3 | 0.29 | I | 2.04 | 0 | 0 |
| X66976 | "M. musculus col8a1 gene, exon 1 (and joined CDS)" | gene | C | N | I | * | 2.5 | 0.29 | I | 1.07 | 0 | 0 |
| D64160 | "Mouse clone Rae-107 mRNA for cell surface protein, com | gene | B | N | I | | 2.5 | 0.29 | I | 0.55 | 0 | 0 |
| M59378 | "Murine tumor necrosis factor 1 receptor (TNFR-1) mRNA, | gene | D | N | I | | 2.4 | 0.29 | I 2.40.28 | NC | | |
| D84096 | "Mouse mRNA for ubiquitin carboxyl-terminal hydrolase ( | gene | B | N | I | * | 2.2 | 0.29 | I 2.1 | 0.2 | 0 | 0 |
| AA003990 | mg89c04.r1 Soares mouse embryo NbMF13.5 14.5 Mus r | est | A | N | I | | 2.1 | 0.29 | I 1.9 | 0.18 | 0 | 0 |
| AA170444 | ms90i10.r1 Soares mouse 3NbMS Mus musculus cDNA clone | est | D | N | I | | 2.1 | 0.29 | I 1.7 | 0.15 | 0 | 0 |
| U03715 | "Mus musculus alpha-1 (XVIII) collagen (COL18A1) gene, | gene | B | N | I | * | 2.1 | 0.29 | I 1.5 | 0.09 | 0 | 0 |
| X17502 | Mouse mRNA overexpressed and amplified in teratocarcino | gene | B | N | I | * | 1.6 | 0.29 | MI 1.5 | 0.08 | 0 | 0 |
| W54584 | md01d12.r1 Soares mouse embryo NbMF13.5 14.5 Mus r | est | A | N | I | * | 2.1 | 0.29 | MI 1.2 | 0.06 | 1.3 | 0.1 |
| L31783 | "Mus musculus uridine kinase mRNA, partial cds" | est | D | N | I | | ~2.6 | 0.29 | NC | D | 0 | |
| W65178 | md78h05.r1 Soares mouse embryo NbMF13.5 14.5 Mus m | est | B | N | I | * | 2.1 | 0.29 | I | 0 | D | 1.5 0 |
| X24674 | "Mus musculus Max interacting protein 1 alternatively spli | gene | A | N | I | * | 2.5 | 0.28 | I | 0 | NC | 0 0.1 |
| X62701 | M. musculus muPAR2 mRNA | gene | A | N | I | * | 2.1 | 0.28 | I 3 | 4.9 | D | 0 |
| W82115 | me98e09.r1 Soares mouse p3NMF19.5 Mus musculus cDN | est | A | N | I | * | 2.1 | 0.28 | I * | 0.75 | MC 1.2 | 2.30.7 |
| AA105763 | m184e01.r1 Soares mouse kidney (#937315) Mus musc | est | D | N | I | * | ~2.5 | 0.28 | I ~3.5 | 0.64 | NC | 0 |
| W53188 | md19a08.r1 Soares mouse embryo NbME13.5 14.5 Mus m | est | D | N | I | | 2 | 0.28 | I 2.4 | 0.53 | NC | 0 |
| X70298 | M. musculus sox-4 mRNA | gene | A | N | MI | | 2.1 | 0.28 | I 2.5 | 0.49 | NC | 0 |
| U74359 | "Mus musculus mothers-against-dpp-related-1 mRNA, cor | gene | C | N | I | * | ~2.4 | 0.28 | I ~2.9 | 0.43 | NC | |
| X61576 | M. musculus mRNA for connexin 43 | gene | D | N | I | | ~2.5 | 0.28 | I ~2.7 | 0.34 | NC | 0 |
| W85566 | "mf49e05.r1 Soares mouse embryo NbME13.5 14.5 Mus m | est | A | D | D | * | ~2.3 | 0.28 | D ~2.3 | 0.29 | NC | 0 |
| AA060704 | j63b03.r1 Soares mouse p3NMF19.5 Mus musculus cDN | est | B | N | D | | 1.7 | 0.28 | D 1.7 | 0.29 | NC | 0 |
| X61506 | Mouse E46 mRNA for E46 protein | | gene | C | Z | I | I | 1.7 | 0.28 | 1.7 | 0.29 NC | 1.3 oI |
| W18308 | "mb6h11.r1 Soares mouse p3NMF19.5 Mus musculus c | est | D | N | I | | 1.4 | 0.28 | I 1.4 | 0.25 | NC | 0 0 |
| U77040 | "Mus musculus LIM protein 3 (mSLIM3) mRNA, complete | est | C | N | I | * | 1.8 | 0.28 | I 1.6 | 0.2 | NC | 0 0 |
| L19932 | "Mouse (beta ig-h3) mRNA, complete cds" | gene | C | N | I | * | 2 | 0.28 | I 1.8 | 0.2 | NC | 0 0 |
| L10106 | "Mus-musculus protein tyrosine phosphate mRNA, comple | gene | D | N | I | | ~2.5 | 0.28 | * | 2.0 | 0.16 NC | 0 0 |
| W15789 | mb51a07.r1 Soares mouse p3NMF1.9.5 Mus musculus cD | est | D | N | I | | 1.8 | 0.28 | I 1.6 | 0.16 | NC | 0 0 |
| X14805 | Mouse mRNA encoding DNA (cytosine-5)-methyltransfera | gene | C | N | I | | 2.2 | 0.28 | I 1.8 | 0.15 | NC | 0 0 |
| M13444 | "Mouse alpha-tubulin isotype M-alpha-4 mRNA, complete | gene | A | N | I | | 2 | 0.28 | I 0.13 | | | |
| Z14986 | M. musculus mRNA encoding adenosylmethionine decarbox | gene | A | N | I | | 2.3 | 0.28NC | 1.6 | 0 | 0 | 1.3 oI |
| D16262 | "Mouse mRNA encoding unknown protein, complete cds" | gene | A | N | I | | 2.1 | 0.28 | NC | 0 | 0 D | 0 |
| U02887 | "Mus musculus DNA repair protein (XRCC1) mRNA, compl | gene | B | N | I | | 2.1 | 0.28 | NC | 0 | 0 | |
| X04367 | Mouse pre-PDGF receptor mRNA (PDGF = platelet-derivec | gene | B | N | I | | 1.9 | 0.28 | NC | 0 D | 1.9 0.4 | 0 |
| U63337 | "Mus musculus cyclin-dependent kinase-2 alpha (Cdk2-alp | gene | C | N | I | | 2.2 | 0.28 | NC | 0 | 0 | 0 |
| U69695 | "Mus musculus hyaluronan synthase homolog mRNA, comp | gen | C | N | I | | ~2.4 | 0.2 | 7I ~7.4 | 2.7 | I | 3.1 1 |
| W30651 | mc14e08.r1 Soares mouse 3NMF19.5 Mus musculus cDN | est | D | N | I | * | 2.3 | 0.27 | I 3.9 | 0.98 | I | 1.7 0.2 |
| AA003554 | mg61d10.r1 Soares mouse embryo NbME.13.5 14.5 Mus m | est | B | A | N | * | 1.7 | 0.2 | 7I 2.2 | 0.59 | I | 1.2 0.1 |
| U17961 | "Mus musculus p62 mRNA, complete cds" | gene | A | N | I | | 2.3 | 0.27 | I 2.8 | 0.48 | I | 0 0 |
| AA068582 | mm45f05.r1 Stratagene mouse melanoma (#937312) Mus | est | C | N | I | | 2.3 | 0.27 | I 2.7 | 0.44 | I | 0 0 |

TABLE 6-continued

ISGs and IRGs identified from mouse embryonic fibroblast incubated
in the presence or absence of IFN-αBBDB in the presence or absence of
encephalomyocarditis virus

| Accession | Description | Type | | | | | | | | | | |
|---|---|---|---|---|---|---|---|---|---|---|---|---|
| M32010 | "Mouse MHC H-2K/t-W5-linked open reading frame mRNA" | gene | D | N | I | 1.8 | 0.27 | I | 2 | 0.41 | 0 | 0 |
| X15267 | "Mouse mRNA for acidic ribosomal phosphoprotein PO" | gene | B | N | D | 1.2 | 0.27 | D | 1.3 | 0.37 | NC | 0 |
| AA003841 | mg78n06.r1 Soares mouse embryo NbME13."5, 14.5 Mus | est | D | N | I | 2.1 | 0.27 | I | 2.3 | 0.33 | NC | 0 |
| M15501 | "Mouse alpha-cardiac actin mRNA, 3' end" | gene | | | * | | | 1.9 | 0.2 | NC | | 0 |
| W13498 | ma84h06.r1 Soares mouse P3NMF19.5 Mus musculus cD | est | C | N | I | 2.4 | 0.27 | I | 2.1 | 0.17 | NC | 0 |
| U37485 | "Mus musculus CDE1-binding protein CDEBP (Cdebp) gen | gene | C | N | I | 1.8 | 0.27 | I | 1.5 | 0.12 | D | 0.1 |
| W51315 | | est | A | Y | | * | 2.3 | 0.27 | * | 0 | 0 | 1.2 |
| L25885 | "Mouse beta 1,4N-acetylgalactosaminyltransferase mRNA | gen | | | | 2.5 | 0.27 | NC | 0 | 0 | NC | 0 |
| X94616 | M. musculus RNA for glycogen synthase | gene | B N | 1 | 1.8 | 0.27 | | | 0 | D | 2 | 0.5 |
| X62940 | M. musculus TSC-22 mRNA | gene | B | N | | 1.6 | NC | NC | 0 | D | NC | 0 |
| X60831 | Moouse ubf gene for transcription factor UBF | gene | B | N | * | 2.4 | 0.27 | NC | 0 | 0 | 0 | 0 |
| X53929 | M. musculus mRNA for PGII (decorin) | gene | B | N | I | * | 2.2 | 0.27 | * | 0 | D | −9.54 |
| X67469 | M. musculus mRNA for AM2 receptor | gene | D | N | I | 1.7 | 0.27 | NC | 0 | 0 | D | 1.1 |
| U73744 | "Mus musculus heat shock 70 protein (Hsc70) gene, com | gene | D | N | 1.4 | 0.27 | | | 0 | NC | 0 | 2.4 | 0 |
| D12618 | "Mouse mRNA for nucleosome assembly protein-1, compl | gene | C | N | I | 1.7 | 0.26 | I | 2.8 | 1.26 | I | 1.6 | 0.4 |
| Z31557 | M. musculus (129/Sv) Cctz mRNA for CCT (chaperonin co | gene | B | N | I | 1.7 | 0.26 | I | 2.2 | 0.76 | I | 1.3 | 0.2 |
| AA003093 | mg51a08.r1 Soares mouse embryo NbME13.5 14.5 Mus m | est | B | N | I | 2 | 0.26 | I | 2.4 | 0.5 | I | 1.2 | 0 |
| D49429 | "Mouse NCBP-29 mRNA for PW29, complete cds" | gene | B | N | I | 2 | 0.26 | MI | 2.5 | 0.49 | | 0 | |
| J04620 | Mouse primase p49 subunit (priA) mRNA, complete cds | gene | A | N | * | 2.4 | 0.26 | I | * | 2.9 | 0.46 | NC | 0 | 0 |
| W78338 | me84b10.r1 Soares mouse embryo NbME13.5 14.5 Mus mu | est | A | N | MI | 1.6 | 0.26 | I | 1.8 | 0.46 | NC | 0 | |
| W13878 | mb36.h02.r1 Soares mouse p3NMF19.5 Mus. musculus cD | est | D | N | I | 1.8 | 0.26 | I | 2.1 | 0.45 | NC | 0 | |
| X04017 | Mouse mRNA for cysteine-rich glycoprotein SPARC | gene | A | N | I | 1.3 | 0.26 | I | 1.4 | 0.39 | NC | 0 | |
| M63848 | "Mouse leukotriene A-4 hydrolase mRNA, complete cds" | gene | D | N | I | 1.8 | 0.26 | I | 1.9 | 0.26 | NC | 0 | |
| AA120716 | mp72h12.r1 Soares mouse embryo NbME13.5 14.5 Mus m | est | C | N | I | 2.1 | 0.26 | I | 2.1 | 0.24 | NC | 0 | |
| AA109714 | mp49e12.r1. Barstead MPLRB1 Mus musculus cDNA clone 574 | est | D | N | I | 1.9 | 0.26 | I | 1.8 | 0.22 | NC | 1.6 | 3 |
| X70067 | M. musculus RNPS1.mRNA for RNA-DNA-binding protein | gene | D | N | I | 1.8 | 0.26 | I | 1.7 | 0.16 | NC | 1.2 | 0.1 |
| W98785 | m912b10.r1 Soares mouse embryo NbME13.5 14.5 Mus m | est | D | N | * | 2.2 | 0.26 | I | 1.6 | 0.09 | NC | 1.6 | 0.2 |
| M63445 | "Mouse NAD-dependent methylenetetrahydrofolate dehyd | gene | A | N | I | 1.9 | 0.26 | | | 0 | 0 | D | | |
| D63707 | "Mouse mRNA for hepatoma derived growth factor (HDGF | gene | D | N | I | 1.6 | 0.26 | NC | 0 | 0 | D | 0.2 | 0.1 |
| X85802 | M. musculus mRNA for testosterone induced transcript | gene | B | N | I | 1.8 | 0.26 | | 0 | 0 | D | 1.7 | 0 |
| AA124405 | mg76b12.r1 Stratagene mouse melanoma (#937312) Mus | est | C | N | * | 2.1 | 0.26 | NC | * | 0 | D | 0.2 | 0.1 |
| L25274 | "Mus musculus transmembrane glycoprotein (DM-GRASP) | gene | D | N | * | ~2.2 | 0.25 | I | ~3.5 | 0.75 | I | 1.6 | 0 |
| U18366 | Mus musculus cardiotrophin-1 mRNA, complete cds" | gene | A | N | * | | 2.2 | 0.25 | D | * | 3 | 0.59 | NC | 0 |
| X81987 | M. musculus mRNA for TAX responsive element binding pr | gene | D | N | D | 1.3 | 0.25 | I | 1.4 | 0.44 | NC | 0 | |
| U58494 | "Mus musculus melanoma cell-derived intracisternal A-part | gene | D | N | I | 2 | 0.25 | I | 2.3 | 0.44 | NC | 0 | |
| M74227 | "Mouse cyclophilin C (cyp C) mRNA, complete cds | gene | A | N | MI | 1.9 | 0.25 | I | 2.1 | 0.42 | NC | 0 | |
| K02927 | "Mouse ribonucleotide reductase subunit M1 mRNA, com | gene | C | N | I | 1.7 | 0.25 | I | 1.9 | 0.37 | NC | 0 | |
| W85321 | "mf48b01.r1 Soares mouse embryo NbME13.5 14.5Mus m | est | B | N | * | 1.9 | 0.25 | I | 2.4 | 0.35 | NC | 0 | |
| D50523 | Mouse mRNA for TI-227 | gene | C | N | I | 2.1 | 0.25I | I | 2.4 | 0.33 | NC | 0 | |
| U47024 | "mh01g11.r1 Soares mouse embryo NbME13.5 14.5 Mus m | est | C | N | I | 1.9 | 0.25 | | | 0.3 | NC | | | |
| AA009169 | "House mouse; Musculus domesticus mRNA for UDP-gala | gene | A | N | I | 2.1 | 0.25 | I | 2 | 0.24 | NC | 0 | 0 |
| D87990 | mf93c05.r1 Soares mouse embryo NbME13.5 14.5 Mus mu | est | C | N | I | 1.7 | 0.25 | I | 1.7 | 0.24 | NC | 0 | 0 |
| W91398 | "md44f11.r1 Soares mouse embryo NbME13.5.14.5 Mus m | est | D | N | I | 1.9 | 0.25 | I | 1.9 | 0.22 | NC | 0 | 0 |
| W54208 | "Mus musculus putative endo/exonuclease MmMre11a (Mr | est | C | N | I | 1.6 | 0.25 | I | 1.6 | 0.2 | NC | 0 | 0 |
| U58987 | M. musculus mRNA for NfiBi-protein (exon 2–12) | gene | B | N | * | 2.4 | 0.25 | * | 2.1 | 0.16 | NC | 0 | 0 |
| Y07685 | m165a03.r1 Stratagene mouse kidney (#937315) Mus musc | gene | C | N | | ~2.2 | 0.25 | I | ~1.8 | 0.15 | NC | 0 | 0 |
| AA062237 | ms39p07.r1 Life Tech mouse embryo 13 5dpc 10666014 | est | C | N | | 2.3 | 0.25 | I | 1.9 | 0.13 | NC | 0 | 0 |
| AA168903 | | est | B | N | | ~2.2 | 0.25 | I | ~1.8 | 0.12 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | |
|---|---|---|---|---|---|---|---|---|---|---|---|---|
| U16818 | "Mus musculus UDP glucuronosyltransferase (UGT1-06) m | gene | A | N | I | * | 2.3 | 0.25 | I | 1.6 | 0.06 | D | 1.5 | 0.1 |
| U27267 | "Mus musculus LPS-induced C-X-C chemokine LIX precurs | gene | A | N | I | | 2.4 | 0.25 | NC | 0 | 0 | D | 1.8 | 0.2 |
| X03505 | Mouse gene exon 2 for serum amyloid A (SAA) 3 protein | gene | A | NI | 2.1 | | 0.24 | I | 2.8 | 0.58 | NC | | | |
| U58033 | "Mus musculus p34 cdc2 kinase mRNA, complete cds" | gene | D | N | I | | 1.7 | 0.24 | I | 2 | 0.45 | NC | 0 | 0 |
| AA105703 | mm66b08.r1 Stratagene mouse macrophage (#937306) Mu | est | C | N | I | | 1.8 | 0.24 | I | 2 | 0.39 | NC | 0 | 0 |
| W97817 | mg03c03.r1 Soares mouse embryo NbME13.5 14.5 Mus m | est | A | N | MI | * | 2.3 | 0.24 | I | ~2.7 | 0.38 | NC | 0 | 0 |
| M27844 | "Mus musculus calmodulin synthesis (CaM) cDNA, comple | gene | D | N | I | | 1.5 | 0.24 | I | 1.6 | 0.31 | NC | 0 | 0 |
| D00659 | "Mouse CYP XIX gene encoding aromatase P450₃ (EC 1.1 | gene | A N | D | * | ~2.2 | 0.24 | D | * | 0.26 | NC | * | 0 | |
| M64403 | "Mus domesticus cyclin-like protein (induced by colony-st | gene | D | N | I | | 1.9 | 0.24 | * | ~2.2 | 1.9 | 0.23 | NC | 0 | |
| L25125 | "Mouse RNA helicase and RNA-dependent ATPase from th | geneA | N | I | 2 | | 0.24 | I | 1.9 | 0.21 | NC | | 0 | |
| X61399 | Mouse F52 mRNA for a novel protein | gene | B | N | I | | 1.7 | 0.24 | I | 1.6 | 0.19 | NC | | |
| X07295 | M. musculus mitochondrial malate dehydrogenase | gene 5'ff gene | D | Y | I | * | ~2.3 | 1.6 | 0.24 | I | ~2.0 | 1.5 | 0.19 | NC | 0 | 0 |
| W51028 | "tnd89g12.r1 Soares mouse embryo NbME13.5 14.5 Mus m | est | D | N | I | | 1.9 | 0.24 | I | * | 1.7 | 0.16 | NC | 0 | 0 |
| W64587 | me74g2.r1 Soares mouse embryo NbME13.5 14.5 Mus m | est | D | N | I | * | 1.6 | 0.24I | | 1.4 | 0.12 | NC | | 0 | 0 |
| W98255 | "Mouse growth arrest specific protein (gas3) mRNA, com | gene | D | N | I | | 1.9 | 0.24 | I | | 1.3 | 0.04 | D | 1.4 | 0.2 |
| M32240 | me45c10.r1 Soares mouse embryo NbME13.5 14.5 Mus r | est | A | N | I | * | 1.8 | 0.24 | I | | 0 | 0 | NC | 0 | 0 |
| W75205 | mg44g07.r1 Soares mouse embryo NbME13.5 14.5.Mus mu | est | B | N | I | | 1.7 | 0.24 | NC | | 0 | 0 | NC | 0 | 0 |
| AA002605 | "Mus musculus Ra b11b mRNA, complete cds" | gene | D | N | I | | 1.8 | 0.24 | NC | | 0 | 0 | NC | 0 | 0 |
| L26528 | Mouse mRNA for H1 histone subtype H1(0) | gene | A | N | I | | ~2.3 | 0.23 | I | | ~4.8 | 1.29 | NC | 1.6 | 0.3 |
| X13171 | "M. musculus (SRP9) signal recognition particle subunit m | gene | C | N | I | | 1.7 | 0.23 | I | | 2.8 | 1.11 | I | | 0 |
| X78304 | mf62h02.rt Soares mouse embryo NbME13.5 14.5 Mus mu | est | B | N | I | | 1.9 | 0.23 | I | | 2.6 | 0.61 | NC | 0 | 0 |
| W89293 | mg38f06.r1 Soares mouse embryo NbME13.5 14.5 Mus m | est | D | N | I | * | ~2.2 | 0.23 | I | * | ~3.2 | 0.58 | NC | 0 | 0 |
| AA002852 | M. musculus MC3 mRNA for proteasome | est | B | N | I | | 1.5 | 0.23 | I | | 1.8 | 0.43 | NC | 0 | 0 |
| X70303 | "Mus musculus RNA helicase mRNA, complete cds" | gene | A | N | I | | 2.3 | 0.23 | * | | 2.9 | 0.4 | NC | 0 | 0 |
| L25126 | M. musculus cadL mRNA | gene | A | N | MI | | | 2 | 0.23 | MI | ~2.3 | 2.3 | 0.39 | NC | | 0 |
| X77557 | "Mus musculus LAF1 transketolase mRNA, complete cds" | gene | B | N | D | * | 1.6 | 0.23 | D | | 1.8 | 0.32 | NC | 0 | 0 |
| U05809 | mp42a09.r1 Barstead MPLRB1 Mus musculus cDNA clone | est | D | N | I | * | ~2.3 | 0.23 | I | * | ~1.9 | 0.13 | NC | * | |
| AA105072 | Mouse mRNA fortalin | est | D | Y | D | | 1.4 | 0.23 | I | | 1.3 | 0.1 | NC | 0 | 0 |
| W57495 | mg13c11.r1 Soares mouse embryo NbME13.5 14.5 Mus r | est | C | N | I | | 1.5 | 0.23 | MI | | 1.3 | 0.09 | NC | 0 | 0 |
| X56123 | "Mus musculus endothelial cell activated protein C recepto | est | A | N | I | * | 1.9 | 0.23 | NC | | 1.5 | 0.09 | NC | 0 | 0 |
| AA002458 | "Mouse murine CD63 mRNA for murine homologue of CD | gene | A | N | I | | 2.3 | 0.23 | NC | | 0 | 0 | D | 0.4 | 1.4 |
| L39017 | mg16c06.r1 Soares mouse embryo NbME13.5 14.5 Mus r | gene | D | N | I | | 1.4 | 0.23 | NC | | 0 | 0 | D | 1.7 | 0.3 |
| D16432 | mq68e09.r1 Soares 2 NbMT Mus musculus cDNA clone 58 | est | A | N | I | * | 1.8 | 0.23 | NC | | 0 | 0 | NC | 0 | 0 |
| W91509 | L95e07.r1 Stratagene mouse embryonic carcinoma (#937 | est | D | N | I | | 1.6 | 0.23 | NC | | 0 | 0 | NC | 0 | 0 |
| AA145829 | m170f08.r1 Soares mouse embryo NbME13.5 14.5 Mus mu | est | D | N | I | * | 2.2 | 0.22 | I | * | ~3.6 | 0.79 | NC | 0 | 0 |
| AA154968 | "Mus musculus Hsp70- related NST-1 (hst.1) mRNA, com | est | B | N | I | * | ~2.1 | 0.22 | I | | 3.2 | 0.62 | NC | 0 | 0 |
| AA035984 | "Mus musculus p21 (Waf1) mRNA, complete cds | gene | B | N | I | | 2.2 | 0.22 | I | | 2 | 0.53 | MI | 1.3 | 0.1 |
| U08215 | mq80b01.r1 Stratagene mouse melanoma (#937312) Mus | gene | A | N | I | | 1.6 | 0.22 | I | | 2.6 | 0.46 | NC | 0 | 0 |
| U09507 | mn42d04.r1 Beddington mouse embryonic region Mus mu | est | A | N | I | | 2 | 0.22 | I | | ~2.8 | 0.38 | NC | 0 | 0 |
| AA137883 | mp97e11.r1 Soares 2NbMT Mus musculus cDNA clone 5 | est | D | N | I | * | ~2.3 | 0.22 | MI | * | 0.25 | NC | | | |
| AA162710 | | est | C | N | I | | ~2.3 | 0.22 | MI | * | 0.25 | NC | | | |
| AA116335 | | est | | | | | | | | | | | | | |
| W83743 | mf32a08.r1 Soares mouse embryo NbME13.5 14.5 Mus mu | est | A | N | I | | 2 | 0.22 | I | | 1.9 | 0.18 | NC | 0 | 0 |
| U07159 | "Mus musculus medium-chain acyl-CdA dehydrogenease mi | gene | A | N | I | | 2.2 | 0.22 | I | | 1.9 | 0.14 | NC | 0 | 0 |
| L07063 | mn10c11.r1 Beddington mouse embryonic region Mus musc | est | A | N | I | | 1.6 | 0.22 | I | | 1.4 | 0.14 | MC | 1.1 | 0 |
| AA118131 | "Mus musculus ret finger protein, mRNA, complete cds" | est | C | N | I | * | 2.1 | 0.22 | * | | 1.5 | 0.05 | NC | 0 | 0 |
| L46855 | | gene | B | NI | 1.8 | | 0.22 | I | | 1.3 | 0.04 | NC | | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | | |
|---|---|---|---|---|---|---|---|---|---|---|---|---|---|
| X63190 | M. musculus PEA3 mRNA | gene | B | N | MI | * | 2.3 | 0.22 | NC | * | 0 | NC | 0 | 0 |
| W17473 | mb60c09.r1 Soares mouse p3NMF19.5 Mus musculus cDN | est | D | N | MD | | 2.1 | 0.22 | NC | * | 0 | NC | 0 | 0 |
| U23789 | "Mus musculus zipper protein kinase (ZPK) mRNA, comple | gene | A | N | I | | 2.2 | 0.22 | D | 3 | 0 | D | 0.7 | 0 |
| W29468 | "mb99d10.r1 Soares mouse p3NMF19.5 Mus musculus cD | est | C | N | I | | 1.7 | 0.22 | D | 1.3 | 0 | D | 0.1 | 0 |
| U03421 | "Mus. musculus interleukin-11 mRNA, complete cds | gene | C | N | I | * | ~2.2 | 0.21 | I | * | ~9.4 | 3.76 | I | 4.2 | 1.9 |
| AA097711 | "mo15h10.r1 Life Tech mouse embryo 13 5dpc 10666014 | est | C | N | I | * | 2 | 0.21 | I | * | 2.8 | 0.54 | NC | 0 | 0 |
| X61433 | M. mulculus mRNA for sodium/potassium ATPase beta su | gene | B | N | I | * | 2 | 0.21 | I | * | 2.4 | 0.36 | NC | 0 | 0 |
| X74856 | M. musculus L28 mRNA for ribosomal protein L28 | gene | D | N | D | | 1.3 | 0.21 | D | | 1.4 | 0.32 | NC | 0 | 0 |
| AA024288 | mh91g06.r1 Soares mouse placenta 4NbMP13.5 14.5 Mus m | est | A | N | I | | 2.1 | 0.21 | I | | 2.3 | 0.3 | NC | 0 | 0 |
| AA144400 | mr98b11.r1 Stratagene mouse embryonic carcinoma (#9.37 | est | D | N | I | | 2 | 0.21 | I | | 1.9 | 0.18 | MC | 0 | 0 |
| AA063858 | mj87f04.r1 Soares mouse p3NMF19.5 Mus musculus cDNA | est | A | N | I | | 2.1 | 0.21 | I | | 2 | 0.17 | NC | 0 | 0 |
| L06144 | "Mus musculus protein kinase (Ptk) mRNA, complete cds" | gene | C | N | I | | 1.8 | 0.21 | I | | 1.7 | 0.16 | NC | 0 | 0 |
| Y09632 | M. musculus mRNA for kinesin-like protein 174 | gene | C | N | I | | 1.8 | 0.21 | I | | 1.6 | 0.16 | NC | 0 | 0 |
| W98413 | mg20g06.r1 Soares mouse embryo NbME13.5 14.5 Mus m | est | A | N | I | * | 1.8 | 0.21 | I | | 1.6 | 0.15 | NC | 0 | 0.2 |
| W08120 | mb40b05.r1 Soares mouse p3NMF19.5 Mus musculus cD | est | B | N | I | | 1.3 | 0.21 | I | | 1.3 | 0.14 | NC | 0 | 0.1 |
| AA073341 | mm93a05.r1 Stratagene mouse heart(#937316) Mus musc | est | C | N | I | | 2.1 | 0.21 | I | | 1.8 | 0.12 | NC | 0 | 0.1 |
| M69042 | "Mouse protein kinase C delta mRNA, complete cds" | gene | A | N | I | | 1.9 | 0.21 | I | | 1.6 | 0.1 | D | 1.2 | 0 |
| W34969 | mc33e08.r1 Soares mouse p3NMF19.5 Mus musculus cDN | est | D | N | D | | ~2.0 | 0.21 | L | | 0 | 0 | NC | 0 | 0 |
| M38314 | "Mouse pulmonary surfactant protein SP-C (SFTP2) gene, | gene | A | N | I | * | ~2.0 | 0.21 | NC | * | 0 | 0 | D | ~4.1 | 1 |
| AA009014 | mg97b12.r1 Soares mouse embryo NbME13.5 14.5 Mus mu | est | A | N | I | * | 2.1 | 0.21 | I | * | 0 | 0 | MC | 1.8 | 0.2 |
| U09419 | "Mus musculus retinoid X receptor interacting protein (RIF | gene | C | N | I | | 1.9 | 0.21 | I | * | 0 | 0 | D | 1.4 | 0.1 |
| W65634 | me14h04.r1 Soares mouse embryo NbME13.5 14.5 Mus m | est | A | N | I | | 1.9 | 0.21 | NC | | 0 | 0 | NC | 1.5 | 0.1 |
| X75313 | M. musculus (C57BL/6) GB-like mRNA | gene | B N | N | D | 1.2 | 0.21 | NC | 0 | NC | 0 | 0 |
| U02304 | "Mus musculus LAF1 glycosaminoglycan N-acetylglucosar | gene | B | N | MI | * | 2.3 | 0.2 | NC | * | 2.1 | 0.54 | D | 1.3 | 0.1 |
| W17589 | mb77a08.r1 Soares mouse p3NMF19.5 Mus musculus cDN | est | B | N | I | | 1.9 | 0.21 | D | | 1.5 | 0.46 | NC | 0 | 0 |
| AA067092 | mm31e06.r1 Stratagene mouse heart (#937313) Mus muscu | est | C | N | D | | ~2.0 | 0.21 | I | | 1.8 | 0.24 | NC | 0 | 0 |
| D87744 | Mouse mRNA for DRPLA protein, complete cds" | gene | A | N | I | * | 2 | 0.2 | NC | * | ~2.0 | 0.19 | D | 0 | 0 |
| AA139602 | "mq40f05.r1 Barstead MPLRB1 Mus musculus cDNA clone | est | A | N | I | | 1.7 | 0.2 | I | | 1.6 | 0.18 | D | 1 | 0 |
| U13705 | "Mus musculus domesticus C57BL/6J plasma glutathione | gene | D | N | D | * | 1.6 | 0.2 | D | | 1.4 | 0.15 | NC | 0 | 0.1 |
| AA064066 | mj62d04.r1 Soares mouse p3NMF19.5 Mus musculus cDN | est | B | N | I | | 1.3 | 0.2 | I | * | ~1.7 | 0.15 | NC | 0 | 0 |
| AA114576 | mo63h09.r1 Stratagene mouse skin (#937316) Mus musc | est | C | N | I | | 1.7 | 0.21 | D | | 1.3 | 0.11 | NC | 0 | 0 |
| U33840 | "Mus musculus TRAF-related protein (TRAFamn) mRNA, c | gene | A | N | I | * | ~2.0 | 0.2 | I | | 0 | 0 | NC | 0 | 0 |
| M23568 | Mus musculus (clone pFT27) transmembrane protein mR | gene | A | N | I | | 1.6 | 0.2 | I | | 0 | 0 | NC | 0 | 0 |
| W54566 | md06c05.r1 Soares mouse embryo NbME13.5 14.5 Mus mu | est | B | N | I | | 1.5 | 0.2 | I | | 0 | 0 | NC | 1.2 | 0 |
| AA007816 | mg66g09.r1 Soares mouse embryo NbME13.5 14.5 Mus m | est | B | N | I | * | ~1.9 | 0.2 | I | | 0 | 0 | NC | 0 | 0 |
| W29434 | mb99f07.r1 Soares mouse p3NMF19.5 Mus musculus cDN | est | D | N | I | | 1.4 | 0.2 | I | | 0 | 0 | NC | 0 | 0 |
| W47728 | mc89f02.r1 Soares mouse embryo NbME13.5 14.5 Mus m | est | A | N | I | | 2.1 | 0.2 | I | | 0 | 0 | D | 1.2 | 0 |
| W48968 | | est | C | Y | D | | ~1.9 | 0.2 | NC | | 0 | 0 | NC | 0 | 0 |
| X65657 | M. musculus (testis) Sox-5 mRNA | gene | C | N | I | | 1.9 | 0.19 | NC | | 0 | 0 | NC | 0 | 0.1 |
| AA170690 | ms85g09.r1 Soares mouse 3NbMS Mus musculus cDNA | est | B | N | I | * | 1.6 | 0.19 | I | | 6.8 | 3.94 | D | 1.3 | 0.1 |
| M22326 | "Mouse growth factor-induced protein (zif/268) mRNA, c | gene | D | N | I | | 1.9 | 0.19 | I | | 1.7 | 0.44 | I | 3.6 | 2.6 |
| U70494 | Mus musculus histone H2A.Z (H2A.Z) mRNA, complete c | gene | A | N | MI | * | 1.4 | 0.19 | I | * | ~2.8 | 0.39 | NC | 1.2 | 0.1 |
| M33467 | Mouse dilute lethal-20J (d-t20J) deletion breakpoint fusio | est | C | N | MI | * | ~2.2 | 0.19 | NC | | 0 | 0 | NC | 0 | 0 |
| AA00574 | mg23g05.r1 Soares mouse embryo NbME13.5 14.5 Mus m | est | B | N | MI | * | 0.19 | I | ~2.6 | 0.36 | | | | |
| | | | | | | ~2.1 | | | | | | | | |
| AA161949 | mr92c02.r1 Stratagene mouse embryonic carcinoma (#93 | est | D | N | I | | 1.4 | 0.19 | I | | 1.6 | 0.33 | NC | 0 | 0 |
| AA163911 | "mn27e02.r1 Soares mouse eNbMS Mus musculus cDNA cl | est | C | N | I | * | 2 | 0.19 | I | | 2.4 | 0.32 | NC | 0 | 0 |
| J05186 | "Mouse protein disulfide isomerase related protein (ERp72 | gene | A | N | I | | 1.5 | 0.19 | I | | 1.6 | 6.3 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | |
|---|---|---|---|---|---|---|---|---|---|---|---|
| L27842 | "Mouse peroxisome assembly factor-1 (PMP35) gene, com | gene | C | N | I | * | 2.1 | I | * | 2.3 | 0.28 | NC | 0 | 0 |
| X80992 | M. musculus Vgr-1 mRNA | gene | A | N | MD | | ~2.1 | D | | ~2.1 | 0.23 | NC | 0 | 0 |
| Z49916 | M. musculus mRNA for CLCN4 | gene | B | N | MI | | 2 | I | | 2.1 | 0.23 | NC | 0 | 0 |
| X55038 | Mouse mCENP-B gene for centromere autoantigene B. (CEN | gene | B | N | I | 1.8 | 0.19 | I | 1.9 | 0.21 | NC | NC | 0 | 0 |
| AA146194 | mq65e10.r1 Soares 2NbMT Mus musculus cDNA clone 5 | est | C | N | I | | 1.9 | MI | | 1.9 | 0.18 | NC | 0 | 0 |
| W46019 | mc77h09.r1 Soares mouse embryo NbME13.5 14.5 Mus m | est | C | N | D | | 1.6 | D | | 1.5 | 0.16 | NC | 0 | 0 |
| L26489 | "Mus musculus furin (FUR) mRNA, complete cds" | gene | D | N | I | | 1.7 | I | | 1.7 | 0.15 | NC | 0 | 0 |
| X16705 | Mouse mRNA for lamin B | gene | D | N | I | * | ~2.2 | I | * | ~2.0 | 0.14 | NC | 0 | 0 |
| U20238 | "Mus musculus GTPase-activating protein GAPIII, mRNA, c | gene | D | N | I | | 1.9 | I | | 1.7 | 0.12 | NC | 0 | 0 |
| M63649 | "Mouse M-twist gene, complete cds" | gene | A | N | I | | 1.9 | I | | 1.7 | 0.11 | NC | 0 | 0 |
| U36384 | "Mus musculus twist-related bHLH protein Dermo-1 mRN | gene | A | N | I | 1.6 | 0.19 | I | 1.3 | 0.08 | NC | NC | 0 | 0 |
| U29055 | "Mus musculus G protein beta 36 subunit mRNA, complet | gene | C | N | I | | 1.5 | I | | 1.1 | 0.03 | D | 1.3 | 0.1 |
| W71558 | me39g12.r1 Soares mouse embryo NbME13.5 14.5 Mus m | est | A | N | I | * | ~2.0 | M | * | 0 | 0 | MI | ~4.1 | 1 |
| AA037997 | m179d03.r1 Soares mouse embryo p3NMF19.5 Mus musculus cDNA | est | B | N | I | * | ~1.9 | NC | * | 0 | 0 | NC | 0 | 0 |
| W56940 | md17f12.r1 Soares mouse embryo NbME13.5 14.5 Mus m | est | A | N | MI | * | 2.2 | NC | * | 0 | 0 | NC | 0 | 0 |
| AA103492 | mo25b07.r1 Life Tech mouse embryo 13 5dpc 10666014 | est | C | N | I | * | 2 | I | | 2 | 0.54 | NC | 0 | 0 |
| X83536 | M. musculus mRNA for membrane-type matrix metalloprote | gene | B | N | I | | 1.5 | I | | 2.3 | 0.51 | MI | 1.3 | 0.1 |
| X93357 | M. musculus mRNA for SYT | gene | C | N | I | | 1.7 | I | | 2 | 0.4 | NC | 0 | 0 |
| AA118729 | mp57g08.r1 Soares 2NbMT Mus musculus cDNA clone 57 | est | C | N | I | | 1.6 | I | | 2.3 | 0.33 | NC | 0 | 0 |
| AA032860 | m125b10.r1 Soares mouse embryo NbME13.5 14.5 Mus mu | est | D | N | I | | 1.9 | I | | 2.1 | 0.29 | NC | 0 | 0 |
| AA106492 | m191a03.r1 Stratagene mouse kidney (#937315) Mus muscu | est | D | N | I | * | 1.8 | I | | 1.9 | 0.24 | NC | 0 | 0 |
| AA036938 | m169g11.r1 Soares mouse embryo NbME13.5 14.5 Mus m | est | A | N | MI | | 1.8 | I | * | ~2.1 | 0.22 | NC | 0 | 0 |
| AA168362 | ms30f06.r1 Stratagene mouse skin (#937313) Mus muscul | est | D | N | I | * | ~2.0 | I | | 1.9 | 0.22 | NC | 0 | 0 |
| J02623 | "Mouse cytosolic aspartate aminotransferase isoenzyme m | gene | B | N | I | | 1.8 | I | | 2.1 | 0.21 | NC | 0 | 0 |
| AA087270 | mo12g12.r1 Life Tech mouse embryo 10 5dpc 10665016 M | est | D | N | I | * | 2 | I | | 1.9 | 0.19 | NC | 0 | 0 |
| D21831 | "Mouse RXR-beta gene, exon 5, 6, 7, 8 and 9" | gene | C | N | MI | * | ~2.0 | NC | * | ~1.8 | 0.15 | NC | 0 | 0 |
| X14206 | Mouse mRNA for poly (ADP-ribose) polymerase (EC 2.4.2 | gene | B | N | I | | 2.1 | I | | 1.7 | 0.1 | NC | 0 | 0 |
| D38162 | Mouse mRNA for mouse a1(XI) collagene chain | gene | C | N | I | * | 2.0 | I | | ~1.6 | 0.09 | NC | 0 | 0 |
| D38581 | Mouse mRNA for VNSP II (vomeronasal secretory protein | gene | C | N | MD | * | ~2.1 | NC | | 0 | 0 | NC | 0 | 0 |
| L23769 | "Mouse microfibril-associated glycoprotein (Magp) mRNA, | gene | B | N | I | | 1.6 | NC | * | 0 | 0 | NC | 0 | 0 |
| D37874 | "Mouse fcrn mRNA for Fc receptor (FcRn), complete cds" | gene | B | N | I | * | 1.7 | NC | * | 0 | 0 | NC | 0 | 0 |
| X66405 | M. musculus mRNA for collagene alpha1 (VI)-collagen | gene | B | N | I | | 1.5 | NC | * | 0 | 0 | D | 1.3 | 0.1 |
| X58251 | Mouse COL1A2 mRNA for pro-alpha-2(I) collagene | gene | B | N | I | | 1.2 | NC | | 0 | 0 | NC | 0 | 0 |
| X70398 | M. musculus P311 mRNA | gene | C | N | MI | * | ~2.1 | NC | * | 0 | 0 | NC | 0 | 0 |
| X80169 | M. musculus mRNA for 200 kD protein | gene | C | N | I | | 1.6 | NC | | 0 | 0 | D | 1.5 | 0.4 |
| W07927 | mb40d05.r1 Soares mouse p3NMF19.5 Mus musculus cD | est | C | N | I | | 1.9 | NC | * | 0 | 0 | NC | 0 | 0 |
| W08269 | mb40b02.r1 Soares mouse p3NMF19.5 Mus musculus cDNA | est | A | N | I | | 1.3 | NC | * | 0 | 0 | NC | 0 | 0 |
| AA097267 | mk16h10.r1 Soares mouse p3NMF19.5 Mus musculus cDN | est | B | N | I | * | 2 | NC | | 0 | 0 | NC | 0 | 0 |
| X06086 | Mouse mRNA for major excreted protein (MEP) | gene | D | N | I | | 1.4 | NC | | 0 | NC | NC | 0 | 0 |
| X69619 | M. musculus mRNA for inhibin beta-A subunit | gene | B | N | I | * | 2 | I | | 7.5 | 3.62 | I | 3.8 | 1.9 |
| L27990 | "Mus musculus Ro protein mRNA, complete cds" | gene | A | N | MI | * | 2 | I | * | 3.8 | 1.01 | MI | 1.9 | 0.3 |
| AA051446 | mj51c10.r1 Soares mouse embryo NbME13.5 14.5 Mus mus | est | B | N | I | | 2 | I | | 3.0 | 0.47 | NC | 0 | 0 |
| W63835 | "md84c11.r1 Soares mouse embryo NbME13.5 14.5 Mus | est | A | N | I | | 2 | I | 2 | 7 | 0.39 | NC | 0 | 0 |
| AA051538 | mj52e04.r1 Soares mouse embryo NbME13.5 14.5 Mus m | est | B | N | MI | | 1.8 | I | | 2.1 | 0.29 | NC | 0 | 0 |
| X06917 | Mus musculus aspartate aminotransferase gene 5'-flank ar | gene | D | N | I | | 1.5 | I | | 1.6 | 0.22 | NC | 0 | 0 |
| D00472 | "Mouse mRNA for cofilin, complete cds and flanks" | gene | D | N | MI | | 1.3 | I | | 1.3 | 0.22 | NC | 0 | 0 |
| J04696 | "Mouse glutathione S-transferase class m (GST5-5) mRN | gene | D | N | MI | | 1.8 | I | | 1.9 | 0.2 | NC | 0 | 0 |
| U62483 | "Mus musculus ubiquitin conjugating enzyme (ubc4) mRN | gene | C | N | I | | 2 | I | | 2 | 0.19 | NC | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | |
|---|---|---|---|---|---|---|---|---|---|---|---|
| AA108866 | m163g07.r1 Stratagene mouse testis (#937308 | Mus mu | est | D | N | * | 1.8 | 0.17 | I | * | 1.9 | 0.19 | NC | 0 | 0 |
| X12944 | Mouse mRNA for HMG-17 chromosomal protein | | gene | B | N | I | 1.4 | 0.17 | I | 1.4 | 0.18 | NC | 0 | 0 | 0 |
| L42177 | "Mus musculus S182 protein mRNA, complete cds" | | gene | D | N | I | 1.9 | 0.17 | I | | 1.9 | 0.17 | NC | 0 | 0 |
| J04694 | "Mus musculus alpha-1 type IV collagene (Col4a-1) mRNA, | | gene | B | N | | 1.5 | 0.17 | I | 1.5 | 0.15 | NC | 0 | 0 |
| U02313 | "Mus musculus MAST205 protein kinase mRNA, complete | | gene | B | N | | 1.7 | 0.17 | I | 1.6 | 0.12 | NC | 0 | 0 |
| D26091 | "House mouse; Musculus domesticus female mammary ca | | gene | D | N | | 1.5 | 0.17 | MI | 1.40.11 | NC | 0 | | |
| D13473 | Mouse mRNA for Rad51 protein | | gene | D | N | | 2 | 0.17 | I | 1.7 | 0.1 | NC | 0 | 0 |
| M93422 | "Mouse adenylyl cyclase type VI mRNA, complete cds" | | gene | D | Y | * | 2 | 0.17 | I | 1.4 | 0.03 | NC | 0 | 0 |
| W51476 | | | est | A | Y | MI | -2.0 | 0.17 | NC | * | 0 | * | 0 | 0 |
| AA108088 | m158e05.r1 Stratagene mouse testis (#937308) Mus mus | | est | C | N | MI | -1.7 | 0.17 | NC | * | 0 | * | 0 | 0 |
| W65511 | me10h02.r1 Soares mouse embryo NbME13.5 14.5 Mus m | | est | A | N | I | 1.8 | 0.17 | NC | * | 0 | NC | 0 | 0 |
| U48972 | "Mus musculus spindlin (Spin) mRNA, complete cds " | | gene | B | N | * | -2.1 | 0.17 | NC | * | 0 | NC | 0 | 0 |
| X65687 | M. musculus mRNA for serine-threonine protein kinase | | est | B | N | 1.5 | 1.9 | 0.17 | NC | 0 | 0 | NC | 0 | 0 |
| W89738 | mf76h09.r1 Soares mouse embryo NbME13.5 14.5 Mus mu | | est | B | N | | 0.16 | 0.17 | NC | 0 | D | 0 | 1.8 | 0.2 |
| U36277 | "Mus musculus I-kappa B alpha chain mRNA, complete cd | | gene | AN | I | -1.9 | 1.8 | I | ~7.1 | 2.6 | I | 2.23 | 3.7 | 1.5 | 1.1 |
| U44088 | "Mus musculus TDAG51 (TDAG51) mRNA, complete cds" | | gene | C | N | I | 1.5 | 0.16 | I | 4.7 | 0.7 | I | | 2.7 | |
| AA103783 | mm91d10.r1 Stratagene mouse embryonic carcinoma RA | | est | C | N | * | 0.16 | I | 2.1 | I | | 1.4 | 0.2 |
| AA154214 | est | | D | N | I | 2 | 0.16 | * | 3 | 0.51 | NC | 0 | 0 |
| mr33e01.r1 Soares mouse 3NbMS Mus musculus cDNA clo | | | | | | | | | | | | | | |
| D90344 | "Mouse mRNA for t-complex polypeptide 1A (Tcp-1a), co | | gene | D | N | I | 0.16 | I | 1.7 | 0.4 | NC | 0 | 0 |
| U43918 | "Mus musculus proliferation-associated protein 1 mRNA, c | | gene | B | N | MI | 1.4 | 1.5 | 0.16 | I | 1.7 | 0.3 | NC | 0 | 0 |
| AA008650 | mg87a07.r1 Soares mouse embryo NbME13.5 14.5 Mus m | | est | B | N | * | 1.8 | 0.16 | I | 2.1 | 0.3 | NC | 0 | 0 |
| Z49085 | M. musculus mRNA for mouse developmental kinase 2 (MD | | gene | A | N | | 1.4 | 0.16 | I | 1.6 | 0.26 | NC | 0 | 0 |
| L24118 | "Mouse primary response gene B94 mRNA, 3' end" | | est | D | N | | 1.8 | 0.16 | I | 2 | 0.24 | NC | 0 | 0 |
| W29756 | mc07e07.r1 Soares mouse p3NMF19.5 Mus musculus cDN | | est | D | N | I | 2 | 0.16 | I | 2.1 | 0.21 | NC | 0 | 0 |
| U30839 | "Mus musculus voltage dependent anion channel 3 mRNA | | gene | C | N | I | 1.4 | 0.16 | I | 1.4 | 0.19 | NC | 0 | 0 |
| D87898 | "House mouse; Musculus domesticus male brain mRNA for | | gene | C | N | I | 1.4 | 0.16 | I | 1.4 | 0.18 | NC | 0 | 0 |
| W41817 | mc63e10.r1 Soares mouse embryo NbME13.514.5 Mus mu | | est | D | N | I | 1.3 | 0.16 | I | 1.3 | 0.15 | NC | 0 | 0 |
| W34756 | "mc32g09.r1 Soares mouse p3NMF19.5 Mus musculus c | | est | C | N | * | 1.8 | 0.16 | I | * | 1.8 | 0.15 | NC | 0 | 0 |
| AA062349 | ml64d11.r1 Soares mouse embryo NbME13.5 14.5 Mus m | | est | D | N | D | 1.8 | 0.16 | D | 1.4 | 0.13 | NC | 0 | 0 |
| X70847 | M. musculus mRNA for adenine nucteotide translocase | | gene | C | N | I | 1.3 | 0.16 | NC | | 1.3 | 0.12 | NC | 0 | 0 |
| D28117 | "Mouse RNA for magnesium dependent protein phosphagene | | A | N | I | 2 | I | 1.8 | 0.11 | NC | 0 | 0 |
| D13545 | "Mouse mRNA for primase large subunit, complete cds" | | gene | A | N | * | 2 | 0.16 | I | * | 1.8 | 0.09 | NC | 0 | 0 |
| U41805 | "Mus musculus putative T1/ST2 receptor binding protein | | gene | B | N | I | 1.6 | 0.16 | * | 1.4 | 0.08 | NC | 0 | 0 |
| AA008793 | mg99d09.r1 Soares mouse embryo NbME13.5 14.5 Mus m | | est | B | N | MD | * | 1.8 | 0.16 | * | 0 | 0 | * | 0 |
| J62091 | md84h04.r1 Soares mouse embryo NbME13.5 14.5 Mus m | | est | A | I | 1.5 | 0.16 | NC | 0 | 0 | D | 1.3 | 0.1 |
| W77121 | "mc61c06.r1 Soares mouse embryo NbME13.5 14.5 Mus m | | est | D | D | 1.5 | 0.16 | NC | 0 | D | 0.77 | 0 | |
| AA154337 | ms61b04.r1 Stratagene mouse embryonic carcinoma | (#193 | est | D | I | -1.8 | 0.15 | I | ~3.5 | 0.53 | I | 1.4 | 0 |
| X62091 | M. musculus Pgp-1 mRNA for CD44 (clone M4) | | gene | C | N | | 1.7 | 0.15 | I | 2.5 | 0.51 | NC | 0 | 0 |
| D87691 | "House mouse; Musculus domesticus mRNA for eRF1, par | | gene | C | N | * | 1.8 | 0.15 | I | 2.6 | 0.45 | I | * | 1.5 | 0.1 |
| AA051736 | mj53a03.r1 Soares mouse embryo NbME13.5 14.5 Mus mu | | est | B | N | * | -1.9 | 0.15 | I | ~2.8 | 0.39 | MI | 1.3 | 0.1 |
| AA096645 | mo05a08.r1 Stratagene mouse lung 937302 Mus muscul | | est | D | N | | 1.7 | 0.15 | * | 2.1 | 0.34 | MI | 1.3 | 0.1 |
| W62036 | "md84c07.r1 Soares mouse embryo NbME13.5 14.5 Mus | | est | D | N | I | 1.8 | 0.15 | I | 2.3 | 0.33 | NC | 0 | 0 |
| X78990 | M. musculus mRNA for testin 2 | | gene | D | I | * | 1.8 | 0.15 | * | 2.2 | | | | |

TABLE 6-continued

ISGs and IRGs identified from mouse embryonic fibroblast incubated in the presence or absence of IFN-αBBDB in the presence or absence of encephalomyocarditis virus

| | | | | | | | | | | | |
|---|---|---|---|---|---|---|---|---|---|---|---|
| M73748 | "Mouse OTS-8 mRNA, complete cds" | gene | D | N | | 1.5 | 0.15 | I | 1.6 | 0.19 | NC | 0 | 0 |
| AA008683 | mg83e03.r1 Soares mouse embryo NbME13.5 14.5 Mus m | est | B | N | | 1.6 | 0.15 | I | 1.6 | 0.18 | NC | 0 | 0 |
| M15525 | "Mouse laminin B1 mRNA, complete cds" | gene | D | N | | 1.6 | 0.15 | I | 1.7 | 0.19 | NC | 0 | 0 |
| U69599 | "Mus musculus interferon gamma receptor second chain (" | gene | C | N | * | 1.9 | 0.15 | I | 2 | 0.17 | NC | 0 | 0 |
| M28540 | "Mouse beta-glucoronidase (Gus-s) mRNA, complete cds" | gene | A | N | | 1.9 | 0.15 | I | 1.9 | 0.15 | NC | 0 | 0 |
| U22399 | "Mus musculus Cdk-inhibitor p57kiP2 (k1P2) mRNA; comp" | gene | A | N | | 1.8 | 0.15 | I | 1.5 | 0.08 | NC | 0 | 0 |
| U34960 | "Mus G protein beta 2 subunit mRNA; complete cds" | gene | D | N | | 1.4 | 0.15 | I | 1.3 | 0.08 | NC | 0 | 0 |
| X16834 | Mouse mRNA for Mac-2 antigene | gene | D | N | | | 1.5 | I | | 1.3 | 0.08 | NC | 0 | 0 |
| AA119665 | mp68h05.r1 Soares 2NbMT Mus musculus cDNA clone 5744 | est | A | N | * | −1.9 | 0.15 | MI | −1.4 | 0.05 | NC | 0 | 0.3 |
| U17343 | "Mus musculus signal recognition particle receptor beta s" | gene | A | N | * | 1.9 | 0.15 | MI | 1.4 | 0.03 | D | 1.4 | 0.1 |
| AAD13526 | mh10h02.r1 Soares mouse placenta 4NbMP13.5 14.5 Mu" | est | B | MI | * | −2.0 | 0.15 | NC | 0 | 0 | NC | 0 | 0.1 |
| U69137 | "Mus musculus T2-cadherin mRNA, partial cds" | gene | C | N | 2 | 0.15 | NC | * | 0 | NC | * | 0 | 0.1 |
| W55117 | | est | A | Y | * | 1.7 | 0.15 | NC | 0 | 0 | NC | 0 | 0 |
| JD526I | "Mouse protective protein (Mo54) mRNA, complete cds" | est | A | N | | 1.4 | 0.15 | NC | 0 | 0 | NC | 0 | 0 |
| W65510 | me10h01.r1 Soares mouse embryo NbME13.5 14.5 Mus m | est | A | N | | 1.4 | 0.15 | NC | 0 | 0 | NC | 0 | 0 |
| X82D67 | M. musculus mRNA for thiol-specific antioxidant | est | B | N | | 1.3 | 0.15 | NC | 0 | 0 | NC | 0 | 0 |
| AA049707 | "mj11gD8.r1 Soares mouse embryo NbMF19.5 Mus | est | B | MI | * | −1.9 | 0.15 | NC | 0 | 0 | NC | 0 | 0 |
| X69025 | M. musculus of PCTAIRE-1 mRNA encoding protein kinase | est | B | N | | 1.7 | 0.15 | NC | 0 | 0 | NC | 0 | 0.1 |
| W08050 | mb38d12.r1 Soares mouse p3NMF19.5. Mus musculus cDN | est | C | N | * | −1.8 | 0.15 | NC | 0 | 0 | NC | 0 | 0 |
| U12473 | "Mus musculus Balb/c conserved helix-loop-helix ubiquitou" | est | B | N | | 1.6 | 0.14 | I | −3.8 | 0.9 | D | 1.5 | 0 |
| U51196 | "Mus musculus APC-binding protein EB1 homolog mRNA," | est | B | N | * | −1.8 | 0.14 | I | 2.1 | 0.35 | D | 0 | 0 |
| J05479 | "Mouse calcineurin catalytic subunit mRNA, complete cds" | gene | D | N | * | −2.0 | 0.14 | I | −2.5 | 0.26 | MI | 1.2 | 0 |
| AA154743 | mt64c04.r1 Soares mouse lymph node NbMLN Mus muscu | est | A | N | | 1.9 | 0.14 | I | 2.2 | 0.24 | NC | 0 | 0 |
| U76546 | "Mus musculus ADP-ribosylation factor-like protein 4 mRN" | est | C | N | * | −1.9 | 0.14 | I | −2.2 | 0.23 | NC | 0 | 0 |
| W82209 | me99f01.r1 Soares mouse embryo p3NMF19.5 Mus musculus cDN | est | A | MI | | 1.4 | 0.14 | I | 1.5 | 0.19 | NC | * | 0.2 |
| AA028877 | mh90g10.r1 Soares mouse placenta 4NbMP13.5 14.5 Mus | est | B | N | | 1.4 | 0.14 | I | 1.5 | 0.17 | NC | 0 | 0 |
| AA039108 | m199d10.r1 Soares mouse embryo NbME13.5 14.5 Mus mu | est | B | MI | * | −1.9 | 0.14 | I | −1.9 | 0.15 | NC | 0 | 0 |
| U35623 | "Mus musculus EAT/MCL-1 mRNA, complete cds" | est | C | N | | 1.7 | 0.14 | I | 1.7 | 0.15 | NC | 0 | 0 |
| AA016424 | mh38l02.r1 Soares mouse placenta 4NbMP13.5 14.5 Mus | est | B | N | | 1.6 | 0.14 | I | 1.6 | 0.12 | NC | 0 | 0 |
| AA015570 | m161f10.r1 Soares mouse embryo NbME13.5 14.5 Mus mus | est | B | N | * | 1.9 | 0.14 | I | 1.7 | 0.08 | NC | 0 | 0 |
| M36120 | "Mouse keratin 19 gene, complete cds" | gene | D | N | | 1.8 | 0.14 | I | 1.4 | 0.04 | NC | 0 | 0 |
| W46019 | mc77h09.r1 Soares mouse embryo NbME13.5 14.5 Mus m | est | C | N | MD | 1.6 | 0.14 | NC | 0 | 0 | NC | 0 | 0 |
| AA10L455 | mp08f02.r1 Life Tech mouse embryo 8 5dpc 10664019 M | est | A | N | MD | 1.4 | 0.14 | NC | 0 | 0 | NC | * | 0 |
| L40459 | "Mus musculus latent transforming growth factor-beta bin | gene | A | N | | 1.6 | 0.14 | NC | 0 | 0 | MD | 1.7 | 0.2 |
| U49739 | "Mus musculus unconventional myosin VI (sv) mRNA, com | gene | B | N | | 1.9 | 0.14 | NC | 0 | 0 | NC | * | 0.5 |
| X69620 | M. musculus mRNA for inhibin beta-B subunit | est | B | N | * | −1.8 | 0.14 | MI | −1.0 | 0 | D | −3.1 | 0.2 |
| X51905 | Mouse Ldh-2 mRNA for lactate dehydrogenease-B (EC 1.1 | gene | C | N | | 1.7 | 0.14 | NC | 0 | 0 | MD | 1.6 | 0 |
| AA073296 | mm83a12.r1 Stratagene mouse embryonic carcinomaRA ( | est | C | N | | 1.7 | 0.14 | NC | 0 | 0 | MD | 0.2 | 0 |
| D10024 | "Mouse mRNA for protein-tyrosine kinase substrate p36 ( | est | D | N | | 1.2 | 0.14 | NC | 0 | 0 | NC | 0 | 0 |
| M32599 | "Mouse glyceraldehyde-3-phosphate dehydrogenease mRN | gene | D | N | | 1.3 | 0.14 | NC | 0 | 0 | NC | 0 | 0.4 |
| W17745 | mb77h01.r1 Soares mouse p3NMF19.5 Mus musculus cD | est | B | N | 1.7 | 1.5 | 0.14 | NC | 0 | 0 | D | 1.7 | 0 |
| L24554 | "Mus musculus adenylosuccinate synthetase mRNA, comp | gene | C | N | * | 0.13 | I | 3.1 | 0.78 | NC | 0 | 0 |
| W07963 | mb45h07.r1 Soares mouse p3NMF19.5 Mus musculus cDN | est | C | N | * | 1.7 | 0.13 | I | 2.8 | 0.63 | NC | 0 | 0 |
| X02452 | Mouse ki-ras cellular oncogene exon 1 from Y1 adrenal tu | gene | B | N | * | −1.8 | 0.13 | I | −2.6 | 0.36 | NC | * | 0 |
| W45817 | mc80d09.r1 Soares mouse embryo NbME13.5 14.5 Mus m | est | D | N | * | −1.7 | 0.13 | I | −2.5 | 0.36 | MI | 1.4 | 0.1 |
| U52951 | "Mus musculus putative transcriptional regulator mEnx-1 | gene | C | N | * | −1.9 | 0.13 | I | −2.4 | 0.26 | NC | 0 | 0 |
| AA014138 | mh29a07.r1 Soares mouse placenta 4NbMP13.5 14.5 Mus | est | B | N | | 1.8 | 0.13 | I | 2.1 | 0.22 | NC | 0 | 0 |

TABLE 6-continued

ISGs and IRGs identified from mouse embryonic fibroblast incubated in the presence or absence of IFN-αBBDB in the presence or absence of encephalomyocarditis virus

| Accession | Description | Type | | | | | | | | | | | |
|---|---|---|---|---|---|---|---|---|---|---|---|---|---|
| W78418 | me84f2.r1 Soares mouse embryo NbM.E13.5 14.5 Mus m | est | A | N | I | | 1.8 | 0.13 | I | 2 | 0.19 | NC | | 0 |
| W17411 | mb58c09.r1 Soares mouse embryo p3NMF19.5 Mus musculus cD | est | D | N | I | | 1.3 | 0.13 | I | 1.3 | 0.19 | NC | | 0 |
| AA104315 | mo50a06.r1 Life Tech mouse embryo 10 5dpc 10665016 | est | C | N | MI | | ~1.7 | 0.13 | I | ~1.9 | 0.18 | NC | * | 0 |
| Z54179 | M. musculus mRNA (evolutionary conserved transcript) | gene | C | N | I | | 1.6 | 0.13 | I | 1.8 | 0.18 | NC | | 0 |
| U41751 | "Mus musculus p53 responsive (Ei24) mRNA, complete cd | gene | B | N | I | | 1.5 | 0.13 | I | 1.5 | 0.11 | NC | | 0 |
| Y09419 | M. musculus mRNA for spermine synthase | gene | C | N | I | | 1.6 | 0.13 | I | 1.5 | 0.11 | NC | | 0 |
| X65553 | M. musculus mRNA for poly(A) binding Protein | gene | C | N | D | | 1.3 | 0.13 | D | 1.2 | 0.1 | NC | | 0 |
| L35528 | "Mus musculus manganese superoxide dismutase (MnSOD | gene | A | N | I | | 1.7 | 0.13 | I | 1.5 | 0.09 | NC | | 0 |
| AA124273 | mq22d04.r1 Barstead MPLRB1 Mus musculus cDNA clone | est | B | N | I | | | 1.6 | 0.13 | I | 1.5 | 0.09 | NC | 0 |
| X80638 | M. musculus rhoC mRNA | gene | B | N | I | | 1.3 | 0.13 | I | 1.3 | 0.08 | NC | | 0 |
| X71422 | M. musculus Hoxd-11 gene | gene | B | N | I | * | ~1.7 | 0.13 | I | ~1.5 | 0.07 | NC | | 0 |
| M98035 | "Mus musculus guanine nucleotide exchange factor delta | gene | A | N | I | 1.6 | 1.4 | MI | | 0.07 | MD | | 1.1 | 0 |
| AA138105 | mq30a03.r1 Barstead MPLRB1 Mus musculus cDNA clone | est | B | N | I | | 0.13 | 0.13 | I | 1.2 | 0.05 | NC | | |
| M90316 | "Mouse S37 (non-leukocyte isoform) mRNA, complete cd | gene | A N | I | | 1.4 | 1.4 | NC | 0 | 0 | D | NC | 1.5 | 0.2 |
| W53694 | md11e11.r1 Soares mouse embryo NbME13.5 14.5 Mus mu | est | A | N | I | | 1.5 | 0.13 | NC | 0 | 0 | NC | | 0 |
| AA068302 | mm62a09.r1 Stratagene mouse embryonic carcinoma (#9 | est | A | N | I | * | 1.6 | 0.13 | NC | 0 | 0 | MD | 2.2 | 1.2 |
| U43836 | "Mus musculus VEGF-related factor mvrf186 precursor mR | gene | B | N | I | | 1.6 | 0.13 | NC | 0 | 0 | D | | 0.50,L & .9 |
| X59846 | M. musculus GAS 6 mRNA associated with growth-arrest | gene | B | N | I | | 1.7 | 0.13 | NC | 0 | 0 | MC | 3.5 | 1.1 |
| U58884 | "Mus musculus SH3-containing protein SH3P7 mRNA, com | gene | C | N | I | | 1.5 | 0.13 | NC | 0 | 0 | D | 1.5 | 0.2 |
| X97796 | M. musculus mRNA homologous to S. cerevisiae RAD54 | gene | C | N | MI | * | 1.9 | 0.13 | NC | 0 | 0 | NC | 0 | 0 |
| AA106625 | mi87g11.r1 Stratagene mouse kidney (#937315) Mus mu | est | C | N | MD | | 1.8 | 0.13 | NC | 0 | 0 | NC | 0 | 0 |
| AA114811 | mn17e12.r1 Beddington mouse embryonic region Mus mus | est | C | N | D | | 1.3 | 0.13 | NC | 0 | 0 | NC | 0 | 0 |
| U64033 | "Mus musculus Tera (Tera) mRNA, complete cds" | gene | C N | I | * | ~1.7 | 0.12 | I | ~3.1 | 0.58 | NC | | 0 | |
| AA002604 | mg44g304.r1 Soares mouse embryo NbME13.5 14.5 Mus m | est | B | N | I | * | ~1.7 | 0.12 | I | ~3.0 | 0.55 | I | 1.7 | 0.1 |
| W17482 | mb60e11.r1 Soares mouse embryo p3NMF19.5 Mus musculus cDN | est | D | N | I | | 1.6 | 0.12 | I | 2.3 | 0.47 | I | 1.4 | 0.2 |
| U16322 | "Mus musculus basic transcription factor MITF-2B mRNA, | gene | B | N | I | * | ~1.7 | 0.12 | I | ~2.4 | 0.3 | NC | 0 | 0 |
| W34965 | mc33d07.r1 Soares mouse embryo p3NMF19.5 Mus musculus cD | est | D | N | I | | 1.5 | 0.12 | I | 1.9 | 0.3 | I | 1.2 | 0.1 |
| M95408 | "Mouse focal adhesion kinase mRNA, complete cds" | gene | C | N | I | | 1.7 | 0.12 | I | 1.8 | 0.16 | NC | 0 | 0 |
| W13461 | mb34g09.r1 Soares mouse embryo NbME13.5 14.5 Mus mu | est | D | N I | 1.4 | | 0.12 | I | 1.4 | 0.15 | NC | | 0 | |
| W71125 | me31h04.r1 Soares mouse embryo NbME13.5 14.5 Musm | est | D | N | I | | 1.3 | 0.12 | I | 1.4 | 0.14 | NC | | 0 |
| AA035951 | m170e-01.r1 Soares mouse embryo NbME13.5 14.5 Mus mu | est | A | N | I | | 1.4 | 0.12 | I | 1.6 | 0.13 | NC | | 0 |
| AA124955 | mp80g04.r1 Soares 2NbMT Mus musculus cDNA clone 57 | est | C | N | I | * | 1.6 | 0.12 | I | 1.4 | 0.13 | NC | | 0 |
| AA120173 | mn33h12.r1 Beddington mouse embryonic region Mus mus | est | B | N | I | * | 1.4 | 0.12 | I | 1.6 | 0.12 | NC | | 0 |
| W13162 | ma74d12.r1 Soares mouse embryo p3NMF19.5 Mus musculus cDN | est | D | N | I | | 1.4 | 0.12 | I | 1.3 | 0.08 | NC | | 0 |
| Z71268 | "Mouse insulin-like growth factor binding protein 2 (IGFBP | gene | C | N | I | | ~1.9 | 0.12 | I | ~1.6 | 0.06 | NC | | 0 |
| U43144 | M. musculus mRNA for CMP-sialic acid transporter | gene | B | N | I | | 1.5 | 0.12 | I | 1.3 | 0.04 | NC | | 0 |
| W57021 | "Mus musculus phospholipase C beta3 mRNA, complete c | gene | B N | MI | | 1.7 | 0.12 | NC | 0 | 0 | D | D | 1.6 | 0.1 |
| U13878 | md52b03.r1 Soares mouse embryo NbME13.5 14.5 Mus m | est | A | N | I | * | ~1.6 | 0.12 | I | ~1.0 | 0 | NC | 0 | 0.1 |
| W71692 | "Mus musculus neural-restrictive silencer factor mRNA, p | est | A | N | I | * | 1.8 | 0.12 | NC | 0 | 0 | NC | 1.3 | 0.1 |
| L05439 | me34f05.r1 Soares mouse embryo NbME13.5 14.5 Mus mu | est | D | N | I | | 1.7 | 0.12 | NC | 0 | 0 | NC | 1.3 | 0 |
| X14972 | "Mouse insulin-like growth factor binding protein 2 (IGFBP | gene | C | N | I | | 1.5 | 0.12 | NC | 0 | 0 | D | | |
| Z31399 | Mouse mRNA for alpha-adaptin (C) | gene | B N | I | 1.5 | | NC | 0 | 0 | NC | | | | |
| W89863 | M. musculus Ccth mRNA for CCT eta subunit (chaperonin | gene | B N | MI | 1.3 | | 0.12 | NC | 0 | 0 | NC | | | |
| AA071662 | nf76107.r1 Soares mouse embryo NbME13.5 14.5 Mus mu | est | B | N | I | | 1.4 | 0.12 | I | 2.3 | 0.35 | MI | 1.4 | 0.1 |
| W29920 | mc08e02.r1 Soares mouse embryo p3NMF19.5 Mus musculus cD | est | C | Y | MI | | 1.7 | 0.11 | I | 2.6 | 0.31 | NC | 0 | 0 |
| AA162215 | mn44b04.r1 Beddington mouse embryonic region Mus mus | est | D | N | I | | 1.7 | 0.11 | D | ~1.5 | | D | | |
| K02138 | "Mouse germline IgM chain gene, mu-delta region" | gene | D | N | D | | 1.8 | 0.11 | | | | | | |

TABLE 6-continued

ISGs and IRGs identified from mouse embryonic fibroblast incubated
in the presence or absence of IFN-αBBDB in the presence or absence of
encephalomyocarditis virus

| | | | | | | | | | | | RNL+/+ IFN/ EMCV |
|---|---|---|---|---|---|---|---|---|---|---|---|
| AA103457 | est | D | N | I | 1.6 | 0.11 | I | 1.6 | 2 | 0.23 | MI | 1.2 | 0 |
| W34066 | est | D | N | I | 1.6 | 0.11 | I | | 0.22 | NC | 0 | 0 | 0 |
| X98475 | gene | C | N | I | 1.6 | 0.11 | I | * | 1.8 | 0.2 | | 0 | 0 |
| AA007747 | est | B | N | 1.4 | 1.8 | 0.11 | I | * | 2 | 0.17 | | 0 | 0 |
| AA116706 | est | B | N | * | 1.5 | 0.11 | MI | * | 1.6 | 0.16 | | 0 | 0 |
| AA168363 | est | A | N | * | 1.8 | 0.11 | I | * | 1.8 | 0.13 | | 0 | 0 |
| D87117 | gene | C/N | 1 | ~1.7 | 0.11 | * | ~1.8 | 0.13 | NC | | 0 | 0 |
| M25149 | gene | D | N | I | 1.4 | 0.11 | I | * | 1.5 | 0.13 | NC | 0 | 0 |
| M85153 | gene | D | N | * | 1.7 | 0.11 | I | * | 1.7 | 0.1 | NC | 0 | 0 |
| M63245 | gene | B | N | MI | 1.5 | 0.11 | I | * | 1.4 | 0.08 | NC | 0 | 0 |
| AA073769 | est | C | N | I | 1.6 | 0.1 | I | * | 1.5 | 0.06 | NC | 0 | 0 |
| M30127 | gene | D | N | * | 1.5 | 0.11 | MI | * | 1.4 | 0.06 | NC | 0 | 0 |
| L36244 | est | B | N | MI | ~1.6 | 0.11 | NC | * | 0 | 0 | NC | 0 | 0.1 |
| M60559 | gene | B | N | MD | 1.8 | 0.11 | NC | * | 0 | 0 | NC | 0 | 0.2 |
| W59540 | est | A | Y | * | ~1.9 | 0.11 | I | * | 0 | 0 | NC | 0 | 0.1 |
| L21973 | gene | A | N | * | 1.7 | 0.1 | I | * | 0 | 0 | MD | 1.2 | 0 |
| W90864 | est | B | N | I | 1.6 | 0.1 | NC | * | 0.44 | 0 | D | 1.4 | 0 |
| M35899 | est | B | N | * | ~1.7 | 0.1 | NC | * | 0 | 0.44 | D | 2.1 | 0 |
| U44940 | gene | B | N | * | ~1.6 | 0.1 | NC | * | ~2.7 | 0.43 | MI | 1.7 | 0.1 |
| AA137902 | gene | D | N | * | ~1.7 | 0.1 | I | * | ~2.8 | 0.27 | NC | 0 | 0 |
| X81464 | gene | B | N | * | 1.6 | 0.1 | I | * | 2.1 | 0.26 | NC | 0 | 0 |
| W64785 | est | B | N | I | ~1.7 | 0.1 | I | * | ~2.2 | 0.25 | NC | 0 | 0 |
| AA119121 | est | B | N | * | 1.6 | 0.1 | I | * | 2 | 0.23 | NC | 0 | 0 |
| AA154444 | est | B | N | * | 1.6 | 0.1 | MI | * | 1.9 | 0.22 | NC | 0 | 0 |
| AA002883 | gene | D | N | * | ~1.6 | 0.1 | I | * | ~2.1 | 0.13 | NC | 0 | 0 |
| W12383 | est | B | N | * | 1.7 | 0.1 | I | * | 1.8 | 0.12 | NC | 0 | 0 |
| M27960 | gene | D | N | I | 1.6 | 0.1 | I | * | 1.7 | 0.11 | NC | 0 | 0 |
| W13875 | gene | C | N | MI | 1.2 | 0.1 | I | * | 1.3 | 0.08 | NC | 0 | 0 |
| AA060106 | est | D | N | * | 1.8 | 0.1 | I | * | 1.7 | 0.07 | NC | 0 | 0 |
| U04299 | gene | C | N | * | 1.6 | 0.1 | MI | * | 1.5 | 0.06 | NC | 0 | 0 |
| U48804 | gene | A | N | MI | 1.6 | 0.1 | I | * | ~1.5 | 0.05 | NC | 0 | 0 |
| W98100 | est | A | N | * | ~1.7 | 0.1 | I | * | ~1.4 | 0.03 | NC | 0 | 0 |
| M24119 | est | D | N | * | 1.5 | 0.1 | I | * | 1.2 | 0.02 | D | 1.4 | 0 |
| L21674 | gene | A | N | * | ~1.8 | 0.1 | I | * | ~1.2 | NC | * | 0 | 0 |
| U04672 | gene | C | N/I | ~1.7 | 0.1 | * | ~1.1 | 0.01 | NC | * | 0 | 0 |
| M64086 | gene | A | N | MI | 1.6 | 0.1 | NC | * | 0 | 0 | MC | 1.4 | 0 |
| AA015076 | gene | A | N | * | 1.5 | 0.1 | NC | * | 0 | 0 | D | 0 | 0 |
| W55789 | est | A | N | * | 1.6 | 0.1 | NC | * | 0 | 0 | D | 1.6 | 0.3 |
| U24700 | est | B | N | * | 1.8 | 0.1 | NC | * | 0 | 0 | D | 1.4 | 0.1 |
| Y83523 | est | B | N | * | 1.3 | 0.1 | NC | * | 0 | 0 | NC | 0 | 0 |
| U27340 | gene | B | N | * | 1.6 | 0.1 | NC | * | 0 | 0 | D | 1.3 | 0.1 |
| X61147 | gene | C | N | I | 1.7 | 0.1 | NC | * | 0 | 0 | NC | 0 | 0 |
| X56690 | gene | C | N | I | 1.3 | 0.1 | NC | * | 0 | 0 | NC | 0 | 0 |
| U40930 | gene | C | N | * | 1.3 | 0.1 | NC | * | 0 | 0 | NC | 0 | 0 |
| W85446 | est | | | | 1.5 | 0.1 | | | 0 | 0 | | 0 | 0 |

| Accession | Type | Description |
|---|---|---|
| AA103457 | est | mo24g05.r1 Life Tech mouse embryo 13 5dpc 10666014 |
| W34066 | est | ma85b11.r1 Soares mouse p3NMF19.5 Mus musculus cD |
| X98475 | gene | M. musculus VASP gene |
| AA007747 | est | mg63a08.r1 Soares mouse embryo NbME13.5 14.5 Mus m |
| AA116706 | est | "mn20h06.r1 Beddington mouse embryonic region Mus mu |
| AA168363 | est | "ms30f07.r1 Stratagene mouse skin (#937313) Mus muscu |
| D87117 | gene | "House mouse; Musculus domesticus brain mRNA for SAF |
| M25149 | gene | "Mouse Tum-P91A antigene gene, complete cds" |
| M85153 | gene | "M. musculus alpha-1,3-galactosyltransferase mRNA, comp |
| M63245 | gene | "Mus musculus amino levulinate synthase (ALAS-H) mRNA |
| AA073769 | est | mm96d12.r1 Stratagene mouse heart (#937316) Mus musc |
| M30127 | gene | "Mouse MHC class 1 tum- transplantation antigene mRNA P |
| L36244 | est | "Mus musculus metalloproteinase matrilysin mRNA, compl |
| M60559 | gene | "Mus musculus Swiss Webster beta-B2 crystallin mRNA, c |
| W59540 | est | |
| L21973 | gene | "Mus musculus F2F1 mRNA, complete cds" |
| W90864 | est | mf79d08.r1 Soares mouse embryo NbME13.5 14.5 Mus m |
| M35899 | est | mc53h11.r1 Soares mouse embryo NbME13.5 14.5 Mus m |
| U44940 | gene | "Mus musculus quaking type I (QKI) mRNA, complete cds" |
| AA137902 | gene | mq01b11.r1.Soares mouse 2NbMT Mus musculus cDNA clone 5 |
| X81464 | gene | M. musculus mRNA for translin |
| W64785 | est | "md 89 d11.r1 Soares mouse embryo NbME13.5.14.5 Mus m |
| AA119121 | est | mp56h01.r1 Soares mouse 2NbMT Mus musculus cDNA clone 57 |
| AA154444 | est | mq47d04.r1 Soares mouse 2NbMT Mus musculus cDNA clone 5818 |
| AA002883 | gene | "tng41d10.r1 Soares mouse embryo NbME13.5 14.5 Mus m |
| W12383 | est | ma67c12.r1 Soares mouse p3NMF19.5 Mus musculus cD |
| M27960 | gene | "Mouse interleukin-4 receptor (secreted form) mRNA, com |
| W13875 | gene | "mb36g03.r1 Soares mouse p3NMF19.5 Mus musculus cDN |
| AA060106 | est | mj71g09.r1 Soares mouse p3NMF19.5 Mus musculus cD |
| U04299 | gene | "Mus musculus BALB/c mannosyl-oligosaccharide alpha-1, |
| U48804 | gene | "Mus musculus Zn-finger protein Pw1 gene, complete cds |
| W98100 | est | me73h07.r1 Soares mouse embryo NbME13.5 14.5 Mus m |
| M24119 | gene | "Mouse glucocerebrosidase mRNA, complete cds" |
| L21674 | gene | "Mouse Eps8 mRNA sequence, complete cds" |
| U04672 | gene | "Mus musculus type I receptor BRK-1 mRNA, complete cd |
| M64086 | gene | "Mouse spl2 proteinase inhibitor (sp12/eb4) mRNA, comp |
| AA015076 | gene | mh15f10.r1 Soares mouse placenta ANbMP13.5 14.5 Mus m |
| W55789 | est | |
| U24700 | est | "Mus musculus protein tyrosine phosphatase (mbptp1b) n |
| Y83523 | est | mf29g05.r1 Soares mouse embryo NbME13.5 14.5 Mus m |
| U27340 | gene | "Mus musculus sulfated glycoprotein (Sgp1) mRNA, comp |
| X61147 | gene | M. musculus mRNA for iron responsive element binding pro |
| X56690 | gene | Mouse mRNA for modifier 1 protein |
| U40930 | gene | "Mus musculus oxidative stress-induced protein mRNA, co |
| W85446 | est | mf45d10.r1 Soares mouse embryo NbME13.5 14.5 Mus m |

TABLE 6-continued

ISGs and IRGs identified from mouse embryonic fibroblast incubated in the presence or absence of IFN-αBBDB in the presence or absence of encephalomyocarditis virus

| | | | | | | | | | |
|---|---|---|---|---|---|---|---|---|---|
| AA123389 | mq73b09.r1 Stratagene.mouse melanoma (#937312) Mus | est | C | N | I | * | ~1.7 | 0.1 | 0 | 0 | 0 |
| D82019 | "Mouse gene for basigin, complete cds (exon1–7)" | gene | D | N | MI | | 1.3 | 0.1 | * | 0 | 0 |
| X97281 | M. musculus mRNA for K+ chanel beta subunit | gene | C | N | I | * | ~1.7 | 0.09 | NC | NC | 0 |
| Z67746 | "M. musculus mRNA for phosphatase 2A catalytic subunit, | gene | B | N | MI | | 1.5 | 0.09 | I | 0.26 | NC |
| J00423 | "Mouse hypoxanthine phosphoribosyltransferase (hprt) mf | gene | A | NI | | 1.4 | 0.09 | I | ~2.4 | 0.2 | NC |
| W98152 | mg13g01.r1 Soares mouse embryo NbME13.5 14.5 Mus mu | est | A | N | I | * | ~1.7 | I | 1.5 | 1.8 | NC |
| U13053 | "Mus musculus Ras-like protein (kir) mRNA, compete cds" | gene | A | N | I | * | ~1.7 | 0.09 | * | 0.18 | NC | 0 |
| X95403 | M. musculus mRNA for GTP-binding protein | gene | C | N | I | | 1.4 | 0.09 | MI | ~1.9 | 0.16 | 0 |
| AA117128 | mn05f10.r1 B | est | | | | | | 0.09 | I | ~1.8 | 0.12 | NC | 0 |
| | eddington mouse embryonic region Mus musc | est | C | N | MI | * | * | ~1.6 | 0.09 | * | 1.5 | 0.11 | NC | 0 |
| | | | | | | | | | 0.09 | I | ~1.7 | 0.11 | NC | 0 |
| X80685 | M. musculus gMCK2-beta gene | gene | B | NI | | 1.3 | 0.09 | MI | 1.2 | NC | 0 | 0 |
| AA000961 | mg38f01.r1 Soares mouse embryo NbME13.5 14.5 Mus m | est | D | N | I | | 1.5 | 0.09 | I | 1.4 | 0.06 | 0 | 0 |
| L01776 | "Mus musculus neuronal dihydropyridine-sensitive L-type | gene | D | N | I | * | ~1.7 | 0.09 | * | ~1.5 | 0.06 | NC | 0 |
| X70842 | M. musculus Flk-1 mRNA | gene | B | N | MI | * | ~1.6 | 0.09 | I | 1.4 | 0.04 | NC | 0 |
| U21103 | "Mus musculus mammary gland factor (Stat5a) mRNA, co | gene | A | N | I | * | ~1.5 | 0.09 | * | ~1.2 | 0.02 | NC | 0 |
| AA050055 | mj17f01.r1 Soares mouse embryo NbME13.5 14.5 Mus m | est | A | N | MI | | 1.4 | 0.09 | NC | 0 | 0 | NC | 0 |
| W54339 | md05f06.r1 Soares mouse embryo NbME13.5 14.5 Mus mu | est | A | N | I | | 1.6 | 0.09 | NC | 0 | 0 | D | 1.3 | 30.5 |
| L04302 | "Mouse thrombospondin 3 (THB SP3) mRNA, complete cd | gene | A | N | I | * | * | 1.7 | 0.09 | NC | 0 | 0 | MD |
| U09874 | "Mus musculus SKD3 mRNA, complete cds" | gene | A | N | MI | | 1.5 | 0.09 | NC | 0 | 0 | NC | 0 |
| U12147 | "Mus musculus laminin-2 alpha2 chain mRNA, complete c | gene | A | N | I | | 1.7 | 0.09 | NC | 0 | 0 | NC | 0 |
| X61432 | mp62a09.r1 Soares 2NbMT Mus musculus cDNA clone 5737 | est | A | N | I | | 1.3 | 0.09 | NC | 0 | 0 | NC | 0 |
| U17297 | M. musculus mRNA for calmodulin | gene | A | N | I | | 1.5 | 0.09 | NC | 0 | 0 | NC | 0 |
| U27315 | "Mus musculus integral membrane phosphoprotein band | gene | A | N | I | * | 1.3 | 0.09 | NC | 0 | 0 | NC | 0.2 |
| D49730 | "Mus musculus adenine nucleotide translocase-1 (Ant1) m | gene | C | N | MI | * | 1.7 | 0.09 | NC | 0 | 0 | D | 1.4 | 0 |
| M21828 | "Mouse mRNA for V1a agrinine vasopression receptor, co | gene | D | N | I | * | 1.7 | 0.09 | NC | 0 | 0 | D | 1.1 | 0 |
| M38337 | "Mouse growth-arrest-specific (gas2) protein mRNA, com | gene | D | N | I | | 1.7 | 0.09 | MI | 1 | 0 | NC | 0 |
| V00836 | "Mouse milk fat globule membrane protein E8 mRNA, com | gene | D | N | I | | 1.3 | ~1.6 | 0.08 | * | ~3.4 | 0.67 | I | 2.10.4 |
| M38381 | Mouse mRNA encoding nerve growth factor (NGF) | gene | A | N | Z | * | * | 0.08 | I | ~2.0 | 0.2 | NC | 0 |
| M23529 | "Mouse serine threonine tyrosine kinase (STY) mRNA, com | gene | A | N | I | * | ~1.5 | 0.08 | I | 1.7 | 0.19 | NC | 0 |
| M17327 | "Mus musculus complement receptor (CRY) mRNA, comp | gene | A | N | I | | 1.4 | 0.08 | I | 1.7 | 0.18 | NC | 0 |
| W33728 | "Mouse endogeneous murine leukemia virus modified polyt | gene | D | N | I | | 1.5 | 1.3 | 0.08 | I | 1.5 | 0.16 | NC | 0 |
| W87078 | mc55h05.r1 Soares mouse embryo NbME13.5 14.5 Mus mus | est | D | N | I | * | * | 0.08 | I | 1.9 | 0.15 | NC | 0 |
| AA023107 | mf56g03.r1 Soares mouse embryo NbME13.5 14.5 Mus mu | est | D | N | I | | 1.6 | 0.08 | I | 1.9 | 0.14 | NC | 0 |
| Z36270 | mh66a12.r1 Soares mouse placenta 4NbMP13.5 14.5 Mus | est | B | N | I | | 1.6 | 0.08 | I | 1.9 | 0.14 | NC | 0 |
| U42190 | M. musculus mRNA for GC Binding Protein | gene | C | N | MI | * | ~1.6 | 0.08 | I | ~1.9 | 0.14 | NC | 0 |
| | "Mus musculus GiT-mismatch binding protein (Gtmbp) mP | gene | | | | | | | | | | | |

TABLE 6-continued

ISGs and IRGs identified from mouse embryonic fibroblast incubated
in the presence or absence of IFN-αBBDB in the presence or absence of
encephalomyocarditis virus

| | | /HLH/Z gene protein (Myn) RNA, complete c | A | N | I | 1.4 | 0.08 | I | 1.5 | 0.12 | NC | | |
|---|---|---|---|---|---|---|---|---|---|---|---|---|---|
| M63903 | "Mus musculus B | | | | | | | | | | | | |
| AA109831 | m198e04.r1 Stratagene mouse kidney (#9.37315) Mus musc | est | C | N | * | 0.08 | I | ~1.7 | 0.1 | I | 0 | 0 |
| W97919 | mg4c10.r1 Soares mouse embryo NbME13.5 14.5 Mus | est | A | N | I | 0.08 | I | ~1.5 | 0.09 | NC | 0 | 0 |
| X76850 | M. musculus mRNA for MAP kinase-activated protein kinase | gene | B | N | I | 0.08 | * | 1.5 | 0.09 | NC | 0 | 0 |
| AA137432 | mq81d03.r1 Stratagene mouse melanoma (#937312) Mus | est | D | N | * | 0.08 | I | ~1.5 | 0.09 | NC | 0 | 0 |
| W13304 | mb17c09.r1 Soares mouse p3NMF19.5 Mus musculus cD | est | D N | I | 1.5 | I | 1.4 | 0.06 | NC | 0 | 0 | | |
| AA000102 | mg31a08.r1 Soares mouse embryo NbME13.5 14.5 Mus | est | D | N | I | 0.08 | * | 1.4 | 0.06 | NC | 0 | 0 |
| L35034 | "Mus musculus ribose 5-phosphate isomerase (RPI) mRNA | gene | A | N | * | 0.08 | I | ~1.4 | 0.04 | NC | 0 | 0 |
| L05670 | "Mus musculus alpha-clustrin and beta-clustrin mRNA, com | gene | A | N | I | 0.08 | I | 1.5 | 0.04 | NC | 0 | 0 |
| X63039 | M. musculus RSP-1 mRNA for p33 protein | gene | C | N | I | 0.08 | I | 1.4 | 0.04 | NC | 0 | 0 |
| U20892 | "Mus musculus glycinamide ribonucleotide synthetase an | gene | C | N | MI | 0.08 | MI | 1.3 | 0.04 | NC | 0 | 0 |
| AA105716 | "mm66f07.r1 Stratagene mouse macrophage (#937306) M | est | C | N | MD | 0.08 | NC | ~1.5 | 0 | NC | 0 | 0 |
| AA137871 | mq75d01.r1 Stratagene mouse melanoma (#937312) Mus | est | C | N | * | 0.08 | NC | 1.3 | 0 | NC | 0 | 0.5 |
| AA044561 | "mj12g04.r1 Soares mouse embryo NbME13.5 14.5 Mus mus | est | A | N | I | 0.08 | NC | 1.7 | 0 | D | 1.7 | 0.1 |
| U13837 | "Mus musculus vacuolar adenosine triphosphatase subuni | gene | B | N | * | 0.08 | NC | 1.3 | 0 | MD | 1.5 | 0 |
| U51167 | "Mus musculus isocitrate dehydrogenease mRNA, complet | gene | B | N | I | 0.08 | NC | 1.5 | 0 | NC | 0 | 0 |
| 570056 | "zeta-crystallin [Mus musculus=mice, liver, mRNA, 2025 | gene | B | N | I | 0.08 | NC | 1.3 | 0 | NC | 0 | 0 |
| X65582 | M. musculus mRNA for alpha-2 collagen VI | gene | B | N | * | 0.08 | NC | 1.2 | 0 | D | 0.2 | 1.3 |
| Z31555 | M. musculus (129 Sv) bcte mRNA for CCT (chaperonin co | gene | B | N | I | 0.08 | NC | 1.3 | 0 | NC | 0 | 0 |
| M33934 | "Mouse IMP dehydrogenease mRNA, complete cds" | gene | C | N | MI | 0.08 | NC | 1.3 | 0 | NC | 0 | 0 |
| X63747 | M. musculus Zfp-38 mRNA | gene | D | N | I | 0.08 | NC | 1.6 | 0 | NC | 0 | 0 |
| U39192 | "Mus musculus heparin-binding epidermal growth factor-III | gene | D | N | I | 0.07 | I | 4.9 | 2.04 | I | 3.2 | 1.7 |
| X06746 | Mouse mRNA for Krox-20 protein containing zinc fingers | gene | D | N | * | 0.07 | I | 3.2 | 0.94 | I | 2.1 | 0.6 |
| AA146248 | m188g08.r1 Stratagene mouse melanoma (#937312) Mus | est | B | N | * | 0.07I | 2.9 | * | 0.41I | 1.7 | 0.1 | | |
| X82786 | M. musculus mRNA for Ki-67 | gene | B | N | * | 0.07 | * | ~2.4 | 0.32 | I | 1.6 | 0.1 |
| U19617 | "Mus musculus Ets-family transcription factor Elf-1 mRNA | gene | C | N | * | 0.07 | * | ~2.5 | 0.32 | MI | 1.6 | 0.1 |
| L10244 | "Mouse spermidine/spermine N1-acetyltransferase (SSAT) | gene | B | N | I | 0.07 | I | 1.7 | 0.28 | I | 1.3 | 0.1 |
| W29163 | mb96c11.r1 Soares mouse p3NMF19.5 Mus musculus cD | est | B | N | I | 0.07 | I | 1.8 | 0.26 | I | 1.3 | 0.1 |
| W61610 | md82e04.r1 Soares mouse embryo NbME13.5 14.5 Mus m | est | D | N | I | 0.07 | I | 1.9 | 0.2 | MI | 0.2 | 0 |
| X55318 | Mus musculus Hox-3.2 gene | gene | A | N | MI | 0.07 | I | 2.2 | 0.19 | MI | 1.3 | 0 |
| L04966 | "Mus musculus ras-related protein (rab18) mRNA, comple | gene | D | N | I | 0.07 | I | ~1.8 | 0.13 | NC | 0 | 0 |
| W78604 | m81g10.r1 Soares mouse embryo NbME13.5 14.5 Mus m | est | A | N | I | 0.07 | I | ~1.8 | 0.11 | NC | 0 | 0 |
| U18996 | "Mus musculus growth factor receptor binding protein (G | gene | A | N | I | 0.07 | I | 1.8 | 0.12 | NC | 0 | 0 |
| X89749 | M. musculus mRNA for mTGIF protein | gene | C | N | I | 0.07 | I | 1.6 | 0.11 | NC | 0 | 0 |
| AA111268 | mo53b03.r1 Life Tech mouse embryo 10 5dpc 10665Q16 M | est | C | N | * | 0.07 | * | ~1.6 | 0.1 | NC | 0 | 0 |
| AA049237 | "mj51a05.r1 Soares mouse embryo NbME13.5 14.5 Mus m | est | B | N | I | 0.07 | I | 1.4 | 0.1 | NC | 0 | 0 |
| W13646 | ma93f05.r1 Soares mouse p3NMF19.5 Mus musculus cD | est | D | N | I | 0.07 | I | 1.2 | 0.1 | NC | 0 | 0 |
| X99641 | M. musculus mRNA for HP1 alpha protein | gene | C | N | * | 0.07 | * | 1.7 | 0.08 | NC | 0 | 0 |
| AA028398 | "m120b02.r1 Soares mouse p3NMF19.5 Mus musculus cD | gene | D | N | I | 0.07 | I | 1.3 | 0.08 | NC | 0 | 0 |
| AA120290 | mn16c06.r1 Beddington mouse embryonic region Mus musc | est | B | N | I | 0.07 | I | 1.4 | 0.04 | NC | 0 | 0 |
| W51237 | M. musculus mRNA for proteinase activated receptor 2 | est | A | Y | I | 0.07 | I | 1.2 | 0.03 | NC | 0 | 0 |
| Z48043 | | gene | B | N | * | 0.07 | NC | ~1.5 | 0 | NC | 0 | 0 |
| AA033424 | m136b07.r1 Soares mouse embryo NbME13.5 14.5 Mus m | est | A | N | I | 0.07 | NC | 1.4 | 0 | NC | 0 | 0 |

TABLE 6-continued

ISGs and IRGs identified from mouse embryonic fibroblast incubated
in the presence or absence of IFN-αBBDB in the presence or absence of
encephalomyocarditis virus

| | | | | | | | | | | | | | |
|---|---|---|---|---|---|---|---|---|---|---|---|---|---|
| W61804 | md82a07.r1 Soares mouse embryo NbME13.5 14.5 Mus m | est | A | Y | MI | * | −1.4 | 0.07 | MI | * | −1.0 | 0 | 0 |
| W62643 | "nm96e05.r1 Stratagene mouse heart (#037316) Mus musc | est | A | N | I | | −1.6 | 0.07 | NC | | 0 | 0 | 0 |
| AA073679 | M. musculus mRNA for C/EBP delta | est | A | N | MI | | 1.5 | 0.07 | NC | | 0 | 0 | 0.1 |
| X61800 | mn44b12.r1 Stratagene mouse melanoma (#937312) Mus | gene | B | N | MI | | 1.3 | 0.07 | MC | | 0 | 1.4 | 0.1 |
| AA067929 | "Mus musculus Golgi 4-transmembrane spanning transport | est | C | N | I | * | 1.5 | 0.07 | NC | | 0 | 1.3 | 0 |
| U34259 | "Mus musculus CTP synthetase homolog (CTPsH) mRNA, | gene | C | N | MI | | 1.2 | 0.07 | NC | | 0 | 0 | 0 |
| U49385 | "Mouse mRNA for STK-1 (serine/threonine kinase), compl | gene | C | N | I | | 1.6 | 0.07 | NC | | 0 | 0 | 0 |
| D21099 | nd89D9.r1 Soares mouse embryo NbME13.5 14.5 Mus m | gene | C | N | I | * | 1.5 | 0.07 | NC | | 0 | 0 | 0 |
| W64791 | ms10c1.r1 Stratagene mouse skin (#937313) Mus muscu | est | D | N | I | | 1.3 | 0.06 | I | | 1.1 | 0 | 0 |
| AA14516 | "Mus musculus parathion hydrolase (phosphotriesterase)- | est | A | N | I | | 1.6 | 0.06 | I | | 2.3 | 1.7 | 0.4 |
| U28016 | "Mouse YL-1 mRNA for YL-1 protein (nuclear protein with | gene | C | N | I | * | 1.5 | 0.06 | I | | 2.7 | 0 | 0 |
| D43643 | me94b11.r1 Soares mouse embryo NbME13.5 14.5 Mus m | est | D | N | I | | 1.4 | 0.06 | I | * | 2.2 | 0 | 0 |
| W54228 | "Mus musculus autoantigene La (SS-B) mRNA, complete cd | gene | D | N | MI | | −1.5 | 0.06 | I | | 1.9 | 0 | 0 |
| L00093 | "Mus musculus homeobox protein (Hoxa11) gene, comple | gene | B | N | I | | 1.6 | 0.06 | I | * | −2.0 | 0 | 0 |
| U20371 | M. musculus keratinocyte growth factor Fgf-7 | est | B | N | I | * | −1.4 | 0.06 | I | | 0.17 | 1.3 | 0 |
| Z22703 | "Mouse mRNA for MDA1, complete cds" | gene | A | N | I | * | −1.5 | 0.06 | I | | 0.16 | 0 | 0 |
| D63784 | "Mus musculus thymidylate synthase mRNA, complete cds" | est | C | N | I | | 1.3 | 0.06 | I | | −1.9 | 0 | 0 |
| M13019 | mf42d05.r1 Soares mouse embryo NbME13.5 14.5 Mus mu | est | D | N | I | | 1.6 | 0.06 | I | | −1.7 | 0 | 0 |
| W85270 | "Mouse cytoskeletal gamma-actin mRNA, complete cds" | est | A | N | I | | 1.5 | 0.06 | I | | 1.5 | 0 | 0 |
| M21495 | "Mouse binding protein 13 (Fkbp13)gene exons 1–5, com | gene | D | N | I | | 1.3 | 0.06 | I | | 1.4 | 0 | 0 |
| M77831 | "Mus musculus ICH-3 mRNA, complete cds" | gene | C | N | I | | 1.4 | 0.06 | I | | 1.2 | 0 | 0 |
| U59463 | "House mouse; Musculus domesticus mRNA for 14-3-3 et | est | C | N | I | * | 1.5 | 0.06 | MI | * | 1.5 | 0 | 0 |
| D87661 | "Mus musculus long-chain acyl-COA dehydrogenease mRN | est | B | N | I | | 1.3 | 0.06 | I | | 1.5 | 0 | 0 |
| U21489 | ma52dD7.r1 Soares mouse p3NMF19.5 Mus musculus cD | gene | D | N | I | | 1.4 | 0.06 | I | | 1.3 | 0 | 0 |
| W12720 | "Mouse small nuclear RNA (Rnu1a-1) mRNA, complete cd | est | D | N | I | * | −1.4 | 0.06 | I | | 1.4 | 0 | 0 |
| L15447 | "Mouse myosin 1 mRNA, complete cds" | gene | D | N | MD | 1.3 | 0.06 | 1 | | NC | 0 | −1.3 | 0 | 0 |
| AA163866 | mj63c07.r1 Life Tech mouse embryo 13 5dpc 10666014 M | est | B | N | MD | | 1.4 | 0.06 | D | 0 | NC | 0.01 | 0 | 0 |
| L00923 | mj63c07.r1 Soares mouse p3NMF19.5 Mus musculus cDN, | gene | A | N | I | * | 1.6 | 0.06 | NC | | 1.1 | 0 | 0 |
| AA059550 | mj67g07.r1 Soares mouse p3NMF19.5 Mus musculus cDN | est | A | N | MI | | 1.4 | 0.06 | NC | * | 0 | 0 | 0 |
| AA064330 | mo60a10.r1 Stratagene mouse Tcell 937311 Mus muscul | est | A | N | MI | * | 1.4 | 0.06 | MI | | 0 | 0 | 0 |
| U17132 | Mouse mRNA for ubiquitin activating enzyme E1 | gene | A | N | I | | 1.5 | 0.06 | I | | 0 | 0 | 0 |
| AA117106 | M. musculus (C57B1/6) Tyro 10 mRNA | est | B | N | I | | 1.2 | 0.06 | NC | * | 0 | 0 | 0 |
| D10576 | mc63b06.r1 Soares mouse embryo NbME13.5 14.5 Mus m | gene | B | N | I | | 1.4 | 0.06 | NC | | 0 | 0 | 0 |
| X76505 | mp74d03.r1 Soares mouse 2NbMT Mus musculus cDNA clone 574 | gene | B | N | I | * | 1.6 | 0.06 | NC | * | 0 | 1.7 | 0.4 |
| M84145 | "Mus musculus type II hair keratin mRNA, 3' end" | gene | A | N | I | | 1.5 | 0.06 | NC | | 0 | 0 | 0 |
| W41745 | "Mouse helix-loop-helix DNA binding protein regulator (Id) | gene | A | N | I | | 1.5 | 0.06 | NC | | 0 | 0 | 0 |
| AA124985 | "Mouse platelet-derived growth factor-inducible KC protein | gene | D | N | I | | 1.3 | 0.05 | I | | 3.8 | 2.9 | 2 |
| M92088 | ma44f11.r1 Soares mouse p3NMF19.5 Mus musculus cDN | est | D | N | I | | −1.5 | 0.05 | I | | −2.8 | 0.4 | 0 |
| M31885 | "M. musculus G protein beta-subunit mRNA, complete cds | gene | A | C | MD | | 1.2 | 0.05 | D | * | 1.5 | 1.3 | 0.1 |
| J04596 | M. musculus CDNap14 mRNA | gene | C | N | I | * | −1.5 | 0.05 | I | | 2 | 1.4 | 0.1 |
| W10459 | "Mus musculus histidyl-mRNA synthetase mRNA, complete | gene | C | N | I | | 1.4 | 0.05 | D | | 1.3 | 1.5 | 0.4 |
| M63658 | mf85c05.r1.Soares mouse embryo NbME13.5 14.5 Mus m | gene | B | Y | I | * | 1.6 | 0.05 | MI | * | 1.6 | 0 | 0 |
| X57337 | me03a03.r1 Soares mouse embryo NbME13.5 14.5 Mus | est | A | N | I | | 1.4 | 0.05 | I | | 1.4 | 0 | 0 |
| U39473 | ms15b04.r Stratagene mouse skin (#937313) Mus muscu | est | B | N | MD | | −1.3 | 0.05 | MC | * | −1.3 | 0 | 0 |
| AA022254 | | est | D | N | D | | −1.4 | 0.05 | MC | * | −1.4 | 0 | 0 |

TABLE 6-continued

ISGs and IRGs identified from mouse embryonic fibroblast incubated in the presence or absence of IFN-αBBDB in the presence or absence of encephalomyocarditis virus

| Accession | Description | Type | Col1 | Col2 | Col3 | Col4 | Col5 | Col6 | Col7 | Col8 | Col9 | Col10 |
|---|---|---|---|---|---|---|---|---|---|---|---|---|
| D14883 | "Mouse mRNA for C33/R2/IA4, complete cds" | gene | A | N | I | * | 1.5 | 0.05 | I | * | 1.3 | 0 |
| AA036574 | "m169e05.r1 Soares mouse embryo NbME13.5 14.5 Mus mu | est | A | N | I | | 1.4 | 0.05 | 0.05 | 1.1 | NC | 0.01 NC |
| U46187 | "Mus musculus KRAB-containing zinc finger protein mRNA | gene | C | N | MI | * | 1.4 | 0.05 | NC | 0 | NC | * 0 |
| AA114623 | mm16d09.r1 Beddington mouse embryonic region Mus mu | est | C | N | I | * | 0.05 | | | NC | NC | * |
| AA153522 | ms61h12.r1 Stratagene mouse embryonic carcinoma (#9 | est | D | N | I | ~1.4 | ~1.6 | 0.05 | NC | 0 | I | * 1.3 |
| L11739 | "Mus musculus homeobox HOX8.1 (Msx2) gene, exon 2 | gene | A | N | MD | * | 1.5 | 0.05 | NC | 0 | NC | 0 |
| U34691 | "Mus musculus uroporphyrinogene decarboxylase mRNA, c | gene | A | N | I | | 1.3 | 0.05 | NC | 0 | NC | 0 |
| AA002979 | mg41c04.r1 Soares mouse embryo NbME13.5 14.5Mus mu | est B | N | I | 1.4 | 0.05 | NC | NC | 0 | 0 | | |
| AA062342 | ml35h10.r1 Stratagene mouse testis (#937308) Mus musc | est B | N | I | ~1.4 | 0.05 | NC | * | 0 | 0 | | |
| Z38015 | "M. musculus DMR-N9 gene, exons 4 and 5, and DM-Pk g | gene | B | N | I | * | 1.5 | 0.05 | NC | 0 | D | ~2.4 0.3 |
| Y00225 | "Murine mRNA for J1 protein, yeast ribosomal protein L3 | gene | B | N | MD | * | 1.1 | 0.05 | NC | 0 | D | 2 0.2 |
| U53455 | "Mus musculus chloride ion current inducer protein (CLCI) | gene | C | N | I | | 1.4 | 0.05 | NC | 0 | NC | 0 0 |
| U49350 | "Mus musculus CTP synthetase mRNA, complete cds" | gene | C | N | MI | | 1.4 | 0.05 | NC | 0 | NC | 0 0 |
| AA087605 | mm88e09.r1 Stratagene mouse embryonic carcinomaRA ( | est | C | N | I | | 1.3 | 0.05 | NC | 0 | NC | 0 0 |
| AA098588 | mm83h08.r1 Stratagene mouse Tcell 937311 Mus muscul | est | C | N | I | * | ~1.5 | 0.05 | NC | 0 | NC | 0 0 |
| Y07711 | M. musculus mRNA for zyxin | gene | C | N | I | | 1.2 | 0.05 | NC | 0 | D | 1.2 0.1 |
| L24755 | "Mus musculus bone morphogenetic protein (Bmp-1) mR | gene | D | N | MI | | 1.3 | 0.05 | NC | 0 | NC | 0 0 |
| W13739 | "mb32b10.r1 Soares mouse p3NMF19.5 Mus musculus cDN | est | D | N | I | | 1.6 | 0.05 | NC | 0 | NC | 0 |
| J05265 | "Mouse interferon gamma receptor mRNA, complete cds" | gene | D | N | MI | | 1.4 | 0.05 | NC | 0 | NC | 0 |
| W71881 | me45h01.r1 Soares mouse embryo NbME13.5 14.5 Mus m | est | D | N | I | * | 1.4 | 0.05 | NC | 0 | I | * 1.7 0.2 |
| M81477 | "Mouse cytoplasmic phosphotyrosine phosphatase mRNA, | gene | D | N | MI | | 1.3 | 0.04 | I | * | I | * 1.3 0.2 |
| L15429 | "Mus musculus L6 antigene mRNA, complete cds" | gene | B | N | MI | | 1.2 | 0.04 | 2.4 | 0.29 | NC | 0 |
| X66295 | M. musculus mRNA for C1q C-chain. | gene | B | N | I | * | ~1.3 | 0.04 | 1.5 | 0.28 | NC | 0 |
| M58691 | "Mouse growth factor-inducible protein mRNA, complete( | gene | A | N | I | | 1.3 | 0.04 | ~2.2 | 0.24 | NC | * 0 |
| D38517 | "Mouse mRNA for Dhm1 protein, complete cds" | gene | B | N | I | | 1.4 | 0.04 | 1.9 | 0.23 | NC | 0 |
| M27073 | "Mus musculus protein phosphatase type 1 (dis2m2) mF | gene | D | N | I | | 1.2 | 0.04 | 1.7 | 0.11 | NC | 0 |
| W42216 | mc69h11.r1 Soares mouse embryo NbME13.5 14.5 Mus m | est | D | N | MI | * | ~1.5 | 0.04 | ~1.9 | 0.11 | NC | * 0 |
| AA146437 | mr05a08.r1 Soares mouse 3NbMS Mus musculus cDNA clo | est | B | N | I | | 1.3 | 0.04 | 1.6 | 0.1 | NC | * 0 |
| X13752 | Murine mRNA for delta-aminolevulinate dehydratase (EC | gene | B | N | I | * | ~1.3 | 0.04 | ~1.4 | 0.06 | NC | * 0 |
| M63660 | "Mouse G-alpha-13 protein mRNA, complete cds" | gene | D | N | I | | 1.3 | 0.04 | 1.3 | 0.05 | NC | 0 |
| M76987 | Mouse alpha-globin transcription factor CP2 mRNA sequen | gene | D | N | I | | ~1.3 | 0.04 | ~1.4 | 0.05 | MD | * 1.1 0.4 |
| M25513 | "Mouse rod transducin alpha subunit (Tr-alpha) gene, exo | gene | A | N | MD | * | ~1.4 | 0.04 | 1.3 | 0.02 | D | 2.3 0 |
| W08715 | mb51a12.r1 Soares mouse p3NMF19.5 Mus musculus cD | est | A | N | MI | | ~1.4 | 0.04 | 0 | 0 | NC | 0 0 |
| AA067335 | mm39e02.r1 Soares mouse embryo melanoma (#9.37312) Mu | est | C | N | I | | ~1.4 | 0.04 | 0 | 0 | D | 1.3 0.1 |
| W11011 | ma47a11.r1 Soares mouse embryo p3NMF19.5 Mus musculus cD | est | C | N | MI | | 1.4 | 0.04 | 0 | 0 | MC | * 1.5 0.1 |
| AA061225 | ml31b12.r1Soares mouse embryo NbME13.5 14.5 Mus m | est | A | N | MI | | 1.4 | 0.04 | 0 | 0 | MC | 1.2 0 |
| AA059517 | mj61c11.r1 Soares mouse embryo NbME13.5.14.5 Mus m | est | A | N | MI | | 1.4 | 0.04 | 0 | 0 | D | 1.3 0.2 |
| AA008043 | mg68e02.r1 Soares mouse embryo NbME13.5 14.5 Mus m | est | A | N | I | | 1.2 | 0.04 | 0 | 0 | NC | 0 0 |
| U25995 | "Mus musculus cell death protein (RIP) mRNA, complete c | gene | A | N | I | * | ~1.5 | 0.04 | 0 | 0 | NC | 0 0 |
| U29173 | "Mus musculus lymphotoxin-beta receptor mRNA, comple | gene | A | N | I | | ~1.4 | 0.04 | 0 | 0 | NC | 0 0 |
| D37801 | Mouse mRNA for protein tyrosine phosphatase | gene | A | N | I | | 1.1 | 0.04 | 0 | 0 | NC | 0 0 |
| L21027 | "Mus musculus TR2 (mTR2) mRNA, partial cds" | gene | A | N | MI | * | ~1.3 | 0.04 | 0 | 0 | NC | 0 0 |
| U30482 | mg54g06.r1 Soares mouse embryo NbME13.5 14.5 Mus mL | est | B | N | I | | 1.3 | 0.04 | 0 | 0 | NC | 0 0 |
| AA002437 | "Mus musculus collagene type XII alpha-1 precursor (Col12 | gene | B | N | I | * | 1.4 | 0.04 | 0 | 0 | NC | 0 0 |
| U25652 | Murine mRNA for neuroendocrine protein 7B2 | gene | B | N | I | | 1.4 | 0.04 | 0 | 0 | NC | 0 0 |
| X15830 | M. musculus siah-2 protein mRNA | gene | C | N | MI | | 1.3 | 0.04 | 0 | 0 | MC | 1.4 0.1 |
| ZI9581 | | | | | | | | | | | | |

TABLE 6-continued

ISGs and IRGs identified from mouse embryonic fibroblast incubated
in the presence or absence of IFN-αBBDB in the presence or absence of
encephalomyocarditis virus

| ID | Description | Type | | | | | | | | | | | | |
|---|---|---|---|---|---|---|---|---|---|---|---|---|---|---|
| J02995 | "Mouse.testis-specific c-abl protein mRNA, complete cds" | gene | D | N | I | | 1.3 | 0.04 | NC | | 0 | 0 | NC | 0 | 0 |
| W29462 | mb99b12.r1 Soares mouse p3NMF19.5 Mus musculus cD | est | D | N | I | | 1.3 | 0.04 | NC | | 0 | 0 | NC | 0 | 0 |
| J05205 | "Mouse junD proto-oncogene mRNA, complete cds" | gene | D | N | MI | 1.2 | 0.04 | NC | 0 | D | 0 | D | | 1.3 | 0.2 |
| X57796 | Mouse mRNA for 55-kDa tumor necrosis factor receptor | gene | D | N | I | | 1.2 | 0.04 | NC | | 0 | 0 | NC | 0 | 0 |
| AA114781 | mn14h10.r1 Beddington mouse embryonic region Mus mu | est | D | N | I | * | −1.3 | 0.03 | I | * | −2.6 | 0.35 | NC | 0 | 0.2 |
| AA170223 | ms60f01.r1 Stratagene mouse embryonic carcinoma (#937 | est | D | N | I | * | −1.3 | 0.03 | I | * | −2.4 | 0.33 | I | 2 | 0 |
| AA027739 | mi14g01.r1 Soares mouse p3NMF19.5 Mus musculus cDNA | est | D | N | I | | 1.3 | 0.03 | I | | 2 | 0.28 | I | 1.5 | 0.2 |
| M37759 | "Mouse serine 1 ultra high sulfur protein gene, complete ( | gene | A | N | MI | | 1.3 | 0.03 | I | | 1.8 | 0.15 | NC | 0 | 0 |
| W33550 | mc52f06.r1 Soares mouse embryo NbME13.5 14.5 Mus mu | est | D | N | I | | 1.2 | 0.03 | I | | 1.4 | 0.07 | NC | 0 | 0 |
| D90173 | "Mouse mRNA for NfJ-B protein, clone NfJ-B2" | gene | C | N | I | * | 1.3 | 0.03 | I | | 1.4 | 0.06 | NC | 0 | 0 |
| D12644 | "Mouse mRNA for KIF2 protein, complete cds" | gene | B | N | I | * | −1.3 | 0.03 | I | | −1.4 | 0.05 | NC | 0 | 0 |
| AA108956 | mp41e04.r1 Barstead MPLRB1 Mus musculus cDNA clone | est | B | N | I | | 1.2 | 0.03 | I | | 1.2 | 0.04 | NC | 0 | 0 |
| X58069 | Mouse mRNA for Histone H2A.X | gene | D | N | I | | 1.2 | 0.03 | I | | 1.2 | 0.04 | NC | 0 | 0 |
| M35662 | "Mouse placental lactogene I (PL-I) mRNA, complete cds" | gene | D | N | D | * | −1.3 | 0.03 | MD | * | −1.3 | 0.03 | NC | 0 | 0 |
| U72141 | "Mus musculus multiple exostoses 2 protein (EXT2) mRN | gene | C | N | I | | 1.2 | 0.03 | I | | 1.2 | 0.03 | NC | 0 | 0 |
| AA142796 | mq63e08.r1 Soares 2NbMT Mus musculus cDNA clone 58 | est | D | N | I | * | 1.3 | 0.03 | I | | 1.3 | 0.02 | NC | 0 | 0.3 |
| U10903 | "Mus musculus zinc finger protein (RP-8) mRNA, complete | gene | A | N | I | | 1.3 | 0.03 | I | | 1.1 | 0.01 | NC | 0 | 0 |
| AA105509 | mo57b06.r1 Life Tech mouse embryo 8 5dpc 10664019 M | est | D | N | I | * | −1.3 | 0.03 | I | | −1.1 | 0.01 | NC | 0 | 0 |
| U10871 | "Mus musculus MAP kinase mRNA, complete cds" | gene | C | N | I | | 1.3 | 0.03 | MI | | 1.2 | 0.01 | NC | 0 | 0 |
| W12919 | ma89f02.r1 Soares mouse p3NMF19.5 Mus musculus cDN | est | D | N | I | * | 1.2 | 0.03 | I | | 1.1 | 0.01 | NC | 0 | 0 |
| W77226 | me63e01.r1 Soares mouse embryo NbME13.5 14.5 Mus m | est | D | N | I | | 1.4 | 0.03 | I | | 1.2 | 0.01 | NC | 0 | 0 |
| AA166391 | ms39n09.r1 Life Tech mouse embryo 13 5dpc 0666014 | est | D | N | I | | −1.2 | 0.03 | I | | −1.0 | 0 | NC | * | 0 |
| D17630 | "Mouse mRNA for interleukin-8 receptor (IL-8R), complet | gene | D | N | MD | * | 1.2 | 0.03 | NC | * | 0 | 0 | NC | * | 0 |
| AA068780 | mmt64g04.r1 Stratagene mouse embryonic carcinoma (#937 | est | A | N | I | | 1.3 | 0.03 | NC | | 0 | 0 | D | 1.7 | 0.3 |
| M74773 | "Mus musculus brain beta spectrin (Spnb-2) mRNA, comp | gene | A | N | MI | * | 1.3 | 0.03 | NC | | 0 | 0 | NC | 0 | 0 |
| W66781 | me17c12.r1 Soares mouse embryo NbME13.5 14.5 Mus m | est | A | N | I | | 1.4 | 0.03 | NC | | 0 | 0 | D | 1.2 | 0.1 |
| 75918 | me82f05.r1 Soares mouse embryo NbME13.5 14.5 Mus mu | est | A | N | I | | 1.3 | 0.03 | NC | | 0 | 0 | NC | 0 | 0 |
| AA063985 | mj31c01.r1 Soares mouse embryo NbME13.5 14.5 Mus mu | est | A | N | I | | 1.3 | 0.03 | I | | −1.0 | 0 | NC | 0 | 0 |
| D49956 | "Mouse mRNA for 8-oxo-dGTPase, complete cds" | gene | A | N | I | | 1.2 | 0.03 | NC | | 0 | 0 | D | 2.6 | 0.4 |
| D38023 | Mouse PIMT mRNA | gene | A | N | I | | 1.4 | 0.03 | NC | | 0 | 0 | D | 1.60.1 | |
| U28807 | "Mus musculus lymphoid-specific transcription factor NFA | gene | B | N | I | | −1.3 | 0.03 | NC | | 0 | 0 | NC | 0 | 0 |
| AA014656 | "mg93g08.r1 Soares mouse embryo NbME13.5 14.5 Mus mu | est | B | N | I | * | −1.3 | 0.02 | I | | −2.3 | 0.21 | MI | 1.9 | 0.2 |
| U04204 | "Mus musculus BALB/c aldose reductase-related protein | gene | B | N | MI | | −1.2 | 0.02 | I | | 1.8 | 0.21 | I | 1.5 | 0.2 |
| AA068350 | mm55c11.r1 Stratagene mouse embryoic carcinoma (#937 | est | B | N | I | | −1.2 | 0.02 | I | | 1.6 | 0.17 | NC | 1.4 | 0.1 |
| AA068847 | mm64a09.r1 Stratagene mouse embryonic carcinoma (#93 | est | C | N | MI | | −1.2 | 0.02 | I | | −1.8 | 0.12 | I | 0 | 0 |
| AA050733 | mj16h08.r1 Soares mouse embryoNbME13.5 14.5 Mus mu | est | A | N | I | | −1.2 | 0.02 | I | | −1.9 | 0.12 | I | 1.5 | 0.1 |
| L33416 | "Mouse (clone p85) secreted protein mRNA, complete cds" | gene | D | N | I | | −1.3 | 0.02 | I | | −1.7 | 0.11 | NC | 0 | 0 |
| AA041826 | mj07d08.r1 Soares mouse embryo NbME13.5 14.5 Mus mu | est | D | N | I | | −1.3 | 0.02 | I | | −1.6 | 0.08 | I | 0 | 0 |
| W18778 | mc05e01.r1 Soares mouse p3NMF19.5 Mus musculus cD | est | D | N | I | | −1.2 | 0.02 | MI | | −1.6 | 0.07 | NC | 0 | 0 |
| AA023591 | mh80b01.r1 Soares mouse placenta 4NbMP13.5 14.5 Mu | est | C | N | I | | −1.2 | 0.02 | MI | | 1.5 | 0.06 | NC | 0 | 0 |
| L29479 | "Mus musculus serine/threonine kinase (sak-a) mRNA, co | gene | C | N | I | * | 1.3 | 0.02 | I | | −1.3 | 0.03 | NC | * | 0 |
| L07101 | "Mus musculus HMG box protein mRNA, complete cds" | gene | A | N | I | | 1.3 | 0.02 | I | | 1.3 | 0.03 | NC | 0 | 0 |
| AA125097 | p77d04.r1 Soares 2NbMT Mus musculus cDNA clone 57 | est | B | Y | I | | −1.2 | 0.02 | I | | | | | | |
| U50734 | "Mus musculus maternal transcript Maid (Maid) mRNA, co | gene | | | | | | | | | | | | | |
| L08266 | "Mouse Facc mRNA, complete cds" | gene | | | | | | | | | | | | | |
| AA108891 | m156c09.r1 Stratagene mouse testis (#937308) Mus muscu | est | | | | | | | | | | | | | |
| W55077 | | est | | | | | | | | | | | | | |
| AA117227 | mo62h09.r1 Stratagene mouse Tcell 937311 Mus musculu | est | | | | | | | | | | | | | |

TABLE 6-continued

ISGs and IRGs identified from mouse embryonic fibroblast incubated in the presence or absence of IFN-αBBDB in the presence or absence of encephalomyocarditis virus

| | | | | | | | | | | | | |
|---|---|---|---|---|---|---|---|---|---|---|---|---|
| AA118162 | mn12f11.r1 Beddington mouse embryonic region Mus mus | est | D | N | I | 1.1 | 0.02 | I | 1.2 | 0.03 | NC | 0 | 0 |
| AA154734 | mr32c06.r1 Soares mouse 3NbMS Mus musculus cDNA c | est | D | N | I | ~1.2 | 0.02 | MI | ~1.2 | 0.02 | NC | * | 0 | 0 |
| U07950 | "Mus musculus BALB/c GbP-dissociation inhibitor (GDI-1) | gene | C | Y | MD | ~1.2 | 0.02 | I | 1.2 | 0.02 | NC | * | 0 | 0 |
| W49039 | | est | A | N | I | ~1.2 | 0.02 | NC | * | 0 | NC | * | 0 | 0.3 |
| W82852 | me93c07.r1 Soares mouse embryo NbME13.5 14.5 Mus m | est | A | N | I | ~1.2 | 0.02 | NC | * | 0 | MC | * | ~2.4 | 0 |
| W78500 | me78h04.r1 Soares mouse embryo NbME13.5 14.5 Mus m | est | A | N | D | ~1.2 | 0.02 | NC | * | 0 | NC | * | 0 | 0 |
| AA036546 | mi50f02.r1 Soares mouse embryo NbME13.5 14.5 Mus m | est | B | N | I | ~1.1 | 0.02 | NC | * | 0 | NC | * | 0 | 0 |
| W81967 | me93h03.r1 Soares mouse embryo NbME13.5 14.5. Mus m | est | B | N | I | ~1.2 | 0.02 | NC | * | 0 | D | * | 2.1 | 0.2 |
| AA064467 | mi49c07.r1 Stratagene mouse testis (#937308) Mus muscul | est | B | N | I | ~1.2 | 0.02 | NC | * | 0 | NC | * | 0 | 0 |
| AA065689 | mn43d07.r1 Stratagene mouse melanoma (#937312) Mus | est | C | N | MI | ~1.2 | 0.02 | NC | * | 0 | NC | * | 0 | 0 |
| M73061 | "Mouse macrophage inflammatory protein-1-alpha gene, c | gene | D | N | D | ~1.2 | 0.02 | NC | * | 0 | I | * | ~1.8 | 0.1 |
| L19311 | | gene | A | N | MI | 1.1 | 0.02 | NC | * | 0 | NC | * | 0 | 0 |
| W61805 | "Mouse spermidine synthase mRNA, complete cds" | est | A | Y | I | ~1.2 | 0.02 | NC | * | 0 | NC | * | 0 | 0 |
| U51866 | | gene | A | N | I | 1.2 | 0.02 | I | 1 | 0 | D | * | 1.3 | 0.1 |
| W64759 | "md89d07.r1 Soares mouse embryo NbME13.5 14.5 Mus m | est | A | N | I | ~1.2 | 0.02 | NC | * | 0 | NC | * | 0 | 0 |
| AA060187 | m65d07.r1 Soares mouse embryo 3NMF19.5 Mus musculus cDNA | est | B | N | I | 1.2 | 0.02 | NC | * | 0 | NC | * | 0 | 0 |
| X65026 | M. musculus mRNA for GTP-binding protein | gene | C | N | I | 1.1 | 0.02 | I | 1 | 0 | NC | * | 0 | 0 |
| AA170104 | ms49a04.r1 Life Tech mouse embryo 13 5dpc 1666014 | est | C | N | I | 1.2 | 0.02 | NC | * | 0 | NC | * | 0 | 0 |
| U68564 | "Mus musculus NAD(H)-specific isocitrate dehydrogenase | gene | D | N | MI | 1.1 | 0.02 | I | 1 | 0 | NC | * | 0 | 0 |
| AA034842 | mi52f10.r1 Soares mouse embryo NbME13.5 14.5 Mus mu | est | D | N | MI | 1.2 | 0.02 | NC | * | 0 | NC | * | 0 | 0 |
| AA061624 | mj90h11.r1 Soares mouse embryo p3NMF19.5 Mus musculus cDNA | est | D | NI | * | 0.01 | I | 0.49 | I | 2.5 | 0.5 |
| M69293 | "Mouse Id2 protein (Id-2) mRNA, 3' end" | gene | A | N | I | 1.2 | 0.01 | I | 2.5 | 0.43 | NC | * | 0 | 0 |
| D00613 | Mouse mRNA for matrix Gla protein (MGP) | gene | D | N | MI | 1.1 | 0.01 | I | 1.3 | 0.15 | I | * | 1.3 | 0.2 |
| W34891 | md62g05.r1 Soares mouse embryo NbME13.5 14.5 Mus m est | D | N | * | ~1.1 | 0.01 | * | 0.11 | NC | 0 | 0 |
| M85078 | "Mus musculus granulocyte-macrophage colony stimulatir | gene | D | N | I | ~1.1 | 0.01 | ~1.6 | 0.06 | NC | * | 0 | 0 |
| X13664 | Mouse mRNA for N-ras protein (exons 1–6 part) | gene | A | N | MD | ~1.1 | 0.01 | I | * | 0 | 0.06 | NC | * | 0 | 0 |
| AA142505 | mq56h11.r1 Soares mouse 2NbMT Mus musculus cDNA clone 58 | est | C | N | I | ~1.2 | 0.01 | I | 1.6 | 0.06 | NC | * | 0 | 0 |
| AA161905 | mn41f03.r1 Beddington mouse embryonic region Mus mus | est | B | N | I | ~1.2 | 0.01 | MI | 1.6 | 0.06 | NC | * | 0 | 0 |
| M59821 | "Mouse growth factor-inducible protein (pip92) mRNA, co | gene | A | N | I | ~1.2 | 0.01 | I | ~1.4 | 0.05 | NC | * | 0 | 0 |
| U44795 | "Mus musculus coagulation factor VII (fVII) mRNA,compl | gene | B | N | MI | 1.2 | 0.01 | MI | 1.3 | 0.04 | NC | * | 0 | 0 |
| W33538 | "mc52e02.r1 Soares mouse embryo NbME13.5 14.5 Mus est | D | N | D | ~1.1 | 0.01 | * | ~1.4 | 0.03 | NC | * | 0 | 0 |
| M37335 | "Mouse myelin proteolipid protein gene, exon 7, clones la | gene | B | N | I | ~1.2 | 0.01 | NC | * | 0 | NC | 0 | 0 |
| M89798 | "Mouse Wnt-5a mRNA, complete cds" | gene | A | N | I | ~1.1 | 0.01 | NC | * | ~1.0 | I | * | 2.7 | 0.4 |
| W59472 | md61c06.r1 Soares mouse embryo NbME13.5 14.5 Mus m | est | A | N | MD | ~1.3 | 0.01 | NC | * | 0 | NC | * | 0 | 0 |
| W98496 | mg13c10.r1 Soares mouse embryo NbME13.5 14.5 Mus m | est | A | N | I | ~1.2 | 0.01 | I | ~1.0 | NC | * | 0 | 0 |
| L37297 | Mus musculus (clone B6) myeloid secondary granule prote | gene | B | N | I | ~1.1 | 0.01 | MI | 1.6 | 0 | NC | * | 0 | 0 |
| AA041873 | mj05c12.r1 Soares mouse embryo NbME13.514.5 Mus mu | est | B | N | I | 1.2 | 0.01 | I | ~1.4 | 0 | NC | * | 0 | 0 |
| U49391 | Mos musculus nucleotide-gated olfactory channel | est | C | N | D | ~1.1 | 0.01 | MI | 1.3 | 0 | NC | * | 0 | 1.40.1 |
| AA169961 | ms48c08.r1 Life Tech mouse embryo 13 5dpc 10666014 M | gene | A | N | I | ~1.1 | 0.01 | * | ~1.4 | 0 | NC | * | 0 | 0 |
| M96823 | "Mouse nucleobindin mRNA, complete cds" | gene | A | N | I | ~1.2 | 0.01 | NC | * | ~1.1 | 0 | NC | 0 | 0 |
| D31842 | "Mouse mRNA for putative protein tyrosine phosphatase | gene | A | N | I | ~1.2 | 0.01 | NC | 0 | D | * | 0 | 0 |
| W85163 | mf37c09.r1 Soares mouse embryo NbME13.5 14.5 Mus m | est | A | N | I | 1.2 | 0.01 | NC | * | 0 | I | * | 0 | 0 |
| U53696 | "Mus musculus class II cytokine receptor 4 (CRF2-4) mRN | gene | B | N | I | 1.1 | 0.01 | I | 0 | 0 | NC | * | 0 | 0 |
| X06340 | Mouse mRNA for P-cadherin | gene | B | N | MI | 1.2 | 0.01 | NC | * | 0 | NC | * | 0 | 0 |
| X63440 | M. musculus mRNA for P19-protein tyrosine phosphatase | gene | B | N | I | ~1.1 | 0.01 | NC | * | 0 | NC | * | 0 | 0 |
| L40632 | "Mus musculus epithelial ankyrin 3 (7kb isoform) mRNA, c | gene | C | N | D | ~1.1 | 0.01 | NC | * | 0 | NC | * | 0 | 0 |
| U60593 | "Mus musculus cytoplasmic protein Ndr1 (Ndr1) mRNA, c | gene | C | N | I | ~1.1 | 0.01 | NC | * | 0 | D | * | 2.2 | 0.5 |
| U29947 | "Mus musculus alpha-D-mannosidase (Man2b1) mRNA, co | gene | C | N | I | 1.1 | 0.01 | NC | * | 0 | NC | * | 0 | 0 |

TABLE 6-continued

ISGs and IRGs identified from mouse embryonic fibroblast incubated in the presence or absence of IFN-αBBDB in the presence or absence of encephalomyocarditis virus

| | | | | | | | | | | | | |
|---|---|---|---|---|---|---|---|---|---|---|---|---|
| U69176 | "Mus musculus laminin alpha 4 chain mRNA, complete cds | gene | C | N | I | * | 1.1 | 0.01 | NC | * | 0 | 0 | 0 |
| AA122619 | mr133d03.r1 Beddington mouse embryonic region Mus mu | est | C | N | I | * | ~1.0 | 0.01 | I | * | ~1.0 | 0 | 0 |
| AA168061 | ms29c05.r1 Stratagene mouse skin (#937313) Mus musc | est | D | N | I | | 1.1 | 0.01 | 1 | | 1 | 0 | 0 |
| AA170018 | "ms58h12.r1 Life Tech mouse embryo 13 5dpc 10666014 | est | D | N | MI | | 1.1 | 0.01 | NC | | 1 | 0 | 0 |
| AA108827 | mp36b01.r1 Barstead MPLRB1 Mus musculus cDNA clone | est | D | N | I | | 1.1 | 0.01 | NC | | 0 | 0 | 0 |
| AA050218 | mj17909.r1 Soares mouse embryo NbME13.5 14.5 Mus m | est | D | N | MI | | 1.1 | 0.01 | NC | | 0 | 0 | 0 |
| W50138 | | est | A | Y | NC | | 0 | 0 | MI | | 20 | 16.94 | * |
| M29015 | "Mouse ribosomal protein L7 (rpL7) gene, complete cds" | gene | A | Y | I | | 0 | 0 | I | | 4.2 | 2.57 | 2.1 | 0.9 |
| W51486 | | est | A | Y | NC | * | 0 | 0 | I | * | ~6.5 | 2.46 | 0 | 0 |
| X63099 | M. musculus mRNA for connexin31 | gene | B | N | I | * | 0 | 0 | MI | * | 6.2 | 2.23 | 1.9 | 0.3 |
| M13522 | Murine serum amyloid A-2 (SAA-2) gene | gene | A | N | NC | * | 0 | 0 | D | * | ~4.5 | 1.77 | 0 | 0 |
| Z29532 | M. musculus mRNA for follistatin | gene | B | N | NC | * | 0 | 0 | I | * | 5.4 | 1.71 | 3 | 0.9 |
| U02298 | "Mus musculus NIH 3T3 chemokine rantes (Scya5) gene, | gene | C | N | NC | * | 0 | 0 | I | * | 4.8 | 1.63 | 4.9 | 2.2 |
| W41622 | mc47a10.r1 Soares mouse p3NMF19.5 Mus musculus | cDN | est | D | N | NC | | 0 | 0 | 0 | | | 3.2 | 1.3 | I | 2.71.5 |
| V00835 | Mouse gene for Metallothionein-1 (three exons) | gene | D | N | NC | | 0 | 0 | D | | 3.2 | 1.16 | D | 3.7 |
| W12946 | ma89h10.r1 Soares mouse p3NMF19.5 Mus musculus cDN | est | D | N | I | * | 0 | 0 | MI | | 3.6 | 1.08 | 2.7 | 0 |
| D30782 | "Mouse mRNA for epiregulin, complete cds" | gene | B | N | NC | * | ~1.0 | 0 | I | * | ~4.0 | 1.01 | 5.4 | 1.7 |
| M83219 | "Mus musculus intracellular calcium-binding protein (MRP- | gene | C | N | NC | * | 0 | 0 | D | | 3.1 | 0.97 | 0 | 0 |
| D78135 | "Mouse mRNA for NDPP-1 protein, complete cds" | gene | A | N | NC | * | 0 | 0 | I | | ~4.1 | 0.95 | 0 | 0 |
| L28117 | Mouse NF-kappa-B (p105) mRNA | gene | B | N | NC | | 0 | 0 | I | * | ~4.2 | 0.94 | 1.5 | 0.1 |
| AA119959 | mp87b08.r1 Soares mouse 2NbMT Mus musculus cDNA clone 57 | est | D | N | NC | | 0 | 0 | MI | * | 2.8 | 0.79 | 0 | 0 |
| M60523 | "Mouse helix-loop-helix protein (Id related) mRNA, comple | gene | D | N | I | * | 0 | 0 | I | | 2.1 | 0.77 | 2.6 | 2.2 |
| D10727 | "Mouse mRNA for NDPP-1 protein, complete cds" | gene | D | N | NC | * | 0 | 0 | D | | ~3.4 | 0.67 | 0 | 0 |
| W75403 | me52t11.r1 Soares mouse embryo N bME13.5 14.5 Mus m | est | A | N | NC | | 0 | 0 | I | | 1.8 | 0.66 | 1.2 | 0.1 |
| W41883 | "mc64g08.r1 Soares mouse embryo NbME13.5 14.5 Mus | est | A | N | NC | * | 0 | 0 | I | 1.6 | 0.65 | I | 1.5 | 0.6 | 0 |
| U79523 | "Mus musculus peptidylglycine alpha-amidating monooxyg | gene | C | N | NC | * | 0 | 0 | 0 | | 3 | 1 | 0 | 0 |
| J03783 | | est | | D | N | NC | | * | | I | * | ~3.2 | 0.64 | * | 6.62.5 |
| W82958 | "Mouse interleukin 6 mRNA, complete cds" | gene | | D | N | NC | | 0 | 0 | NC | | 3.4 | 0.62 | I | 0 |
| AA42453 | mf08d08.r1 Soares mouse p3NMF19.5 Mus musculus cDNA | est | A | N | NC | * | 0 | 0 | I | * | 3 | 0.61 | 0 | 0 |
| AA144240 | mp96a02.r1 Soares mouse 2NbMT Mus musculus cDNA clone 577 | est | C | N | NC | * | 0 | 0 | I | * | 3 | 0.58 | 1.3 | 0.1 |
| U34245 | "mr78c07.r1 Stratagene mouse heart (#937316) Mus mu | est | D | N | NC | | 0 | 0 | MI | * | 3.1 | 0.57 | 1.9 | 0.3 |
| AA060840 | "Mus musculus fos-related antigen-1 (Fra-1) mRNA, comp | gene | B | N | NC | * | 0 | 0 | MI | | 2.7 | 0.56 | 1.3 | 0.1 |
| W13693 | mj80d05.r1 Soares mouse p3NMF19.5 Mus musculus cDNA | est | D | N | NC | | 0 | 0 | D | * | 3.1 | 0.54 | 2.2 | 0.4 |
| AA028701 | ma94g01.r1 Soares mouse p3NMF19.5 Mus musculus cDNA | est | D | N | NC | * | 0 | 0 | I | | 3.3 | 0.54 | 0 | 0 |
| U63386 | "Mus musculus nuclear transcriptional repressor Mph1 mR | gene | B | N | NC | * | 0 | 0 | I | | 3.2 | 0.53 | 2.2 | 0.4 |
| X16995 | Mouse N10 gene for a nuclear hormonal binding receptor | gene | A | N | NC | * | 0 | 0 | NC | | 2.5 | 0.48 | 1.7 | 0.2 |
| W83337 | mf25h11.r1 Soares mouse embryo NbME13.5 14.5 Mus mus | est | C | N | NC | * | 0 | 0 | D | | 1.6 | 0.48 | 1.2 | 0.1 |
| U39066 | "Murine MAP kinase kinase 6c mRNA, complete cds" | gene | A | N | NC | | 0 | 0 | MI | * | 2.9 | 0.46 | 1.7 | 0.1 |
| W89900 | mf77h05.r1 Soares mouse embryo NbME13.5 14.5 Mus mus | est | C | N | NC | | 0 | 0 | D | | 2 | 0.43 | 1.4 | 0.1 |
| AA071689 | | est | A | T | NC | | 0 | 0 | D | | 2 | 0.41 | 0 | 0 |
| AA068364 | mm53c08.r1 Stratagene mouse embryonic carcinoma (#937 | est | C | N | NC | | 0 | 0 | I | * | ~2.9 | 0.41 | 0 | 0 |
| L43326 | "Mus musculus kinectin (CG-1) mRNA, complete cds" | gene | C | N | NC | * | 0 | 0 | I | | 2.8 | 0.4 | 2.1 | 0.2 |
| AA071792 | mm72a03.r1 Stratagene mouse macrophage (#937306) Mu | est | C | N | NC | | 0 | 0 | D | * | ~2.6 | 0.4 | 0 | 0 |
| W98609 | "ng14h05.r1 Soares mouse embryo NbME13.5 14.5 Mus | est | B | N | NC | | 0 | 0 | D | | 2.8 | 0.39 | D | 2.1 | 0.2 |
| U50378 | "Mus musculus DNA repair enzyme (Ku 70) gene, exon 1 | gene | D | N | NC | * | 0 | 0 | NC | | ~2.7 | 0.38 | 0 | 0 |
| AA028701 | mi12g10.r1 Soares mouse p3NMF19.5 Mus musculus cDN | est | B | N | NC | * | 0 | 0 | I | | 1.9 | 0.37 | 0 | 0 |
| U72881 | "Mus musculus RGS-r protein mRNA, complete cds" | gene | C | N | NC | * | 0 | 0 | I | * | ~2.0 | 0.37 | I | ~3.7 | 1.5 |
| W46019 | mc77h09.r1 Soares mouse embryo NbME13.5 14.5 Mus m | est | C | N | NC | * | 0 | 0 | D | | 2.1 | 0.36 | 1.4 | 0.2 |
| X73359 | M. musculus mAES-1 mRNA | gene | A | N | NC | | 0 | 0 | MD | | 1.7 | 0.36 | | |

TABLE 6-continued

ISGs and IRGs identified from mouse embryonic fibroblast incubated
in the presence or absence of IFN-αBBDB in the presence or absence of
encephalomyocarditis virus

| | | | | | | | | | | | | | |
|---|---|---|---|---|---|---|---|---|---|---|---|---|---|
| J03023 | "Murine macrophage gene, encoding bmk (B cell/myeloid | gene | D | N | NC | * | 0 | 0 | I | * | 2.6 | 0.35 | MI | * | 1.8 | 0.2 |
| W14352 | mb33h03.r1 Soares mouse p3NMF19.5 Mus musculus cD | est | D | N | NC | * | 0 | 0 | MI | * | 2.7 | 0.35 | NC | | 0 | 0 |
| AA016431 | mh38h02.r1 Soares mouse placenta 4NbMP13.5 1.4.5 Mu | est | B | N | NC | | 0 | 0 | D | | 1.7 | 0.34 | D | | 1.4 | 0.1 |
| L38971 | "Mus musculus (E25) mRNA, complete cds" | gene | C | N | NC | | 0 | 0 | D | | 1.9 | 0.34 | I | | 1.7 | 0.3 |
| U54803 | "Mus musculus cysteine protease (Lice) gene, exons 3–7, | gene | D | N | NC | * | 0 | 0 | I | | 2.4 | 0.34 | D | | 2.6 | 0.6 |
| AA152695 | "ms12a04.r1 Stratagene mouse skin (#93713) Mus muscu | est | D | N | NC | | 0 | 0 | MI | * | ~2.4 | 0.32 | MI | * | 3 | 0.6 |
| W09323 | ma06h08.r1 Soares mouse p3NMF19.5 Mus musculus cD | est | D | N | NC | * | 0 | 0 | MD | * | ~2.3 | 0.32 | NC | | 0 | 0 |
| X64550 | M. musculus mNRA RHAMM | gene | C | N | NC | | 0 | 0 | I | * | 2.5 | 0.31 | MI | | 1.8 | 0.2 |
| M31419 | "Mouse 204 interferon-activatable protein mRNA, comple | gene | C | N | NC | * | 0 | 0 | I | * | ~2.5 | 0.31 | I | | 0 | 0 |
| D50494 | "Mouse mRNA for murine RCK, complete cds" | gene | C | N | NC | | 0 | 0 | I | | 1.9 | 0.3 | I | | 1.8 | 0.3 |
| U33198 | "Mus musculus intranuclear protein mRNA, complete cds" | gene | B | N | NC | | 0 | 0 | I | | ~2.6 | 0.29 | NC | * | 0 | 0 |
| AA034714 | "m155h03.r1 Soares mouse embryo NbME13.5 14.5 Mus m | est | A | N | NC | * | 0 | 0 | D | | 1.3 | 0.28 | D | | 1.3 | 0.3 |
| U19118 | "Mus musculus transcription factor LRG-21 mRNA, comple | gene | B | N | NC | | 0 | 0 | I | * | ~2.4 | 0.28 | I | * | 1.8 | 0.2 |
| AA060550 | mj69q11.r1 Soares mouse p3NMF19.5 Mus musculus cDN | est | B | N | NC | * | 0 | 0 | D | | 1.8 | 0.28 | I | | 1.5 | 0.2 |
| AA144887 | mr11d06.r1 Soares mouse 3NbMS Mus musculus cDNA clon | est | D | N | I | * | 0 | 0 | ~2.5 | 0.28 | NC | | | | 0 | 0 |
| U17259 | "Mus musculus p19 mRNA, complete cds" | gene | A | N | NC | | 0 | 0 | D | | 2.4 | 0.27 | D | | 1.4 | 0.1 |
| U05241 | "Mus musculus c-Src kinase (Csk) mRNA, complete cds" | gene | A | Y | NC | | 0 | 0 | D | | 1.9 | 0.27 | I | | ~1.0 | 0 |
| W50127 | | est | A | N | NC | * | 0 | 0 | C | | ~1.6 | 0.26 | NC | * | 0 | 0 |
| J03877 | "Mouse gamma-renin mRNA; complete cds" | gene | C | N | NC | * | 0 | 0 | MD | * | ~2.3 | 0.26 | D | | 1.6 | 0.3 |
| U02997 | "Mus musculus 129 cryptidin-2 (Defcr2) gene, exon 2 and | gene | A | N | NC | | 0 | 0 | I | | 1.7 | 0.26 | I | | 0 | 0 |
| U26176 | "Mus musculus somatostatin receptor type 4 (SSTR4) gen | gene | A | N | NC | * | 0 | 0 | MI | * | 2.2 | 0.26 | NC | | 0 | 0 |
| V00727 | Mouse c-fos oncogene | gene | B | N | I | * | 0 | 0 | I | * | ~2.3 | 0.26 | I | | 2.4 | 0.3 |
| U12961 | "Mus musculus NAD(P)H:menadione oxidoreductase (Nmo | gene | AN | NC | * | 0 | 0 | I | * | ~2.3 | 0.25 | NC | | | | 0 | 0 |
| AA035993 | m171c05.r1 Soares mouse embryo NbME13.5 14.5 Mus m | est | D | N | NC | | 0 | 0 | * | | ~2.2 | 0.25 | I | | 0 | 0.6 |
| U38940 | "Mus musculus asparagine synthetase mRNA, complete cd | gene | B | N | NC | * | 0 | 0 | MD | * | 1.5 | 0.24 | NC | | 3 | 0 |
| W58941 | md53e02.r1 Soares mouse embryo NbME13.5 14.5 Mus m | est | A | N | NC | | 0 | 0 | I | | 1.6 | 0.23 | NC | | 0 | 0 |
| U14135 | "Mus musculus CD1 integrin alpha v subunit mRNA, comp | gene | B | N | NC | * | 0 | 0 | I | * | ~2.3 | 0.23 | I | | 0 | 0 |
| AA030421 | m128f03.r1 Soares mouse embryo NbME13.5 14.5 Mus mu | est | B | N | NC | | 0 | 0 | I | | 2.1 | 0.23 | MI | | 1.6 | 0.1 |
| D16464 | Mouse helix-loop-helix factor HES-1 gene | gene | B | N | NC | | 0 | 0 | I | | 1.7 | 0.23 | NC | | 1.4 | 0.1 |
| X72310 | M. musculus mRNA for DRTF-polypeptide-1 (DP-1) | gene | B | N | NC | * | 0 | 0 | I | | 2 | 0.23 | NC | | 0 | |
| AA061016 | mj88f06.r1 Soares mouse p3NMF19.5 Mus musculus cDN | est | B | N | NC | * | 0 | 0 | ~2.3 | 0.23 | D | | 3.5 | 0.7 | | |
| U34277 | "Mus musculus PAF acetylhydrolase mRNA, complete cds" | gene | A | N | NC | * | 0 | 0 | MI | * | ~2.3 | | NC | | 0 | |
| X61940 | Mouse mRNA for a growth factor-inducible immediate ear | gene | B | N | NC | | 0 | 0 | MI | | 1.8 | 0.22 | NC | | 0 | 0 |
| AA169951 | ms44ct04.r1 Life Tech mouse embryo 13 5dpc, 10666014 | est | C | N | NC | | 0 | 0 | D | | 1.5 | 0.22 | I | | 1.3 | 0.1 |
| J03168 | "Mouse interferon regulatory factor-2 mRNA, complete cd | gene | D | N | I | * | ~1.0 | 0 | I | | ~2.2 | 0.22 | D | | 2.5 | 0.4 |
| W47863 | mc84h02.r1 Soares mouse embryo NbME13.5 14.5 Mus m | est | A | N | NC | | 0 | 0 | D | | 1.6 | 0.21 | NC | * | 0 | 0 |
| AA120203 | mn35d09.r1 Beddington muse embryonic region Mus mus | est | D | N | NC | | 0 | 0 | D | | 2.3 | 0.21 | NC | * | 0 | 0 |
| AA138791 | mr02c08.r1 Soares mouse 3NbMS Mus musculus cDNA cl | est | D | N | NC | | 0 | 0 | I | * | 2.1 | 0.2 | I | * | 1.7 | 0.2 |
| D32167 | Mouse zic mRNA for Zic protein, complete cds" | gene | A | N | NC | * | 0 | 0 | I | | 2.2 | 0.21 | NC | | 0 | 0 |
| AA051341 | mj40d10.r1 Soares mouse embryo NbME13.5 14.5 Mus m | est | B | N | NC | | 0I | 0 | * | | ~2.1 | MI | | 2.1 | | |
| U49351 | "Mus musculus lysosomal alpha-glucosidase mRNA, compl | gene | C | N | NC | | 0 | 0 | D | | 1.6 | 0.21 | D | | 0.2 | 0.1 |
| AA008463 | "mg83c09.r1 Soares mouse embryo NbME13.5 14.5 Mus | est | B | N | NC | | 0 | 0 | MD | | 2 | 0.2 | NC | | 1.3 | 0 |
| U25096 | "Mus musculus Kruppel-like factor LKLF mRNA, complete | gene | B | N | NC | * | 0 | 0 | I | | 1.9 | 0.2 | NC | * | 0 | 0 |
| AA061915 | mj84a02.r1 Soares mouse p3NMF19.5 Mus musculus cDN | est | C | N | NC | * | 0 | 0 | MD | | 1.6 | 0.2 | MD | | 1.5 | 0.2 |
| AA064021 | mj61f02.r1 Soares mouse embryo NbME13.5 14.5 Mus mu | est | C | N | NC | * | 0 | 0 | D | | 1.4 | 0.2 | D | | 1.3 | 0.2 |
| AA066424 | mn30c05.r1 Stratagene mouse skin (#93713) Mus mus | est | C | N | I | * | ~1.0 | 0 | I | * | ~1.9 | 0.19 | MI | * | 2.5 | 0.3 |
| AA111592 | mo32h08.r1 Life Tech mouse embryo 13 5dpc 10666014 M | est | C | N | NC | | 0 | 0 | MD | * | 1.9 | 0.19 | NC | | 0 | 0 |

TABLE 6-continued

ISGs and IRGs identified from mouse embryonic fibroblast incubated in the presence or absence of IFN-αBBDB in the presence or absence of encephalomyocarditis virus

| Accession | Description | Type | C1 | C2 | C3 | C4 | C5 | C6 | C7 | C8 | C9 | C10 | C11 | C12 |
|---|---|---|---|---|---|---|---|---|---|---|---|---|---|---|
| AA153484 | "mr84h03.r1 Stratagene mouse heart (#937316) Mus muscl | est | D | N | I | * | ~1.0 | 0 | I | ~1.8 | 0.19 | NC | 0 | 0 |
| W41072 | mc39f08.r1 Soares mouse p3NMF19.5 Mus musculus cDN | est | D | N | NC |  | 0 | 0 | I | 1.8 | 0.19 | NC |  0 | 0 |
| U36757 | "Mus musculus thrombin receptor (Cf2r) gene, exon 2 an | gene | A | N | I | * | 0 | 0 | MI | 2 | 0.18 | NC | * | 0.4 |
| U21951 | "Mus musculus apolipoprotein B mRNA-editing componen | gene | A | N | I | * | ~1.0 | 0 | I | ~1.8 | 0.18 | NC | * | 0 |
| U59864 | "Mus musculus TRAF-interacting protein t-TRAF mRNA, cc | gene | C | N | NC |  | 0 | 0 | I | ~2.1 | 0.18 | MI | * | 2.6 |
| W16201 | mb63d06.r1 Soares mouse p3NMF19.5 Mus musculus cD | est | D | N | NC | * | 0 | 0 | I | 2.1 | 0.18 | MI | * | 1.6 |
| X52886 | M. musculus mRNA for cathepsin D | gene | B | N | NC | * | 0 | 0 | D | 1.5 | 0.17 | D |  | 1.6 |
| W12204 | ma65c11.r1 Soares mouse p3NMF19.5 Mus musculus cD | est | D | N | NC | * | 0 | 0 | I | ~2.0 | 0.17 | I |  | 2.1 |
| D83206 | "Mouse mRNA for P24 protein, complete cds" | gene | D | N | NC | * | 0 | 0 | MI | 2.1 | 0.16 | NC | * | 0 |
| D76440 | "Mouse gene necdin, complete cds and promoter sequ | gene | A | N | NC | * | 0 | 0 | D | 1.5 | 0.16 | D |  | 1.3 |
| L22472 | "Mouse Bax alpha mRNA, complete cds" | gene | A | N | I | * | 0 | 0 | I | 1.4 | 0.16 | D |  | 1.7 |
| X77731 | M. musculus mRNA for Deoxycytidine kinase | gene | B | N | NC | * | 0 | 0 | I | ~2.0 | 0.16 | I |  | 2.2 |
| W89699 | mt79b10.r1 Soares mouse embryo NbME13.5 14.5 Mus m | est | C | N | NC |  | 0 | 0 | I | 1.9 | 0.16 | NC |  | 0 |
| AA087334 | "mn95W9.r1 Stratagene mouse lung 937302 Mus musculu | est | C | N | NC |  | 0 | 0 | I | 1.5 | 0.16 | NC |  | 0 |
| M62418 | "Mouse clathrin-associated protein 19 (AP19) mRNA, com | gene | D | N | NC |  | 0 | 0 | D | ~1.9 | 0.15 | MD | * | ~2.2 |
| X15378 | Mouse gene for the light and heavy chains of myeloperoxi | gene | B | N | NC | * | 0 | 0 | MI | ~1.9 | 0.15 | NC |  | 0 |
| AA064355 | mt47a02.r1 Stratagene mouse testis (#937308) Mus musc | est | C | N | NC | * | 0 | 0 | MD | 1.2 | 0.14 | NC |  | 0 |
| W83519 | "tnf29f08.r1 Soares mouse embryo NbME13.5 14.5 Mus mu | est | B | N | NC |  | 0 | 0 | I | 1.6 | 0.14 | NC |  | 0 |
| AA033333 | "mi43e02.r1 Soares mouse embryo NbME13.5 14.5 Mus m | est | B | N | NC | * | 0 | 0 | I | 1.4 | 0.14 | NC |  | 0 |
| W41861 | mc64a04.r1 Soares mouse embryo NbME13.5 14.5 Mus m | est | D | N | NC |  | 0 | 0 | I | 0.13 | 0.14 | * | 0 | 0 |
| X67677 | M. musculus c-yes mRNA | gene | B | N | NC | * | 0 | 0 | I | ~1.9 | NC | I | * | 1.9 |
| AA098525 | "tnk18a12.r1 Soares mouse p3NMF19.5 Mus musculus cD | est | A | N | NC | * | 0 | 0 | I | 1.6 | 0.13 | NC |  | 0 |
| U09928 | "Mus musculus DBA/2J interferon-inducible RNA-dependen | gene | A | N | NC | * | 0 | 0 | I | 1.8 | 0.13 | NC |  | 0 |
| W65616 | me12b10.r1 Soares mouse embryo NbME13.5 14.5 Mus mu | est | B | N | NC |  | 0 | 0 | I | 1.3 | 0.13 | NC |  | 0 |
| W34296 | ma99e05.r1 Soares mouse p3NMF19.5 Mus musculus cD | est | B | N | NC |  | 0 | 0 | I | ~1.9 | 0.13 | NC |  | 0 |
| AA024297 | mh91a08.r1 Soares mouse placenta 4NbMP13.5 14.5 Mu | est | C | N | NC |  | 0 | 0 | I | 1.8 | 0.13 | NC |  | 0 |
| AA073986 | "mn95d03.r1 Stratagene mouse heart (#937316) Mus mus | est | D | N | NC | * | 0 | 0 | I | 1.6 | 0.13 | NC |  | 1.6 |
| M11686 | "Mouse endo B cytokeratin mRNA, complete cds" | gene | D | N | NC |  |  |  | I | ~2.0 | 0.13 | I |  | 1.6 |
| M21050 | "Mouse lysozyme M gene, exon 4" | gene | A | N | NC | * | 0 | 0 | MD | 1.6 | 0.12 | NC |  | 0 |
| M23504 | "Mus musculus T cell secreted protein (P600) mRNA, con | gene | B | N | NC |  | 0 | 0 | MI | ~1.7 | 0.12 | I | * | 1.1 |
| U37351 | "Mus musculus Paneth cell enhanced expression PCEE mR | gene | C | N | NC | * | 0 | 0 | I | 1.6 | 0.12 | NC |  | 0 |
| AA087787 | "mn86a12.r1 Stratagene mouse embryonic carcinoma RA | est | D | N | NC |  | 0 | 0 | I | 1.2 | 0.12 | NC |  | 0 |
| D00812 | "Mouse mRNA for 30-KDa subunit of replication protein A | gene | D | N | NC |  | 0 | 0 | I | 1.7 | 0.12 | NC |  | 0 |
| L17076 | Mus musculus (clones EcDNA1 and EcDNA4) RNA-binding | gene | A | N | NC | * | 0 | 0 | I | 1.6 | 0.12 | NC |  | 0 |
| W91095 | mf84a04.r1 Soares mouse embryo NbME13.5 14.5 Mus m | est | A | NC |  |  |  |  | MD | 1.8 | 0.11 | NC |  | 0 |
| AA097936 | "mn82f02.r1 Stratagene mouse Tcell 937311 Mus muscul | est | C | N | NC | * | 0 | 0 | MI | 1.7 | 0.11 | NC | * | 0 |
| W99019 | mf92g05.r1 Soares mouse embryo NbME13.5 14.5 Mus mu | est | D | N | NC | * | 0 | 0 | I | ~1.8 | 0.11 | NC | * | 0 |
| W34743 | mc62h02.r1 Soares mouse embryo NbME13.5 14.5 Mus m | est | D | N | NC | * | 0 | 0 | MI | ~1.7 | 0.11 | NC | * | 0 |
| W13196 | mb33a06.r1 Soares mouse p3NMF19.5 Mus musculus cD | est | B | N | NC | * | 0 | 0 | I | 1.7 | 0.11 | NC |  | 0 |
| X73523 | "M. musculus mRNA for Gal beta1, 3GalNAc alpha213-sialy | gene | B | N | NC | * | 0 | 0 | I | *1.8 | NC | 0 |  | 0 |
| X71327 | M. musculus mRNA for MRE-binding transcription factor | gene | B | N | NC |  | 0 | 0 | I | 1.8 | 0.11 | NC |  | 0 |
| U05837 | "Mus gene musculus mouse beta-N-acetylhex-osaminidase alph | B | N | NC |  | 0 | 0 | D | 1.5 | D | 1.9 |  | 0.4 |  |

TABLE 6-continued

ISGs and IRGs identified from mouse embryonic fibroblast incubated
in the presence or absence of IFN-αBBDB in the presence or absence of
encephalomyocarditis virus

| | | | | | | | | | | | |
|---|---|---|---|---|---|---|---|---|---|---|---|
| U28423 | "Mus musculus protein kinase inhibitor p58 mRNA1, comple | gene | C | N | I | * | ~1.0 | 0 | I | * | ~1.5 | 0.11 | NC | | 0 | 0 |
| X94444 | M. musculus mRNA for preprocathepsin K | gene | C | N | NC | | 0 | 0 | I | | 1.6 | 0.11 | NC | | 0 | 0 |
| W14370 | mb36f09.r1 Soares mouse p3NMF19.5 Mus musculus cD | est | A | Y | NC | | 0 | 0 | I | | 1.4 | 0.11 | I | 0 | 1.5 | 0.3 |
| W54637 | | est | A | N | NC | | 0 | 0 | | 1.6 | 0.11 | | 0 | | | |
| X74145 | M. musculus mRNA for protein kinase.crk4 | gene | B | N | NC | | 0 | 0 | I | | 1.6 | 0.1 | NC | | 0 | 0 |
| X75888 | M. musculus mRNA for cyclin E | gene | C | N | NC | | 0 | 0 | I | | 1.5 | 0.1 | NC | | 0 | 0 |
| X80339 | M. musculus Six1 mRNA | gene | C | N | NC | | 0 | 0 | I | | 1.7 | 0.1 | NC | | 0 | 0 |
| U60987 | "Mus musculus FAD-linked glycerol-3-phosphate dehydro | gene | C | N I | * | ~1.0 | 0 | I | * | ~1.7 | 0.1 | NC | | 0 | 0.1 |
| AA144649 | "mr70f07.r1 Stratagene mouse testis (#937308) Mus musc | est | C | N | | 0 | I | | 1.6 | 0.1 | MI | 0 | 1.5 | |
| | | | | NC | | | | | | | | | | | |
| AA14438 | mr69l02.r1 Stratagene mouse testis (#937308) Mus musc | est D | N | NC | | 0 | 0 | MI | * | 0.1 | NC | | 0 | 0 |
| W62420 | md99g06.r1 Soares mouse embryo NbME13.5 14.5 Mus m | est | A | N | N | 0 | 0 | MI | | 1.6 | 0.09 | NC | | 0 | 0 |
| W64413 | "me03g03.r1 Soares mouse embryo NbME13.5 14.5 Mus m | est A | N | NC | | 0 | MI | 1.6 | 0.09 | NC | | 0 | |
| | | | | NC | | | | | | | | | | | |
| X78683 | M. musculus mRNA for B-cell receptor associated protein ( | gene | B | N | NC | | 0 | 0 | I | | 1.3 | 0.09 | NC | | 0 | 0 |
| AA034761 | mi44d12.r1 Soares mouse embryo NbME13.5 14.5 Mus m | est | B | N | NC | * | 0 | 0 | I | | 1.5 | 0.09 | I | 0 | 1.5 | 0.1 |
| AA098138 | mm84c07.r1 Stratagene mouse Tcell 937311 Mus musculu | est | C N | NC | | 0 | 1 | I | 1.6 | 0.09 | NC | | 0 | |
| U27457 | "Mus musculus origin recognition complex protein 2 homol | gene | C | N | NC | * | 0 | 0 | I | * | ~1.7 | 0.09 | NC | | 0 | 0.1 |
| AA163902 | mr27a01.r1 Soares mouse 3NbMS Mus musculus cDNA cl | est | D | N | NC | | 0 | 0 | I | | 1.6 | 0.09 | I | 0 | 1.5 | 0.1 |
| M28312 | "Mus musculus 3/10 metalloproteinase inhibitor gene, exc | gene | A | N | NC | | 0 | 0 | I | | 1.2 | 0.09 | I | 0 | 1.3 | 0.2 |
| U11075 | "M. musculus inwardly-rectifying K+ channel protein (mb | gene | B | Y | NC | | 0 | 0 | MI | * | ~1.7 | 0.08 | NC | * | 0 | 0 |
| AA020069 | | est | C | N | I | * | 0 | 0 | MD | * | ~1.6 | 0.08 | NC | * | 0 | 0.3 |
| AA118151 | mn11b10.r1 Beddington mouse embryonic region muscl | est | D | N I | * | ~1.0 | 1 | I | * | ~1.5 | 0.08 | I | * | 2.5 | 0 |
| AA120674 | mp75d12.r1 Soares mouse 2NbMT Mus musculus cDNA clone 575 | est | D | N | NC | * | 0 | 0 | I | * | 0.08 | MI | * | 1.8 | 0.2 |
| W41627 | "3mc47c09.r1 Soares mouse p3NMF19.5 Mus musculus cD | est | B | N | NC | * | 0 | 0 | I | * | ~1.5 | 0.08 | NC | * | 0 | 0 |
| X87671 | "M. musculus mRNA for 3BP-1, an SH3 domain binding pro | gene | D | N | NC | * | 0 | 0 | MI | * | ~1.6 | 0.08 | NC | * | 0 | 0 |
| U56909 | "Mus musculus multiple testis transcript (mtt1) mRNA, cc | gene | C | N | NC | * | 0 | 0 | I | * | 1.7 | 0.08 | NC | * | 0 | 0 |
| AA124052 | "mp98f06.r1 Soares mouse 2NbMT Mus musculus cDNA clone 5 | est | C | N | NC | * | 0 | 0 | MI | * | 1.6 | 0.08 | MI | * | 1.4 | 0.1 |
| U35456 | "Mus musculus glutathione synthetase type A1 mRNA, cc | gene | B | N | NC | * | 0 | 0 | I | * | ~1.5 | 0.07 | I | * | ~2.5 | 0.3 |
| X72711 | "M. musculus mRNA for replication factor C, large subunit" | gene | B | N | NC | * | 0 | 0 | I | * | ~1.6 | 0.07 | I | * | 1.8 | 0.1 |
| Z46966 | M. musculus mRNA for imogene 44 | gene | B | N | NC | * | 0 | 0 | MI | * | ~1.7 | 0.07 | NC | * | 0 | 0 |
| D49473 | "House mouse: Musculus domesticus adult tests mRNA f | gene | C | N | NC | * | 0 | 0 | I | * | 1.5 | 0.07 | NC | * | 0 | 0 |
| M28489 | "Mus musculus (clone Mt6a) ribosomal protein S6 kinase | gene | A | N | NC | * | 0 | 0 | I | * | ~1.6 | 0.07 | NC | * | 0 | 0 |
| U00689 | "Mus musculus TIA mRNA, complete cds" | gene | A | N | NC | * | 0 | 0 | I | * | 1.6 | 0.07 | NC | * | 0 | 0 |
| U25051 | "Mus musculus phosphatidylethanolamine-N-methyltransfe | gene | C | N | NC | * | 0 | 0 | D | * | 1.2 | 0.07 | D | * | 2.6 | 0.5 |
| D00208 | "Mouse pEl98 protein mRNA which is enhanced in establ | gene | A | N | NC | * | 0 | 0 | MD | * | 1.6 | 0.07 | D | * | 2.6 | 0.5 |
| AA137737 | mq99a08.r1 Soares mouse 3NbMS Mus musculus cDNA clo | est | D | N | NC | * | 0 | 0 | MI | * | 1.4 | 0.07 | NC | * | 0 | 0 |
| AA109109 | "mo31a10.r1 Life Tech mouse embryo 13 5dpc 10666014 | est | D | N | NC | * | 0 | 0 | I | * | 1.6 | 0.07 | NC | * | 0 | 0 |
| W09664 | ma03d05.r1 Soares mouse p3NMF19.5 Mus musculus cDNA | est | D | N | I | * | ~1.0 | 0 | I | * | ~1.6 | 0.07 | NC | * | 0 | 0 |
| W53731 | md15g07.r1 Soares mouse embryo NbME13.5 14.5 Mus mu | est | D | N | NC | * | 0 | 0 | I | * | ~1.6 | 0.07 | NC | * | 0 | 0 |
| AA021788 | mh86h07.r1 Soares mouse placenta 4NbMP13.514.5 Mu | est | A | N | NC | * | 0 | 0 | MI | * | ~1.6 | 0.06 | NC | * | 0 | 0 |
| W64800 | md88f02.r1 Soares mouse embryo NbME13.5 14.5 Mus m | est | B | N | NC | * | 0 | 0 | I | * | 1.5 | 0.06 | NC | * | 0 | 0 |
| AA138324 | mq96d09.r1 Stratagene mouse heart (#937316) Mus musc | est | B | N | NC | * | 0 | 0 | I | * | ~1.6 | 0.06 | NC | * | 0 | 0 |
| AA050934 | mg72g12.r1 Soares mouse embryo NbME 13.5 1.45 Mus m | est | B | N | NC | * | 0 | 0 | I | * | 1.5 | 0.06 | NC | * | 0 | 0 |
| AA089111 | "ml57d05.r1 Stratagene mouse testis (#937308) Mus musc | est | A | Y | NC | * | 0 | 0 | I | * | ~1.5 | 0.06 | NC | * | 0 | 0 |
| W55814 | "mb23g09.r1 Soares mouse p3NMF19.5 Mus musculus c | est | B | N | NC | * | 0 | 0 | I | * | 1.2 | 0.06 | NC | * | 0 | 0 |
| X75285 | M. musculus mRNA for fibulin-2 | gene | C | N | NC | * | 0 | 0 | MD | * | 1.1 | 0.06 | NC | * | 0 | 0 |

TABLE 6-continued

ISGs and IRGs identified from mouse embryonic fibroblast incubated in the presence or absence of IFN-αBBDB in the presence or absence of encephalomyocarditis virus

| ID | Description | col3 | col4 | col5 | col6 | col7 | col8 | col9 | col10 | col11 | col12 | col13 |
|---|---|---|---|---|---|---|---|---|---|---|---|---|
| D29639 | "Mouse embryonal carcinoma cell mRNA for 3-hydroxyacy | gene | C | N | NC | | 0 | MI | 1.3 | 0.06 | NC | | 0 | 0 |
| AA105621 | "mm68b06.r1 Stratagene mouse macrophage (#937306) M | est | C | N | NC | | 0 | MI | 1.2 | 0.06 | NC | | 0 | 0 |
| L26320 | "Mouse flap endonuclease-1 (FEN-1) mRNA, complete cds" | gene | D | N | NC | | 0 | I | 1.4 | 0.06 | NC | | 0 | 0 |
| W13263 | mb31d10.r1 Soares mouse p3NMF19.5 Mus musculus cDN | est | D | N | NC | * | 0 | I | 1.5 | 0.06 | I | | 1.8 | 0.2 |
| W0059 | "nc26b04.r1 Soares mouse p3NMF19.5 Mus musculus cD | est | C | N | NC | | 0 | MI | ~1.4 | 0.05 | NC | | 0 | 0 |
| U55057 | "Mus musculus receptor protein tyrosine phosphatase-lam | gene | C | N | NC | * | 0 | I | 1.5 | 0.05 | MI | * | 1.5 | 0.1 |
| AA109999 | "ml60a02.r1 Stratagene mouse testis (#937308) Mus mus | est | D | N | NC | | 0 | D | ~1.4 | 0.05 | D | | 1.3 | 0.2 |
| AA068735 | "mm59d02.r1 Stratagene mouse embryonic carcinoma (#9 | est | A | N | NC | * | 0 | MD | 1.2 | 0.05 | I | | 1.3 | 0.1 |
| AA034714 | "m155h03.r1 Soares mouse embryo NbME13.5 14.5 Mus m | est | D | N | NC | | 0 | I | 1.5 | 0.05 | NC | | 0 | 0 |
| AA119194 | mp63a03.r1 Soares 2NbMT Mus musculus cDNA clone 57 | est | B | N | NC | | 0 | I | 1.3 | 0.05 | NC | | 1.4 | 0.1 |
| W42234 | mc37a06.r1 Soares mouse p3NMF19.5 Mus musculus cD | est | B | N | I | * | 0 | MI | ~1.4 | 0.05 | NC | | 0 | 0 |
| X74351 | M. musculus mRNA for XPAC Xeroderma Pigmentosum gro | gene | B | N | NC | | 0 | I | 1.3,0.05 NC | | 1.3 | 0 |
| AA107514 | mp05g07.r1 Life Tech mouse embryo 8 5dpc 10664019 | est | C | N | NC | | 0 | D | 1.3 | 0.05 | D | | 0 | 0 |
| AA086698 | mm93b06.r1 Soares mouse Tcell 937311 Mus musculu | est | C | N | NC | * | 0 | MI | 1.5 | 0.05 | NC | | 0 | 0 |
| X92411 | M. musculus mRNA for MHR23B | gene | C | N | NC | | 0 | I | 1.5 | 0.05 | NC | | 1.4 | 0.1 |
| AA104940 | mm67e02.r1 Stratagene mouse macrophage (#937306) Mu | est | B | N | I | * | ~1.0 | * | ~1.4 | 0.05 | I | | 1.4 | 0 |
| X96859 | M. musculus mRNA for ubiquitin-conjugating enzyme | gene | C | N | NC | | 0 | I | 1.5 | 0.05 | NC | | 0 | 0 |
| U60330 | "Mus musculus Ki antigene mRNA, complete cds" | gene | C | N | NC | | 0 | D | 1.3 | 0.05 | NC | 0 | 0 | |
| AA146282 | "mr06e08.r1 Soares mouse 3NbMS Mus musculus cDNA | est | C | N | I | * | 0 | MI | ~1.4 | 0.05 | NC | | 0 | 0 |
| AA168283 | ms22d05.r1 Stratagene mouse skin (#937313) Mus musc | est D | N | N | * | ~1.0 | * | ~1.4 | 0.05 | NC | 0 | | 0 |
| M73741 | "Mouse alpha-B2-crystallin gene, complete cds" | gene | D | N | NC | | 0 | I | 1.3 | 0.05 | NC | | 0 | 0 |
| W36586 | mb86c07.r1 Soares mouse p3NMF19.5 Mus musculus cDN | est | B | N | NC | * | 0 | 1.3 | 0.05 | I | | 1.8 | 0.1 |
| U14332 | "Mus musculus interleukin 15 (IL15) mRNA, complete cds" | gene | A | N | MI | * | 0 | I | ~1.3 | 0.04 | I | * | 0 | 0 |
| AA027669 | "1m109g01.r1 Soares mouse p3NMF19.5 Mus musculus cds | est | B | N | NC | * | 0 | MI | ~1.4 | 0.04 | NC | | 0 | 0 |
| L49502 | "Mus musculus phosphoprotein (p150TSP) mRNA, comple | gene | B | N | NC | * | ~1.0 | I | 1.4 | 0.04 | NC | | 0 | 0 |
| W46752 | "Mouse mRNA for plexin 1, complete cds" | est | B | Y | NC | | 0 | I | ~1.3 | 0.04 | NC | | 0 | 0 |
| D86948 | ms35a08.r1 Stratagene mouse heart (#937316) Mus muse | gene | C | N | MI | * | 0 | MI | ~1.4 | 0.04 | NC | | 0 | 0 |
| AA168694 | m177e10.r1 Soares mouse p3NMF19.5 Mus musculus cD | est | D | N | NC | * | 0 | I | ~1.3 | 0.04 | NC | | 0 | 0 |
| AA037945 | mm66c11.r1 Stratagene mouse macrophage (#937306) M | gene | D | N | I | * | 0 | MI | ~1.3 | 0.04 | NC | | 0 | 0 |
| AA104477 | "Mus musculus secreted T cell protein (H400, SIS-gamma | est | D | N | NC | * | 0 | I | ~1.2 | 0.04 | NC | | 0 | 0 |
| M23503 | "Mus musculus MEK kinase mRNA, complete cds" | gene | B | N | NC | * | 0 | MI | ~1.4 | 0.04 | I | | 1.4 | 0 |
| L13103 | "Mus musculus angiogenein precursor (Ang) gene, complet | gene | B | N | NC | * | 0 | I | ~1.4 | 0.04 | NC | | 0 | 0 |
| U22516 | "Mouse oncogene (ect2) mRNA, complete cds" | gene | C | N | NC | * | 0 | I | ~1.4 | 0.04 | NC | | 0 | 0 |
| AA015354 | mh13h07.r1 Soares mouse placenta 4NbMP13.5 14.5 Mus | est | D | N | MI | * | 0 | MI | ~1.3 | 0.04 | NC | | 0 | 0 |
| U48737 | "Mus musculus serine/threonine-protein kinase PRP4m (Pf | est | D | N | I | * | 0 | MI | ~1.3 | 0.04 | NC | | 0 | 0 |
| D87899 | "House mouse; Musculus domesticus male brain mRNA for | gene | D | N | I | * | ~1.0 | I | 1.4 | 0.04 | NC | | 0 | 0 |
| AA103078 | "mo20g01.r1 Life Tech mouse embryo 13 5dpc 10666014 | est | C | N | NC | * | 0 | I | ~1.4 | 0.04 | I | | 2.2 | 0.3 |
| AA117313 | m19c12.r1 Beddington mouse embryonic region Mus muse | est | D | N | NC | * | 0 | I | ~1.4 | 0.04 | NC | | 0 | 0 |
| AA140026 | mq39h04.r1 Barstead MPLRB1 Mus musculus cDNA clone | gene | B | N | NC | * | 0 | I | 1.3 | 0.04 | NC | | 0 | 0 |
| AA059763 | "mj77e11.r1 Soares mouse p3NMF19.5 Mus musculus cD | est | D | N | NC | * | 0 | I | 1.2 | 0.04 | I | | 1.4 | 0.2 |
| L11316 | "Mouse oncogene (ect2) mRNA, complete cds" | gene | D | N | I | * | ~1.0 | * | ~1.4 | 0.04 | NC | | 0 | 0 |
| D26090 | "Mouse mRNA for mCDC46 protein, complete cds" | gene | D | N | NC | | 1 | MI | ~1.3 | 0.04 | NC | | 0 | 0 |
| AA003162 | mg51a09.r1 Soares mouse embryo NbME13.5 14.5 Mus m | est | D | N | I | * | ~1.0 | I | 1.3 | 0.04 | NC | | 0 | 0 |
| L38677 | "Mus musculus alpha 2,8-sialyltransferase (GD3 synthase) | gene | B | N | I | * | 0 | MI | ~1.2 | 0.03 | NC | * | 0 | 0 |
| X96793 | M. musculus mRNA for placenta growth factor | gene | B | N | I | * | 0 | * | ~1.2 | 0.03NC | | 0.03NC | * | 0 | 0 |
| X63162 | M. musculus mRNA for transin-1 | gene | B | N | I | * | 0 0 | * | 1.4 | 0.03 | NC | * | 0 | 0 |
| U61363 | "Mus musculus groucho-related gene 4 protein (Grg4) mR | gene | C | N | NC | * | 0 | MD | ~1.2 | 0.03 | NC | | 0 | 0 |
| U64199 | "Mus musculus Il-12 receptor beta2 mRNA, complete cds" | gene | C | N | NC | | 0 | * | ~1.3 | 0.03 | NC | | 0 | 0 |

TABLE 6-continued

ISGs and IRGs identified from mouse embryonic fibroblast incubated
in the presence or absence of IFN-αBBDB in the presence or absence of
encephalomyocarditis virus

| | | | | | | | | | | | |
|---|---|---|---|---|---|---|---|---|---|---|---|
| X14029 | Mouse MuIFN-beta gene for beta-interferon | gene | D | N | NC | * | 0 | 0 | I | * | ~1.2 | 0.03 | I | * | ~3.3 | 0.8 |
| X53953 | M. musculus ets-1 mRNA | gene | A | N | NC | | 0 | 9 | I | | ~1.3 | 0.03 | NC | | 0 | 0 |
| U12922 | "Mus musculus CD1 geranylgeranyl transferase beta subu | gene | C | N | NC | | 0 | 0 | I | | 1.2 | 0.03 | NC | * | 0 | 0 |
| U58888 | "Mus musculus SH3-containing protein SH3P2 mRNA, par | gene | C | N | NC | | 0 | 0 | MI | | 1.1 | 0.03 | MI | | 1.2 | 0 |
| W41974 | mc68h11.r1 Soares mouse embryo NbME13.5 14.5 Mus | est | D | N | NC | * | 0 | 0 | I | | 1.3 | 0.03 | NC | | 0 | 0 |
| X56461 | Murine Hox2.2 mRNA for a homeobox protein | gene | D | N | NC | | 0 | 0 | I | * | ~1.4 | 0.03 | NC | | 0 | 0 |
| W20901 | mb95a12.r1 Soares mouse p3NMF19.5 Mus musculus cD | est | D | N | I | * | ~1.0 | 0 | I | | ~1.3 | 0.02 | NC | | 0 | 0 |
| M33467 | Mouse dilute lethal-20J (d-120J) deletion breakpoint fusio | est | A | N | NC | | 0 | 0 | MI | * | ~1.1 | 0.02 | NC | * | 0 | 0 |
| D28941 | "Mouse mRNA for alpha-2,3-sialyltransferase, complete cc | gene | A | N | I | | 0 | 0 | I | | ~1.3 | 0.02 | NC | * | 0 | 0 |
| W89740 | mf77a09.r1 Soares mouse embryo NbME13.5 14.5 Mus m | est | B | N | NC | * | ~1.0 | 0 | MI | * | ~1.1 | 0.02 | NC | * | 0 | 0 |
| D00622 | Mouse mRNA for heparin binding protein 44 | gene | B | N | NC | | 0 | 0 | I | | 1.2 | 0.02 | NC | * | 1.4 | 0 |
| L49433 | "Mus musculus TNFR2-TRAF signalling complex protein m | gene | B | N | I | * | ~1.0 | 0 | I | * | ~1.1 | 0.02 | NC | * | 0 | 0.1 |
| U43321 | "Mus musculus putative transmembrane receptor (frizzled | gene | B | N | NC | | 0 | 0 | MI | | ~1.2 | 0.02 | MI | * | ~2.0 | 0.2 |
| AA023087 | mh67a10.r1 Soares mouse placenta ANbMp13.5 14.5 Mus m | est | B | N | NC | * | 0 | 0 | I | * | 1.3 | 0.02 | NC | * | ~2.1 | 0 |
| X84797 | M. musculus mRNA similar to human hematopoeitic specifi | gene/ B | N | NC | * | 0 | 1 | * | ~1.2 | 0.02 | I | * | 0 | 1.70.1 |
| X75018 | M. musculus mRNA for Id4 helix-loop-helix protein | gene | C | N | I | * | ~1.0 | 0 | I | * | ~1.1 | 0.02 | I | * | 0 | 0 |
| U42385 | Mus musculus fibroblast growth fadtor inducible gene 16 | gene | C | N | I | | ~1.0 | 0 | I | * | ~1.1 | 0.02 | MI | * | 0 | 0 |
| AA103507 | mo25e04.r1 Life Tech mouse embryo 13 5dpc 10666014 M | est | C | N | NC | | 0 | 0 | MI | * | 1.1 | 0.02 | NC | | 0 | 0 |
| J03535 | "Mouse Ig-related glycoprotein-70 mRNA, complete cds" | gene | D | N | NC | * | ~1.0 | 0 | I | * | * | ~1.2 | 0.02 | I | | * | 1.70.1 |
| J03733 | "Mouse ornithing decarboxylase gene, complete cds" | gene | A | N | * | 0 | 0 | I | | 1.1 | 0.02 | NC | | 0 | 0 |
| AA021664 | mi03d01.r1 Soares mouse placenta 4NbMP13.5 14.5 Mus m | est | B | Y | I | * | 0 | 0 | MI | * | ~1.2 | 0.02 | NC | * | 0 | 0 |
| AA027404 | ml77b11.r1 Soares mouse embryo kidney (#937315) Mus muc | est | C | N | I | | 0 | 0 | I | | ~1.1 | 0.02 | NC | * | 0 | 0 |
| AA068062 | mi61g04.r1 Soares mouse embryo NbMF13.5 1A.5 Mus m | est | C | N | NC | | 0 | 0 | MI | | 1.2 | 0.02 | NC | * | 0 | 0 |
| AA015331 | "ms11t03s1 Stratagene mouse embryo skin (#937313) Mus muscul | est | D | N | I | * | 0 | 0 | I | | 1.1 | 0.02 | NC | | 0 | 0.4 |
| AA154013 | ms60c07.r1 Stratagene mouse embryonic carcinoma (#93 | est | D | N | NC | | ~1.0 | 0 | MI | | ~1.2 | 0.02 | I | * | 1.5 | 0.1 |
| AA170375 | ms16d09.r1 Soares mouse p3NMF19.5 Mus musculus cDN | est | D | N | NC | | 0 | 0 | I | | 1.2 | 0.02 | MI | * | 1.3 | 0 |
| M17790 | "Mouse SAA4 gene encoding serum amyloid A, exons 3 a | gene | A | N | I | * | 0 | 0 | MI | * | ~1.1 | 0.01 | NC | * | 0 | 0 |
| AA078994 | "mg65e12.r1 Soares mouse embryo NbME13.5 14.5 Mus mu | est | B | N | NC | * | ~1.0 | 0 | I | | 1.2 | 0.01 | NC | * | 0 | 0 |
| X55573 | M. musculus brain-derived neurotrophic factor mRNA | gene | B | N | NC | | 1 | 0 | I | * | ~1.1 | 0.01 | NC | * | 0 | 0 |
| Z22649 | M. musculus c-mpl mRNA | gene | B | N | NC | * | 0 | 0 | MI | | 1.2 | 0.01 | NC | * | 0 | 0 |
| AA073278 | mm82g03.r1 Stratagene mouse embryonic carcinoma RA | est | C | N | I | * | ~1.0 | 0 | I | * | ~1.1 | 0.01 | NC | * | 0 | 0 |
| AA107515 | mp05g08.r1 Life Tech mouse embryo 8 5dpc 10664019 Mu | est | C | N | NC | | 0 | 0 | I | | 1.1 | 0.01 | NC | | 0 | 0 |
| AA120368 | mn17d01.r1 Beddington mouse embryonic region Mus mu | est | C | N | NC | * | 0 | 0 | I | * | ~1.2 | 0.01 | MI | * | 0 | 0 |
| X82457 | M. musculus es64 mRNA | gene | B | N | NC | | 0 | 0 | I | | 1.1 | 0.01 | MI | | 1.3 | 0.1 |
| X57277 | M. musculus rac1 gene | gene | C | N | NC | | 0 | 0 | I | | 1.1 | 0.01 | NC | | 0 | 0 |
| U56773 | "Mus musculus pelle-like protein kinase mRNA, complete c | gene | C | N | I | | 0 | 0 | I | | 1.1 | 0.01 | NC | | 0 | 0 |
| U66849 | "Mus musculus hereditary haemochromatosis homolog mP | gene | C | N | MI | * | ~1.0 | 0 | MI | | 1.2 | 0.01 | NC | | 0 | 0 |
| U30838 | Mus musculus voltage dependent anion channel 2 mRNA | gene | C | N | I | | 1 | 0 | I | | 1.1 | 0.01 | NC | | 0 | 0 |
| AA162290 | ms27c12.r1 Stratagene mouse embryo skin (#937313) Mus muscl | est | D | N | NC | | 0 | 0 | MI | | ~1.2 | 0.01 | NC | | 0 | 0 |
| W90837 | mf78g07.r1 Soares mouse embryo NbME13.5 14.5 Mus m | est | D | N | NC | | 0 | 0 | I | | 1.1 | 0.01 | I | | 1.3 | 0.1 |

TABLE 6-continued

ISGs and IRGs identified from mouse embryonic fibroblast incubated in the presence or absence of IFN-αBBDB in the presence or absence of encephalomyocarditis virus

| Accession | Description | | | | | | | | | |
|---|---|---|---|---|---|---|---|---|---|---|
| M13963 | "Mouse inhibitory G protein of adenylate cyclase, alpha ch gene | D | N | NC | 0 | 0 | I | 1.1 | 0.01 | NC | 0 | 0 |
| M57696 | "Mouse lyn A protein tyrosine kinase (lynA) mRNA, compl gene | D | N | NC | * | 0 | I | * | 1.2 | 0.01 | NC | 0 | 0 |
| D38417 | "Mouse mRNA for arylhydrocarbon receptor, complete cd gene | D | N | I | * | 0 | I | * | ~1.1 | 0.01 | 1 | 1.7 | 0.1 |
| L21768 | "Mus musculus eps15 mRNA, complete cds" gene | D | N | I | * | ~1.0 | I | * | ~1.1 | 0.01 | NC | 0 | 0 |

1 - untreated RNL +/30
2 - IFNA - 18 h
3 - IFNA - 18 h + EMCV 6 h

TABLE 7

MURINE GENES INDUCED BY IFN-α

| Apoptosis | Immune | Growth Regulation |
|---|---|---|
| ICH-3 (Caspase-11) | Modulation | P204 |
| | | |
| PML | ISG-15 | PML |
| MyD88 | MIG | GTP binding Proteins |
| | | |
| Signaling | CyCAP | LRG-47 |
| | | |
| IRF-1 & 7 | RANTES | GTP2 |
| STAT 1 | MCP-5 | Miscellaneous |
| | | |
| PML | IAP | Thymidylate kinase hom. |
| G3BP | Antigen Processing | Apolipoprotein D |
| | | |
| MyD88 | LMP 2 & 7 | GARGs |
| ISGF3-γ | PA 28 α and β | |
| Endoglin | HAM 1 | |
| IKB-α | TAP 2 | |
| Rpt-1 r | | |

TABLE 8

EMCV-enhancement of gene expression in interferon-treated cells

| | |
|---|---|
| TK Homologue | Growth Factor Inducible Prot. |
| GARGs | Inhibin β A subunit |
| G/H synthase | Inhibin β B subunit |
| Squalene epoxidase | IKB-α |
| Cell. Retinoic acid BP | EGF-like growth factor |
| Hyaluronan Synth. Hom. | RANTES |
| PG2 (decorin) | Epiregulin |
| IL-11 | IL-6 |
| Pulmonary Surfactant Prot. | IFN-β |

What is claimed is:

1. An array for identifying agents which mimic or inhibit the activity of interferons comprising:

a) gene probes that hybridize with from about 50 to about 10,000 interferon-stimulated and interferon-repressed gene transcripts, and b) a substrate to which said gene probes are attached;

wherein the array comprises gene probes that hybridize to transcripts of no more than 99 genes whose expression is known not to be stimulated or repressed by interferon treatment, and wherein the array comprises a probe that hybridizes with the transcript of human phospholipid scramblase.

2. The array of claim 1 wherein the gene probes are selected from the group consisting of oligonucleotides, cDNA molecules, and synthetic gene probes comprising nucleobases.

3. The array of claim 1 wherein the array comprises a plurality of the genes listed in Table 2.

4. The array of claim 1 wherein the array comprises a plurality of the genes listed in Table 3.

5. An array for identifying agents which mimic or inhibit the activity of interferons comprising:

a) gene probes that hybridize with from about 50 to about 10,000 interferon-stimulated and interferon-repressed gene transcripts, and b) a substrate to which said gene probes are attached;

wherein the array comprises gene probes that hybridize to transcripts of no more than 99 genes whose expression is known not to be stimulated or repressed by interferon treatment, and wherein the array comprises a probe that hybridizes with the transcript of human 52 kD SS A-Ro autoantigen.

6. The array of claim 5 wherein the gene probes are selected from the group consisting of oligonucleotides, cDNA molecules, and synthetic gene probes comprising nucleobases.

7. The array of claim 5 wherein the array comprises a plurality of the genes listed in Table 2.

8. The array of claim 5 wherein the array comprises a plurality of the genes listed in Table 3.

* * * * *